US011167010B2

(12) United States Patent
Wang et al.

(10) Patent No.: US 11,167,010 B2
(45) Date of Patent: Nov. 9, 2021

(54) TREFOIL FAMILY FACTOR PROTEINS AND USES THEREOF

(71) Applicant: THE TRUSTEES OF COLUMBIA UNIVERSITY IN THE CITY OF NEW YORK, New York, NY (US)

(72) Inventors: Timothy C. Wang, New York, NY (US); Jan K. Kitajewski, Ridgewood, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 16/189,868

(22) Filed: Nov. 13, 2018

(65) Prior Publication Data

US 2019/0298798 A1 Oct. 3, 2019

Related U.S. Application Data

(63) Continuation of application No. 15/367,958, filed on Dec. 2, 2016, now Pat. No. 10,124,037, which is a continuation of application No. 14/550,246, filed on Nov. 21, 2014, now abandoned, which is a continuation-in-part of application No. PCT/US2013/034981, filed on Apr. 2, 2013.

(60) Provisional application No. 61/649,767, filed on May 21, 2012.

(51) Int. Cl.

*A61K 38/17* (2006.01)
*G01N 33/574* (2006.01)
*A61K 38/22* (2006.01)

(52) U.S. Cl.

CPC .......... *A61K 38/1709* (2013.01); *A61K 38/22* (2013.01); *G01N 33/57419* (2013.01); *G01N 33/57446* (2013.01); *G01N 2333/4704* (2013.01)

(58) Field of Classification Search

CPC ............... A61K 38/1709; A61K 38/22; G01N 33/57446; G01N 33/57419

See application file for complete search history.

(56) References Cited

U.S. PATENT DOCUMENTS

| | | | |
|---|---|---|---|
| 10,124,037 | B2 | 11/2018 | Wang |
| 2003/0166911 | A1 | 9/2003 | Ebner |
| 2003/0186880 | A1 | 10/2003 | Podolsky |

OTHER PUBLICATIONS

Otto et al. (Identification of blottin: A novel gastric trefoil factor family-2 binding protein; Proteomics, vol. 6, No. 15, pp. 4235-4245, Aug. 2006 (Year: 2006).*

*Homo sapiens* trefoil factor 2; *Homo sapiens* trefoil factor 2 (TFF2), mRNA; NCBI Reference Sequence: NM_005423.4; www.ncbi.nlm.nih.gov/nuccore/195234777?sat=14&satkey=9004569; pp. 1-5, available Mar. 11, 2011.

Mundy-Bosse et al.; Distinct myeloid suppressor cell subsets correlate with plasma IL-6 and IL-10 and reduced interferon-alpha signaling in CD4+ T cells from patients with GI malignancy; Cancer Immunol Immunother (2011) 60:1269-1279; published online May 21, 2011.

Jul. 11, 2017 Office Action issued in connection with U.S. Appl. No. 15/367,958.

Nov. 20, 2017 Amendment in Response dated Jul. 11, 2017 Office Action filed in connection with U.S. Appl. No. 15/367,958.

Declaration of Dr. Anil K. Rustgi Under 35 U.S.C. § 1.132 (excluding Exhibits 2-7) filed Nov. 20, 2017 in connection with U.S. Appl. No. 15/367,958.

Jan. 18, 2018 Final Office Action issued in connection with U.S. Appl. No. 15/367,958.

May 16, 2018 Amendment in Response to Jan. 18, 2018 Final Office Action filed in connection with U.S. Appl. No. 15/367,958.

May 23, 2018 Advisory Action issued in connection with U.S. Appl. No. 15/367,958.

Jun. 25, 2018 Notice of Allowance issued in connection with U.S. Appl. No. 15/367,958.

* cited by examiner

*Primary Examiner* — Antonio Galisteo Gonzalez
(74) *Attorney, Agent, or Firm* — John P. White

(57) ABSTRACT

The invention provides for methods for treating an inflammatory disease of the digestive system in a subject by administering a trefoil family molecule. The invention provides for methods for treating a digestive system cancer in a subject by administering a trefoil family molecule. The invention provides for methods for cell proliferation in a subject by administering a trefoil family molecule.

5 Claims, 70 Drawing Sheets

Specification includes a Sequence Listing.

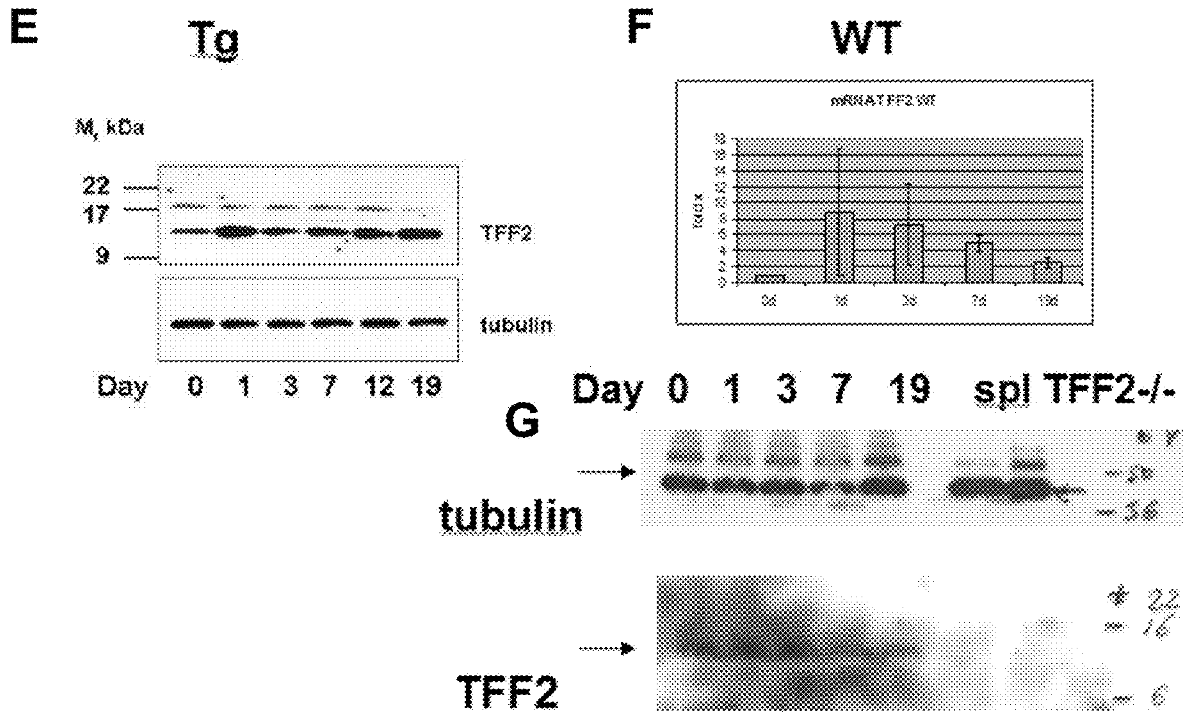
FIGS. 1E-G g h

H
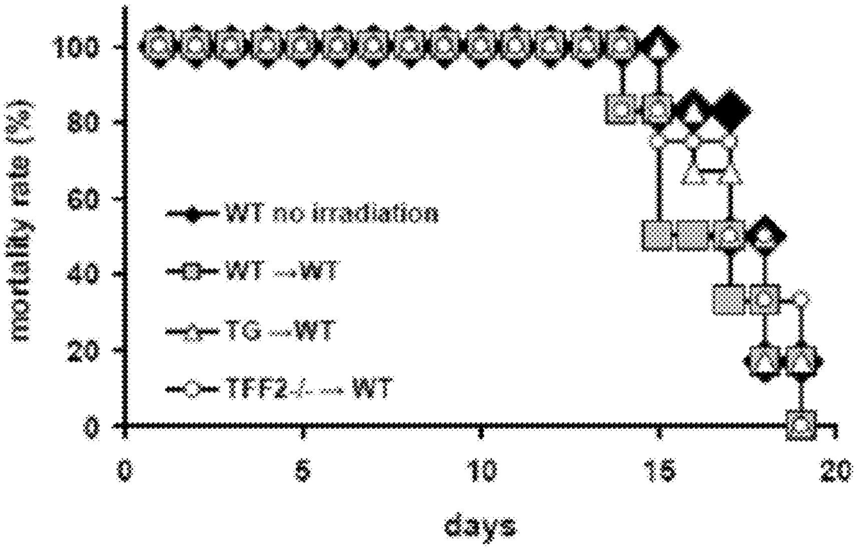
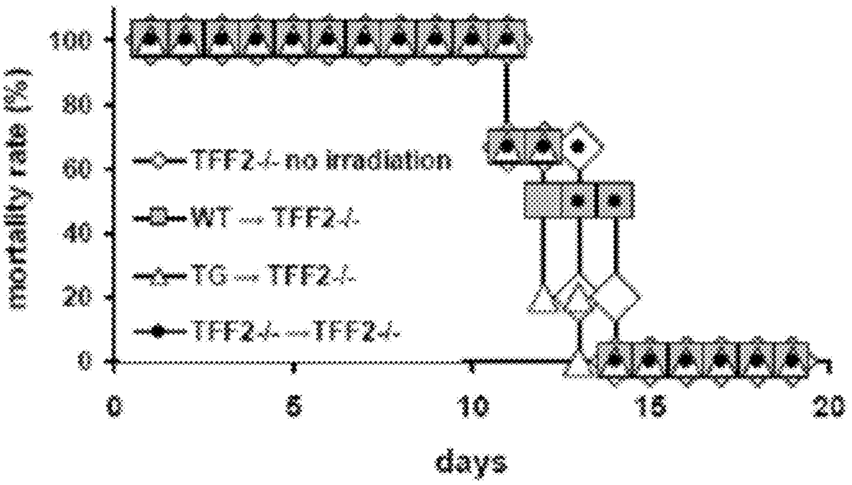
*FIG. 6H*

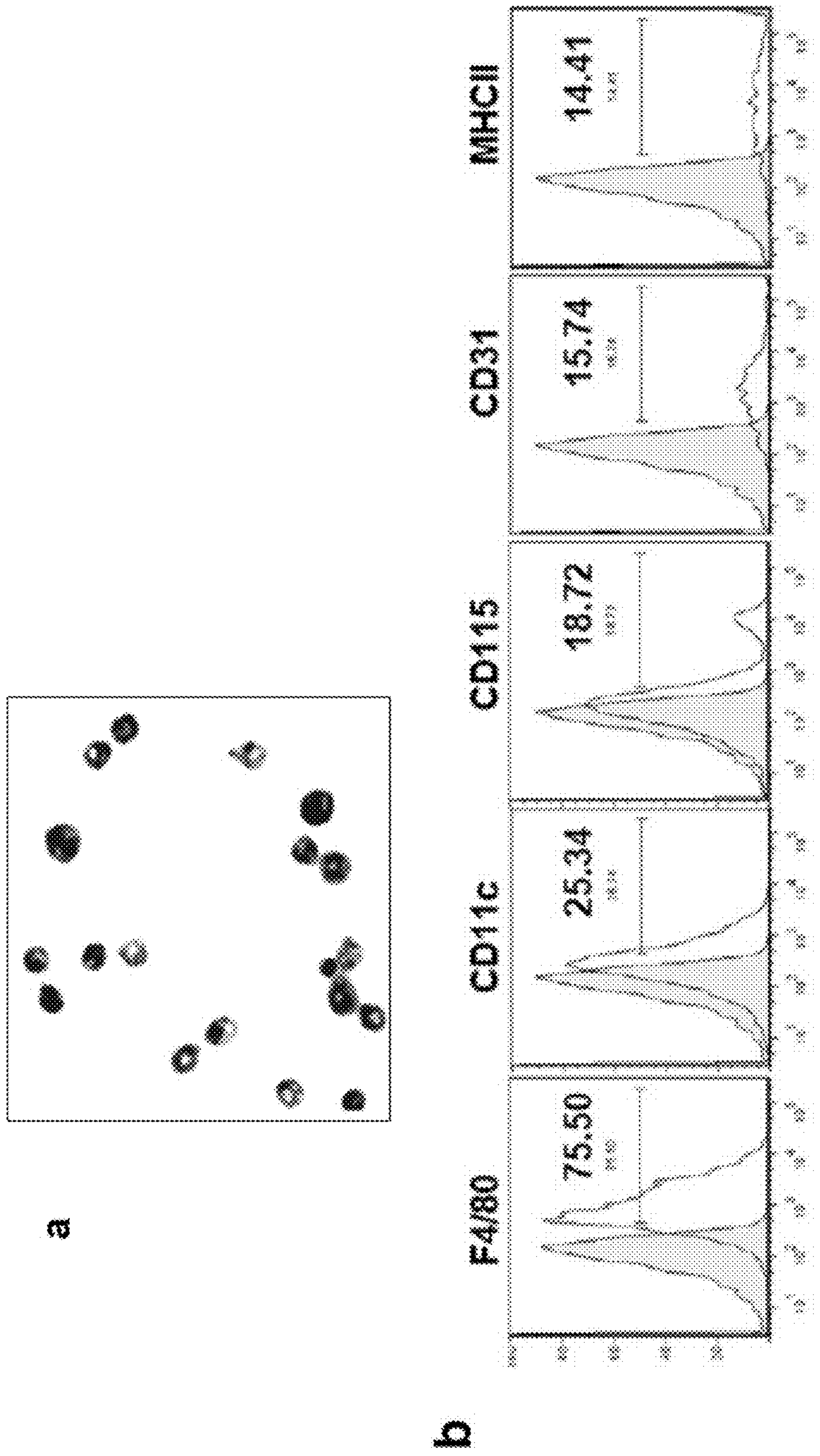
FIGS. 9A-B

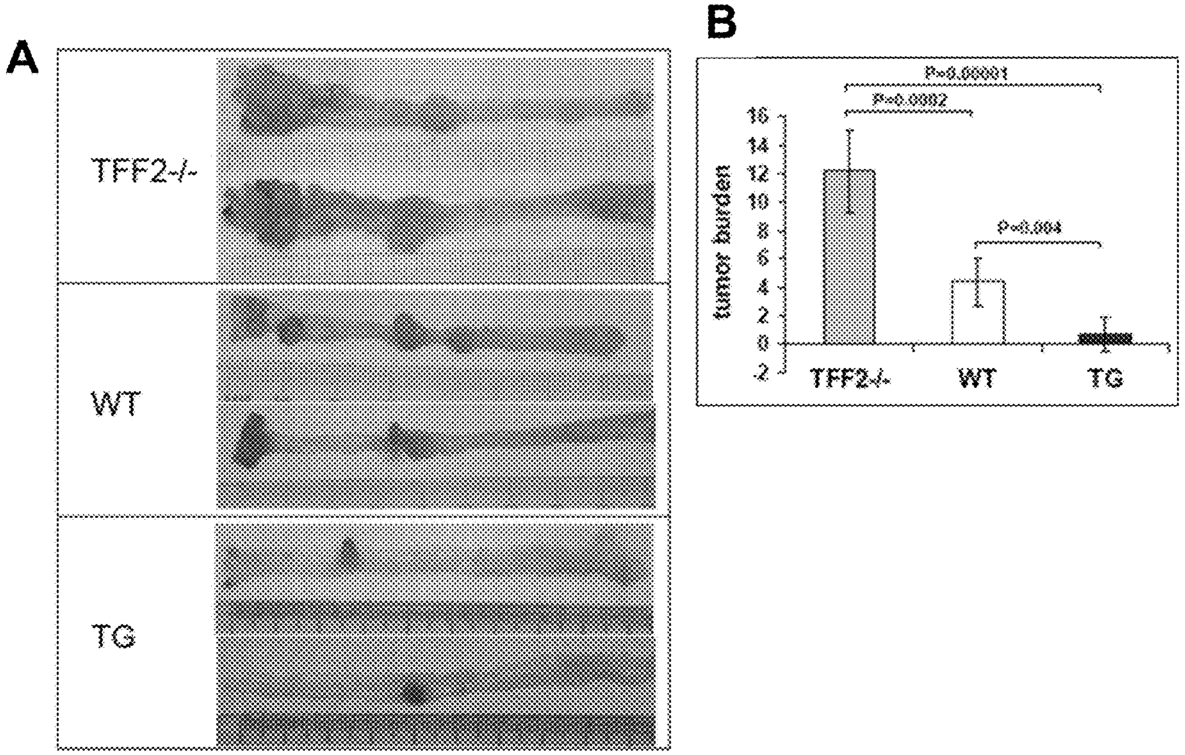
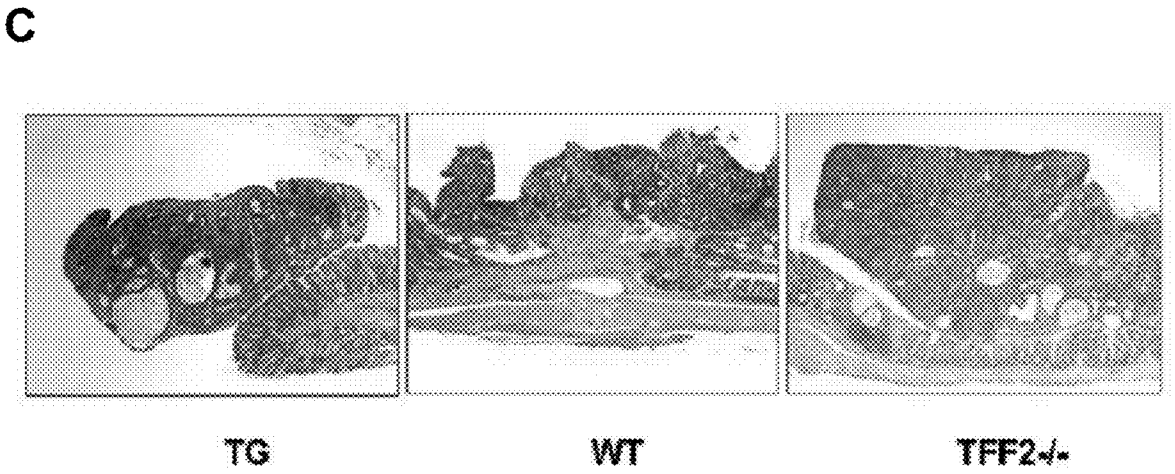
*FIGS. 11A-11C*

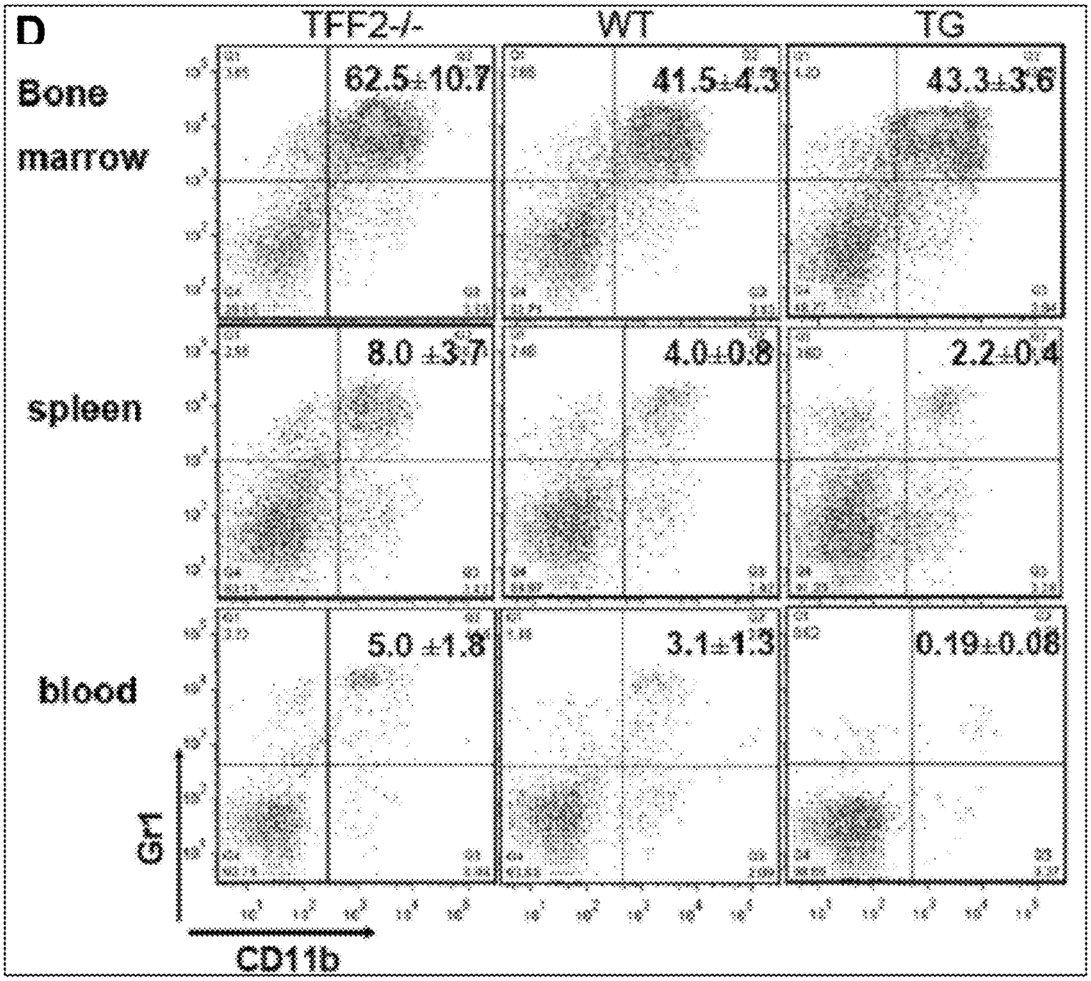
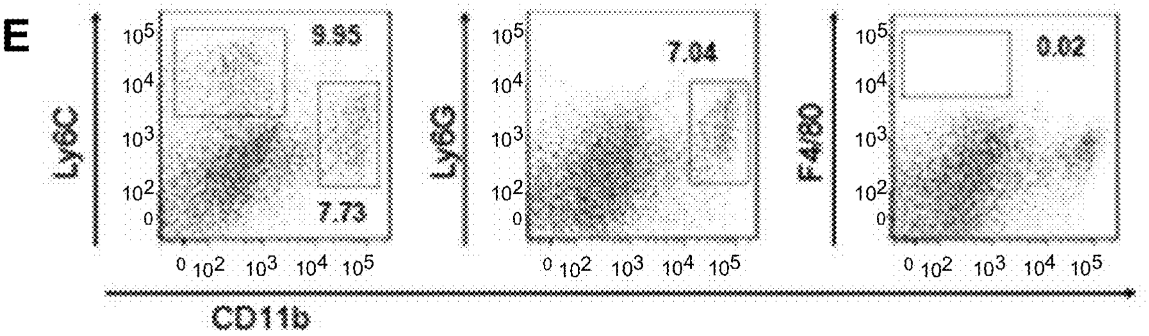
FIGS. 11D-E

6% DSS

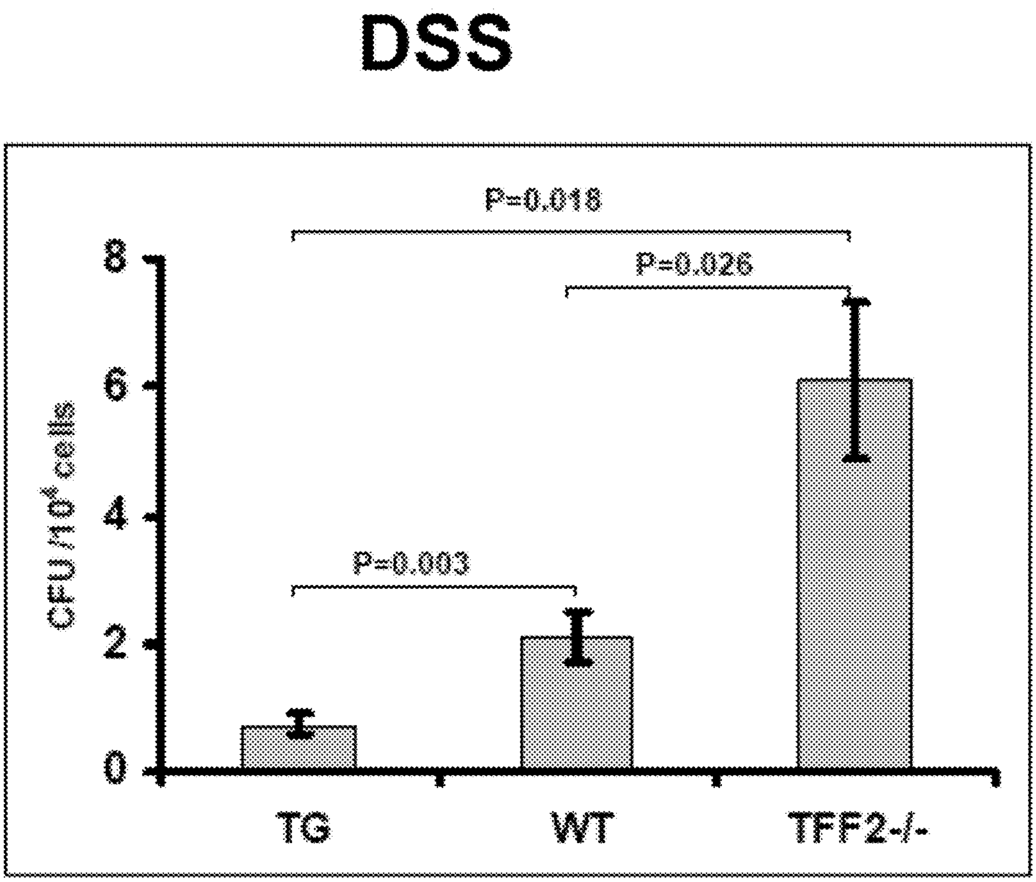
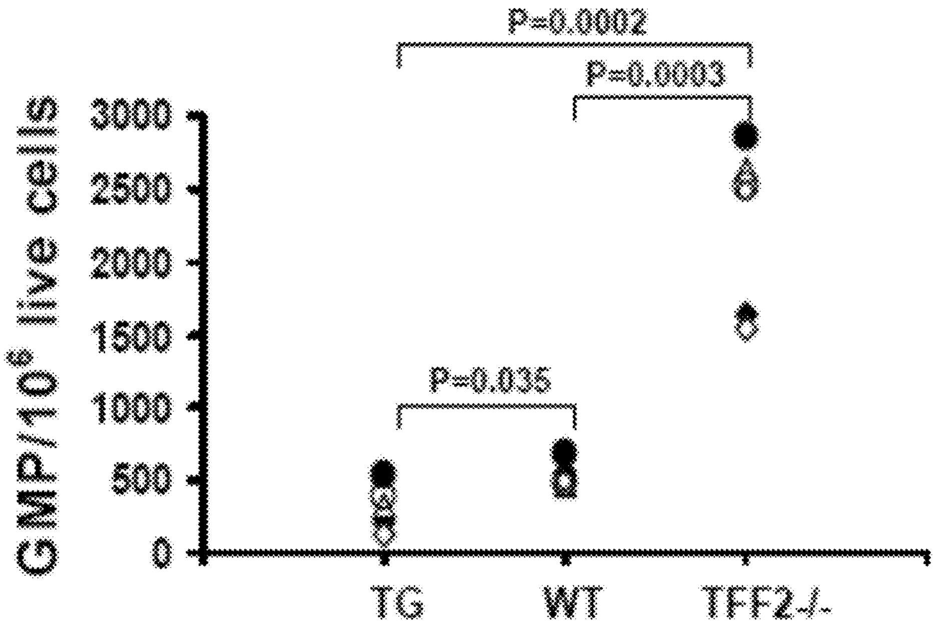
*FIG. 40*

| Symbol | Description | Fold Change |
|---|---|---|
| Myb(x3) | myeloblastosis oncogene | 6.54 |
| Gfi1 | growth factor independent 1 | 6.08 |
| Fos | FBJ osteosarcoma oncogene | 4.09 |
| Prdm1 | PR domain containing 1, with ZNF domain | 3.95 |
| Lyl1 | lymphoblastomic leukemia 1 | 3.93 |
| Hoxa9 | homeobox A9 | 3.82 |
| Klf5 | Kruppel-like factor 5 | 3.16 |
| XXXXXXXX | XXXXXXXXXXXXXXXXXXXXXXXXXXXXXXXXXXXXXXXXXXXX | XXXXXXXX |
| Junb | Jun-B oncogene | 1.89 |

AP-1

Co-Factor

Bcl3 B cell leukemia/lymphoma 3 2.62

FIG. 44

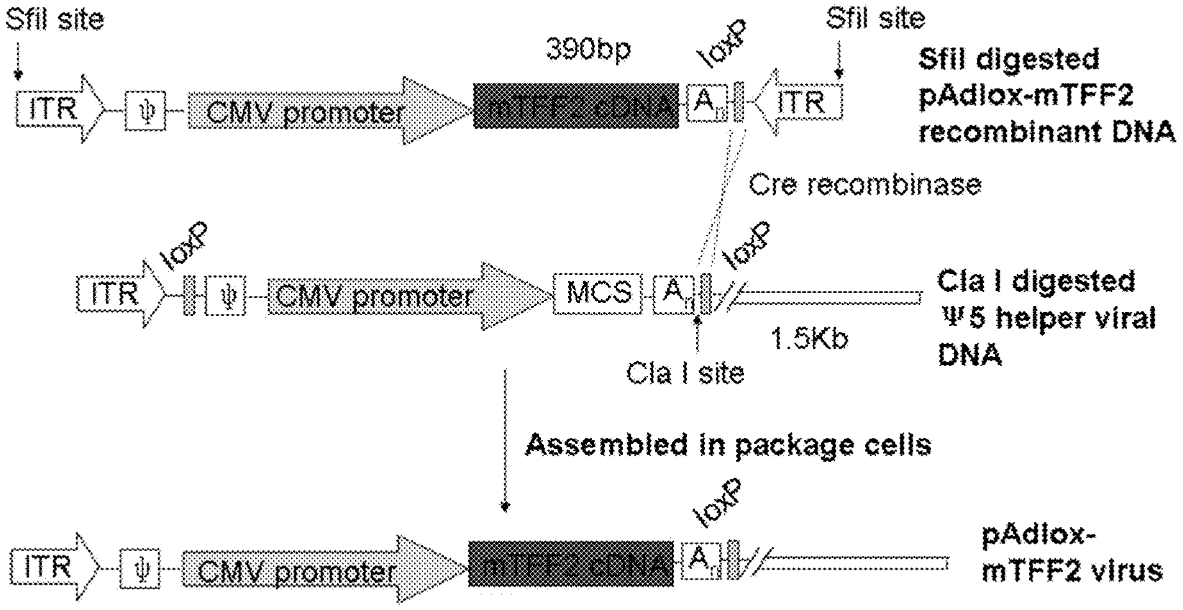
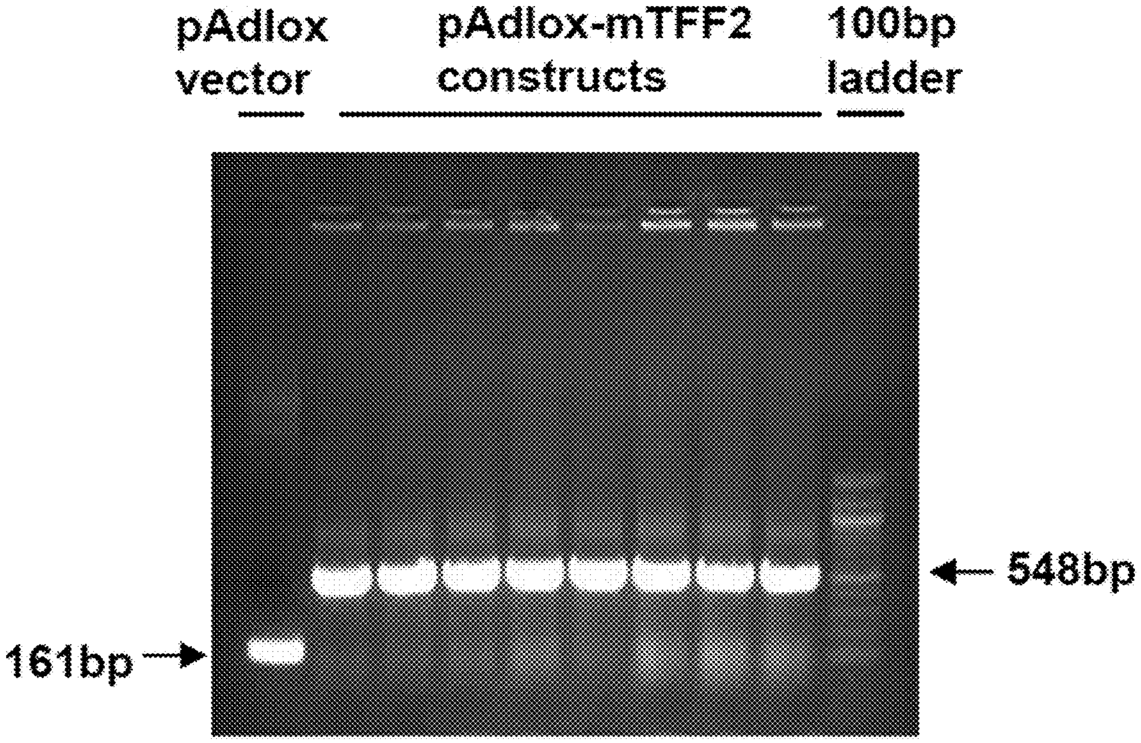
FIG. 47

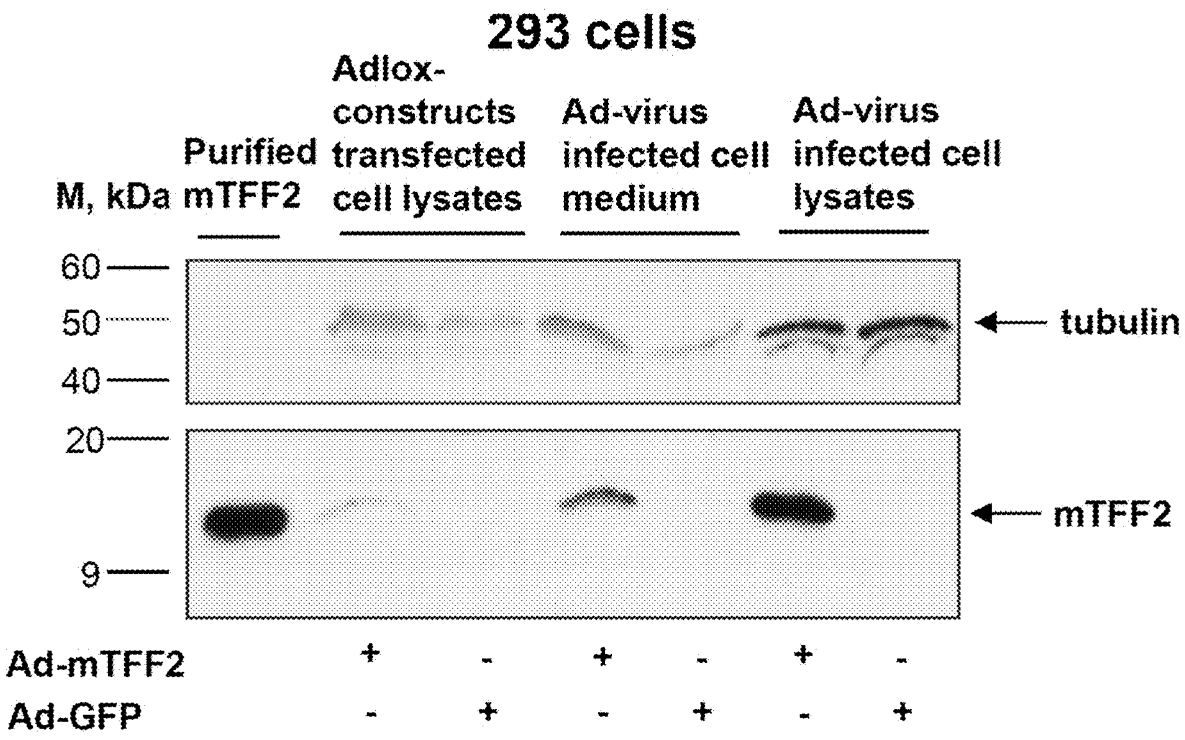
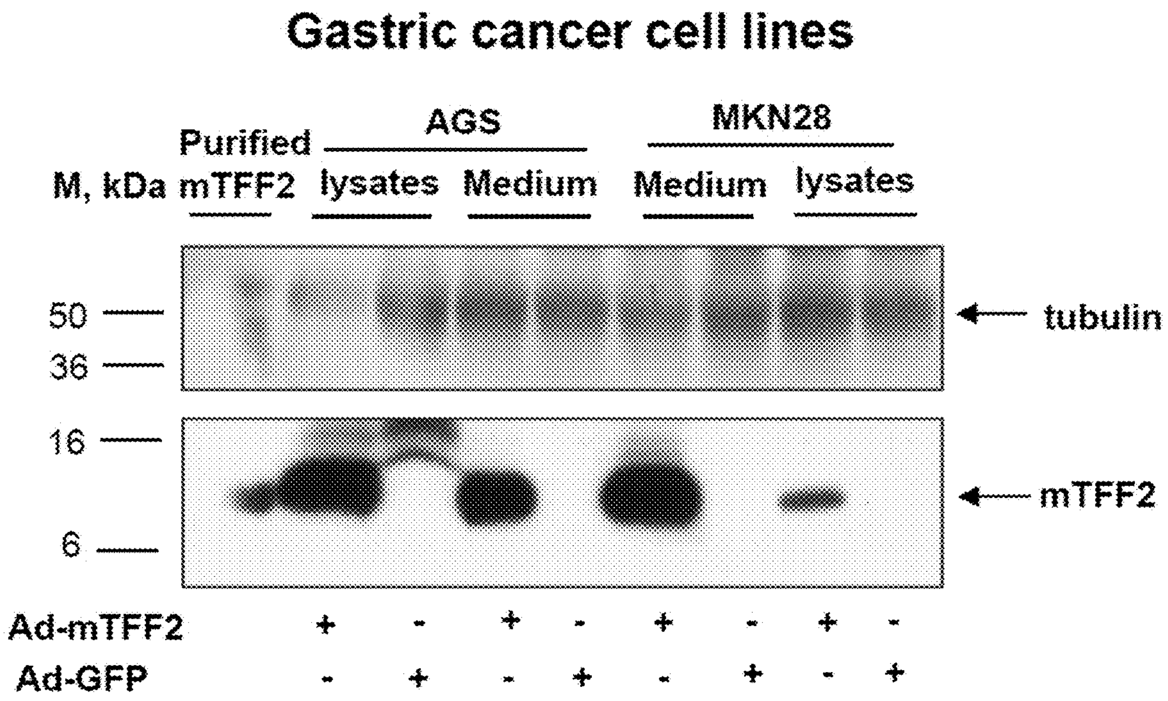
FIG. 50

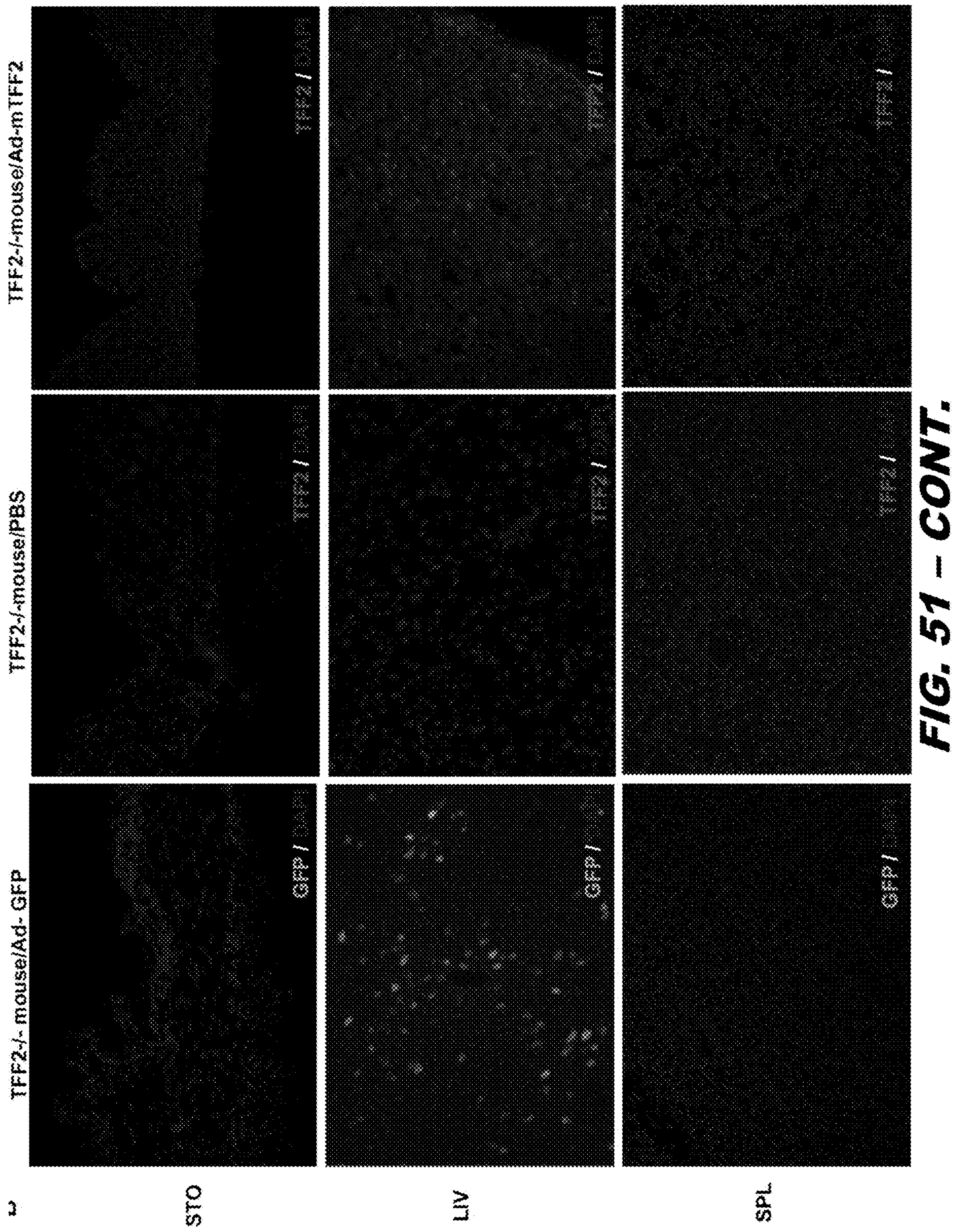
FIG. 51 – CONT.

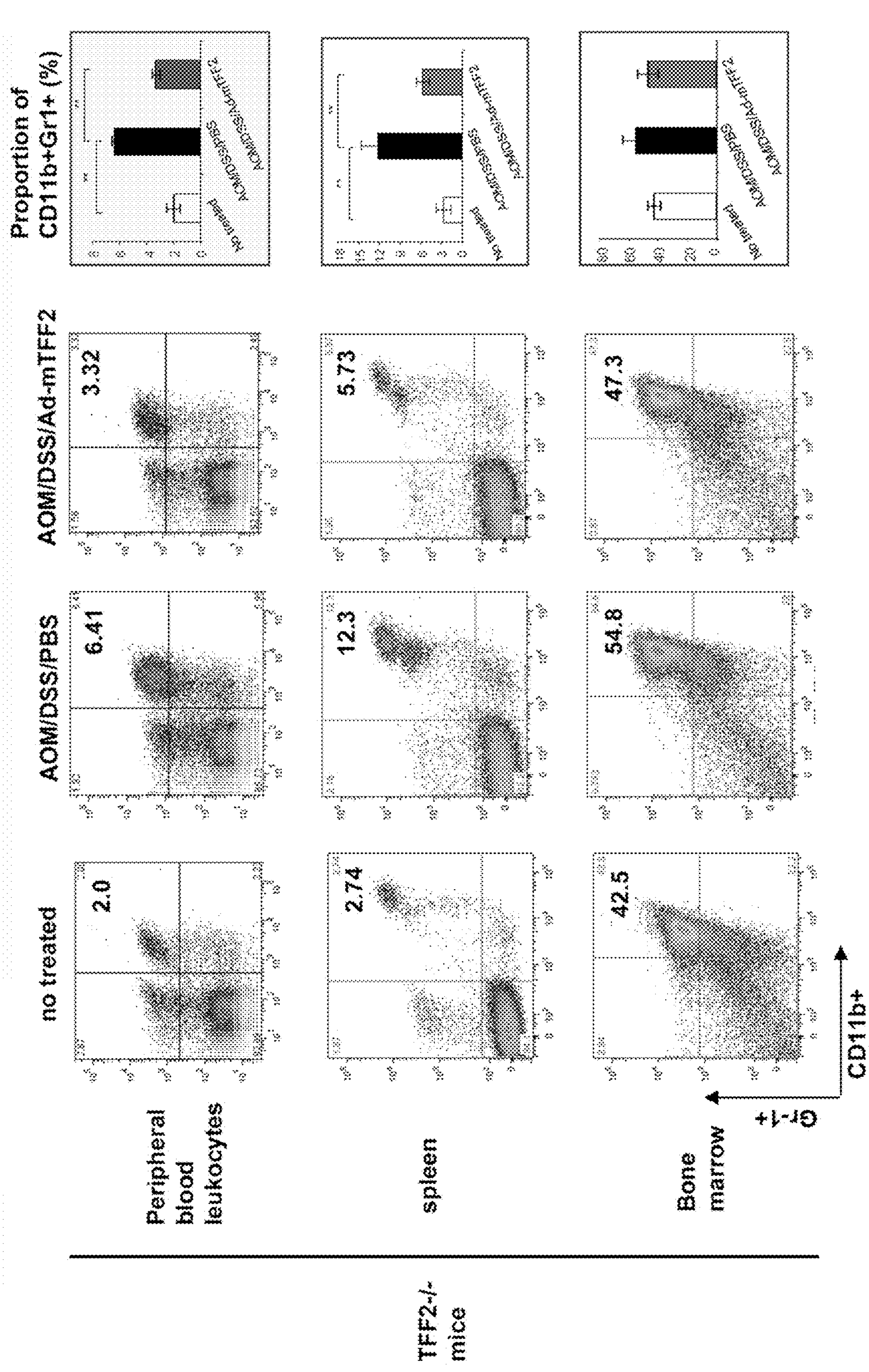
FIG. 56 – Cont.

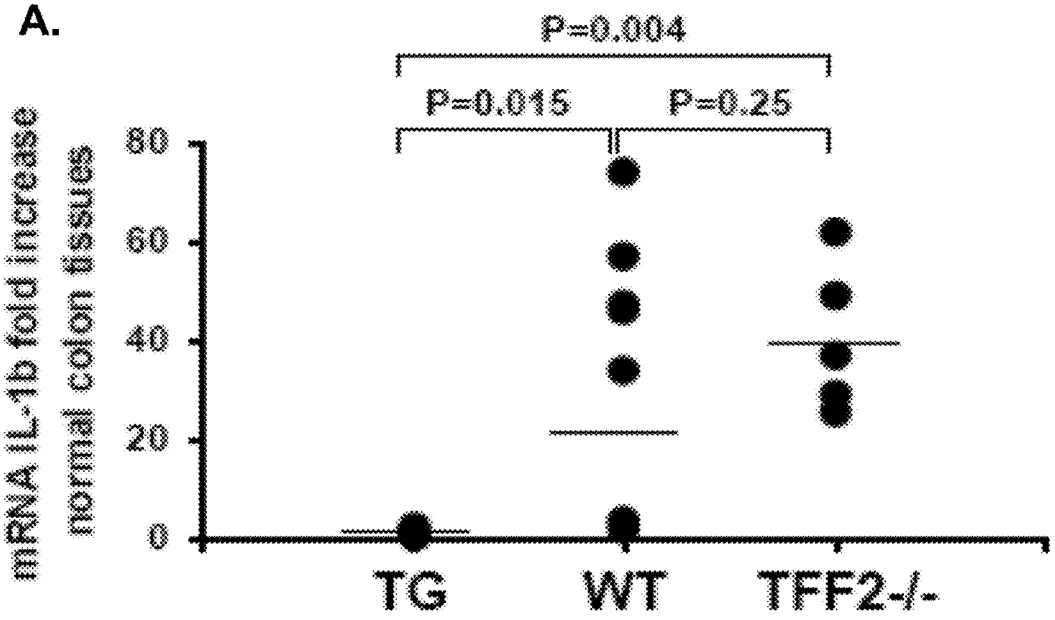
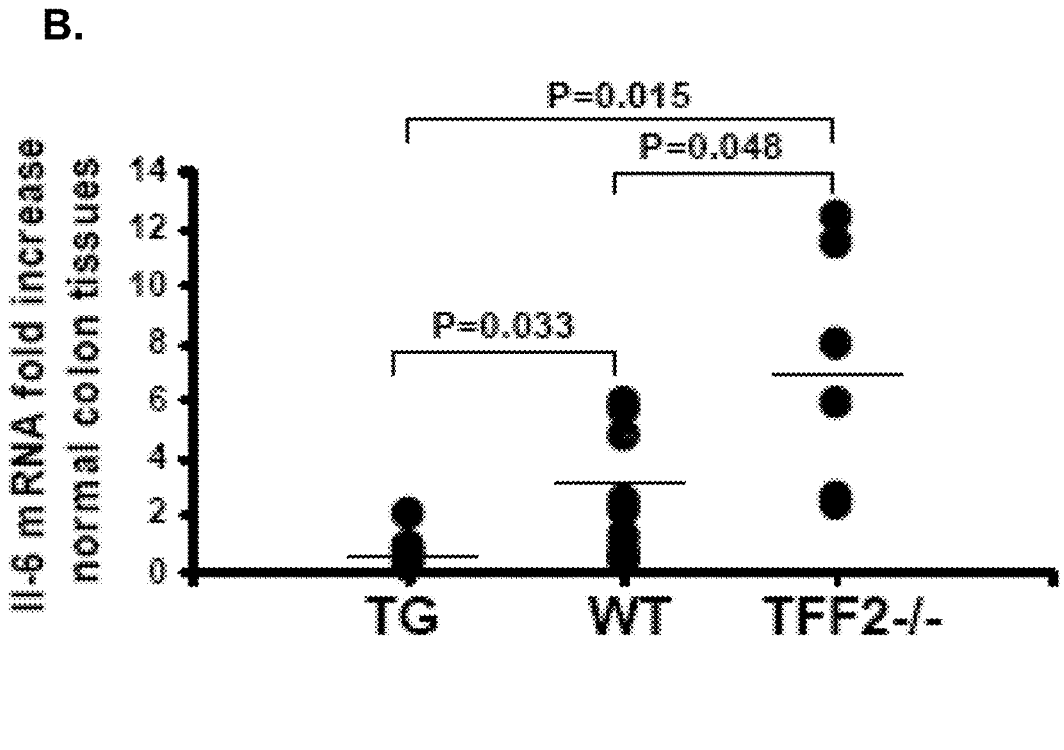
*FIGS. 59A-B*

C.
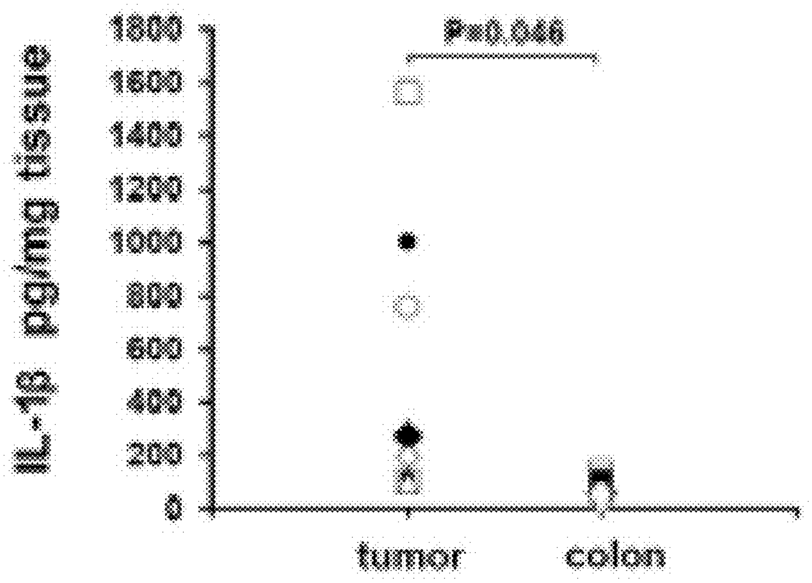
D.
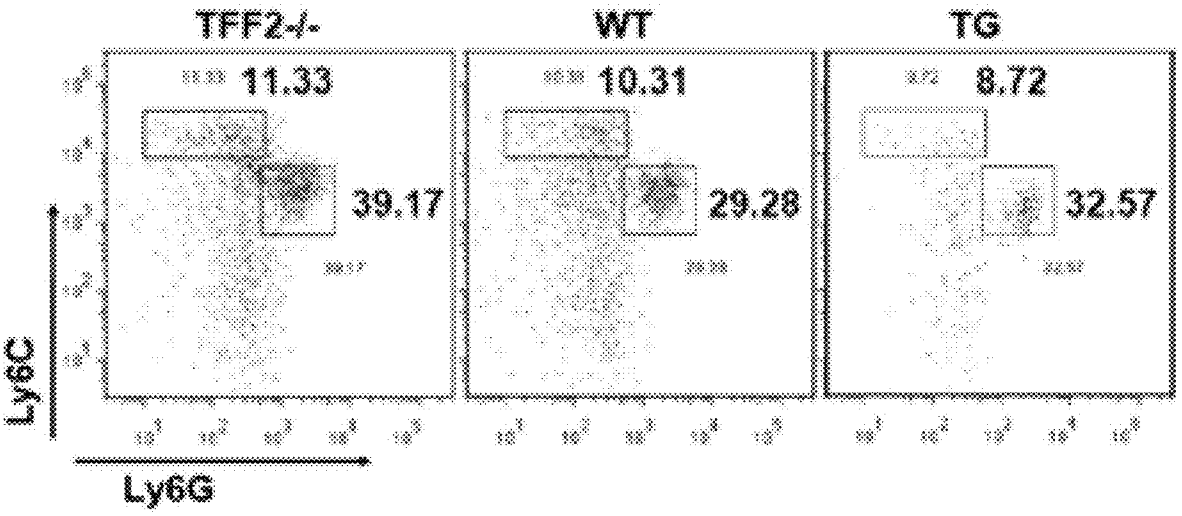
FIGS. 59C-D

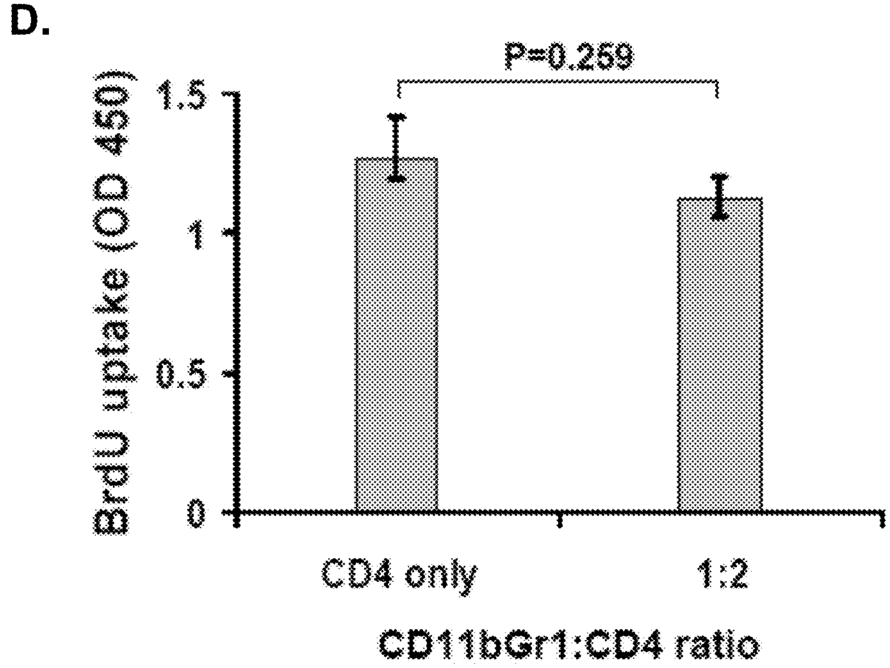
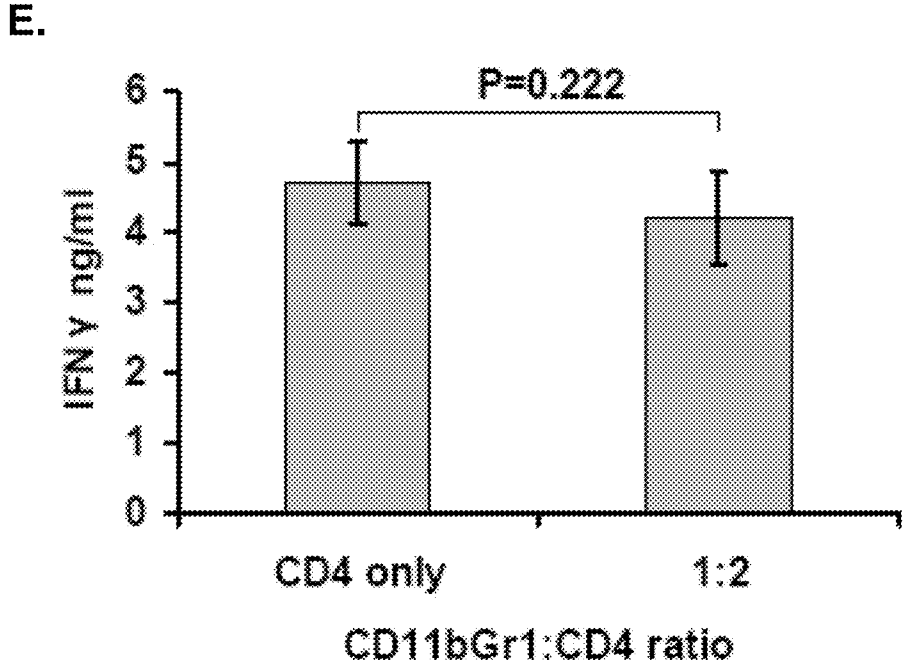
*FIGS. 61D-E*

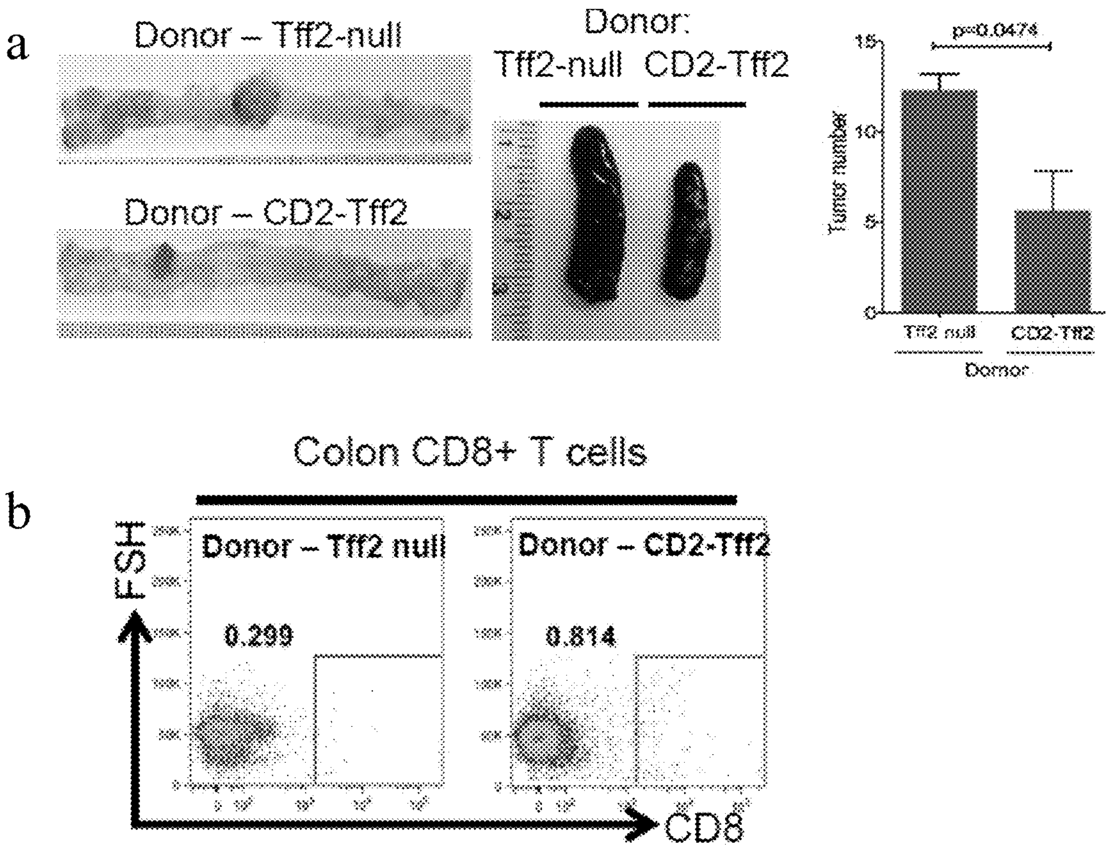
*FIGS. 68A-B*

SEQUENCE LISTING

```
<160> NUMBER OF SEQ ID NOS: 25

<210> SEQ ID NO 1
<211> LENGTH: 84
<212> TYPE: PRT
<213> ORGANISM: Homo sapiens

<400> SEQUENCE: 1

Met Ala Thr Met Glu Asn Lys Val Ile Cys Ala Leu Val Leu Val Ser
1               5                   10                  15

Met Leu Ala Leu Gly Thr Leu Ala Glu Ala Gln Thr Glu Thr Cys Thr
            20                  25                  30

Val Ala Pro Arg Glu Arg Gln Asn Cys Gly Phe Pro Gly Val Thr Pro
        35                  40                  45

Ser Gln Cys Ala Asn Lys Gly Cys Cys Phe Asp Asp Thr Val Arg Gly
    50                  55                  60

Val Pro Trp Cys Phe Tyr Pro Asn Thr Ile Asp Val Pro Pro Glu Glu
65                  70                  75                  80

Glu Cys Glu Phe


<210> SEQ ID NO 2
<211> LENGTH: 508
<212> TYPE: DNA
<213> ORGANISM: Homo sapiens

<400> SEQUENCE: 2
```

-continued

```
atccctgact cggggtcgcc tttggagcag agaggaggca atggccacca tggagaacaa     60

ggtgatctgc gccctggtcc tggtgtccat gctggccctc ggcaccctgg ccgaggccca    120

gacagagacg tgtacagtgg ccccccgtga aagacagaat tgtggttttc ctggtgtcac    180

gccctcccag tgtgcaaata agggctgctg tttcgacgac accgttcgtg gggtcccctg    240

gtgcttctat cctaatacca tcgacgtccc tccagaagag gagtgtgaat tttagacact    300

tctgcaggga tctgcctgca tcctgacgcg gtgccgtccc cagcacggtg attagtccca    360

gagctcggct gccacctcca ccggacacct cagacacgct tctgcagctg tgcctcggct    420

cacaacacag attgactgct ctgactttga ctactcaaaa ttggcctaaa aattaaaaga    480

gatcgatatt aaaaaaaaaa aaaaaaaa                                         508
```

<210> SEQ ID NO 3
<211> LENGTH: 129
<212> TYPE: PRT
<213> ORGANISM: Homo sapiens

<400> SEQUENCE: 3

```
Met Gly Arg Arg Asp Ala Gln Leu Leu Ala Ala Leu Leu Val Leu Gly
1               5                   10                  15

Leu Cys Ala Leu Ala Gly Ser Glu Lys Pro Ser Pro Cys Gln Cys Ser
            20                  25                  30

Arg Leu Ser Pro His Asn Arg Thr Asn Cys Gly Phe Pro Gly Ile Thr
        35                  40                  45

Ser Asp Gln Cys Phe Asp Asn Gly Cys Cys Phe Asp Ser Ser Val Thr
    50                  55                  60

Gly Val Pro Trp Cys Phe His Pro Leu Pro Lys Gln Glu Ser Asp Gln
65                  70                  75                  80

Cys Val Met Glu Val Ser Asp Arg Arg Asn Cys Gly Tyr Pro Gly Ile
                85                  90                  95

Ser Pro Glu Glu Cys Ala Ser Arg Lys Cys Cys Phe Ser Asn Phe Ile
            100                 105                 110

Phe Glu Val Pro Trp Cys Phe Phe Pro Lys Ser Val Glu Asp Cys His
        115                 120                 125

Tyr
```

<210> SEQ ID NO 4
<211> LENGTH: 717
<212> TYPE: DNA
<213> ORGANISM: Homo sapiens

<400> SEQUENCE: 4

```
cacggtggaa gggctggggc cacggggcag agaagaaagg ttatctctgc ttgttggaca     60

aacagagggg agattataaa acatacccgg cagtggacac catgcattct gcaagccacc    120

ctggggtgca gctgagctag acatgggacg gcgagacgcc cagctcctgg cagcgctcct    180

cgtcctgggg ctatgtgccc tggcggggag tgagaaaccc tccccctgcc agtgctccag    240

gctgagcccc cataacagga cgaactgcgg cttccctgga atcaccagtg accagtgttt    300

tgacaatgga tgctgtttcg actccagtgt cactggggtc ccctggtgtt tccacccccct   360

cccaaagcaa gagtcggatc agtgcgtcat ggaggtctca gaccgaagaa actgtggcta    420

cccgggcatc agccccgagg aatgcgcctc tcggaagtgc tgcttctcca acttcatctt    480

tgaagtgccc tggtgcttct tcccgaagtc tgtggaagac tgccattact aagagaggct    540

ggttccagag gatgcatctg gctcaccggg tgttccgaaa ccaaagaaga aacttcgcct    600
```

tatcagcttc atacttcatg aaatcctggg ttttcttaac catcttttcc tcattttcaa 660
tggtttaaca tataatttct ttaaataaaa cccttaaaat ctgctaaaaa aaaaaaa 717

<210> SEQ ID NO 5
<211> LENGTH: 94
<212> TYPE: PRT
<213> ORGANISM: Homo sapiens

<400> SEQUENCE: 5

Met Lys Arg Val Leu Ser Cys Val Pro Glu Pro Thr Val Val Met Ala
1 5 10 15

Ala Arg Ala Leu Cys Met Leu Gly Leu Val Leu Ala Leu Leu Ser Ser
20 25 30

Ser Ser Ala Glu Glu Tyr Val Gly Leu Ser Ala Asn Gln Cys Ala Val
35 40 45

Pro Ala Lys Asp Arg Val Asp Cys Gly Tyr Pro His Val Thr Pro Lys
50 55 60

Glu Cys Asn Asn Arg Gly Cys Cys Phe Asp Ser Arg Ile Pro Gly Val
65 70 75 80

Pro Trp Cys Phe Lys Pro Leu Gln Glu Ala Glu Cys Thr Phe
85 90

<210> SEQ ID NO 6
<211> LENGTH: 1054
<212> TYPE: DNA
<213> ORGANISM: Homo sapiens

<400> SEQUENCE: 6
gccaaaacag tgggggctga actgacctct ccccttttggg agagaaaaac tgtctgggag 60
cttgacaaag gcatgcagga gagaacagga gcagccacag ccaggaggga gagccttccc 120
caagcaaaca atccagagca gctgtgcaaa caacggtgca taaatgaggc ctcctggacc 180
atgaagcgag tcctgagctg cgtcccggag cccacggtgg tcatggctgc cagagcgctc 240
tgcatgctgg ggctggtcct ggccttgctg tcctccagct ctgctgagga gtacgtgggc 300
ctgtctgcaa accagtgtgc cgtgccagcc aaggacaggg tggactgcgg ctacccccat 360
gtcaccccca aggagtgcaa caaccggggc tgctgctttg actccaggat ccctggagtg 420
ccttggtgtt tcaagcccct gcaggaagca gaatgcacct tctgaggcac ctccagctgc 480
ccccggccgg gggatgcgag gctcggagca cccttgcccg gctgtgattg ctgccaggca 540
ctgttcatct cagcttttct gtccctttgc tcccggcaag cgcttctgct gaaagttcat 600
atctggagcc tgatgtctta acgaataaag gtcccatgct ccacccgagg acagttcttc 660
gtgcctgaga ctttctgagg ttgtgcttta tttctgctgc gtcgtgggag agggcgggag 720
ggtgtcaggg gagagtctgc ccaggcctca agggcaggaa aagactccct aaggagctgc 780
agtgcatgca aggatatttt gaatccagac tggcacccac gtcacaggaa agcctaggaa 840
cactgtaagt gccgcttcct cgggaaagca gaaaaaatac atttcaggta gaagttttca 900
aaaatcacaa gtctttcttg gtgaagacag caagccaata aaactgtctt ccaaagtggt 960
cctttatttc acaaccactc tcgctactgt tcaatacttg tactattcct gggttttgtt 1020
tctttgtaca gtaaacatta tgaacaaaca ggca 1054

<210> SEQ ID NO 7
<211> LENGTH: 33
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 7

attgaattcg ccaccatgcg acctcgagat gcc                                33


<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

aattgaattc tcagtagtga caatcttcca cagac                              35


<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

taagctctcg gggtgtggac tc                                            22


<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10

gaagtgggtg gaaacaccaa gg                                            22


<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11

tctccaaaga attcgccacc at                                            22


<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12

ggttggaaaa gcagcagttt cg                                            22


<210> SEQ ID NO 13
<211> LENGTH: 21
<212> TYPE: DNA
<213> ORGANISM: Artificial Sequence
```

<220> FEATURE:
<223> OTHER INFORMATION: Description of Artificial Sequence: Synthetic
primer

<400> SEQUENCE: 13
gctggactgc cgccatgaga a 21

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 14
tgccgccaca cttgaccagc 20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 15
tgctcagcgt tgggctgctg 20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 16
tgggacccaa gcgaggatgc 20

<210> SEQ ID NO 17
<211> LENGTH: 24
<212> TYPE: DNA
<213> ORGANISM: Mus musculus

<400> SEQUENCE: 17
accacacctt ctacaatgag ctgc 24

<210> SEQ ID NO 18
<211> LENGTH: 22
<212> TYPE: DNA
<213> ORGANISM: Mus musculus

<400> SEQUENCE: 18
cttctctttg atgtcacgca cg 22

<210> SEQ ID NO 19
<211> LENGTH: 35
<212> TYPE: PRT
<213> ORGANISM: Homo sapiens

<400> SEQUENCE: 19

Gly Ser Pro Arg Phe Gln Asp Ser Ser Ser Ser Lys Ala Pro Pro Pro
1 5 10 15

Ser Leu Pro Ser Pro Ser Arg Leu Pro Gly Pro Ser Asp Thr Pro Ile

```
            20                  25                  30

Leu Pro Gln
        35


<210> SEQ ID NO 20
<211> LENGTH: 108
<212> TYPE: DNA
<213> ORGANISM: Homo sapiens

<400> SEQUENCE: 20

ggatcaccac gcttccagga ctcctcttcc tcaaaggccc ctcctcctag ccttccaagc      60

ccatcccgac tcccggggcc ctcggacact ccgatcctcc cacaataa                  108


<210> SEQ ID NO 21
<211> LENGTH: 274
<212> TYPE: PRT
<213> ORGANISM: Homo sapiens

<400> SEQUENCE: 21

Met Trp Gly Trp Lys Cys Leu Leu Phe Trp Ala Val Leu Val Thr Ala
1               5                   10                  15

Thr Leu Cys Thr Ala Arg Pro Ala Pro Thr Leu Pro Glu Gln Ala Gln
            20                  25                  30

Gln Ser Thr Arg Ala Asp Leu Gly Pro Gly Glu Pro Lys Ser Cys Asp
        35                  40                  45

Lys Thr His Thr Cys Pro Pro Cys Pro Ala Pro Glu Leu Leu Gly Gly
    50                  55                  60

Pro Ser Val Phe Leu Phe Pro Pro Lys Pro Lys Asp Thr Leu Met Ile
65                  70                  75                  80

Ser Arg Thr Pro Glu Val Thr Cys Val Val Val Asp Val Ser His Glu
                85                  90                  95

Asp Pro Glu Val Lys Phe Asn Trp Tyr Val Asp Gly Val Glu Val His
            100                 105                 110

Asn Ala Lys Thr Lys Pro Arg Glu Glu Gln Tyr Asn Ser Thr Tyr Arg
        115                 120                 125

Val Val Ser Val Leu Thr Val Leu His Gln Asp Trp Leu Asn Gly Lys
    130                 135                 140

Glu Tyr Lys Cys Lys Val Ser Asn Lys Ala Leu Pro Ala Pro Ile Glu
145                 150                 155                 160

Lys Thr Ile Ser Lys Ala Lys Gly Gln Pro Arg Glu Pro Gln Val Tyr
                165                 170                 175

Thr Leu Pro Pro Ser Arg Asp Glu Leu Thr Lys Asn Gln Val Ser Leu
            180                 185                 190

Thr Cys Leu Val Lys Gly Phe Tyr Pro Ser Asp Ile Ala Val Glu Trp
        195                 200                 205

Glu Ser Asn Gly Gln Pro Glu Asn Asn Tyr Lys Thr Thr Pro Pro Val
    210                 215                 220

Leu Asp Ser Asp Gly Ser Phe Phe Leu Tyr Ser Lys Leu Thr Val Asp
225                 230                 235                 240

Lys Ser Arg Trp Gln Gln Gly Asn Val Phe Ser Cys Ser Val Met His
                245                 250                 255

Glu Ala Leu His Asn His Tyr Thr Gln Lys Ser Leu Ser Leu Ser Pro
            260                 265                 270

Gly Lys
```

<210> SEQ ID NO 22
<211> LENGTH: 822
<212> TYPE: DNA
<213> ORGANISM: Homo sapiens

<400> SEQUENCE: 22

```
atgtggggct ggaagtgcct cctcttctgg gctgtgctgg tcacagccac tctctgcact     60

gccaggccag ccccaacctt gcccgaacaa gctcagcagt cgacgcgcgc agatctgggc    120

ccgggcgagc ccaaatcttg tgacaaaact cacacatgcc caccgtgccc agcacctgaa    180

ctcctggggg gaccgtcagt cttcctcttc cccccaaaac ccaaggacac cctcatgatc    240

tcccggaccc ctgaggtcac atgcgtggtg gtggacgtga gccacgaaga ccctgaggtc    300

aagttcaact ggtacgtgga cggcgtggag gtgcataatg ccaagacaaa gccgcgggag    360

gagcagtaca acagcacgta ccgtgtggtc agcgtcctca ccgtcctgca ccaggactgg    420

ctgaatggca aggagtacaa gtgcaaggtc tccaacaaag ccctcccagc ccccatcgag    480

aaaaccatct ccaaagccaa agggcagccc cgagaaccac aggtgtacac cctgccccca    540

tcccgggatg agctgaccaa gaaccaggtc agcctgacct gcctggtcaa aggcttctat    600

cccagcgaca tcgccgtgga gtgggagagc aatgggcagc cggagaacaa ctacaagacc    660

acgcctcccg tgctggactc cgacggctcc ttcttcctct acagcaagct caccgtggac    720

aagagcaggt ggcagcaggg gaacgtcttc tcatgctccg tgatgcatga ggctctgcac    780

aaccactaca cgcagaagag cctctccctg tctccgggta aa                       822
```

<210> SEQ ID NO 23
<211> LENGTH: 309
<212> TYPE: PRT
<213> ORGANISM: Homo sapiens

<400> SEQUENCE: 23

```
Met Trp Gly Trp Lys Cys Leu Leu Phe Trp Ala Val Leu Val Thr Ala
1               5                   10                  15

Thr Leu Cys Thr Ala Arg Pro Ala Pro Thr Leu Pro Glu Gln Ala Gln
            20                  25                  30

Gln Ser Thr Arg Ala Asp Leu Gly Pro Gly Glu Pro Lys Ser Cys Asp
        35                  40                  45

Lys Thr His Thr Cys Pro Pro Cys Pro Ala Pro Glu Leu Leu Gly Gly
    50                  55                  60

Pro Ser Val Phe Leu Phe Pro Pro Lys Pro Lys Asp Thr Leu Met Ile
65                  70                  75                  80

Ser Arg Thr Pro Glu Val Thr Cys Val Val Val Asp Val Ser His Glu
                85                  90                  95

Asp Pro Glu Val Lys Phe Asn Trp Tyr Val Asp Gly Val Glu Val His
            100                 105                 110

Asn Ala Lys Thr Lys Pro Arg Glu Glu Gln Tyr Asn Ser Thr Tyr Arg
        115                 120                 125

Val Val Ser Val Leu Thr Val Leu His Gln Asp Trp Leu Asn Gly Lys
    130                 135                 140

Glu Tyr Lys Cys Lys Val Ser Asn Lys Ala Leu Pro Ala Pro Ile Glu
145                 150                 155                 160

Lys Thr Ile Ser Lys Ala Lys Gly Gln Pro Arg Glu Pro Gln Val Tyr
                165                 170                 175

Thr Leu Pro Pro Ser Arg Asp Glu Leu Thr Lys Asn Gln Val Ser Leu
            180                 185                 190
```

-continued

```
Thr Cys Leu Val Lys Gly Phe Tyr Pro Ser Asp Ile Ala Val Glu Trp
        195                 200                 205

Glu Ser Asn Gly Gln Pro Glu Asn Asn Tyr Lys Thr Thr Pro Pro Val
    210                 215                 220

Leu Asp Ser Asp Gly Ser Phe Phe Leu Tyr Ser Lys Leu Thr Val Asp
225                 230                 235                 240

Lys Ser Arg Trp Gln Gln Gly Asn Val Phe Ser Cys Ser Val Met His
                245                 250                 255

Glu Ala Leu His Asn His Tyr Thr Gln Lys Ser Leu Ser Leu Ser Pro
            260                 265                 270

Gly Lys Gly Ser Pro Arg Phe Gln Asp Ser Ser Ser Ser Lys Ala Pro
        275                 280                 285

Pro Pro Ser Leu Pro Ser Pro Ser Arg Leu Pro Gly Pro Ser Asp Thr
    290                 295                 300

Pro Ile Leu Pro Gln
305


<210> SEQ ID NO 24
<211> LENGTH: 930
<212> TYPE: DNA
<213> ORGANISM: Homo sapiens

<400> SEQUENCE: 24

atgtggggct ggaagtgcct cctcttctgg gctgtgctgg tcacagccac tctctgcact      60

gccaggccag ccccaacctt gcccgaacaa gctcagcagt cgacgcgcgc agatctgggc     120

ccgggcgagc ccaaatcttg tgacaaaact cacacatgcc caccgtgccc agcacctgaa     180

ctcctggggg gaccgtcagt cttcctcttc cccccaaaac ccaaggacac cctcatgatc     240

tcccggaccc ctgaggtcac atgcgtggtg gtggacgtga gccacgaaga ccctgaggtc     300

aagttcaact ggtacgtgga cggcgtggag gtgcataatg ccaagacaaa gccgcgggag     360

gagcagtaca acagcacgta ccgtgtggtc agcgtcctca ccgtcctgca ccaggactgg     420

ctgaatggca aggagtacaa gtgcaaggtc tccaacaaag ccctcccagc ccccatcgag     480

aaaaccatct ccaaagccaa agggcagccc cgagaaccac aggtgtacac cctgccccca     540

tcccgggatg agctgaccaa gaaccaggtc agcctgacct gcctggtcaa aggcttctat     600

cccagcgaca tcgccgtgga gtgggagagc aatgggcagc cggagaacaa ctacaagacc     660

acgcctcccg tgctggactc cgacggctcc ttcttcctct acagcaagct caccgtggac     720

aagagcaggt ggcagcaggg gaacgtcttc tcatgctccg tgatgcatga ggctctgcac     780

aaccactaca cgcagaagag cctctccctg tctccgggta aaggatcacc acgcttccag     840

gactcctctt cctcaaaggc ccctcctcct agccttccaa gcccatcccg actcccgggg     900

ccctcggaca ctccgatcct cccacaataa                                      930


<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 25

His His His His His His
1               5
```

TREFOIL FAMILY FACTOR PROTEINS AND USES THEREOF

This application is a continuation of U.S. Ser. No. 15/367,958, filed Dec. 2, 2016, now U.S. Pat. No. 10,124,037, issued Nov. 13, 2018, which is a continuation-of U.S. Ser. No. 14/550,246, filed Nov. 21, 2014, which is a continuation-in-part of International Application No. PCT/US2013/034981, filed Apr. 2, 2013, which claims priority of U.S. Provisional Application No. 61/649,767, filed on May 21, 2012, the contents of each of which is hereby incorporated by reference in its entirety.

GOVERNMENT SUPPORT

This invention was made with government support under Grant No. NIH 5R01 DK060758-10 awarded by the National Institute of Health and the National Institute of Diabetes and Digestive and Kidney Diseases. The Government has certain rights in the invention.

All patents, patent applications and publications, and non-patent publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

REFERENCE TO SEQUENCE LISTING

This application incorporates-by-reference nucleotide and/or amino acid sequences which are present in the file named "181113_87665-PCT-AA-US_SubstituteSequenceListing_DH.txt," which is 17,347 bytes in size, and which was created Nov. 13, 2018 in the IBM-PC machine format, having an operating system compatibility with MS-Windows, which is contained in the text file filed Nov. 13, 2018 as part of this application.

BACKGROUND OF THE INVENTION

Trefoil factor 2 (TFF2) is a small secreted protein that is expressed in gastrointestinal mucosa where it functions to protect and repair mucosa, but it is also expressed at low levels in splenic immune cells where its role has been unclear. The Tff2 gene is epigenetically silenced in digestive system cancers and thus has been postulated to protect against cancer development through multiple mechanisms.

SUMMARY OF THE INVENTION

The present invention provides for the use of TFF2, delivered as a recombinant peptide or using a viral vector or modified peptide (for example, a fusion protein for increased stability) to treat advanced cancer or dysplasia by specifically suppressing myeloid proliferation with this approach. TFF2 can be a new and useful cancer therapy that works by targeting the tumor microenvironment, specifically the myeloid cells (e.g. MDSC, tumor associated macrophages, neutrophils) that support cancer. In addition, it can be a form of replacement of a tumor suppressor gene product that is normally downregulated in many cancers.

In one aspect, the invention provides for a method of treating or preventing a cancer in a subject, the method comprising administering to the subject a therapeutically effective amount of TFF2 protein, thereby treating or preventing the cancer. In one embodiment, the cancer is colon cancer. In another embodiment, the cancer is rectal cancer. In one embodiment, the cancer is gastric cancer. In another embodiment, the cancer is stomach cancer.

In one embodiment, the TFF2 protein is a human TFF2 protein. In one embodiment, the TFF2 protein is a recombinant protein.

In one embodiment, the treating or preventing comprises inhibiting the proliferation of myeloid-derived suppressor cells (MDSCs).

In one aspect, the invention provides for a method of treating an inflammatory disease of the digestive system in a subject, the method comprising administering to a subject a trefoil family molecule. In one embodiment, the inflammatory disease of the digestive system comprises esophagitis, inflammatory bowel disease, Crohn's disease, ulcerative colitis, colitis, irritable bowel syndrome, celiac disease, gastritis, or a combination thereof. In another embodiment, the inflammatory disease of the digestive system is colitis.

In one aspect, the invention provides for a method of treating a digestive system cancer in a subject, the method comprising administering to a subject a trefoil family molecule. In one embodiment, the digestive system cancer is selected from the group consisting of mouth cancer, pharynx cancer, esophageal cancer, and stomach cancer. In another embodiment, the digestive system cancer is selected from the group consisting of small intestine cancer, large intestine cancer, colon cancer, rectal cancer, and anal cancer. In another embodiment, the digestive system cancer is selected from the group consisting of liver cancer, pancreatic cancer, and gall bladder. In a further embodiment, the digestive system cancer is colon cancer.

In one aspect, the invention provides for a method of decreasing cell proliferation in a subject, the method comprising administering to a subject a trefoil family molecule, thus decreasing cell proliferation. In one embodiment, the cell is a myeloid-derived suppressor cell. In another embodiment, the myeloid-derived suppressor cell is a tumor associated myeloid-derived suppressor cell. In another embodiment, the myeloid-derived suppressor cell is a myeloid-derived suppressor cell associated with a tumor. In further embodiments, the myeloid-derived suppressor cell expresses a MDSC-specific surface marker. In one embodiment, the myeloid derived suppressor cell does not express a MDSC-specific surface marker. In another embodiment, the surface marker is Grl1, CD11b, or a combination thereof. In another embodiment, the surface marker is CD14, CD15, CD33, or a combination thereof. In another embodiment the surface marker is HLA-DR.

In one aspect, the invention provides a method of decreasing tumor growth in a subject, the method comprising administering to a subject a trefoil family molecule, thus decreasing tumor growth. In one embodiment, the tumor is a tumor of the digestive system.

In one aspect, the invention provides a method of treating dysplasia of the digestive system in a subject, the method comprising administering to the subject a trefoil family molecule.

In one aspect, the invention provides a kit for treating a trefoil family protein disorder, the kit comprising a trefoil family molecule, to administer to a subject and instructions of use.

In one aspect, the invention provides a method of determining the presence of, or predisposition to, a trefoil family molecule disorder in a sample from a subject, the method comprising: (a) detecting the presence, absence or reduction of a trefoil family molecule in the sample, wherein absence, or reduction of the molecule indicates the presence of, or predisposition to, a trefoil family molecule disorder. In one embodiment, the method further comprises: (b) administering a trefoil family molecule to the subject where a trefoil family molecule was not detected. In one embodiment, the method further comprises incubating the sample with an agent that binds a trefoil family molecule, or fragment thereof. In one embodiment, the agent is an antibody to a trefoil family molecule. In another embodiment, the sample is digestive system cancer cells. In further embodiments, the digestive system cancer is selected from the group consisting of mouth cancer, pharynx cancer, esophageal cancer, and stomach cancer. In yet another embodiment, the digestive system cancer is selected from the group consisting of small intestine cancer, large intestine cancer, colon cancer, rectal cancer, and anal cancer. In another embodiment, the digestive system cancer is selected from the group consisting of liver cancer, pancreatic cancer, and gall bladder. In one embodiment, the digestive system cancer is colon cancer.

In one embodiment, administering the trefoil family molecule is conducted simultaneously with the administering of a chemotherapy drug. In another embodiment, administering the trefoil family molecule is conducted sequentially in any order with the administering of a chemotherapy drug. Non-limiting examples of conventional chemotherapy drugs include: aminoglutethimide, amsacrine, asparaginase, bcg, anastrozole, bleomycin, buserelin, bicalutamide, busulfan, capecitabine, carboplatin, camptothecin, chlorambucil, cisplatin, carmustine, cladribine, colchicine, cyclophosphamide, cytarabine, dacarbazine, cyproterone, clodronate, daunorubicin, diethylstilbestrol, docetaxel, dactinomycin, doxorubicin, dienestrol, etoposide, exemestane, filgrastim, fluorouracil, fludarabine, fludrocortisone, epirubicin, estradiol, gemcitabine, genistein, estramustine, fluoxymesterone, flutamide, goserelin, leuprolide, hydroxyurea, idarubicin, levamisole, imatinib, lomustine, ifosfamide, megestrol, melphalan, interferon, irinotecan, letrozole, leucovorin, ironotecan, mitoxantrone, nilutamide, medroxyprogesterone, mechlorethamine, mercaptopurine, mitotane, nocodazole, octreotide, methotrexate, mitomycin, paclitaxel, oxaliplatin, temozolomide, pentostatin, plicamycin, suramin, tamoxifen, porfimer, mesna, pamidronate, streptozocin, teniposide, procarbazine, titanocene dichloride, raltitrexed, rituximab, testosterone, thioguanine, vincristine, vindesine, thiotepa, topotecan, tretinoin, vinblastine, trastuzumab, and vinorelbine. In one embodiment, the chemotherapy drug is an alkylating agent (e.g. busulfan, cisplatin, carboplatin, chlorambucil, cyclophosphamide, ifosfamide, dacarbazine (DTIC), mechlorethamine (nitrogen mustard), melphalan, and temozolomide), a nitrosourea, an anti-metabolite (e.g. 5-fluorouracil, capecitabine, 6-mercaptopurine, methotrexate, gemcitabine, cytarabine (ara-C), fludarabine, or pemetrexed), a topoisomerase inhibitor (e.g. topotecan, irinotecan, etoposide (VP-16), or teniposide), a mitotic inhibitor, an anthracycline (e.g. daunorubicin, doxorubicin (Adriamycin), epirubicin, idarubicin, or mitoxantrone), a corticosteroid hormone, a sex hormone, or a targeted anti-tumor compound (e.g. imatinib (Gleevec), gefitinib (Iressa), erlotinib (Tarceva), rituximab (Rituxan), or bevacizumab (Avastin)).

In one embodiment, administering the trefoil family molecule is conducted simultaneously with the administering of radiation therapy. In another embodiment, administering the trefoil family molecule is conducted sequentially in any order with the administering of radiation therapy. Non-limiting examples of conventional radiation therapy include: external beam radiation therapy, sealed source radiation therapy, unsealed source radiation therapy, particle therapy, and radioisotope therapy.

In one embodiment, administering the trefoil family molecule is conducted simultaneously with the administering of cancer immunotherapy. In another embodiment, administering the trefoil family molecule is conducted sequentially in any order with the administering of cancer immunotherapy. Non-limiting examples of cancer immunotherapy include: cancer vaccines, therapeutic antibodies, such as monoclonal antibody therapy (e.g., Bevacizumab, Cetuximab, and Panitumumab), cell based immunotherapy, and adoptive cell based immunotherapy.

In one embodiment, administering the trefoil family molecule is conducted simultaneously with the administering of an anti-inflammatory drug. In another embodiment, the trefoil family molecule is conducted sequentially in any order with the administering of an anti-inflammatory drug. Non-limiting examples of anti-inflammatory drugs include: anti-inflammatory steroids (corticosteroids) (e.g. prednisone), aminosalicylates (e.g., mesalazine), non-steroidal anti-inflammatory drugs (NSAIDs) (e.g. aspirin, ibuprofen, naproxen) and immune selective anti-inflammatory derivatives (ImSAIDs). An anti-inflammatory drug also includes antibodies or molecules that target cytokines and chemokines including, but not limited to, anti-TNFα antibodies (e.g. infliximab (Remicade), adalimumab (Humira), certolizumab pegol (Cimzia), golimumab (Simponi), etanercept (Enbrel)), anti-IL12 antibodies, anti-IL2 antibodies (basiliximab (Simulect), daclizumab (Zenapax), azathioprine (Imuran®, Azasan®), 6-mercaptopurine (6-MP, Purinethol®), cyclosporine A (Sandimmune®, Neoral®), tacrolimus (Prograf®), and anti-GM-CSF antibodies.

In one aspect, the invention provides a diagnostic kit for determining the presence of, or predisposition to, a trefoil family molecule disorder, the kit comprising an agent that binds to a trefoil family molecule, and instructions for use. In one embodiment, the agent is an antibody to a trefoil family molecule.

In one embodiment, the trefoil family molecule is TFF1. In another embodiment, the trefoil family molecule is TFF2. In a further embodiment, the trefoil family molecule is TFF3.

In one embodiment, the subject is a human. In another embodiment, the subject is a cat. In a further embodiment, the subject is a dog.

In one embodiment, the trefoil family molecule is a nucleic acid. In another embodiment, the nucleic acid is delivered as a viral vector. In one embodiment, the nucleic acid comprises the nucleotide sequence of SEQ ID NO: 2. In another embodiment, the nucleic acid comprises the nucleotide sequence of SEQ ID NO: 4. In a further embodiment, the nucleic acid comprises the nucleotide sequence of SEQ ID NO: 6.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIG. 1A. Detection of TFF2 protein in the mouse stomach and spleen by western blot analysis. Detection of TFF2 in spleen by immunoprecipitation. Total splenic extracts from five wild type mice were combined and used for this experiment. A half of extracts was precipitated by TFF2 antibodies while another half was precipitated by IgG isolated from pre-immune serum. Protein A—bounded with agarose beads was added and incubated for 24 h at 4° C. Precipitates were resolved in gel-electrophoresis, and revealed by WB analysis using anti-mouse TFF2 antibodies. Stomach extracts from wild-type mouse was used as positive control. The position of TFF2 is indicated by arrow, positions of molecular weight markers (Mr, kDa) are shown on the right. FIG. 1B. Detection of TFF2 protein in the mouse stomach and spleen by western blot analysis. Detection of TFF2 in mouse tissue extracts (stomach, spleen, thymus) by Western blot by using SuperSignal® West Femto Trial Kit. The position of TFF2 is indicated by arrow, positions of molecular weight markers (Mr, kDa) are shown on the left. FIG. 1C. Detection of TFF2 mRNA in T-cells by semi-quantitative RT-PCR. Total mRNA was isolated from splenic T and B cells (lanes T and B, top panel), reverse transcribed and amplified by PCR by using primers, which are specific for mTFF2 (top panel); T-cells marker Thy 1.2 (second panel); B-cells marker CD19 (third panel); actin (loading control, bottom panel). The resulted products were resolved by agarose gel electrophoresis as shown. The positions of 100 bp DNA ladders (M) are shown on the right. FIG. 1D. Upregulation of TFF2 mRNA expression by mitogenic stimuli in mouse splenocytes. Mouse splenocytes were activated by concavalin A (ConA, 1 μg/ml), bacterial lipopolysaccharides (LPS, 100 ng/ml) or left unstimulated (unst) for 24 h. The relative abundance of TFF2 mRNA was measured in the splenocytes and stomach (positive control) by real-time PCR.

FIG. 1E-G. TFF2 is upregulated in spleen upon DSS treatment. FIG. 1E Western blot of splenic tissues obtained from TG mice after DSS administration. Time-course change of TFF2 peptide in spleen upon DSS in CD2-TFF2 transgenic mice FIG. 1F RT-PCR analysis of WT mice spleen tissues during administration of 3% DSS water showed increased levels of TFF2 mRNA expression. TFF2 is increased in spleen of WT mice upon DSS administration. FIG. 1G Western blot of splenic tissues obtained from wild type mice after DSS administration. Time-course change of TFF2 peptide in spleen upon DSS in wild type mice.

FIG. 2A. Scheme of cloning TFF2 into the hCD2-TFF2 cassette. The full-length gene of murine TFF2 was cloned into a unique EcoRI site of the hCD2 minigene cassette, which contains the promoter, polyadenylation site, and locus control region elements from the human CD2 gene. FIG. 2B. RT-PCR analysis of TFF2 mRNA expression under control of hCD2 promoter in spleen and thymus of CD2-TFF2 transgenic mice. Upper panel, the spleen and thymus cells of the offspring of founders possessed CD2-TFF2 mRNA, 1,2—spleen and thymus from wild type, 3 and 4, 5 and 6—spleen and thymus accordingly from transgenic mice, 7,8—water. Middle panel, controls consisted of samples without reverse transcriptase were negative for presence of CD2-TFF2 mRNA. Bottom panel, the expression level of TFF2 mRNA was normalized for GAPDH mRNA.

FIG. 3A. Kaplan-Meier survival curves of TFF2−/−, TG and WT mice administered 3% DSS. Representative data of one of two independent experiments (n=12 per TFF2−/−, n=8 per WT, n=7 per TG mice). FIG. 3B. Colitis was induced in mice by administration of 3% DSS in drinking water for 5 days, mice were sacrificed and analyzed on day 19. Quantification of colon size of wild type, transgenic and TFF2−/− mice. FIG. 3C. Representative spleen appearance of transgenic, wild type and TFF2−/− mice upon 2.5% DSS treatment. FIG. 3D. Representative colon appearance of wild type, transgenic and TFF2−/− mice upon 2.5% DSS treatment. FIG. 3E. Quantification of spleen mass of transgenic, wild type and TFF2−/− mice upon 2.5% DSS treatment.

FIG. 3F. Microscopic evaluation of DSS-induced colon damage. WT, TFF2−/− and TG mice were administrated 2.5% DSS for 5 days followed by tap water for the next two weeks. Colons were obtained on day 19 from each group. Results are representative of two independent experiments (4-6 animals per group). Colons were stained with haematoxylin and eosin. Panels: upper—TFF2−/−, middle—WT, bottom—TG, no DSS (left), atrophy and inflammation upon DSS treatment (right). FIG. 3G. Inflammatory score of colon tissue after DSS treatment (day 19).

FIG. 6H are plots that show the survival rate of wild type (upper panel) and TFF2−/− (lower panel) chimaeras with bone marrow transplanted from WT, TG and TFF2−/− mice (FIG. 6H).

FIGS. 7A-B. show immunohistochemical staining of spleens from TFF2−/−, WT and TG mice on day 19 after DSS treatment. Spleens are stained with anti-Ki67 (nuclear proliferating antigen, brown) and anti-Gr1 (red) antibodies. Note an expansion of red pulp and a partially overlapped staining for Gr1 and Ki67 markers in spleen of TFF2−/− mouse Magnification ×40 (FIG. 7A) and ×200 (FIG. 7B).

FIG. 7E. BrdU uptake by Gr1+CD11b+ cells from TFF2−/−, wild type and transgenic mice.

FIG. 8A TFF2 inhibits BrdU uptake by Gr1+CD11b+ cells. Isolated Gr1+CD11b+ cells ($2\times10^5$/well) were cultured 7 days in presence of 10 or 5 ng/ml of GM-CSF. FIG. 8B Effect of TFF2 protein on Gr1+CD11b+ cell survival and death. Sorted Gr1+CD11b+ cells (more then 95% of pure cells) were grown with 5 ng/ml of GM-CSF with addition of TFF2 in indicated concentrations for 8 days. FIG. 8C Proliferation was measured in triplicate by BrdU uptake after 24 h pulse and expressed in arbitrary units (AU at 450 nm).

FIG. 9A shows phenotypical characterization of Gr1+CD11b+ cells. Morphology of sorted Gr1+CD11b+ cells. Splenocytes cells from TFF2−/− mice with DSS treatment were labeled for Gr1 and CD11b antigen and sorted on sorter FACSAria. Purity of sorted cells was more than 95%.

FIG. 9B shows phenotypical characterization of Gr1+CD11b+ cells. Phenotype of Gr1+CD11b+ cells. Cells were stained for indicated antigen for flow cytometry analysis. Cells were gated on viable Gr1+CD11b+ population and expression of various markers was analyzed. Isotype control is shown as shaded and antigen staining as unshaded histogram accordingly. Representative data on antigen expression of sorted Gr1+CD11b+ cells.

FIG. 10A. TFF2 inhibits BrdU uptake by Gr1+CD11b+ cells. Isolated Gr1+CD11b+ cells ($2\times10^5$/well) were cultured 7 days in presence of 10 or 5 ng/ml of GM-CSF. Proliferation was measured in triplicate by BrdU uptake after 24 h pulse and expressed in arbitrary units (AU at 450 nm). FIG. 10B. Effect of TFF2 protein on Gr1+CD11b+ cells survival and death. Sorted Gr1+CD11b+ cells (more than 95% of pure cells) were grown with 5 ng/ml of GM-CSF with addition of TFF2 in indicated concentrations for 7 days. TFF2 directly suppresses growth by IMC in response to GM-CSF, in vitro IMCs were sorted from spleen of TFF2−/− mice treated with DSS and cultured in presence of GM-CSF for 7 days.

FIGS. 11A-B. TFF2−/− mice are more susceptible while TG mice are more resistant to azoxymethane-DSS-induced colonic tumorigenesis. FIG. 11A Representative colons of TFF2−/−, WT and TG (upper, middle and lower panels accordingly) mice after AOM/DSS treatment at 5 months. FIG. 11B Tumor burden of TFF2−/−, WT and TG mice. Each group of mice included 4-7 animals, 3 independent experiments were done.

FIG. 11C is a photomicrograph of H&E stained colonic tumors in TFF2−/−, wild type and CD2-TFF2 mice.

FIG. 11D is a plot showing that AOM+DSS treatment resulted into higher accumulation of Gr1+CD11b+ cells in bone marrow, spleen and blood in TFF2−/− mice compare with wild type and transgenic animals. Spleen, bone marrow and blood were harvested from mice and analyzed for Gr1+CD11b+ cells. Representative dot plots of flow cytometry data of CD11b1+ staining versus Gr1+ staining gated on live cells. Proportions of Gr1+CD11b+ cells in spleen, blood and bone marrow. Data are pooled from 5-6 mice of each group of mice and represent data from 3 independent experiments.

FIG. 11E is a plot showing CD11b-Ly6C+, CD11b+ Ly6C− and CD11b+Ly6G− cells in tumor tissue. Tumor from TFF2−/− mice was digested with collagenase IV, cells were stained with antibody CD11b, Ly6C, Ly6G and F4/80 and analyzed by flow cytometry.

FIG. 14A are plots showing FACS analysis of splenic CD11b+GR1+ cells in WT and CD2-TFF2 transgenic (TG) mice at 14 days and 19 days after starting DSS treatment. WT mice show a significant increase in IMCs while TG mice do not. FIG. 14B. shows FACS analysis for FOXP3+ cells in the spleens of WT and TG mice after DSS treatment.

FIG. 26A. Tumor from TFF2−/− mice was digested with collagenase IV and DNAase I. CD11b+Gr1+ were gated on live CD45+ cells. FIG. 26B. Preponderance of CD11b+ Ly6G+ population in colon tumor tissue of TFF2−/−mice. Single cells from tumor were obtained as above. Cells were gated on Ly6C and Ly6G positive subsets on CD11b+ population among CD45+ live cells.

FIG. 40 is a bar graph (top) and plot (bottom) showing TFF2-deficiency results in a higher number of splenic CFU and GMP in the DSS model.

FIG. 44 shows a schematic of seven transcription factors unregulated (>3-fold) by TFF2 in CD11bGr1 cells.

FIG. 47. Diagram of the adenoviral construct expressing tagged TFF2 and evidence for expression of the recombinant product. The full-length mTFF2 cDNA fragment was generated through PCR amplification using the pCMV3-mTFF2 construct, then was subcloned into pAdlox vector to generate the pAdlox-mTFF2 construct and packaged in HEK293 cells (top). The Ad-mTFF2 constructs were verified by PCR and DNA sequencing (bottom).

FIG. 50. Expression of murine TFF2 in 293 cells and gastric cancer cell lines. Western blot showing recombinant mTFF2 expression in 293 cells, after Adlox-mTFF2 construct transfection or Ad-GFP infection (top). Western blot showing recombinant mTFF2 expression in AGS/MKN28 cells, after Ad-mTFF2 or Ad-GFP infection (bottom).

FIGS. 59A-D. mRNA level of IL-1β (FIG. 59A) and IL-6 (FIG. 59B) in colon without visible tumor obtained from TFF2-deficient, TG and wild type mice. Gene expression was normalized on GAPDH levels and the expression of each gene relative to untreated colon tissues of wild type mice is depicted. FIG. 59C. Higher level of IL-1β in tumor tissue compare with colon without visible in tumor in TFF2−/− mice. FIG. 59D. Flow cytometry analysis of Ly6C+ and Ly6G+ cells after gating on CD11b+ cells in spleen of tumor-bearing TFF2−/− mice.

FIGS. 61A-E are plots and graphs showing FACS analysis of CD11b+Gr1+ splenic cells for other MDSC markers, including F4/80, CD11c, CD115, CD31, MHCII, CD86, CD40 and CD80 (FIGS. 61A, 61C). FIG. 61B shows analysis by FACS of Ly6C versus Ly6G cells. Both are suppressed in TG mice. FIG. 61D shows the effect of MDSCs on CD4 proliferation and IFNgamma secretion in response to stimulation.

Immunofluorescence of CD4+CD44hiCD62Llo memory T cells with antibodies to CD44 (green) and TFF2 (red) showing co-localization.

Figure 64:
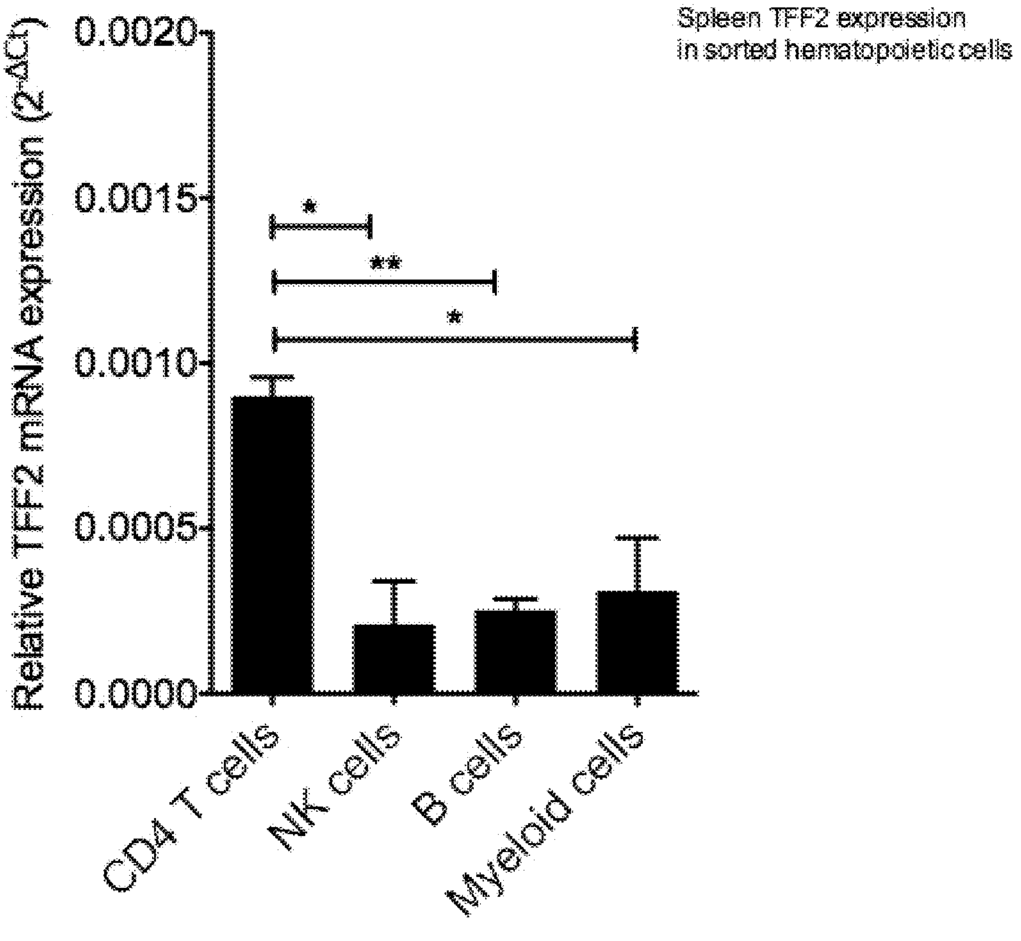

FIG. 64. TFF2 mRNA expression in immune cells in the spleen.

Figure 65:
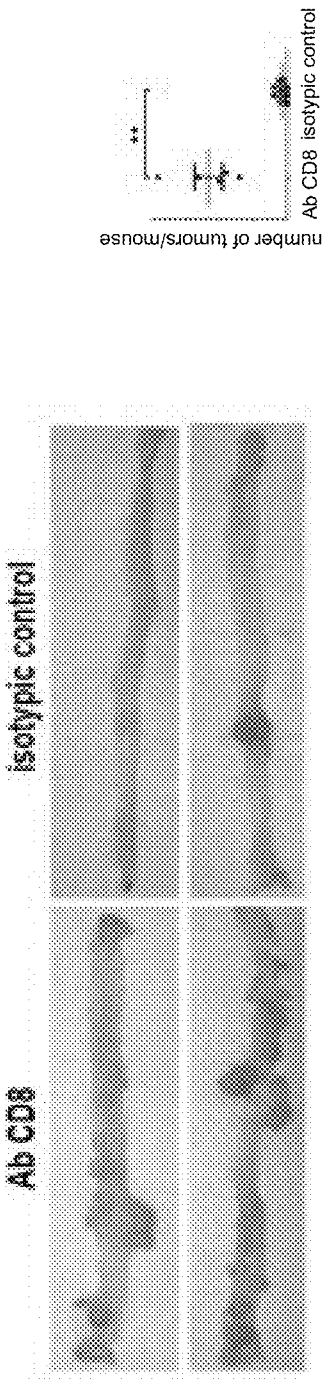

FIG. 65. CD8 T-cells play role in TFF2-mediated protection of colon from tumor development. CD2-Tff2 mice were injected with AOM following DSS treatment. Four weeks later CD8 antibody (300 ug/mouse) was injected intraperitoneally twice a week and mice were sacrificed 12 weeks later. (Right) bars present number of tumors/mouse in mice received CD8 Ab vs mice received isotypic control.

Figure 66:
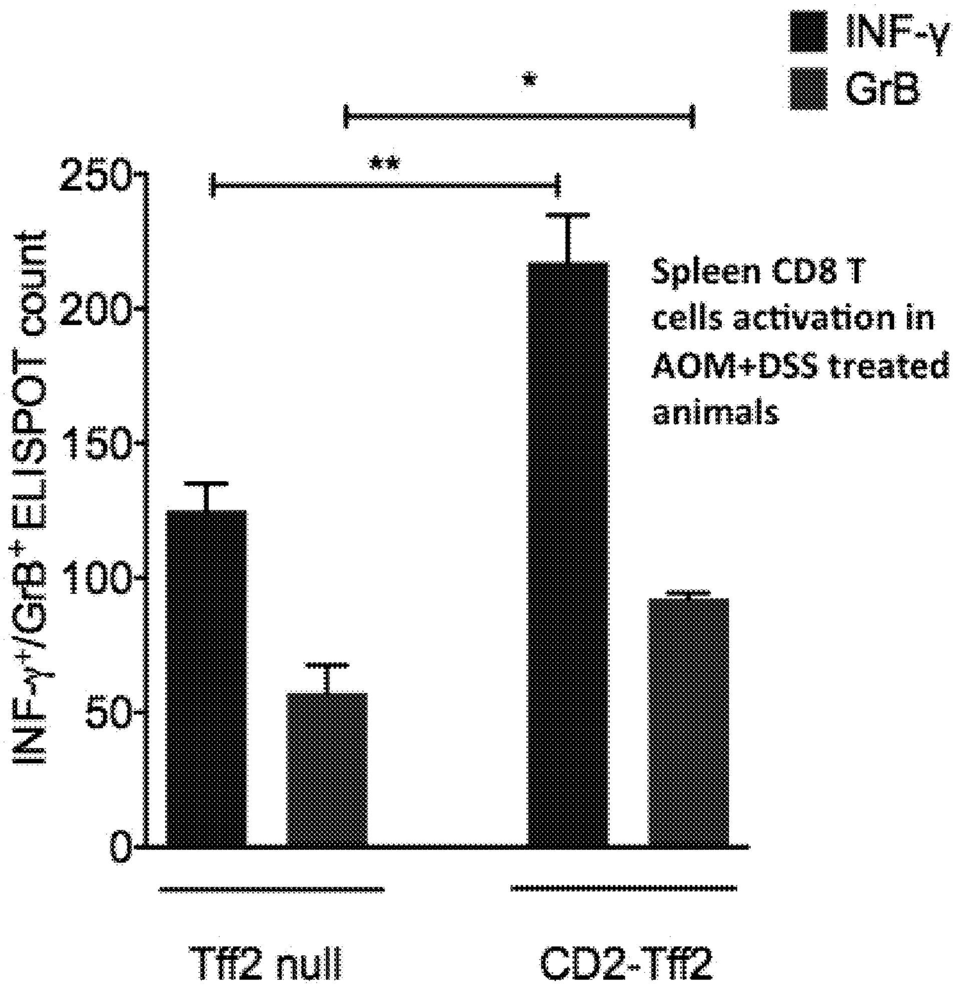

FIG. 66. Increased activated CD8+ T cells in the spleens of CD2-TFF2 transgenic mice. ELISPOT for IFN-g and Granzyme B from sorted CD8+ T cells from CD2-TFF2 and TFF2−/− mice after AOM/DSS.

Figure 67A:
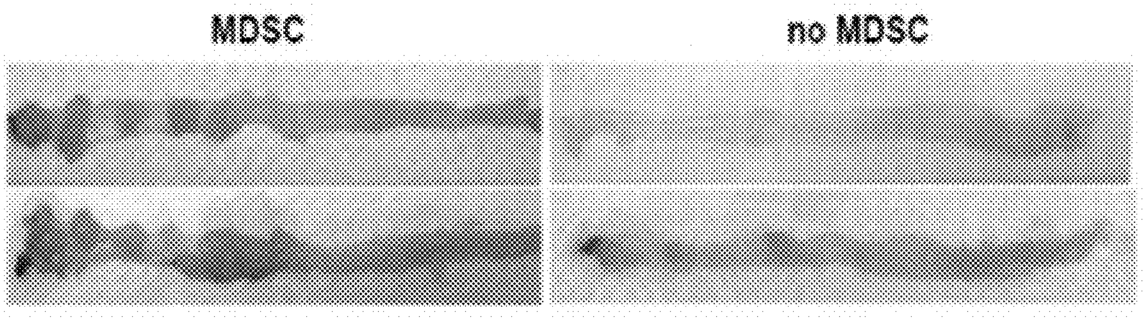
Figure 67B:
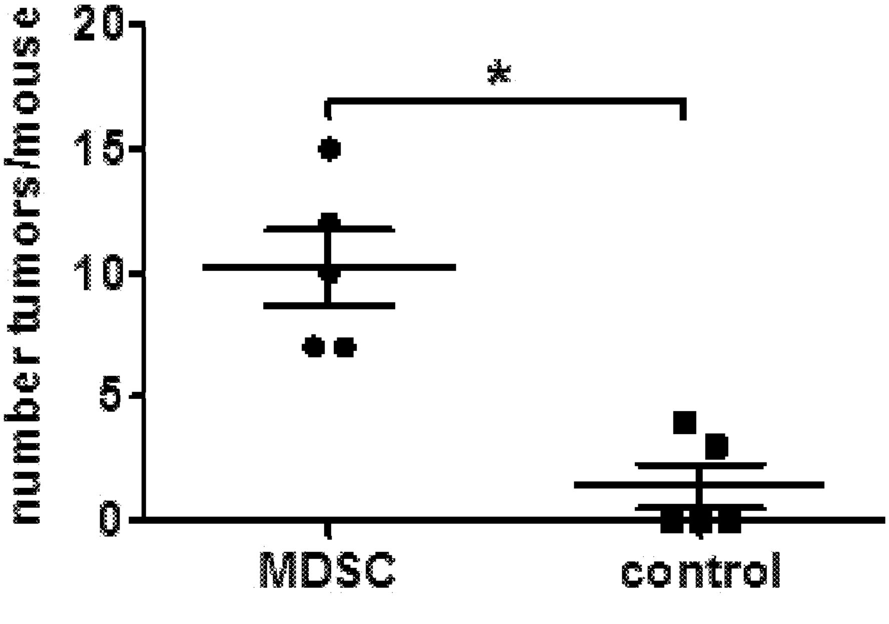

FIGS. 67A-B. MDSCs contribute to carcinogenesis in AOM/DSS-induced colon cancer model. Adoptive transfer of MDSC results into tumor progression in CD2-Tff2 mice. CD2-Tff2 mice were injected with AOM following DSS water for 7 days. After 4 weeks 5 mice were subjected intravenous tail injection once a week with 2-3×$10^6$ MDSC sorted from spleen and bone marrow from tumor-bearing Tff2-null mice and 5 mice from control group received PBS injection. (A) representative pictures of colon from control group and group received MDSC. (B) bars present number of tumor/mouse in mice received MDSC vs. mice received PBS.

FIGS. 68A-B. Splenic IMC from Tff2-null mice show higher contribution in tumorigenesis vs. splenic IMC from CD2-Tff2 mice. WT CD45.1 mice were treated with AOM/DSS, 13 weeks after, recipient mice were infused with 3×106 CD11b+Gr1+ cells sorted from either Tff2-null or CD2-tff2 mice spleen. 5 weeks after adoptive transfer, recipient mice were killed, colon tumor number were counted, MDSCs and CD8+ T cells were analyzed by FACS. Wildtype mice that received IMC from spleen of Tff2-nulls mice develop more tumors in colon and bigger spleens (A) and lower CD8 T-cells in colon tissues (B).

DETAILED DESCRIPTION OF THE INVENTION

Abbreviations and Definitions

The singular forms “a”, “an” and “the” include plural reference unless the context clearly dictates otherwise. The use of the word “a” or “an” when used in conjunction with the term “comprising” in the claims and/or the specification may mean “one,” but it is also consistent with the meaning of “one or more,” “at least one,” and “one or more than one.”

As used herein the term “about” is used herein to mean approximately, roughly, around, or in the region of. When the term “about” is used in conjunction with a numerical range, it modifies that range by extending the boundaries above and below the numerical values set forth. In general, the term “about” is used herein to modify a numerical value above and below the stated value by a variance of 20 percent up or down (higher or lower).

The invention is directed to methods of treating diseases of the digestive system in a subject comprising administering a trefoil family molecule. For example, the invention is directed to methods for treating an inflammatory disease of the digestive system in a subject. The invention is also directed to methods for treating a digestive system cancer. The invention is also directed to methods of decreasing tumor growth. The invention is also directed to treating dysplasia of the digestive system. The invention further encompasses methods of decreasing cell proliferation in a subject comprising administering a trefoil family molecule. For example, the invention is directed to methods of decreasing the proliferation of myeloid-derived suppressor cells.

As would be apparent to one of ordinary skill in the art, any method or composition described herein can be implemented with respect to any other method or composition described herein.

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

Diseases of the Digestive System

The present invention provides methods for treating diseases of the digestive system. In one embodiment the digestive system comprises the gastrointestinal tract including structures from the mouth to the anus, and the accessory organs. For example, this includes, but is not limited to, the mouth, the pharynx, the esophagus, the stomach, the small intestine, including the duodenum, jejunum, and ileum, the large intestine including the cecum, colon, and rectum, and the anus. In further embodiments, the accessory organs of the digestive system include, but are not limited to, the liver, the pancreas, and the gall bladder.

The present invention provides methods for treating an inflammatory disease of the digestive system in a subject comprising administering a trefoil family molecule. In one embodiment, the inflammatory disease of the digestive system includes, but is not limited to, esophagitis, inflammatory bowel disease, Crohn’s disease, ulcerative colitis, colitis, irritable bowel syndrome, celiac disease, and gastritis.

In some embodiments, the subject is already suspected to have an inflammatory disease of the digestive system. In other embodiments, the subject is being treated for an inflammatory disease of the digestive system, before being treated according to the methods of the invention. In other embodiments, the subject is not being treated for an inflammatory disease of the digestive system, before being treated according to the methods of the invention.

The present invention provides methods for treating a digestive system cancer in a subject comprising administering a trefoil family molecule. In one embodiment, the digestive system cancer includes, but is not limited to, mouth cancer, pharynx cancer, esophageal cancer, stomach cancer, small intestine cancer, large intestine cancer, colon cancer, rectal cancer, anal cancer, liver cancer, pancreatic cancer, and gall bladder cancer.

In some embodiments, the subject is already suspected to have a digestive system cancer. In other embodiments, the subject is being treated for a digestive system cancer, before being treated according to the methods of the invention. In other embodiments, the subject is not being treated for a digestive system cancer, before being treated according to the methods of the invention.

The present invention also provides methods for decreasing tumor growth in a subject comprising administering a trefoil family molecule. In one embodiment, the tumor is a tumor of the digestive system. Tumor growth can be measured in a variety of ways, known to one of skill in the art. For example, tumor growth can be measured by measuring the tumor volume over time. Tumor volume can be measured in a variety of ways, known to one of skill in the art including, but not limited to, positron emission tomography and computed tomography (PET-CT), single-photon emission computed tomography (SPECT-CT), magnetic resonance spectroscopy (MR), X-ray computed tomography (CT), and molecular imaging.

The present invention provides methods for treating dysplasia of the digestive system in a subject comprising administering a trefoil family molecule. Dysplasia is a condition where there is a morphologically identifiable local tissue abnormality at a given site. Dysplasia can have characteristics including, but not limited to, increased cell number, nuclear abnormalities, and cellular differentiation abnormalities, compared to normal cells. A dysplasia can precede the development of any neoplasm, benign or malignant.

The present invention provides methods for decreasing cell proliferation in a subject comprising administering a trefoil family molecule. In one embodiment, the cells are myeloid-derived suppressor cells (also referred to throughout as "MDSC"). In another embodiment the myeloid-derived suppressor cells are tumor associated. In another embodiment, the myeloid-derived suppressor cell is a myeloid-derived suppressor cell associated with a tumor. For example, the tumor can be any solid tumor associated with myeloid-derived suppressor cells. A tumor is a growth of tissue forming an abnormal mass, and can be benign, pre-malignant, or malignant. In one embodiment, the tumor is a breast tumor. In another embodiment, the tumor is a prostate tumor. In another embodiment, the tumor is a lung tumor. In a further embodiment, the tumor is a skin tumor. In one embodiment the tumor can be a tumor of the digestive system. In one embodiment, the tumor of the digestive system includes, but is not limited to, a mouth tumor, a pharynx tumor, an esophageal tumor, a stomach tumor, a small intestine tumor, a large intestine tumor, a colon tumor, a rectal tumor, an anal tumor, a liver tumor, a pancreatic tumor, and a gall bladder tumor.

In a further embodiment MDSC express a surface marker. In yet another embodiment MDSC do not express a surface marker. In one embodiment, MDSC express the surface marker Grl1, CD11b, or a combination thereof. In one embodiment, MDSC express the surface marker CD14, CD15, CD33, or a combination thereof. In another embodiment, MDSC do not express the surface marker HLA-DR. In a further embodiment, MDSC express the surface marker CD14, CD15, CD33, and do not express the surface marker HLA-DR, or a combination thereof.

MDSC are a heterogeneous population of early myeloid progenitors, such as immature granulocytes, macrophages, and dendritic cells. As used herein "MDSC" includes both M-MDSC (monocytic-MDSC) or G-MDSC (granulocytic-MDSC), or a combination thereof. MDSC may or may not express surface markers. For example, in mice, MDSC can express CD11b, Gr1, or a combination thereof. In mice, MDSC can express other surface markers including, but not limited to Ly-6G, Ly-6C, CD49d, or a combination thereof. In one embodiment, mouse MDSC express CD11b, Gr1, and Ly-6G and do not express Ly-6C and CD49d. In another embodiment, mouse MDSC express CD80, CD11b, Grl1, Ly-6C and CD49d and do not express Ly-6G. In humans, MDSC can express CD14, CD15, CD33, or a combination thereof. In humans, MDSC may not express HLA-DR. In one embodiment, human MDSC express CD14, CD33 and do not express HLA-DR. In another embodiment, human MDSC express CD15, CD33 and do not express HLA-DR. In humans, MDSC can express other surface markers including, but not limited to, CD11b, CD124, S100A9, Stat, CD80, CD83, DC-Sign, SSC, or a combination thereof. In humans, MDSC may not express other surface markers, including, but not limited to, Lin (Lin refers to Lineage markers specific for T and B cells). In one embodiment, MDSC can be associated with tumors. In another embodiment MDSC can reside in the tumor microenvironment. The tumor microenvironment comprises the normal cells and molecules that surround a tumor or cancer cell. Characteristics of MDSC will be known to one of skill in the art, for further information the reader is referred to Lindau D. et al. 2013 Immunology 138(2):105-115.

The present invention also provides a kit for treating a trefoil family molecule disorder in a subject. A trefoil family molecule disorder comprises an inflammatory disease of the digestive system, a cancer of the digestive system, or a dysplasia of the digestive system. In one embodiment, the kit for treating a trefoil family molecule disorder comprises a trefoil family molecule, to administer to a subject and instructions of use.

The present invention also provide a method of determining the presence of, or predisposition to, a trefoil family molecule disorder in a subject. A trefoil family molecule disorder comprises an inflammatory disease of the digestive system, a cancer of the digestive system, or a dysplasia of the digestive system. In one embodiment, the presence of, or predisposition to a trefoil family molecule disorder in a subject is determined by extracting a sample from a subject and detecting the presence, absence or reduction of a trefoil family molecule in the sample, wherein absence, or reduction of the molecule indicates the presence of, or predisposition to, a trefoil family molecule disorder. In a further embodiment, the method further comprises administering a trefoil family molecule to the subject where a trefoil family protein was not detected. In one embodiment the sample is digestive system cancer cells. In one embodiment, a reduction of a trefoil family molecule in the sample comprises detecting a lower amount of a trefoil family molecule in the sample than the amount of a trefoil family molecule in a control sample. In one embodiment, the control sample is from a subject without a trefoil family molecule disorder. In another embodiment, the control sample are not cancer cells. In one embodiment, the trefoil family molecule is detected by incubating the sample with an agent that binds to a trefoil family molecule. In a further embodiment, the agent is an antibody to a trefoil family molecule.

The present invention also provides a diagnostic kit for determining the presence of, or predisposition to, a trefoil family protein disorder, the kit comprising an agent that binds to a trefoil family molecule, and instructions for use. A trefoil family molecule disorder comprises an inflammatory disease of the digestive system, a cancer of the digestive system, or a dysplasia of the digestive system. In one embodiment, the agent is an antibody to a trefoil family molecule.

In one embodiment, the subject is an animal. In another embodiment, the subject is an animal that has or is diagnosed with a disease of the digestive system. In one embodiment, the subject is a human. In other embodiments, the subject is a mammal. In one embodiment, the subject is a dog. In another embodiment, the subject is a cat. In some embodiments, the subject is a rodent, such as a mouse or a rat. In some embodiments, the subject is a cow, pig, sheep, goat, cat, horse, dog, and/or any other species of animal used as livestock or kept as pets.

Trefoil Family Molecules

As used herein, a "trefoil family molecule" refers to a trefoil family protein, or a fragment thereof. A "trefoil family molecule" can also refer to a nucleic acid (including, for example, genomic DNA, complementary DNA (cDNA), synthetic DNA, as well as any form of corresponding RNA) which encodes a polypeptide corresponding to a trefoil family protein, or fragment thereof. For example, a trefoil family molecule can include TFF1 (e.g., comprising the amino acid sequence shown in SEQ ID NO: 1, or comprising the nucleic acid sequence shown in SEQ ID NO: 2), TFF2 (e.g., comprising the amino acid sequence shown in SEQ ID NO: 3, or comprising the nucleic acid sequence shown in SEQ ID NO: 4), or TFF3 (e.g., comprising the amino acid sequence shown in SEQ ID NO: 5, or comprising the nucleic acid sequence shown in SEQ ID NO: 6). For example, a trefoil family molecule can be encoded by a recombinant nucleic acid encoding a trefoil family protein, or fragment thereof. The trefoil family molecules of the invention can be obtained from various sources and can be produced according to various techniques known in the art. For example, a nucleic acid that encodes a trefoil family molecule can be obtained by screening DNA libraries, or by amplification from a natural source. A trefoil family molecule can include a fragment or portion of a trefoil family protein. A trefoil family molecule can include a variant of the above described examples, such as a fragment thereof. Such a variant can comprise a naturally-occurring variant due to allelic variations between individuals (e.g., polymorphisms), mutated alleles, or alternative splicing forms. In one embodiment, a trefoil family molecule is encoded by a nucleic acid variant of the nucleic acid having the sequence shown in SEQ ID NOS: 2, 4, or 6 wherein the variant has a nucleotide sequence identity to SEQ ID NOS:2, 4, or 6 of at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%. In another embodiment, a variant of the trefoil family protein comprises a protein or polypeptide encoded by a trefoil family nucleic acid sequence, such as the sequence shown in SEQ ID NOS: 2, 4, or 6. A trefoil family molecule can also include a trefoil family protein, or fragment thereof, that is modified by the addition of a carboxy-terminal peptide (CTP) domain for increased stability.

The nucleic acid can be any type of nucleic acid, including genomic DNA, complementary DNA (cDNA), synthetic or semi-synthetic DNA, as well as any form of corresponding RNA. For example, a nucleic acid encoding a trefoil family protein can comprise a recombinant nucleic acid encoding such a protein. The nucleic acid can be a non-naturally occurring nucleic acid created artificially (such as by assembling, cutting, ligating or amplifying sequences). It can be double-stranded or single-stranded.

The invention further provides for nucleic acids that are complementary to a trefoil family molecule. Complementary nucleic acids can hybridize to the nucleic acid sequence described above under stringent hybridization conditions. Non-limiting examples of stringent hybridization conditions include temperatures above 30° C., above 35° C., in excess of 42° C., and/or salinity of less than about 500 mM, or less than 200 mM. Hybridization conditions can be adjusted by the skilled artisan via modifying the temperature, salinity and/or the concentration of other reagents such as SDS or SSC.

According to the invention, protein variants can include amino acid sequence modifications. For example, amino acid sequence modifications fall into one or more of three classes: substitutional, insertional or deletional variants. Insertions can include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. These variants ordinarily are prepared by site-specific mutagenesis of nucleotides in the DNA encoding the protein, thereby producing DNA encoding the variant, and thereafter expressing the DNA in recombinant cell culture. In one embodiment, a trefoil family molecule can be modified with an amino acid sequence inserted as a carboxyl terminal fusion. For example, carboxyl terminal fusions may be used to increase the stability of a trefoil family molecule.

In one embodiment, a trefoil family molecule comprises a protein or polypeptide encoded by a nucleic acid sequence encoding a trefoil family protein, such as the sequences shown in SEQ ID NOS: 2, 4, or 6. In another embodiment, the polypeptide can be modified, such as by glycosylations and/or acetylations and/or chemical reaction or coupling, and can contain one or several non-natural or synthetic amino acids. An example of a trefoil family molecule is the polypeptide having the amino acid sequence shown in SEQ ID NOS: 1, 3, or 5. Such variants can include those having at least from about 46% to about 50% identity to SEQ ID NOS: 1, 3, or 5 or having at least from about 50.1% to about 55% identity to SEQ ID NOS: 1, 3, or 5, or having at least from about 55.1% to about 60% identity to SEQ ID NOS: 1, 3, or 5, or having from at least about 60.1% to about 65% identity to SEQ ID NOS: 1, 3, or 5, or having from about 65.1% to about 70% identity to SEQ ID NOS: 1, 3, or 5, or having at least from about 70.1% to about 75% identity to SEQ ID NOS: 1, 3, or 5, or having at least from about 75.1% to about 80% identity to SEQ ID NOS: 1, 3, or 5, or having at least from about 80.1% to about 85% identity to SEQ ID NOS: 1, 3, or 5, or having at least from about 85.1% to about 90% identity to SEQ ID NOS: 1, 3, or 5, or having at least from about 90.1% to about 95% identity to SEQ ID NOS: 1, 3, or 5, or having at least from about 95.1% to about 97% identity to SEQ ID NOS: 1, 3, or 5, or having at least from about 97.1% to about 99% identity to SEQ ID NOS: 1, 3, or 5. In another embodiment, a trefoil family molecule can be a fragment of a trefoil family protein.

In one embodiment, a trefoil family molecule, according to the methods described herein can be administered to a subject as a recombinant protein. In another embodiment, a trefoil family molecule, can be administered to a subject as a modified recombinant protein. For example, a trefoil family protein, or fragment thereof, can be modified by the addition of a carboxy-terminal peptide (CTP) domain for increased stability. In a further embodiment, a trefoil family molecule, according to the methods described herein can be administered to a subject by delivery of a nucleic acid encoding a trefoil family protein, or fragment thereof. For example, nucleic acids can be delivered to a subject using a viral vector.

Polypeptides can be susceptible to denaturation or enzymatic degradation in the blood, liver or kidney. Accordingly, polypeptides can be unstable and have short biological half-lives. Polypeptides can be modified to increase their stability, for example, a fusion protein can be generated for increased stability. In one embodiment, an isolated polypeptide can comprise a carboxy-terminal peptide (CTP) domain fused to a trefoil family molecule. The addition of the CTP domain to a trefoil family molecule can be used to stabilize the trefoil family molecule and cause a longer biological half-life to the polypeptides in circulation. In one embodiment, the CTP comprises the C-terminal domain of the beta subunit of the human chorionic gonadotrophin (hCG).

The term "biological half-life" is the time required for the activity of a substance taken into the body to lose one half its initial pharmacologic, physiologic, or biologic activity.

In one embodiment, a trefoil family molecule of the present invention comprises an isolated polypeptide comprising a carboxy-terminal peptide (CTP) domain fused to a trefoil family molecule. In one embodiment, fusing a CTP domain to a trefoil family molecule (for example, TFF1, TFF2, or TFF3) can result in increased glycosylation and/or protein stability. In some embodiments, one CTP domain is added to the N-terminus of a trefoil family molecule. In other embodiments, two CTP domains are added to the N-terminus of a trefoil family molecule. In further embodiments, three CTP domains are added to the N-terminus of a trefoil family molecule. In some embodiments, one CTP domain is added to the C-terminus of a trefoil family molecule. In other embodiments, two CTP domains are added to the C-terminus of a trefoil family molecule. In further embodiments, three CTP domains are added to the C-terminus of a trefoil family molecule. In some embodiments, at least one CTP domain is added to the N-terminus and/or C-terminus of a trefoil family molecule. In other embodiments, at least two CTP domains are added to the N-terminus and/or C-terminus of a trefoil family molecule. In further embodiments, at least three CTP domains are added to the N-terminus and/or C-terminus of a trefoil family molecule. In some embodiments, the CTP domains are added in tandem.

In one embodiment, a trefoil family molecule of the present invention comprises an isolated polypeptide comprising a Fc domain fused to a trefoil family molecule. A Fc domain is the fragment crystallizable region of an antibody. In one embodiment, fusing a Fc domain to a trefoil family molecule (for example, TFF1, TFF2, or TFF3) can result in dimerization, and/or protein stability, and/or increased protein activity, and/or improved protein purification. In some embodiments, one Fc domain is added to the N-terminus of a trefoil family molecule. In other embodiments, two Fc domains are added to the N-terminus of a trefoil family molecule. In further embodiments, three Fc domains are added to the N-terminus of a trefoil family molecule. In some embodiments, one Fc domain is added to the C-terminus of a trefoil family molecule. In other embodiments, two Fc domains are added to the C-terminus of a trefoil family molecule. In further embodiments, three Fc domains are added to the C-terminus of a trefoil family molecule. In some embodiments, at least one Fc domain is added to the N-terminus and/or C-terminus of a trefoil family molecule. In other embodiments, at least two Fc domains are added to the N-terminus and/or C-terminus of a trefoil family molecule. In further embodiments, at least three Fc domains are added to the N-terminus and/or C-terminus of a trefoil family molecule. In some embodiments, the Fc domains are added in tandem.

In one embodiment, a trefoil family molecule of the present invention comprises an isolated polypeptide comprising a CTP domain and a Fc domain fused to a trefoil family molecule. In one embodiment, fusing a CTP domain and a Fc domain to a trefoil family molecule (for example, TFF1, TFF2, or TFF3) can result in dimerization, and/or protein stability, and/or increased protein activity, and/or improved protein purification. In some embodiments, a CTP domain and a Fc domain are added to the N-terminus of a trefoil family molecule. In some embodiments, a CTP domain and a Fc domain are added to the C-terminus of a trefoil family molecule. In some embodiments, at least one Fc domain is added to the N-terminus and/or C-terminus of a trefoil family molecule and at least one CTP domain is added to the N-terminus and/or C-terminus of a trefoil family molecule. In other embodiments, at least one Fc domain is added to the N-terminus and/or C-terminus of a trefoil family molecule and at least two CTP domains are added to the N-terminus and/or C-terminus of a trefoil family molecule. In further embodiments, at least one Fc domain are added to the N-terminus and/or C-terminus of a trefoil family molecule and at least three CTP domain is added to the N-terminus and/or C-terminus of a trefoil family molecule. In some embodiments, the Fc domains and CTP domains are added in tandem and can be in any order.

SEQ ID NO: 19 depicts the amino acid sequence of a CTP domain:

```
GSPRFQDSSSSKAPPPSLPSPSRLPGPSDTPILPQ
```

SEQ ID NO: 20 depicts the nucleic acid sequence encoding a CTP domain:

```
ggatcaccacgcttccaggactcctcttcctcaaaggcccctcctcctag
ccttccaagcccatcccgactcccggggccctcggacactccgatcctcc
cacaataa
```

SEQ ID NO: 21 depicts the amino acid sequence of a Fc domain:

```
  1 MWGWKCLLFW AVLVTATLCT ARPAPTLPEQ AQQSTRADLG
    PGEPKSCDKT HTCPPCPAPE
 61 LLGGPSVFLF PPKPKDTLMI SRTPEVTCVV VDVSHEDPEV
    KFNWYVDGVE VHNAKTKPRE
121 EQYNSTYRVV SVLTVLHQDW LNGKEYKCKV SNKALPAPIE
    KTISKAKGQP REPQVYTLPP
181 SRDELTKNQV SLTCLVKGFY PSDIAVEWES NGQPENNYKT
    TPPVLDSDGS FFLYSKLTVD
241 KSRWQQGNVF SCSVMHEALH NHYTQKSLSL SPGK
```

SEQ ID NO: 22 depicts the nucleic acid sequence encoding a Fc domain:

```
  1 atgtggggct ggaagtgcct cctcttctgg gctgtgctgg
    tcacagccac tctctgcact
 61 gccaggccag ccccaacctt gcccgaacaa gctcagcagt
    cgacgcgcgc agatctgggc
```

-continued

```
121 ccgggcgagc ccaaatcttg tgacaaaact cacacatgcc
    caccgtgccc agcacctgaa
181 ctcctggggg gaccgtcagt cttcctcttc cccccaaaac
    ccaaggacac cctcatgatc
241 tcccggaccc ctgaggtcac atgcgtggtg gtggacgtga
    gccacgaaga ccctgaggtc
301 aagttcaact ggtacgtgga cggcgtggag gtgcataatg
    ccaagacaaa gccgcgggag
361 gagcagtaca acagcacgta ccgtgtggtc agcgtcctca
    ccgtcctgca ccaggactgg
421 ctgaatggca aggagtacaa gtgcaaggtc tccaacaaag
    ccctcccagc ccccatcgag
481 aaaaccatct ccaaagccaa agggcagccc cgagaaccac
    aggtgtacac cctgccccca
541 tcccgggatg agctgaccaa gaaccaggtc agcctgacct
    gcctggtcaa aggcttctat
601 cccagcgaca tcgccgtgga gtgggagagc aatgggcagc
    cggagaacaa ctacaagacc
661 acgcctcccg tgctggactc cgacggctcc ttcttcctct
    acagcaagct caccgtggac
721 aagagcaggt ggcagcaggg gaacgtcttc tcatgctccg
    tgatgcatga ggctctgcac
781 aaccactaca cgcagaagag cctctccctg tctccgggta
    aa
```

SEQ ID NO: 23 depicts the amino acid sequence of a FcCTP where the CTP domain is underlined and bold:

```
1   MWGWKCLLFW AVLVTATLCT ARPAPTLPEQ AQQSTRADLG
    PGEPKSCDKT HTCPPCPAPE
61  LLGGPSVFLF PPKPKDTLMI SRTPEVTCVV VDVSHEDPEV
    KFNWYVDGVE VHNAKTKPRE
121 EQYNSTYRVV SVLTVLHQDW LNGKEYKCKV SNKALPAPIE
    KTISKAKGQP REPQVYTLPP
181 SRDELTKNQV SLTCLVKGFY PSDIAVEWES NGQPENNYKT
    TPPVLDSDGS FFLYSKLTVD
241 KSRWQQGNVF SCSVMHEALH NHYTQKSLSL SPGKGSPRFQ
    DSSSSKAPPP SLPSPSRLPG
301 PSDTPILPQ
```

SEQ ID NO: 24 depicts the nucleic acid sequence encoding a FcCTP where the CTP domain is underlined and bold:

```
1   atgtggggct ggaagtgcct cctcttctgg gctgtgctgg
    tcacagccac tctctgcact
61  gccaggccag ccccaacctt gcccgaacaa gctcagcagt
    cgacgcgcgc agatctgggc
121 ccgggcgagc ccaaatcttg tgacaaaact cacacatgcc
    caccgtgccc agcacctgaa
181 ctcctggggg gaccgtcagt cttcctcttc cccccaaaac
    ccaaggacac cctcatgatc
241 tcccggaccc ctgaggtcac atgcgtggtg gtggacgtga
    gccacgaaga ccctgaggtc
301 aagttcaact ggtacgtgga cggcgtggag gtgcataatg
    ccaagacaaa gccgcgggag
361 gagcagtaca acagcacgta ccgtgtggtc agcgtcctca
    ccgtcctgca ccaggactgg
421 ctgaatggca aggagtacaa gtgcaaggtc tccaacaaag
    ccctcccagc ccccatcgag
481 aaaaccatct ccaaagccaa agggcagccc cgagaaccac
    aggtgtacac cctgccccca
541 tcccgggatg agctgaccaa gaaccaggtc agcctgacct
    gcctggtcaa aggcttctat
601 cccagcgaca tcgccgtgga gtgggagagc aatgggcagc
    cggagaacaa ctacaagacc
661 acgcctcccg tgctggactc cgacggctcc ttcttcctct
    acagcaagct caccgtggac
721 aagagcaggt ggcagcaggg gaacgtcttc tcatgctccg
    tgatgcatga ggctctgcac
781 aaccactaca cgcagaagag cctctccctg tctccgggta
    aaggatcacc acgcttccag
841 gactcctctt cctcaaaggc ccctcctcct agccttccaa
    gcccatcccg actcccgggg
901 ccctcggaca ctccgatcct cccacaataa
```

The invention provides for a nucleic acid encoding a trefoil family protein, or fragment thereof, such as a TFF1 molecule, a TFF2 molecule, or a TFF3 molecule.

For example, the polypeptide sequence of human TFF1 is depicted in SEQ ID NO: 1. The nucleotide sequence of human TFF1 is shown in SEQ ID NO: 2. Sequence information related to TFF1 is accessible in public databases by GenBank Accession numbers NP_003216.1 (protein) and NM_003225.2 (nucleic acid).

SEQ ID NO: 1 is the human wild type amino acid sequence corresponding to TFF1 (residues 1-84):

```
1   MATMENKVIC ALVLVSMLAL GTLAEAQTET CTVAPRERQN
    CGFPGVTPSQ CANKGCCFDD
61  TVRGVPWCFY PNTIDVPPEE ECEF
```

SEQ ID NO: 2 is the human wild type nucleotide sequence corresponding to TFF1 (nucleotides 1-508), wherein the underscored bolded "ATG" denotes the beginning of the open reading frame:

```
1   atccctgact cggggtcgcc tttggagcag agaggaggca
    atggccacca tggagaacaa
61  ggtgatctgc gccctggtcc tggtgtccat gctggccctc
    ggcaccctgg ccgaggccca
121 gacagagacg tgtacagtgg ccccccgtga aagacagaat
    tgtggttttc ctggtgtcac
181 gccctcccag tgtgcaaata agggctgctg tttcgacgac
    accgttcgtg gggtcccctg
241 gtgcttctat cctaatacca tcgacgtccc tccagaagag
    gagtgtgaat tttagacact
301 tctgcaggga tctgcctgca tcctgacgcg gtgccgtccc
    cagcacggtg attagtccca
361 gagctcggct gccacctcca ccggacacct cagacacgct
    tctgcagctg tgcctcggct
421 cacaacacag attgactgct ctgactttga ctactcaaaa
    ttggcctaaa aattaaaaga
481 gatcgatatt aaaaaaaaaa aaaaaaaa
```

For example, the polypeptide sequence of human TFF2 is depicted in SEQ ID NO: 3. The nucleotide sequence of human TFF2 is shown in SEQ ID NO: 4. Sequence information related to TFF2 is accessible in public databases by GenBank Accession numbers NP_005414.1 (protein) and NM_005423.4 (nucleic acid).

SEQ ID NO: 3 is the human wild type amino acid sequence corresponding to TFF2 (residues 1-129):

```
1   MGRRDAQLLA ALLVLGLCAL AGSEKPSPCQ CSRLSPHNRT
    NCGFPGITSD QCFDNGCCFD
61  SSVTGVPWCF HPLPKQESDQ CVMEVSDRRN CGYPGISPEE
    CASRKCCFSN FIFEVPWCFF
121 PKSVEDCHY
```

SEQ ID NO: 4 is the human wild type nucleotide sequence corresponding to TFF2 (nucleotides 1-717), wherein the underscored bolded "ATG" denotes the beginning of the open reading frame:

```
1   cacggtggaa gggctggggc cacggggcag agaagaaagg
    ttatctctgc ttgttggaca
61  aacagagggg agattataaa acatacccgg cagtggacac
    catgcattct gcaagccacc
121 ctggggtgca gctgagctag acatgggacg gcgagacgcc
    cagctcctgg cagcgctcct
181 cgtcctgggg ctatgtgccc tggcggggag tgagaaaccc
    tccccctgcc agtgctccag
241 gctgagcccc cataacagga cgaactgcgg cttccctgga
    atcaccagtg accagtgttt
301 tgacaatgga tgctgtttcg actccagtgt cactggggtc
    ccctggtgtt tccacccccct
361 cccaaagcaa gagtcggatc agtgcgtcat ggaggtctca
    gaccgaagaa actgtggcta
421 cccgggcatc agccccgagg aatgcgcctc tcggaagtgc
    tgcttctcca acttcatctt
481 tgaagtgccc tggtgcttct tcccgaagtc tgtggaagac
    tgccattact aagagaggct
541 ggttccagag gatgcatctg gctcaccggg tgttccgaaa
    ccaaagaaga aacttcgcct
601 tatcagcttc atacttcatg aaatcctggg ttttcttaac
    catcttttcc tcattttcaa
661 tggtttaaca tataatttct ttaaataaaa cccttaaaat
    ctgctaaaaa aaaaaaa
```

For example, the polypeptide sequence of human TFF3 is depicted in SEQ ID NO: 5. The nucleotide sequence of human TFF3 is shown in SEQ ID NO: 6. Sequence information related to TFF3 is accessible in public databases by GenBank Accession numbers NP_003217.3 (protein) and NM_003226.3 (nucleic acid).

SEQ ID NO: 5 is the human wild type amino acid sequence corresponding to TFF3 (residues 1-94):

```
1   MKRVLSCVPE PTVVMAARAL CMLGLVLALL SSSSAEEYVG
    LSANQCAVPA KDRVDCGYPH
61  VTPKECNNRG CCFDSRIPGV PWCFKPLQEA ECTF
```

SEQ ID NO: 6 is the human wild type nucleotide sequence corresponding to TFF3 (nucleotides 1-1054), wherein the underscored bolded "ATG" denotes the beginning of the open reading frame:

```
1   gccaaaacag tgggggctga actgacctct cccctttggg
    agagaaaaac tgtctgggag
61  cttgacaaag gcatgcagga gagaacagga gcagccacag
    ccaggaggga gagccttccc
```

```
                        -continued
 121  caagcaaaca atccagagca gctgtgcaaa caacggtgca

      taaatgaggc ctcctggacc

 181  atgaagcgag tcctgagctg cgtcccggag cccacggtgg

      tcatggctgc cagagcgctc

 241  tgcatgctgg ggctggtcct ggccttgctg tcctccagct

      ctgctgagga gtacgtgggc

 301  ctgtctgcaa accagtgtgc cgtgccagcc aaggacaggg

      tggactgcgg ctacccccat

 361  gtcaccccca aggagtgcaa caaccggggc tgctgctttg

      actccaggat ccctggagtg

 421  ccttggtgtt tcaagcccct gcaggaagca gaatgcacct

      tctgaggcac ctccagctgc

 481  ccccggccgg gggatgcgag gctcggagca cccttgcccg

      gctgtgattg ctgccaggca

 541  ctgttcatct cagcttttct gtccctttgc tcccggcaag

      cgcttctgct gaaagttcat

 601  atctggagcc tgatgtctta acgaataaag gtcccatgct

      ccacccgagg acagttcttc

 661  gtgcctgaga ctttctgagg ttgtgcttta tttctgctgc

      gtcgtgggag agggcgggag

 721  ggtgtcaggg gagagtctgc ccaggcctca agggcaggaa

      aagactccct aaggagctgc

 781  agtgcatgca aggatatttt gaatccagac tggcacccac

      gtcacaggaa agcctaggaa

 841  cactgtaagt gccgcttcct cgggaaagca gaaaaaatac

      atttcaggta gaagttttca

 901  aaaatcacaa gtctttcttg gtgaagacag caagccaata

      aaactgtctt ccaaagtggt

 961  cctttatttc acaaccactc tcgctactgt tcaatacttg

      tactattcct gggttttgtt

1021  tctttgtaca gtaaacatta tgaacaaaca ggca
```

A trefoil family molecule can also encompass ortholog genes, which are genes conserved among different biological species such as humans, dogs, cats, mice, and rats, that encode proteins (for example, homologs (including splice variants), mutants, and derivatives) having biologically equivalent functions as the human-derived protein. Orthologs of a trefoil family protein include any mammalian ortholog inclusive of the ortholog in humans and other primates, experimental mammals (such as mice, rats, hamsters and guinea pigs), mammals of commercial significance (such as horses, cows, camels, pigs and sheep), and also companion mammals (such as domestic animals, e.g., rabbits, ferrets, dogs, and cats). A trefoil family molecule can comprise a protein encoded by a nucleic acid sequence homologous to the human nucleic acid, wherein the nucleic acid is found in a different species and wherein that homolog encodes a protein similar to a trefoil family protein.

The invention utilizes conventional molecular biology, microbiology, and recombinant DNA techniques available to one of ordinary skill in the art. Such techniques are well known to the skilled worker and are explained fully in the literature. See, e.g., Maniatis, Fritsch & Sambrook, "*DNA Cloning: A Practical Approach*," Volumes I and II (D. N. Glover, ed., 1985); "Oligonucleotide Synthesis" (M. J. Gait, ed., 1984); "*Nucleic Acid Hybridization*" (B. D. Hames & S. J. Higgins, eds., 1985); "*Transcription and Translation*" (B. D. Hames & S. J. Higgins, eds., 1984); "*Animal Cell Culture*" (R. I. Freshney, ed., 1986); "*Immobilized Cells and Enzymes*" (IRL Press, 1986): B. Perbal, "*A Practical Guide to Molecular Cloning*" (1984), and Sambrook, et al., "*Molecular Cloning: a Laboratory Manual*" (2001).

One skilled in the art can obtain a trefoil family molecule, (e.g., TFF1, TFF2, or TFF3) in several ways, which include, but are not limited to, isolating the protein via biochemical means or expressing a nucleotide sequence encoding the protein of interest by genetic engineering methods.

The invention provides for a trefoil family molecule that are encoded by nucleotide sequences. The trefoil family molecule can be a polypeptide encoded by a nucleic acid (including genomic DNA, complementary DNA (cDNA), synthetic DNA, as well as any form of corresponding RNA). For example, a trefoil family molecule can be encoded by a recombinant nucleic acid encoding a human trefoil family protein, or fragment thereof. The trefoil family molecules of the invention can be obtained from various sources and can be produced according to various techniques known in the art. For example, a nucleic acid that encodes a trefoil family molecule can be obtained by screening DNA libraries, or by amplification from a natural source. The trefoil family molecule of the invention can be produced via recombinant DNA technology and such recombinant nucleic acids can be prepared by conventional techniques, including chemical synthesis, genetic engineering, enzymatic techniques, or a combination thereof. A trefoil family molecule of this invention can also encompasses variants of the human trefoil family proteins. The variants can comprise naturally-occurring variants due to allelic variations between individuals (e.g., polymorphisms), mutated alleles, or alternative splicing forms.

In one embodiment, a fragment of a nucleic acid sequence that comprises a trefoil family molecule (such as, e.g., TFF1, TFF2, or TFF3) can encompass any portion of at least about 8 consecutive nucleotides of SEQ ID NO: 2, 4, or 6. In one embodiment, the fragment can comprise at least about 10 nucleotides, at least about 15 nucleotides, at least about 20 nucleotides, or at least about 30 nucleotides of SEQ ID NO: 2, 4, or 6. Fragments include all possible nucleotide lengths between about 8 and about 100 nucleotides, for example, lengths between about 15 and about 100 nucleotides, or between about 20 and about 100 nucleotides.

A trefoil family molecule, can be a fragment of a trefoil family protein, such as, e.g., TFF1, TFF2, or TFF3. For example, the trefoil family protein fragment can encompass any portion of at least about 8 consecutive amino acids of SEQ ID NO: 1, 3, or 5. The fragment can comprise at least about 10 consecutive amino acids, at least about 20 consecutive amino acids, at least about 30 consecutive amino acids, at least about 40 consecutive amino acids, a least about 50 consecutive amino acids, at least about 60 consecutive amino acids, at least about 70 consecutive amino acids, at least about 80 consecutive amino acids, at least about 90 consecutive amino acids, at least about 100 consecutive amino acids, at least about 110 consecutive amino acids, or at least about 120 consecutive amino acids of SEQ ID NOS: 1, 3, or 5. Fragments include all possible amino acid lengths between about 8 and 80 about amino acids, for example, lengths between about 10 and about 80 amino acids, between about 15 and about 80 amino acids, between about 20 and about 80 amino acids, between about 35 and about 80 amino acids, between about 40 and about 80 amino acids, between about 50 and about 80 amino acids, or between about 70 and about 80 amino acids.

Recombinant Proteins

One skilled in the art understands that polypeptides (for example TFF1, TFF2, TFF3, and the like) can be obtained in several ways, which include but are not limited to, expressing a nucleotide sequence encoding the protein of interest, or fragment thereof, by genetic engineering methods.

In one embodiment, the nucleic acid is expressed in an expression cassette, for example, to achieve overexpression in a cell. The nucleic acids of the invention can be an RNA, cDNA, cDNA-like, or a DNA of interest in an expressible format, such as an expression cassette, which can be expressed from the natural promoter or an entirely heterologous promoter. The nucleic acid of interest can encode a protein, and may or may not include introns. Any recombinant expression system can be used, including, but not limited to, bacterial, mammalian, yeast, insect, or plant cell expression systems.

Host cells transformed with a nucleic acid sequence encoding a trefoil family molecule (such as, e.g., TFF1, TFF2, or TFF3), can be cultured under conditions suitable for the expression and recovery of the protein from cell culture. The polypeptide produced by a transformed cell can be secreted or contained intracellularly depending on the sequence and/or the vector used. Expression vectors containing a nucleic acid sequence encoding a trefoil family molecule can be designed to contain signal sequences which direct secretion of soluble polypeptide molecules encoded by a trefoil family molecule (such as, e.g., TFF1, TFF2, or TFF3), through a prokaryotic or eukaryotic cell membrane.

Nucleic acid sequences comprising a trefoil family molecule (such as, e.g., TFF1, TFF2, or TFF3) that encode a polypeptide can be synthesized, in whole or in part, using chemical methods known in the art. Alternatively, a trefoil family molecule can be produced using chemical methods to synthesize its amino acid sequence, such as by direct peptide synthesis using solid-phase techniques. Protein synthesis can either be performed using manual techniques or by automation. Automated synthesis can be achieved, for example, using Applied Biosystems 431A Peptide Synthesizer (Perkin Elmer). Optionally, fragments of a trefoil family molecule can be separately synthesized and combined using chemical methods to produce a full-length molecule.

A synthetic peptide can be substantially purified via high performance liquid chromatography (HPLC). The composition of a synthetic a trefoil family molecule can be confirmed by amino acid analysis or sequencing. Additionally, any portion of an amino acid sequence comprising a protein encoded by a trefoil family molecule (e.g., TFF1, TFF2, or TFF3) can be altered during direct synthesis and/or combined using chemical methods with sequences from other proteins to produce a variant polypeptide or a fusion protein.

The invention further encompasses methods for using a protein or polypeptide encoded by a nucleic acid sequence of a trefoil family molecule, such as the sequences shown in SEQ ID NOS: 1, 3, or 5. In another embodiment, the polypeptide can be modified, such as by glycosylations and/or acetylations and/or chemical reaction or coupling, and can contain one or several non-natural or synthetic amino acids. An example of a trefoil family molecule has the amino acid sequence shown in either SEQ ID NO: 1, 3, or 5. In certain embodiments, the invention encompasses variants of a human protein encoded by a trefoil family molecule (such as, e.g., TFF1, TFF2, and TFF3).

Expression Systems

Bacterial Expression Systems.

One skilled in the art understands that expression of desired protein products in prokaryotes is most often carried out in *E. coli* with vectors that contain constitutive or inducible promoters. Some non-limiting examples of bacterial cells for transformation include the bacterial cell line *E. coli* strains DH5α or MC1061/p3 (Invitrogen Corp., San Diego, Calif.), which can be transformed using standard procedures practiced in the art, and colonies can then be screened for the appropriate plasmid expression. In bacterial systems, a number of expression vectors can be selected. Non-limiting examples of such vectors include multifunctional *E. coli* cloning and expression vectors such as BLUESCRIPT (Stratagene). Some *E. coli* expression vectors (also known in the art as fusion-vectors) are designed to add a number of amino acid residues, usually to the N-terminus of the expressed recombinant protein. Such fusion vectors can serve three functions: 1) to increase the solubility of the desired recombinant protein; 2) to increase expression of the recombinant protein of interest; and 3) to aid in recombinant protein purification by acting as a ligand in affinity purification. In some instances, vectors, which direct the expression of high levels of fusion protein products that are readily purified, may also be used. Some non-limiting examples of fusion expression vectors include pGEX, which fuse glutathione S-tranferase (GST) to desired protein; pcDNA 3.1N5-His A B & C (Invitrogen Corp, Carlsbad, Calif.) which fuse 6x-His (SEQ ID NO:25) to the recombinant proteins of interest; pMAL (New England Biolabs, MA) which fuse maltose E binding protein to the target recombinant protein; the *E. coli* expression vector pUR278 (Ruther et al., (1983) EMBO 12:1791), wherein the coding sequence may be ligated individually into the vector in frame with the lac Z coding region in order to generate a fusion protein; and pIN vectors (Inouye et al., (1985) *Nucleic Acids Res.* 13:3101-3109; Van Heeke et al., (1989) *J. Biol. Chem.* 24:5503-5509. Fusion proteins generated by the likes of the above-mentioned vectors are generally soluble and can be purified easily from lysed cells via adsorption and binding of the fusion protein to an affinity matrix. For example, fusion proteins can be purified from lysed cells via adsorption and binding to a matrix of glutathione agarose beads subsequently followed by elution in the presence of free glutathione. For example, the pGEX vectors are designed to include thrombin or factor Xa protease cleavage sites so that the cloned target can be released from the GST moiety.

Plant, Insect, and Yeast Expression Systems.

Other suitable cell lines, in addition to microorganisms such as bacteria (e.g., *E. coli* and *B. subtilis*) transformed with recombinant bacteriophage DNA, plasmid DNA or cosmid DNA expression vectors containing coding sequences for a trefoil family molecule may alternatively be used to produce the molecule of interest. A non-limiting example includes plant cell systems infected with recombinant virus expression vectors (for example, tobacco mosaic virus, TMV; cauliflower mosaic virus, CaMV) or transformed with recombinant plasmid expression vectors (e.g., Ti plasmid) containing coding sequences for a trefoil family molecule. If plant expression vectors are used, the expression of sequences encoding a trefoil family molecule can be driven by any of a number of promoters. For example, viral promoters such as the 35S and 19S promoters of CaMV can be used alone or in combination with the omega leader sequence from tobacco mosaic virus TMV. Alternatively, plant promoters such as the small subunit of RUBISCO or heat shock promoters, can be used. These constructs can be introduced into plant cells by direct DNA transformation or by pathogen-mediated transfection.

In another embodiment, an insect system also can be used to express a trefoil family molecule. For example, in one such system *Autographa californica* nuclear polyhedrosis virus (AcNPV) is used as a vector to express foreign genes in *Spodoptera frugiperda* cells or in *Trichoplusia* larvae. Sequences encoding a trefoil family molecule can be cloned into a non-essential region of the virus, such as the polyhedrin gene, and placed under control of the polyhedrin promoter. Successful insertion of the nucleic acid sequences of a trefoil family molecule will render the polyhedrin gene inactive and produce recombinant virus lacking coat protein. The recombinant viruses can then be used to infect *S. frugiperda* cells or *Trichoplusia* larvae in which a trefoil family molecule can be expressed.

In another embodiment, a yeast (for example, *Saccharomyces* sp., *Pichia* sp.) system also can be used to express a trefoil family molecule. Yeast can be transformed with recombinant yeast expression vectors containing coding sequences for a trefoil family molecule.

Mammalian Expression Systems.

Mammalian cells (such as BHK cells, VERO cells, CHO cells and the like) can also contain an expression vector (for example, one that harbors a nucleotide sequence encoding a trefoil family molecule) for expression of a desired product. Expression vectors containing such a nucleic acid sequence linked to at least one regulatory sequence in a manner that allows expression of the nucleotide sequence in a host cell can be introduced via methods known in the art. A number of viral-based expression systems can be used to express a trefoil family molecule in mammalian host cells. The vector can be a recombinant DNA or RNA vector, and includes DNA plasmids or viral vectors. For example, if an adenovirus is used as an expression vector, sequences encoding a trefoil family molecule can be ligated into an adenovirus transcription/translation complex comprising the late promoter and tripartite leader sequence. Insertion into a non-essential E1 or E3 region of the viral genome can be used to obtain a viable virus which is capable of expressing a trefoil family molecule in infected host cells. Transcription enhancers, such as the Rous sarcoma virus (RSV) enhancer, can also be used to increase expression in mammalian host cells. In addition, viral vectors can be constructed based on, but not limited to, adeno-associated virus, retrovirus, adenovirus, lentivirus or alphavirus.

Regulatory sequences are well known in the art, and can be selected to direct the expression of a protein or polypeptide of interest (such as a trefoil family molecule) in an appropriate host cell as described in Goeddel, *Gene Expression Technology: Methods in Enzymology* 185, Academic Press, San Diego, Calif. (1990). Non-limiting examples of regulatory sequences include: polyadenylation signals, promoters (such as CMV, ASV, SV40, or other viral promoters such as those derived from bovine papilloma, polyoma, and Adenovirus 2 viruses (Fiers, et al., 1973, Nature 273:113; Hager G L, et al., *Curr Opin Genet Dev,* 2002, 12(2):137-41) enhancers, and other expression control elements. Practitioners in the art understand that designing an expression vector can depend on factors, such as the choice of host cell to be transfected and/or the type and/or amount of desired protein to be expressed.

Enhancer regions, which are those sequences found upstream or downstream of the promoter region in non-coding DNA regions, are also known in the art to be important in optimizing expression. If needed, origins of replication from viral sources can be employed, such as if a prokaryotic host is utilized for introduction of plasmid DNA. However, in eukaryotic organisms, chromosome integration is a common mechanism for DNA replication.

For stable transfection of mammalian cells, a small fraction of cells can integrate introduced DNA into their genomes. The expression vector and transfection method utilized can be factors that contribute to a successful integration event. For stable amplification and expression of a desired protein, a vector containing DNA encoding a protein of interest (for example, a trefoil family molecule) is stably integrated into the genome of eukaryotic cells (for example mammalian cells, such as HEK293 cells), resulting in the stable expression of transfected genes. An exogenous nucleic acid sequence can be introduced into a cell (such as a mammalian cell, either a primary or secondary cell) by homologous recombination as disclosed in U.S. Pat. No. 5,641,670, the contents of which are herein incorporated by reference.

A gene that encodes a selectable marker (for example, resistance to antibiotics or drugs, such as ampicillin, neomycin, G418, and hygromycin) can be introduced into host cells along with the gene of interest in order to identify and select clones that stably express a gene encoding a protein of interest. The gene encoding a selectable marker can be introduced into a host cell on the same plasmid as the gene of interest or can be introduced on a separate plasmid. Cells containing the gene of interest can be identified by drug selection wherein cells that have incorporated the selectable marker gene will survive in the presence of the drug. Cells that have not incorporated the gene for the selectable marker die. Surviving cells can then be screened for the production of the desired protein molecule (for example, a trefoil family molecule).

A host cell strain can be chosen for its ability to modulate the expression of the inserted sequences or to process the expressed trefoil family molecule (such as, e.g., TFF1, TFF2, or TFF3) in the desired fashion. Such modifications of the polypeptide include, but are not limited to, acetylation, carboxylation, glycosylation, phosphorylation, lipidation, and acylation. Post-translational processing which cleaves a "prepro" form of the polypeptide also can be used to facilitate correct insertion, folding and/or function. Different host cells which have specific cellular machinery and characteristic mechanisms for post-translational activities (e.g., CHO, HeLa, MDCK, HEK293, and W138), are available from the American Type Culture Collection (ATCC; 10801 University Boulevard, Manassas, Va. 20110-2209) and can be chosen to ensure the correct modification and processing of the foreign protein.

An exogenous nucleic acid can be introduced into a cell via a variety of techniques known in the art, such as lipofection, microinjection, calcium phosphate or calcium chloride precipitation, DEAE-dextrin-mediated transfection, or electroporation. Electroporation is carried out at approximate voltage and capacitance to result in entry of the DNA construct(s) into cells of interest. Other methods used to transfect cells can also include modified calcium phosphate precipitation, polybrene precipitation, liposome fusion, and receptor-mediated gene delivery.

Animal or mammalian host cells capable of harboring, expressing, and secreting large quantities of a trefoil family molecule of interest into the culture medium for subsequent isolation and/or purification include, but are not limited to, Human Embryonic Kidney 293 cells (HEK-293) (ATCC CRL-1573); Chinese hamster ovary cells (CHO), such as CHO-K1 (ATCC CCL-61), DG44 (Chasin et al., (1986) *Som. Cell Molec. Genet,* 12:555-556; Kolkekar et al., (1997) *Biochemistry,* 36:10901-10909; and WO 01/92337 A2), dihydrofolate reductase negative CHO cells (CHO/dhfr−, Urlaub et al., (1980) *Proc. Natl. Acad. Sci. USA.,* 77:4216), and dp12.CHO cells (U.S. Pat. No. 5,721,121); monkey kidney CV1 cells transformed by SV40 (COS cells, COS-7, ATCC CRL-1651); human embryonic kidney cells (e.g., 293 cells, or 293 cells subcloned for growth in suspension culture, Graham et al., (1977) *J. Gen. Virol.,* 36:59); baby hamster kidney cells (BHK, ATCC CCL-10); monkey kidney cells (CV1, ATCC CCL-70); African green monkey kidney cells (VERO-76, ATCC CRL-1587; VERO, ATCC CCL-81); mouse sertoli cells (TM4; Mather (1980) *Biol. Reprod.,* 23:243-251); human cervical carcinoma cells (HELA, ATCC CCL-2); canine kidney cells (MDCK, ATCC CCL-34); human lung cells (W138, ATCC CCL-75); human hepatoma cells (HEP-G2, HB 8065); mouse mammary tumor cells (MMT 060562, ATCC CCL-51); buffalo rat liver cells (BRL 3A, ATCC CRL-1442); TRI cells (Mather (1982) *Annals NY Acad Sci.,* 383:44-68); MCR 5 cells; FS4 cells. A cell line transformed to produce a trefoil family molecule can also be an immortalized mammalian cell line of lymphoid origin, which include but are not limited to, a myeloma, hybridoma, trioma or quadroma cell line. The cell line can also comprise a normal lymphoid cell, such as a B cell, which has been immortalized by transformation with a virus, such as the Epstein Barr virus (such as a myeloma cell line or a derivative thereof).

A host cell strain, which modulates the expression of the inserted sequences, or modifies and processes the nucleic acid in a specific fashion desired also may be chosen. Such modifications (for example, glycosylation and other post-translational modifications) and processing (for example, cleavage) of protein products may be important for the function of the protein. Different host cell strains have characteristic and specific mechanisms for the post-translational processing and modification of proteins and gene products. As such, appropriate host systems or cell lines can be chosen to ensure the correct modification and processing of the foreign protein expressed, such as a trefoil family molecule. Thus, eukaryotic host cells possessing the cellular machinery for proper processing of the primary transcript, glycosylation, and phosphorylation of the gene product may be used. Non-limiting examples of mammalian host cells include HEK-293, 3T3, W138, BT483, Hs578T, CHO, VERY, BHK, Hela, COS, BT2O, T47D, NS0 (a murine myeloma cell line that does not endogenously produce any immunoglobulin chains), CRL7O3O, MDCK, 293, HTB2, and HsS78Bst cells.

Various culturing parameters can be used with respect to the host cell being cultured. Appropriate culture conditions for mammalian cells are well known in the art (Cleveland W L, et al., *J Immunol Methods,* 1983, 56(2): 221-234) or can be determined by the skilled artisan (see, for example, *Animal Cell Culture: A Practical Approach* 2nd *Ed*., Rickwood, D. and Hames, B. D., eds. (Oxford University Press: New York, 1992)). Cell culturing conditions can vary according to the type of host cell selected. Commercially available medium can be utilized.

Cells suitable for culturing can contain introduced expression vectors, such as plasmids or viruses. The expression vector constructs can be introduced via transformation, microinjection, transfection, lipofection, electroporation, or infection. The expression vectors can contain coding sequences, or portions thereof, encoding the proteins for expression and production. Expression vectors containing sequences encoding the produced proteins and polypeptides, as well as the appropriate transcriptional and translational control elements, can be generated using methods well known to and practiced by those skilled in the art. These methods include synthetic techniques, in vitro recombinant DNA techniques, and in vivo genetic recombination which are described in J. Sambrook et al., 201*, Molecular Cloning, A Laboratory Manual*, Cold Spring Harbor Press, Cold Spring Harbor, N.Y. and in F. M. Ausubel et al., 1989*, Current Protocols in Molecular Biology*, John Wiley & Sons, New York, N.Y.

Purification of Recombinant Proteins

A trefoil family molecule (such as, e.g., TFF1, TFF2, or TFF3) can be purified from any human or non-human cell which expresses the polypeptide, including those which have been transfected with expression constructs that express a trefoil family molecule. A purified trefoil family molecule (such as, e.g., TFF1, TFF2, or TFF3) can be separated from other compounds which normally associate with the trefoil family molecules, in the cell, such as certain proteins, carbohydrates, or lipids, using methods practiced in the art. For protein recovery, isolation and/or purification, the cell culture medium or cell lysate is centrifuged to remove particulate cells and cell debris. The desired polypeptide molecule (for example, a trefoil family molecule) is isolated or purified away from contaminating soluble proteins and polypeptides by suitable purification techniques. Non-limiting purification methods for proteins include: size exclusion chromatography; affinity chromatography; ion exchange chromatography; ethanol precipitation; reverse phase HPLC; chromatography on a resin, such as silica, or cation exchange resin, e.g., DEAE; chromatofocusing; SDS-PAGE; ammonium sulfate precipitation; gel filtration using, e.g., Sephadex G-75, Sepharose; protein A sepharose chromatography for removal of immunoglobulin contaminants; and the like. Other additives, such as protease inhibitors (e.g., PMSF or proteinase K) can be used to inhibit proteolytic degradation during purification. Purification procedures that can select for carbohydrates can also be used, e.g., ion-exchange soft gel chromatography, or HPLC using cation- or anion-exchange resins, in which the more acidic fraction(s) is/are collected.

Methods of Administration

Nucleic Acid Delivery Methods.

The invention provides methods for treating a disease of the digestive system in a subject, e.g., an inflammatory disease of the digestive system, or a digestive system cancer. In one embodiment, the method can comprise administering to the subject a trefoil family molecule (e.g, a trefoil family polypeptide or a trefoil family polynucleotide).

Various approaches can be carried out to restore the activity or function of a trefoil family molecule (such as, e.g., TFF1, TFF2, or TFF3) in a subject, such as those carrying an altered trefoil family gene locus. For example, supplying wild-type trefoil family gene function (such as, e.g., TFF1, TFF2, TFF3) to such subjects can treat inflammatory diseases of the digestive system, treat a cancer of the digestive system, treat dysplasia of the digestive system, decrease tumor growth, or decrease cell proliferation (e.g., myeloid-derived suppressor cell proliferation). Increasing a trefoil family gene expression level or activity (such as, e.g., TFF1, TFF2, or TFF3) can be accomplished through gene or protein therapy.

A nucleic acid encoding a trefoil family molecule can be introduced into the cells of a subject. For example, the wild-type gene (or fragment thereof) can also be introduced into the cells of the subject in need thereof using a vector as described herein. The vector can be a viral vector or a plasmid. The gene can also be introduced as naked DNA. The gene can be provided so as to integrate into the genome of the recipient host cells, or to remain extrachromosomal. Integration can occur randomly or at precisely defined sites, such as through homologous recombination. For example, a functional copy of a trefoil family molecule can be inserted in replacement of an altered version in a cell, through homologous recombination. Further techniques include gene gun, liposome-mediated transfection, or cationic lipid-mediated transfection. Gene therapy can be accomplished by direct gene injection, or by administering ex vivo prepared genetically modified cells expressing a functional polypeptide.

Delivery of nucleic acids into viable cells can be effected ex vivo, in situ, or in vivo by use of vectors, and more particularly viral vectors (e.g., lentivirus, adenovirus, adeno-associated virus, or a retrovirus), or ex vivo by use of physical DNA transfer methods (e.g., liposomes or chemical treatments). Non-limiting techniques suitable for the transfer of nucleic acid into mammalian cells in vitro include the use of liposomes, electroporation, microinjection, cell fusion, DEAE-dextran, and the calcium phosphate precipitation method (see, for example, Anderson, Nature, supplement to vol. 392, no. 6679, pp. 25-20 (1998)). Introduction of a nucleic acid or a gene encoding a polypeptide of the invention can also be accomplished with extrachromosomal substrates (transient expression) or artificial chromosomes (stable expression). Cells may also be cultured ex vivo in the presence of therapeutic compositions of the present invention in order to proliferate or to produce a desired effect on or activity in such cells. Treated cells can then be introduced in vivo for therapeutic purposes.

Nucleic acids can be inserted into vectors and used as gene therapy vectors. A number of viruses have been used as gene transfer vectors, including papovaviruses, e.g., SV40 (Madzak et al., (1992) *J Gen Virol.* 73(Pt 6):1533-6), adenovirus (Berkner (1992) *Curr Top Microbiol Immunol.* 158: 39-66; Berkner (1988) *Biotechniques,* 6(7):616-29; Gorziglia and Kapikian (1992) *J Virol.* 66(7):4407-12; Quantin et al., (1992) *Proc Natl Acad Sci USA.* 89(7):2581-4; Rosenfeld et al., (1992) *Cell.* 68(1):143-55; Wilkinson et al., (1992) *Nucleic Acids Res.* 20(9):2233-9; Stratford-Perricaudet et al., (1990) *Hum Gene Ther.* 1(3):241-56), vaccinia virus (Moss (1992) *Curr Opin Biotechnol.* 3(5):518-22), adeno-associated virus (Muzyczka, (1992) *Curr Top Microbiol Immunol.* 158:97-129; Ohi et al., (1990) *Gene.* 89(2): 279-82), herpesviruses including HSV and EBV (Margolskee (1992) *Curr Top Microbiol Immunol.* 158:67-95; Johnson et al., (1992) *Brain Res Mol Brain Res* 0.12(1-3): 95-102; Fink et al., (1992) *Hum Gene Ther.* 3(1):11-9; Breakefield and Geller (1987) *Mol Neurobiol.* 1(4):339-71; Freese et al., (1990) *Biochem Pharmacol.* 40(10):2189-99), and retroviruses of avian (Bandyopadhyay and Temin (1984) *Mol Cell Biol.* 4(4):749-54; Petropoulos et al., (1992) *J Virol.* 66(6):3391-7), murine (Miller et al. (1992) *Mol Cell Biol.* 12(7):3262-72; Miller et al., (1985) *J Virol.* 55(3):521-6; Sorge et al., (1984) *Mol Cell Biol.* 4(9):1730-7; Mann and Baltimore (1985) *J Virol.* 54(2):401-7; Miller et al., (1988) *J Virol.* 62(11):4337-45), and human origin (Shimada et al., (1991) *J Clin Invest.* 88(3):1043-7; Helseth et al., (1990) *J Virol.* 64(12):6314-8; Page et al., (1990) *J Virol.* 64(11): 5270-6; Buchschacher and Panganiban (1992) *J* Virol. 66(5):2731-9).

Non-limiting examples of in vivo gene transfer techniques include transfection with viral (typically retroviral) vectors (see U.S. Pat. No. 5,252,479, which is incorporated by reference in its entirety) and viral coat protein-liposome mediated transfection (Dzau et al., Trends in Biotechnology 11:205-210 (1993), incorporated entirely by reference). For example, naked DNA vaccines are generally known in the art; see Brower, Nature Biotechnology, 16:1304-1305 (1998), which is incorporated by reference in its entirety. Gene therapy vectors can be delivered to a subject by, for example, intravenous injection, local administration (see, e.g., U.S. Pat. No. 5,328,470) or by stereotactic injection (see, e.g., Chen, et al., 1994. Proc. Natl. Acad. Sci. USA 91: 3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

For reviews of gene therapy protocols and methods see Anderson et al., Science 256:808-813 (1992); U.S. Pat. Nos. 5,252,479, 5,747,469, 6,017,524, 6,143,290, 6,410,010 6,511,847; 8,398,968; and 8,404,653 which are all hereby incorporated by reference in their entireties. For an example of gene therapy treatment in humans see Porter et al., NEJM 2011 365:725-733 and Kalos et al. Sci. Transl. Med. 2011. 201 3(95):95. For additional reviews of gene therapy technology, see Friedmann, Science, 244:1275-1281 (1989); Verma, Scientific American: 68-84 (1990); Miller, Nature, 357: 455-460 (1992); Kikuchi et al., J Dermatol Sci. 2008 May; 50(2):87-98; Isaka et al., Expert Opin Drug Deliv. 2007 September; 4(5):561-71; Jager et al., Curr Gene Ther. 2007 August; 7(4):272-83; Waehler et al., Nat Rev Genet. 2007 August; 8(8):573-87; Jensen et al., Ann Med. 2007; 39(2):108-15; Herweijer et al., Gene Ther. 2007 January; 14(2):99-107; Eliyahu et al., Molecules, 2005 Jan. 31; 10(1):34-64; and Altaras et al., Adv Biochem Eng Biotechnol. 2005; 99:193-260, all of which are hereby incorporated by reference in their entireties.

These methods described herein are by no means all-inclusive, and further methods to suit the specific application is understood by the ordinary skilled artisan. Moreover, the effective amount of the compositions can be further approximated through analogy to compounds known to exert the desired effect.

Protein Delivery Methods.

Protein replacement therapy can increase the amount of protein by exogenously introducing wild-type or biologically functional protein by way of infusion. A replacement polypeptide can be synthesized according to known chemical techniques or may be produced and purified via known molecular biological techniques. Protein replacement therapy has been developed for various disorders. For example, a wild-type protein can be purified from a recombinant cellular expression system (e.g., mammalian cells or insect cells-see U.S. Pat. No. 5,580,757 to Desnick et al.; U.S. Pat. Nos. 6,395,884 and 6,458,574 to Selden et al.; U.S. Pat. No. 6,461,609 to Calhoun et al.; U.S. Pat. No. 6,210,666 to Miyamura et al.; U.S. Pat. No. 6,083,725 to Selden et al.; U.S. Pat. No. 6,451,600 to Rasmussen et al.; U.S. Pat. No. 5,236,838 to Rasmussen et al. and U.S. Pat. No. 5,879,680 to Ginns et al.), human placenta, or animal milk (see U.S. Pat. No. 6,188,045 to Reuser et al.), or other sources known in the art. After the infusion, the exogenous protein can be taken up by tissues through non-specific or receptor-mediated mechanism.

A trefoil family molecule can also be delivered in a controlled release system. For example, the trefoil family molecule can be administered using intravenous infusion, an implantable osmotic pump, a transdermal patch, liposomes, or other modes of administration. In one embodiment, a pump can be used (see Sefton (1987) *Biomed. Eng.* 14:201; Buchwald et al. (1980) *Surgery* 88:507; Saudek et al. (1989) *N. Engl. J Med.* 321:574). In another embodiment, polymeric materials can be used (see *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger and Peppas, (1983) *J. Macromol. Sci. Rev. Macromol. Chem.* 23:61; see also Levy et al. (1985) *Science* 228:190; During et al. (1989) *Ann. Neurol.* 25:351; Howard et al. (1989) *J. Neurosurg.* 71:105). In yet another embodiment, a controlled release system can be placed in proximity of the therapeutic target thus requiring only a fraction of the systemic dose (see, e.g., Goodson, in *Medical Applications of Controlled Release*, supra, vol. 2, pp. 115-138 (1984)). Other controlled release systems are discussed in the review by Langer (*Science* (1990) 249:1527-1533).

Pharmaceutical Compositions and Methods of Administration

In some embodiments, a trefoil family molecule can be supplied in the form of a pharmaceutical composition, comprising an isotonic excipient prepared under sufficiently sterile conditions for human administration. Choice of the excipient and any accompanying elements of the composition comprising a trefoil family molecule will be adapted in accordance with the route and device used for administration. In some embodiments, a composition comprising a trefoil family molecule can also comprise, or be accompanied with, one or more other ingredients that facilitate the delivery or functional mobilization of the trefoil family molecule.

These methods described herein are by no means all-inclusive, and further methods to suit the specific application is understood by the ordinary skilled artisan. Moreover, the effective amount of the compositions can be further approximated through analogy to compounds known to exert the desired effect.

According to the invention, a pharmaceutically acceptable carrier can comprise any and all solvents, dispersion media, coatings, antibacterial and antifungal agents, isotonic and absorption delaying agents, and the like, compatible with pharmaceutical administration. The use of such media and agents for pharmaceutically active substances is well known in the art. Any conventional media or agent that is compatible with the active compound can be used. Supplementary active compounds can also be incorporated into the compositions.

A trefoil family molecule (such as, e.g., TFF1, TFF2, and TFF3) can be administered to the subject one time (e.g., as a single injection or deposition). Alternatively, a trefoil family molecule can be administered once or twice daily to a subject in need thereof for a period of from about 2 to about 28 days, or from about 7 to about 10 days, or from about 7 to about 15 days. It can also be administered once or twice daily to a subject for a period of 1, 2, 3, 4, 5, 6, 7, 8, 9, 10, 11, 12 times per year, or a combination thereof. Furthermore, a trefoil family molecule can be co-administrated with another therapeutic.

In one embodiment, a trefoil family molecule can be co-administrated with a chemotherapy drug. Some non-limiting examples of conventional chemotherapy drugs include: aminoglutethimide, amsacrine, asparaginase, bcg, anastrozole, bleomycin, buserelin, bicalutamide, busulfan, capecitabine, carboplatin, camptothecin, chlorambucil, cisplatin, carmustine, cladribine, colchicine, cyclophosphamide, cytarabine, dacarbazine, cyproterone, clodronate, daunorubicin, diethylstilbestrol, docetaxel, dactinomycin, doxorubicin, dienestrol, etoposide, exemestane, filgrastim, fluorouracil, fludarabine, fludrocortisone, epirubicin, estradiol, gemcitabine, genistein, estramustine, fluoxymesterone, flutamide, goserelin, leuprolide, hydroxyurea, idarubicin, levamisole, imatinib, lomustine, ifosfamide, megestrol, melphalan, interferon, irinotecan, letrozole, leucovorin, ironotecan, mitoxantrone, nilutamide, medroxyprogesterone, mechlorethamine, mercaptopurine, mitotane, nocodazole, octreotide, methotrexate, mitomycin, paclitaxel, oxaliplatin, temozolomide, pentostatin, plicamycin, suramin, tamoxifen, porfimer, mesna, pamidronate, streptozocin, teniposide, procarbazine, titanocene dichloride, raltitrexed, rituximab, testosterone, thioguanine, vincristine, vindesine, thiotepa, topotecan, tretinoin, vinblastine, trastuzumab, and vinorelbine.

In one embodiment, the chemotherapy drug is an alkylating agent, a nitrosourea, an anti-metabolite, a topoisomerase inhibitor, a mitotic inhibitor, an anthracycline, a corticosteroid hormone, a sex hormone, or a targeted anti-tumor compound.

A targeted anti-tumor compound is a drug designed to attack cancer cells more specifically than standard chemotherapy drugs can. Most of these compounds attack cells that harbor mutations of certain genes, or cells that overexpress copies of these genes. In one embodiment, the anti-tumor compound can be imatinib (Gleevec), gefitinib (Iressa), erlotinib (Tarceva), rituximab (Rittman), or bevacizumab (Avastin).

An alkylating agent works directly on DNA to prevent the cancer cell from propagating. These agents are not specific to any particular phase of the cell cycle. In one embodiment, alkylating agents can be selected from busulfan, cisplatin, carboplatin, chlorambucil, cyclophosphamide, ifosfamide, dacarbazine (DTIC), mechlorethamine (nitrogen mustard), melphalan, and temozolomide.

An antimetabolite makes up the class of drugs that interfere with DNA and RNA synthesis. These agents work during the S phase of the cell cycle and are commonly used to treat leukemia, tumors of the breast, ovary, and the gastrointestinal tract, as well as other cancers. In one embodiment, an antimetabolite can be 5-fluorouracil, capecitabine, 6-mercaptopurine, methotrexate, gemcitabine, cytarabine (ara-C), fludarabine, or pemetrexed.

Topoisomerase inhibitors are drugs that interfere with the topoisomerase enzymes that are important in DNA replication. Some examples of topoisomerase I inhibitors include topotecan and irinotecan while some representative examples of topoisomerase II inhibitors include etoposide (VP-16) and teniposide.

Anthracyclines are chemotherapy drugs that also interfere with enzymes involved in DNA replication. These agents work in all phases of the cell cycle and thus, are widely used as a treatment for a variety of cancers. In one embodiment, an anthracycline used with respect to the invention can be daunorubicin, doxorubicin (Adriamycin), epirubicin, idarubicin, or mitoxantrone.

In one embodiment, a trefoil family molecule can be co-administrated with an anti-inflammatory drug. Some non-limiting examples of anti-inflammatory drugs include: anti-inflammatory steroids (corticosteroids) (e.g. prednisone), aminosalicylates (e.g., mesalazine), non-steroidal anti-inflammatory drugs (NSAIDs) (e.g. aspirin, ibuprofen, naproxen) and immune selective anti-inflammatory derivatives (ImSAIDs). An anti-inflammatory drug also includes antibodies or molecules that target cytokines and chemokines including, but not limited to, anti-TNFα antibodies (e.g. infliximab (Remicade), adalimumab (Humira), certolizumab pegol (Cimzia), golimumab (Simponi), etanercept (Enbrel)), anti-IL12 antibodies, anti-IL2 antibodies (basiliximab (Simulect), daclizumab (Zenapax), azathioprine (Imuran®, Azasan®), 6-mercaptopurine (6-MP, Purinethol®), cyclosporine A (Sandimmune®, Neoral®), tacrolimus (Prograf®), and anti-GM-CSF antibodies.

In one embodiment, a trefoil family molecule can be co-administrated with radiation therapy. Some non-limiting examples of conventional radiation therapy include: external beam radiation therapy, sealed source radiation therapy, unsealed source radiation therapy, particle therapy, and radioisotope therapy.

In one embodiment, a trefoil family molecule can be co-administrated with a cancer immunotherapy. Cancer immunotherapy comprises using the immune system of the subject to treat a cancer. For example, the immune system of a subject can be stimulated to recognize and eliminate cancer cells. Some non-limiting examples of cancer immunotherapy include: cancer vaccines, therapeutic antibodies, such as monoclonal antibody therapy (e.g., Bevacizumab, Cetuximab, and Panitumumab), cell based immunotherapy, and adoptive cell based immunotherapy.

A trefoil family molecule may also be used in combination with surgical or other interventional treatment regimens used for the treatment disease of the digestive system.

A trefoil family molecule can be administered to a subject by any means suitable for delivering the protein, nucleic acid or compound to cells of the subject. For example, it can be administered by methods suitable to transfect cells. Transfection methods for eukaryotic cells are well known in the art, and include direct injection of the nucleic acid into the nucleus or pronucleus of a cell; electroporation; liposome transfer or transfer mediated by lipophilic materials; receptor mediated nucleic acid delivery, bioballistic or particle acceleration; calcium phosphate precipitation, and transfection mediated by viral vectors.

The compositions of this invention can be formulated and administered to reduce the symptoms associated with a disease of the digestive system by any means that produce contact of the active ingredient with the agent's site of action in the body of a human or non-human subject. For example, the compositions of this invention can be formulated and administered to reduce the symptoms associated with an inflammatory disease of the digestive system, a digestive system cancer, or a dysplasia of the digestive system, or cause a decrease in cell proliferation, or a decrease in tumor growth. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

Pharmaceutical compositions for use in accordance with the invention can be formulated in conventional manner using one or more physiologically acceptable carriers or excipients. The therapeutic compositions of the invention can be formulated for a variety of routes of administration, including systemic and topical or localized administration. Techniques and formulations generally can be found in *Remmington's Pharmaceutical Sciences*, Meade Publishing Co., Easton, Pa. ($20^{th}$ ed., 2000), the entire disclosure of which is herein incorporated by reference. For systemic administration, an injection is useful, including intramuscular, intravenous, intraperitoneal, and subcutaneous. For injection, the therapeutic compositions of the invention can be formulated in liquid solutions, for example in physiologically compatible buffers, such as PBS, Hank's solution, or Ringer's solution. In addition, the therapeutic compositions can be formulated in solid form and redissolved or suspended immediately prior to use. Lyophilized forms are also included. Pharmaceutical compositions of the present invention are characterized as being at least sterile and pyrogen-free. These pharmaceutical formulations include formulations for human and veterinary use.

Any of the therapeutic applications described herein can be applied to any subject in need of such therapy, including, for example, a mammal such as a dog, a cat, a cow, a horse, a rabbit, a monkey, a pig, a sheep, a goat, or a human.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EM™ (BASF, Parsippany, N.J.) or phosphate buffered saline (PBS). The composition must be sterile and fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, a pharmaceutically acceptable polyol like glycerol, propylene glycol, liquid polyetheylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, and thimerosal. In many cases, it can be useful to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the trefoil family molecule in the required amount in an appropriate solvent with one or a combination of ingredients enumerated herein, as required, followed by filtered sterilization. Dispersions are prepared by incorporating the active compound into a sterile vehicle which contains a basic dispersion medium and the required other ingredients from those enumerated herein. In the case of sterile powders for the preparation of sterile injectable solutions, examples of useful preparation methods are vacuum drying and freeze-drying which yields a powder of the active ingredient plus any additional desired ingredient from a previously sterile-filtered solution thereof.

Oral compositions include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as known in the art A composition of the invention can be administered to a subject in need thereof. Subjects in need thereof can include but are not limited to, for example, a mammal such as a dog, a cat, a cow, a horse, a rabbit, a monkey, a pig, a sheep, a goat, or a human.

A composition of the invention can also be formulated as a sustained and/or timed release formulation. Such sustained and/or timed release formulations can be made by sustained release means or delivery devices that are well known to those of ordinary skill in the art, such as those described in U.S. Pat. Nos. 3,845,770; 3,916,899; 3,536,809; 3,598,123; 4,008,719; 4,710,384; 5,674,533; 5,059,595; 5,591,767; 5,120,548; 5,073,543; 5,639,476; 5,354,556; and 5,733,566, the disclosures of which are each incorporated herein by reference. The pharmaceutical compositions of the invention (e.g., that have a therapeutic effect) can be used to provide slow or sustained release of one or more of the active ingredients using, for example, hydropropylmethyl cellulose, other polymer matrices, gels, permeable membranes, osmotic systems, multilayer coatings, microparticles, liposomes, microspheres, or the like, or a combination thereof to provide the desired release profile in varying proportions. Suitable sustained release formulations known to those of ordinary skill in the art, including those described herein, can be readily selected for use with the pharmaceutical compositions of the invention. Single unit dosage forms suitable for oral administration, such as, but not limited to, tablets, capsules, gel-caps, caplets, or powders, that are adapted for sustained release are encompassed by the invention.

In the methods described herein, a trefoil family molecule, can be administered to the subject either as RNA, in conjunction with a delivery reagent, or as a nucleic acid (e.g., a recombinant plasmid or viral vector) comprising sequences which express the gene product. Suitable delivery reagents for administration of the a trefoil family molecule, include the Mirus Transit TKO lipophilic reagent; lipofectin; lipofectamine; cellfectin; or polycations (e.g., polylysine), or liposomes.

The dosage administered can be a therapeutically effective amount of the composition sufficient to result in treatment of an inflammatory disease of the digestive system, treatment of an of a digestive system cancer, a decrease in cell proliferation, a decrease in tumor growth, or treatment of dysplasia of the digestive system, and can vary depending upon known factors such as the pharmacodynamic characteristics of the active ingredient and its mode and route of administration; time of administration of active ingredient; age, sex, health and weight of the recipient; nature and extent of symptoms; kind of concurrent treatment, frequency of treatment and the effect desired; and rate of excretion.

In some embodiments, the effective amount of the administered trefoil family molecule is at least about 0.01 μg/kg body weight, at least about 0.025 μg/kg body weight, at least about 0.05 μg/kg body weight, at least about 0.075 μg/kg body weight, at least about 0.1 μg/kg body weight, at least about 0.25 μg/kg body weight, at least about 0.5 μg/kg body weight, at least about 0.75 μg/kg body weight, at least about 1 μg/kg body weight, at least about 5 μg/kg body weight, at least about 10 μg/kg body weight, at least about 25 μg/kg body weight, at least about 50 μg/kg body weight, at least about 75 μg/kg body weight, at least about 100 μg/kg body weight, at least about 150 μg/kg body weight, at least about 200 μg/kg body weight, at least about 250 μg/kg body weight, at least about 300 μg/kg body weight, at least about 350 μg/kg body weight, at least about 400 μg/kg body weight, at least about 450 μg/kg body weight, at least about 500 μg/kg body weight, at least about 550 μg/kg body weight, at least about 600 μg/kg body weight, at least about 650 μg/kg body weight, at least about 700 μg/kg body weight, at least about 750 μg/kg body weight, at least about 800 μg/kg body weight, at least about 850 μg/kg body weight, at least about 900 μg/kg body weight, at least about 950 μg/kg body weight, at least about 1000 μg/kg body weight, at least about 1500 μg/kg body weight, at least about 2000 μg/kg body weight, at least about 2500 μg/kg body weight, at least about 3000 μg/kg body weight, at least about 3500 μg/kg body weight, at least about 4000 μg/kg body weight, at least about 4500 μg/kg body weight, at least about 5000 μg/kg body weight, at least about 5500 μg/kg body weight, at least about 6000 μg/kg body weight, at least about 6500 μg/kg body weight, at least about 7000 μg/kg body weight, at least about 7500 μg/kg body weight, at least about 8000 μg/kg body weight, at least about 8500 μg/kg body weight, at least about 9000 μg/kg body weight, at least about 9500 μg/kg body weight, or at least about 10000 μg/kg body weight.

In one embodiment, a trefoil family molecule is administered at least once daily. In another embodiment, a trefoil family molecule is administered at least twice daily. In some embodiments, a trefoil family molecule is administered for at least 1 week, for at least 2 weeks, for at least 3 weeks, for at least 4 weeks, for at least 5 weeks, for at least 6 weeks, for at least 8 weeks, for at least 10 weeks, for at least 12 weeks, for at least 18 weeks, for at least 24 weeks, for at least 36 weeks, for at least 48 weeks, or for at least 60 weeks. In further embodiments, a trefoil family molecule is administered in combination with a second therapeutic agent.

Toxicity and therapeutic efficacy of therapeutic compositions of the present invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Therapeutic agents that exhibit large therapeutic indices are useful. Therapeutic compositions that exhibit some toxic side effects can be used.

Experimental animals can be used as models for human disease. For example, mice can be used as a mammalian model system. The physiological systems that mammals possess can be found in mice, and in humans, for example. Certain diseases can be induced in mice by manipulating their environment, genome, or a combination of both. For example, the AOM/DSS mouse model is a model for human colon cancer. In another example, the DSS mouse model is a model for human colitis. Other mouse models of carcinogenesis include the two-stage DMBA/TPA model of skin cancer, the DEN/CCL4 model of liver cancer, and the *H. felis*/MNU model of gastric cancer. In addition, there are numerous genetically engineered models of cancer, such as the KPC model of pancreatic cancer.

Administration of a trefoil family molecule is not restricted to a single route, but may encompass administration by multiple routes. Multiple administrations may be sequential or concurrent. Other modes of application by multiple routes will be apparent to one of skill in the art.

Methods of Detection

Embodiments of the invention provide for detecting expression of a trefoil family molecule (such as, e.g., TFF1, TFF2, TFF3). In one embodiment, a gene alteration can result in increased or reduced protein expression and/or activity. The alteration can be determined at the level of the DNA, RNA, or polypeptide.

In some embodiments, the detecting comprises detecting in a biological sample whether there is a reduction in an mRNA encoding a trefoil family protein, or a reduction in a trefoil family protein, or a combination thereof. In further embodiments, the detecting comprises detecting in a biological sample whether there is a reduction in an mRNA encoding a trefoil family protein, or a reduction in a trefoil family protein, or a combination thereof. The presence of such an alteration is indicative of the presence or predisposition to a digestive system cancer (e.g., colon cancer) or an inflammatory disease of the digestive system.

Methods for detecting and quantifying trefoil family molecules, (such as, e.g., TFF1, TFF2, TFF3 proteins and polynucleotides) in biological samples are known the art. For example, protocols for detecting and measuring the expression of a polypeptide encoded by a trefoil family molecule, such as TFF1, TFF2, TFF3, using either polyclonal or monoclonal antibodies specific for the polypeptide are well established. Non-limiting examples include Western blot, enzyme-linked immunosorbent assay (ELISA), radioimmunoassay (RIA), and fluorescence activated cell sorting (FACS).

In one embodiment, a biological sample comprises, a blood sample, serum, cells (including whole cells, cell fractions, cell extracts, and cultured cells or cell lines), tissues (including tissues obtained by biopsy), body fluids (e.g., urine, sputum, amniotic fluid, synovial fluid), or from media (from cultured cells or cell lines). The methods of detecting or quantifying trefoil family molecules (such as, e.g., TFF1, TFF2, TFF3) include, but are not limited to, amplification-based assays with (signal amplification) hybridization based assays and combination amplification-hybridization assays. For detecting and quantifying trefoil family molecules (such as, e.g., TFF1, TFF2, TFF3), an exemplary method is an immunoassay that utilizes an antibody or other binding agents that specifically bind to a trefoil family protein (such as, e.g., TFF1, TFF2, or TFF3) or epitope of such, for example, Western blot or ELISA assays.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention.

Those skilled in the art will recognize, or be able to ascertain, using no more than routine experimentation, numerous equivalents to the specific substances and procedures described herein. Such equivalents are considered to be within the scope of this invention, and are covered by the following claims.

All publications and other references mentioned herein are incorporated by reference in their entirety, as if each individual publication or reference were specifically and individually indicated to be incorporated by reference. Publications and references cited herein are not admitted to be prior art.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1: Generation of TFF2 Transgenic Mice

A knock out the trefoil factor family 2 (TFF2) gene in mice showed that loss of TFF2 resulted in increased inflammation in response to DSS colitis or *Helicobacter* gastritis, suggesting that TFF2 dampened inflammatory responses. In addition, other results showed that TFF2 was specifically silenced in many cancers, suggesting it was a tumor suppressor gene. Most recently, it was shown that TFF2 is normally expressed by a subset of T cells, and that such TFF2 expression acts to regulate myeloid progenitors. In response to the induction of cancer, myeloid progenitors proliferate and are markedly amplified, resulting in increase myeloid derived suppressor cells (MDSC) that promote cancer growth. Thus, in TFF2 knockout mice these cells are much increased. A TFF2 overexpressing mouse was generated, where TFF2 was highly expressed in all T cells, and found that in response to carcinogens, myeloid proliferation was suppressed and the mice did not develop cancer. Accumulating evidence has indicated that blocking myeloid cell expansion (e.g. using an antibody to GM-CSF) can inhibit cancer initiation and progression.

TFF2 can be used, delivered as a recombinant peptide or using a viral vector or modified peptide (for increased stability) to treat advanced cancer (or dysplasia) by specifically suppressing myeloid proliferation with this approach. More potent means of delivery are being developed.

TFF2 can be a new and useful cancer therapy that works by targeting the tumor microenvironment, specifically the myeloid cells (e.g. MDSC, tumor associated macrophages, neutrophils) that support cancer. In addition, it can be a form of replacement of a tumor suppressor gene product that is normally downregulated in many cancers.

TFF2 differs from other myeloid therapies, such as anti-CSF or anti-GM-CSF, in that it would be a natural peptide and not a monoclonal antibody. While most useful potentially in treatment of advanced cancer, it can also be used in cancer prevention therapy in high risk individuals.

Example 2: TFF2 is a Novel Tumor Suppressor that Inhibits Expansion of Gr1+CD11b+ Myeloid Derived Suppressor Cells (MDSC) and Blocks Colon Carcinogenesis Trefoil factor 2 (TFF2) is a small secreted protein that is expressed in gastrointestinal mucosa where it functions to protect and repair mucosa. It is, however, also expressed at low levels in splenic immune cells where its role has been unclear. TFF2 is epigenetically silenced in gastric cancer and thus has been postulated to protect against cancer development through multiple mechanisms. Since TFF2 is normally expressed in splenic T-cells the specific contribution of T-cell related TFF2 production in the modulation of tumorigenesis was investigated. It was discovered that TFF2 is a critical modulator of the aberrant inflammatory response that promotes carcinogenesis.

Methods:

Transgenic (TG) mice that overexpress TFF2 under the control of the human CD2 promoter (specific to T-cells) were created. These TG mice were compared to TFF2−/− (knockout) and wild-type (WT) mice in inflammation and inflammatory carcinogenesis models (including the DSS colitis model and the AOM/DSS colon cancer model). The contribution of T-cell TFF2 production on tumor development and the associated immune response was examined in vivo and mechanisms analyzed in vitro.

Results:

DSS colitis caused a marked early (day 1-3) upregulation of TFF2 production in the spleen, absent in TFF2−/− mice. Compared to the WT mice, the null mice displayed a dramatically amplified inflammatory response to DSS with increased splenic cell proliferation and associated increases in MDSCs (Gr1+CD11b+) detected in both the spleen and bone marrow. In contrast, the proliferation and expansion of Gr1+CD11b+ cells seen with DSS was markedly suppressed in the TFF2 overexpressing TG mice. This was consistent with an immune modulatory role of T-cell TFF2. Interestingly, this aberrant inflammatory response to DSS seen in the TFF2 null mice, translated into an ordered difference in ultimate tumor development in the AOM/DSS model with TFF2−/− mice developing more colonic tumors then WT mice, which in turn developed more than the TG mice. The TG mice showed almost complete suppression of colonic tumorigenesis ($P<0.05$). To identify the cellular target of TFF2, a eukaryotic TFF2 expression construct was generated using the pMIG vector to express mouse TFF2 (mTFF2) in CHO-KI cells. Recombinant mTFF2 was properly folded in this system and subsequently purified. It was found that mTFF2 suppressed, in a dose-dependent manner, the proliferation of Gr1+CD11b+ cells (MDSCs) in vitro. Thus, potentially revealing the mechanism through which TFF2 modulated the immune response and reduced inflammatory carcinogenesis.

Conclusion:

Overexpression of TFF2 markedly suppressed tumor growth by curtailing the proliferation and expansion of myeloid progenitors that give rise to MDSCs. This novel mechanism for suppressing myeloid cells may have implications for cancer prevention and therapy.

Example 3: TFF2 Inhibits Expansion of Gr1+CD11b+ Myeloid-Derived Suppressor Cells and Blocks Colon Carcinogenesis Trefoil factor 2 (TFF2) is a small secreted protein that is expressed in gastrointestinal mucosa where it functions to protect and repair mucosa, but it is also expressed at low levels in splenic immune cells where its role has been unclear. The Tff2 gene is epigenetically silenced in gastric cancers and thus has been postulated to protect against cancer development through multiple mechanisms.

The aims include:

Identify the cell target of TFF2 in suppressing tumor development.

Determine the specific contribution of T cell-derived TFF2 in the modulation of tumorigenesis.

Methods

Transgenic (TG) mice that overexpress TFF2 under the control of the human CD2 promoter, T cells-specific promoter were created. These TG mice were compared to Tff2−/− and wild-type (WT) mice in inflammation and inflammatory carcinogenesis models (including the DSS—induced colitis model and the AOM/DSS colon cancer model). The contribution of T cell derived TFF2 on tumor development and the associated immune response was examined in vivo and mechanisms analyzed in vitro.

Results

DSS administration (colitis) caused a marked early (day 1-3) upregulation of TFF2 expression (production) in the spleen. Compared to the WT mice, TFF2−/− mice displayed worse inflammatory response to DSS with increased proportion of Gr1+CD11b+ cells (myeloid-derived suppressor cells [MDSCs]) in the spleen and bone marrow. In contrast, the proliferation and expansion of Gr1+CD11b+ cells seen with DSS treatment was markedly suppressed in the TFF2 overexpressing TG mice. Consistently TFF2−/− mice developed more colonic tumors than WT mice, which in turn developed more than the TG mice in AOM/DSS model. The TG mice showed almost complete suppression of colonic tumorigenesis ($p<0.05$) with normal proportion of MDSCs in spleen in contrast to TFF2−/− deficient mice which all develop tumor and display expansion of IMC in spleen and bone marrow. To identify the cellular target of TFF2, a eukaryotic TFF2 expression construct was generated using the pMIG vector to express mouse TFF2 (mTFF2) in CHO-KI cells. Recombinant mTFF2 was properly expressed in this system and subsequently purified. We found that recombinant mTFF2 suppressed, in a dose-dependent manner, the proliferation of Gr1+CD11b+ cells (MDSCs) in vitro, thus potentially revealing the mechanism through which TFF2 modulates the immune response and reduces inflammatory carcinogenesis.

Conclusion

Overexpression of TFF2 markedly suppressed tumor growth by curtailing the proliferation and expansion of myeloid progenitors that give rise to MDSCs. This novel mechanism for suppressing myeloid cells may have implications for cancer prevention and therapy.

Example 4: TFF2 Inhibits Expansion of Gr1+CD11b+ Myeloid-Derived Suppressor Cells and Blocks Colon Carcinogenesis Trefoil factor 2 (TFF2) is a small secreted protein that is expressed in gastrointestinal mucosa where it functions to protect and repair mucosa. It is also expressed at low levels in splenic immune cells where its role has been unclear. The Tff2 gene is epigenetically silenced in gastric cancers and thus has been postulated to protect against cancer development through multiple mechanisms.

Methods

The aims include:

Determine the specific contribution of T cell-derived TFF2 in carcinogenesis.

Identify the cells targeted by TFF2 to reduce tumor development.

Generation of Transgenic Mice

Transgenic (TG) mice that overexpress TFF2 under the control of the human CD2 promoter (a T cell-specific promoter, FIG. 2A) were created. These TG mice were compared to TFF2−/− and wild-type (WT) mice in inflammation and inflammatory carcinogenesis models (including the DSS-induced colitis model and the AOM/DSS colon cancer model). The contribution of T cell derived TFF2 on tumor development and the associated immune response was examined in vivo and mechanisms analyzed in vitro.

Generation of Mice Chimaeras

WT mice were lethally irradiated and transplanted with bone marrow from WT, TFF2−/− and TG mice. The chimaeras were given 5% DSS water for 5 days and tap water for the remaining days. They were sacrificed on day 19 and differences in clinical disease parameters were measured.

Results

TFF2 is Upregulated Upon Splenic T Cells Activation

Figures 1A, 1B, 1C, 1D:
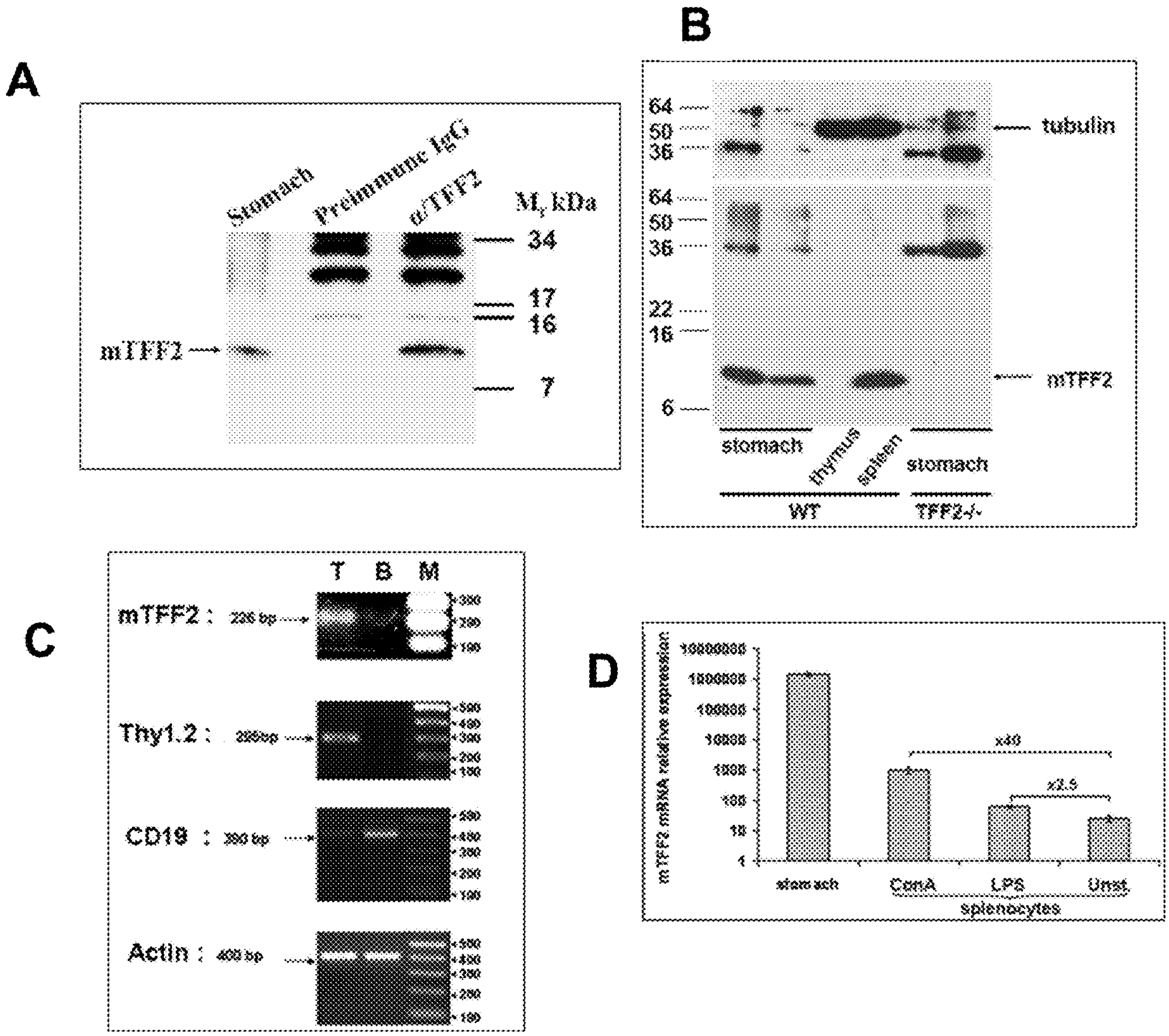
FIGS. 1A-D. TFF2 is expressed in splenic T-cells and upregulated upon T-cells activation.

TFF2 is expressed in the stomach and spleen of WT mice (FIG. 1B). Robust TFF2 mRNA expression was detected in resting splenic T cells from WT mice (FIG. 1C). There was minimal expression in B cells at baseline. When murine splenocytes were stimulated with concavalin A (Con A), a T cell-specific stimulant, and lipopolysaccharides (LPS), a B cell-activator, a 40- and 2.5-fold increase was observed in TFF2 mRNA expression respectively over unstimulated splenocytes (FIG. 1D). An upregulation of TFF2 expression in WT spleen was also detected after administration of 3% DSS water (FIG. 1F).

TFF2−/− Mice have More Severe DSS-Induced Inflammation

Figures 3A, 3B, 3C, 3D, 3E:
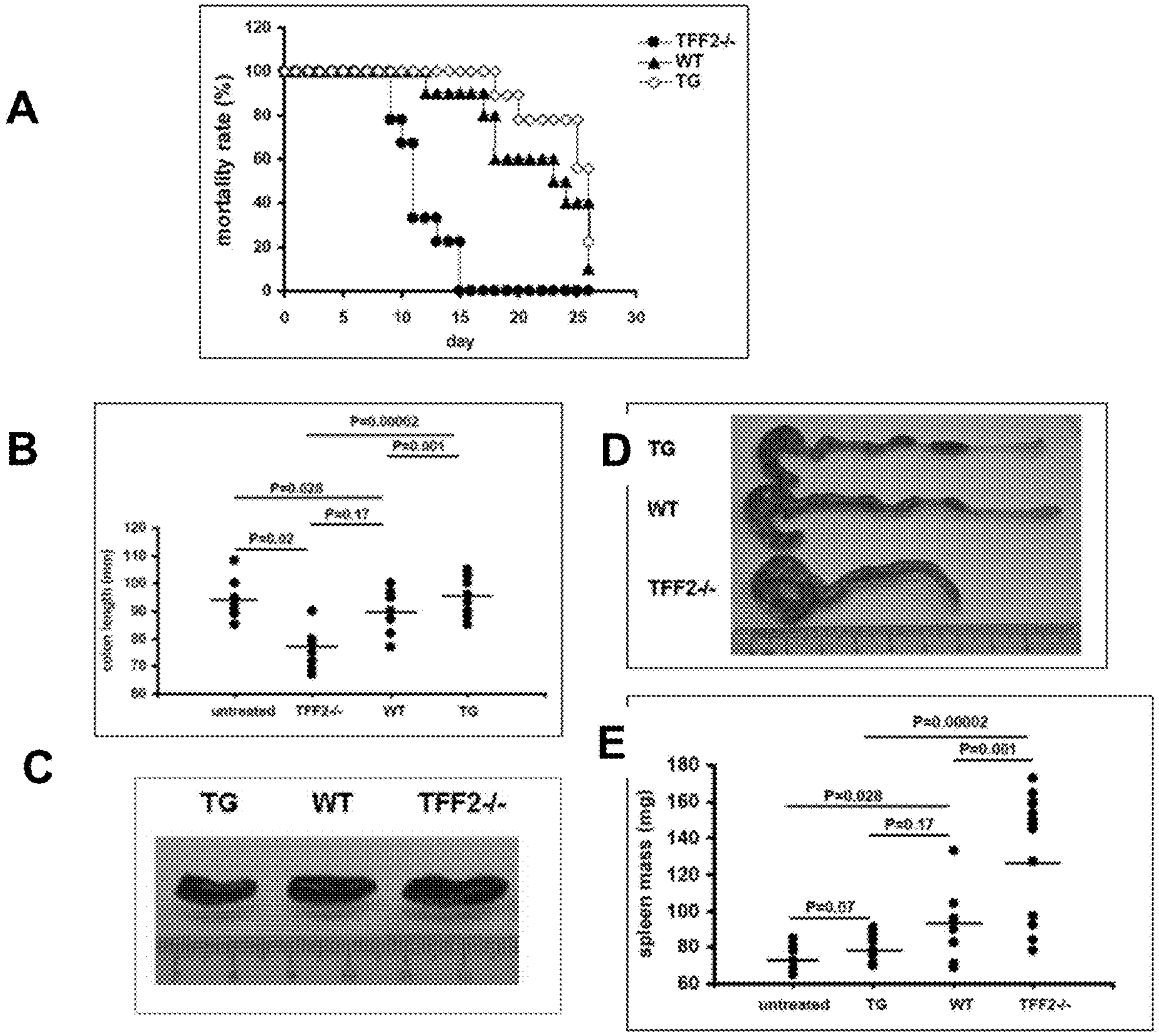
FIGS. 3A-E. TFF2-deficiency results in more severe inflammation upon DSS challenge.

TFF2 deficient mice had more severe inflammation and higher mortality rate than TG and WT mice after DSS administration (FIG. 3A). TFF2−/− mice had greater reactive splenomegaly compared to TG and WT upon 2.5% DSS regimen (FIG. 3E).

Transgenic Mice Overexpressing TFF2 in T Cells (TG Mice) Show Attenuated DSS Colitis Unlike TFF2−/− mice, TG mice showed attenuated DSS colitis. Tff2−/− showed an upregulation of inflammatory cytokines IL-1b at day 19 (FIG. 4A) and myeloperoxidase (MPO) activity at acute phase of colitis on day 6 after DSS administration (FIG. 4E) suggesting the role of TFF2 in modulating inflammation.

WT Mice Reconstituted with Bone Marrow from TFF2−/− Showed More Acute Inflammatory Response Following bone marrow (BM) transplantation and DSS, WT recipients of TFF2−/−donor BM were most affected. They lost more weight (FIG. 5A), had shorter colons (FIG. 5B), more severe splenomegaly (FIG. 5D) and greater increase of IL-1β in colon (FIG. 5E) at day 19 compared to recipients of TG or WT BM. Highlighting the importance of hematopoietic TFF2 production.

Figures 7A, 7B:
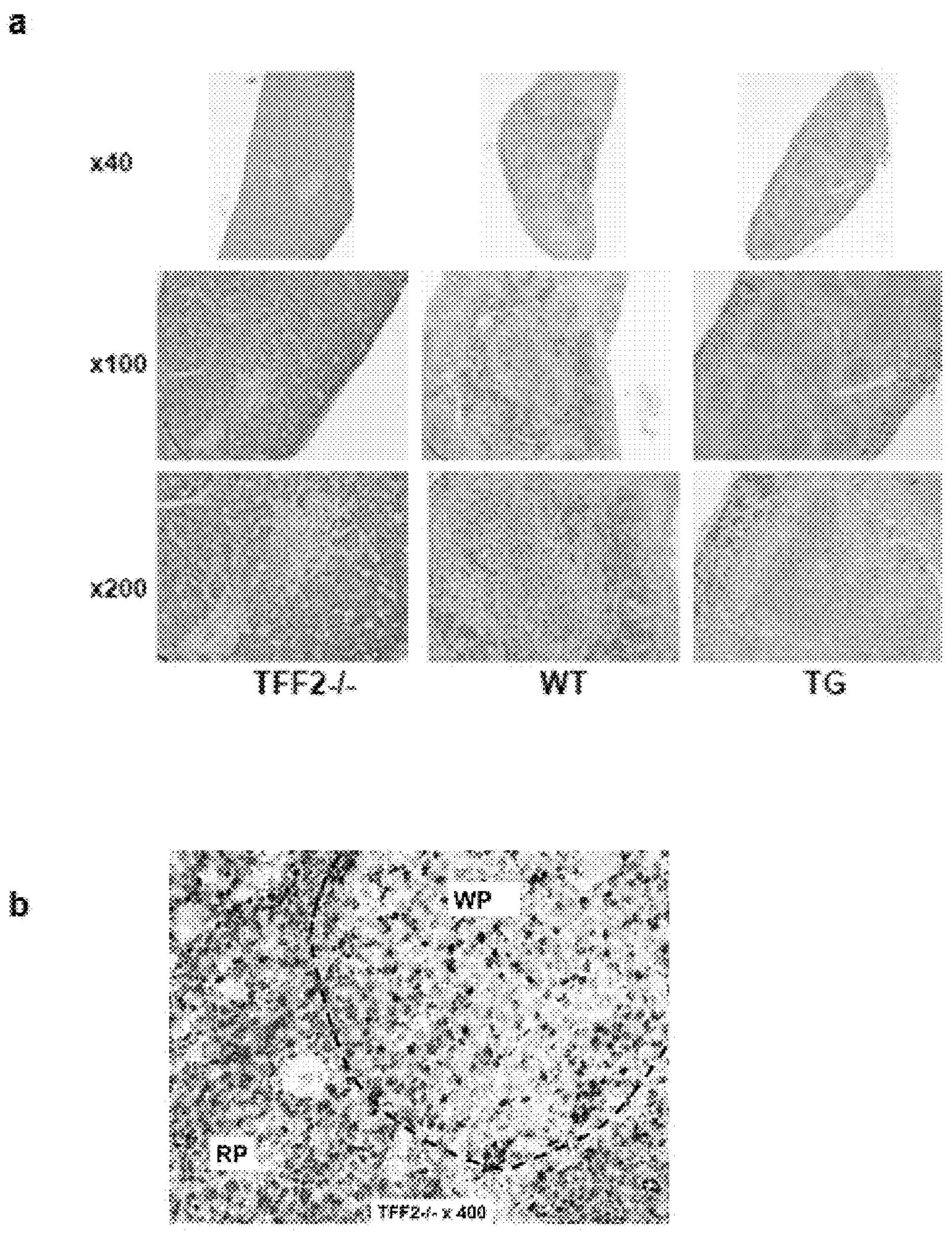
FIGS. 7A-B. Accumulation of CD11b+Gr1+ cells in spleens from DSS-treated TFF2−/− and WT mice.

DSS Treatment Increased Gr1+CD11b+ (Myeloid-Derived Suppressor Cells, MDSCs) Cells in the Spleen of TFF2−/− and WT but not in the Spleen of TG Mice In comparison to WT and TG groups, TFF2−/− mice had more significant splenic myeloid proliferation following DSS treatment ((examined by Ki67 (brown, proliferation) and Gr1 (red, myeloid marker) coimmunostaining) (FIG. 7A). Coimmunostaining was localized to the red pulp zone, where myeloid cells reside (FIG. 7B). FACS analysis showed TFF2 expression-dependent expansion of CD11b+ Gr1+ cells in the spleen and bone marrow of the mice (FIGS. 7C, 7D) after DSS-treatment. Thus, splenomegaly in DSS-treated TFF2−/− mice resulted from the expansion of immature myeloid cells due to extramedullary hematopoiesis.

TFF2 Inhibits Proliferation of Gr1+CD11b+ Cells

Figures 8A, 8B, 8C:
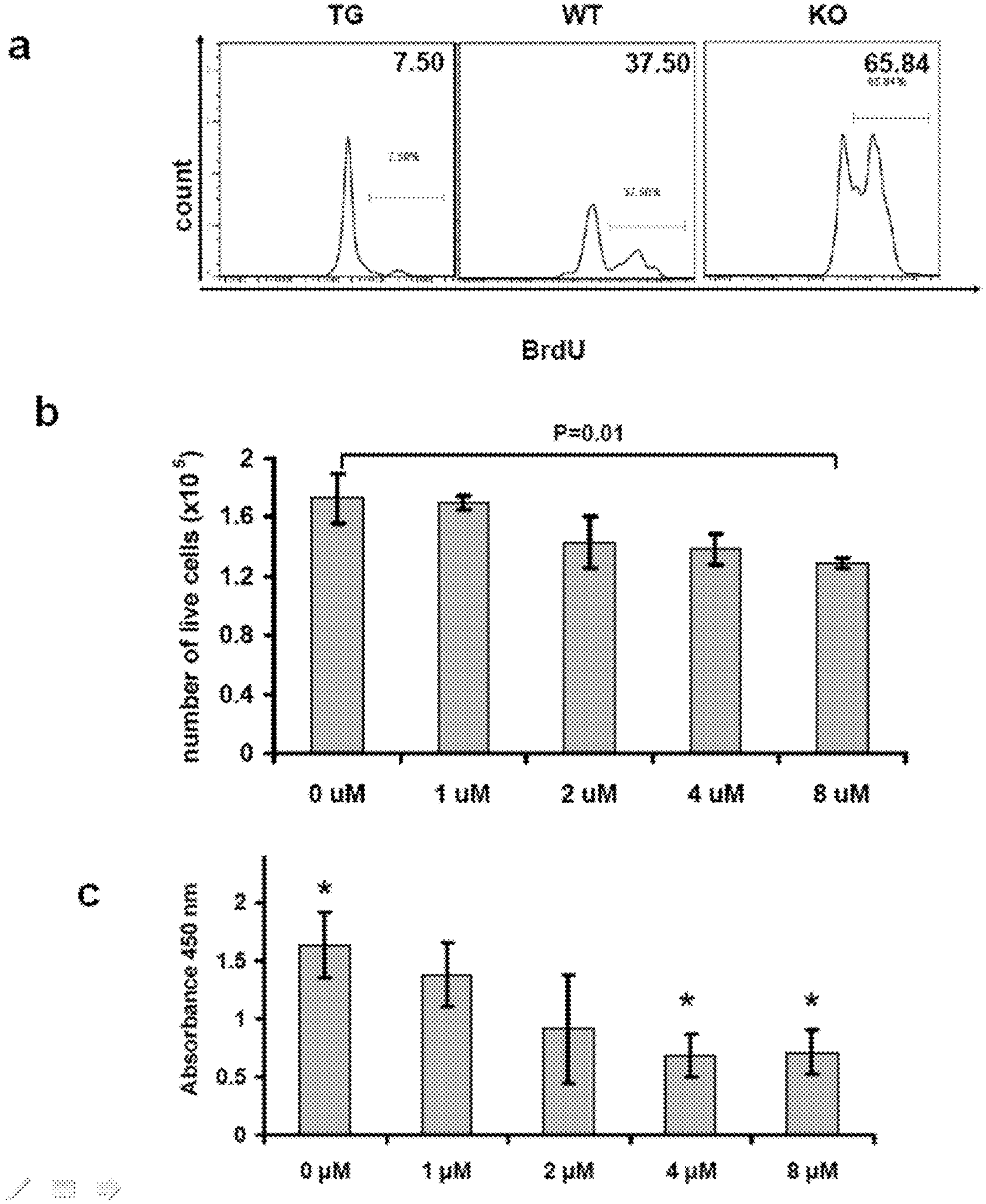
FIGS. 8A-C. Recombinant mouse TFF2 inhibits proliferation of sorted Gr1+CD11b+ cells in vitro. Spleens were obtained from TFF2−/− on day 19 after starting DSS water. Splenic cells from TFF2−/− mice were labeled for Gr1 and CD11b antigen and sorted on sorter FACSAria.

Using BrdU uptake as another measure of proliferation, it was found that following DSS TFF2−/− mice showed greatest, WT mice intermediate and TG mice least proliferation of Gr1+CD11b+ cells (D+19, FIG. 8A). Gr1+CD11b+ cells cultured with increasing concentrations of rTFF2 (murine) also showed a dose-dependent decrease in viability (FIG. 8C).

Expression of TFF2 by Splenic T Cells Suppressed the Development of Colon and Rectal Tumors in AOM/DSS Model.

AOM/DSS treatment showed a similar gradient of Gr1+ CD11b+ cell number in BM, spleen and blood relative to the TFF2 sufficiency of the host (TFF2−/−>WT>TG, FIG. 11D). TFF2−/− mice developed more colonic tumors (FIG. 11A, B) and increased colonic inflammation (FIG. 11C) than WT and TG mice following AOM/DSS model of colonic tumorigenesis.

Conclusion

TFF2 suppresses tumorigenesis by inhibiting the expansion of MDSCs. This novel mechanism has implications for cancer prevention and therapy.

Example 5: TFF2 Secreted by Splenic T-Cells Dampens Inflammation and Inhibits Carcinogenesis Through Suppression of Immature CD11b+Gr1+ Myeloid Cells Trefoil factor 2 (TFF2) is a small protease resistant peptide secreted by the stomach that plays a prominent role in mucosal protection. Here, evidence that TFF2 is also produced by lymphoid T-cells and suppresses tumorigenesis associated with inflammation is provided. Transgenic mice (CD2-TFF2) overexpressing TFF2 in splenic T-cells are more resistant to DSS colitis, while TFF2-deficient mice show greater systemic and colonic inflammatory responses. Transplant of TFF2-deficient bone marrow into wild-type mice reproduces the DSS-injury susceptibility phenotype, while transplant of bone marrow from CD2-TFF2 transgenic mice reduces inflammatory responses. Following DSS treatment, TFF2-deficient mice accumulate a greater number of Gr1+CD11b+ immature myeloid cells (IMC) in the spleen and bone marrow, while CD2-TFF2 transgenic mice show minimal increases in splenic IMC. The expansion of splenic IMC in TFF2-deficient mice was associated with higher number of granulocyte-macrophage precursors and an increase in proliferating Gr-1+ myeloid cells, which was suppressed in CD2-TFF2 transgenic mice. Consistently, number of colony-forming units obtained from spleen of TFF2−/−-deficient mice has been found significantly higher while in TG mice it was much less compare with wild type counterparts. An addition of recombinant TFF2 suppressed proliferation of Gr1+CD11b+ cells in vitro experiments. Furthermore, all TFF2−/− deficient mice develop colon tumors in model AOM/DSS and show higher tumor burden compared with wild type mice and transgenic mice. Only 30% of transgenic mice develop tumors with a very low tumor burden. The number of colony-forming units in the spleen of TFF2 knockout mice was found to be much higher compared with wild-type while transgenic mice showed the lowest number of colony-forming units and granulocyte-macrophage cells as well. Taken together, these data show that TFF2 restricts expansion of Gr1+CD11b+ cells through inhibition of proliferation of myeloid progenitors/precursors. This accounts for less tumorigenesis associated with inflammation.

Introduction

Tumor growth and progression can be accompanied by expansion of myeloid-derived suppressive cells (MDSCs) that are commonly characterized as a heterogeneous population expressing surface markers Gr1 and CD11b in mice. These cells suppress host immune response through inhibition of T-cells and natural killer cells function (1). At present there are several known tumor-derived factors that regulate the function and biology of MDSC. Growth factors GM-CSF and G-CSF along with cytokine IL-6 greatly modulate suppressive functions of myeloid cells through transcription factor C/EBPβ (2-5). 1L-1b, TGF-b (6,7), IL-10, vascular endothelial growth factor (8), and prostaglandin E2 are also identified as factors promoting expansion of Gr1+CD11b+ cells.

The trefoil factor family in mammals comprises a group of three secreted proteins that all contain a highly conserved triple loop structure (the trefoil domain). In the gastrointestinal tract, trefoil factor family 1 (TFF1) is normally produced in the epithelium of gastric surface pits, while trefoil peptide 2 (TFF2) is most abundant in the stomach/duodenum, where, along with TFF1, it plays a role in the maintenance of mucus layer integrity as well as in stimulation of mucosal restitution, in part through a motogenic effect on epithelial cells (9-11). TFF3 is highly expressed in the apical part of goblet cells in the intestine and colon but not in normal gastric mucosa (9-11).

TFF2 and TFF3-deficiency does not result in obviously changed phenotype, however these mice have increased susceptibility to DSS treatment compared with wild type counterparts (12,13). In contrast, all TFF1-deficient mice developed adenoma and 30% of them showed carcinoma (14,15). From clinical research it is well known that TFF1 expression is lost in 40-60% of human gastric tumors (16). In addition, inactivation of TFF1 by deletion, missence mutation or promoter methylation results to tumor incidence in mice (17).

In contrast TFF1 the role of TFF2 as a gastric tumor suppressive gene was not so clear. However, the loss of TFF2 during progression of intestinal-type gastric cancer in human samples has been also reported (18,19). Like TFF1 the downregulation of TFF2 expression occurred likely due to aberrant promoter methylation (20,21). Importantly TFF2-deficient mice progressed more quickly to dysplasia in the setting of *H. pylori* infection or when crossed to gp130F/F mice (21,22). Considering direct link between cancer and inflammation and the anti-inflammatory nature of TFF2 there is a potential role of TFF2 as a gastric tumor suppressive gene however, there is still no direct experimental proof of the anti-tumor effect of TFF2.

The anti-inflammatory effect of TFF2 has been proven in numerous studies on experimental rodent models with induced colitis although the mechanism is not clearly understood. In contrast to the rat where TFF2 expression is observed in colon tissue, in mice neither TFF2 peptide nor mRNA is produced in the large intestine, even under inflammatory conditions (23). Nevertheless, administration of recombinant TFF2 ameliorates the severity of experimental colitis induced with bowel irritants such as dextran sodium sulfate (DSS), ethanol or indomethacin in rodents (24-28). Additionally, TFF2-deficient mice have more severe DSS-induced colitis (and delayed recovery) in comparison with wild type animals (13). Analysis of the distribution of endogenous trefoil peptides along the various compartments of the gastrointestinal tract revealed that TFF2 peptide is detectable in normal human luminal contents from the distal and proximal part of the gut. This finding suggests an effective transit and remarkable stability of gastric TFF2 peptide along the whole gastrointestinal tract (29,30). Presumably, gastric TFF2 may exert its protective effect in mouse colitis model in part due to a potentiation of mucin barrier function (31). Indeed, radiolabeled TFF2 injected intravenously in rats is specifically taken up by TFF2-producing cells and then transferred to the mucus where TFF2 presumably mediates its protective function (10,32, 33).

However, expression of trefoil factors is not restricted solely to gastrointestinal epithelial cells. It has been shown TFF2 mRNA expression at much lower levels in primary and secondary lymphatic organs thymus and spleen, where their expression increased upon LPS treatment (13,34). Since then it has been suggested that trefoil factors are intimately involved in the regulation of immune responses. Indeed, TFF2 exhibits chemotactic activity for human monocytes (34), inhibits LPS-induced nitric oxide production by a monocyte cell line in vitro (35), inhibits myeloperoxidase activity in a model of DSS-induced colitis (25,28), and decreases leukocyte recruitment by reducing the expression of vascular adhesion component-1 (VACM-1) (24). Furthermore, TFF2 deficiency results in the upregulation of expression of several genes that have been implicated in immune regulation, including MHCI, MHCII, cryptdin family members, etc. (36). In addition, splenic T cells from TFF2-deficient mice were found to be hyper-responsive to IL-1β stimulation, suggesting a specific role in negative regulation of IL-1β receptor—mediated signaling (13). Finally, it was recently demonstrated that TFF2 was able to dampen SDF-1 induced signaling in vitro and in vivo studies through CXCR4 receptor (37,38). Indeed, in transgenic mice overexpression of SDF-1 in gastric mucosa increased gastric epithelial proliferation and hyperplasia, however TFF2-deficient mice crossed with transgenic SDF-1 mice developed markedly more severe inflammation, hyperplasia and metaplasia conforming that TFF2 as a partial antagonist of SDF-1 in vivo. Very recently it has been shown that TFF2 through CXCR4 receptor induces IL-33 release from lung epithelial, dendritic cells and macrophages resulting in the development of type 2 immune response in asthma (39).

Nevertheless, data on effect of trefoil factors on function of primary immune cells are still limited, and most of them are derived primarily from in vitro experiments that do not reproduce the inflammatory microenvironment in vivo (13, 40). Moreover, it is possible that trefoil factors modulate function of target cells indirectly by affecting other cell populations or through the interaction with partner(s). Included in this example, the function of secreted TFF2 in the immune compartment through the generation of a transgenic mouse bearing an expression cassette consisting of mTFF2 open reading frame inserted under the control of human CD2 gene promoter that targets T-cell specific transgene expression (41) is explored. CD2-TFF2 transgenic mice and TFF2−/− deficient mice were used as experimental models to investigate the role of TFF2 in colonic inflammation and colitis-associated cancerogenesis (tumorigenesis associated with inflammation). Analysis of the CD2-TFF2 transgenic mice, along with the TFF2−/− mice, points to a critical role of TFF2 in the generation of myeloid-derived suppressor cells (MDSC) during inflammatory and carcinogenic stimuli. Without being bound by theory there is strong evidence that myeloid Gr+CD11b+ cells are the mediators/targets of TFF2 anti-inflammatory function in vivo.

Materials and Methods

Mice

Wild type C57/BL6 mice (7-12 weeks) were purchased from Jackson Laboratories (Bar Harbor, Me.), TFF2-deficient mice (TFF2−/−) on C57/BL6 background were described earlier, CD2-TFF2 mice (TG) were generated in current study. Mice were group housed under a controlled temperature (25° C.) and photoperiod (12:12-h light-dark cycle). To discriminate the role of TFF2 expressed by epithelial and immune cells bone marrow transplantation were performed using TFF2−/− deficient, WT and CD2-TFF2 transgenic mice as recipients or donors of bone marrow (hematopoietic) cells in various combinations.

Cloning mTFF2 into hCD2 Cassette, Generation of CD2-TFF2 Transgenic Mice and Screening for CD2-TFF2 Transgene.

Mouse gene TFF2 was cloned downstream into hCD2 promoter into EcoRI site of expressing vector. For this purpose the site for EcoRI was incorporated in primers for PCR amplification of mouse TFF2 sequence using respective mouse cDNA library (Open Biosystem).

The forward primer was ATTGAATTC GCC ACC ATG CGA CCT CGA GAT GCC (SEQ ID NO: 7) (Tm=60.6C). The reverse primer was AATTGAATTC TCA GTA GTG ACA ATC TTC CACAGA C (SEQ ID NO: 8) (Tm=56.2C) Site for EcoRI is shown in bold. PCR amplification produced 406 bp fragment of intact mTFF2. After cloning the resulting construct was transfected into *E. coli* Stbl2 competent cells. Clones were verified for presence and proper orientation of TFF2 gene by sequencing using forward primer located in CD2 and reverse primer located within TFF2 sequence (see below).

Transgenic mouse lines expressing the TFF2 protein were generated in Transgenic Core Facility of Columbia University as follows. The DNA of pCD2-TFF2 was digested by SalI/NotI to remove vector sequence and the fragment with CD2 cassette was purified by gel electrophoresis. The fragment was microinjected into pronuclei of fertilized mouse eggs and the injected embryos were implanted into pseudo-pregnant outbred females.

The offspring were screened for transgene integration by PCR analysis of tail DNA using primers selected for promoter part of CD2 gene and TFF2 gene. Forward primer was 5'-TAAGCTCTCGGGGTGTGGACTC-3' (SEQ ID NO: 9), Reverse primer was: GAAGTGGGTGGAAACACCAAGG (SEQ ID NO: 10). The correct size of amplified fragment was 472 bp. PCR amplification was performed for 30 cycles using following conditions: denaturation for 20 sec at 94° C., annealing at 65° C. for 20 sec, and elongation at 72° C. for 40 sec, followed by a final 7 min extension at 72° C.

Four founder mice were produced. These mice were bred with C57BL/6 mice. The offspring of the founders were tested for presence of transgenic CD2-TFF2 mRNA transcript expression in spleen and thymus as follows. Total RNA was isolated from whole spleen and thymus, using a Trizol reagent (Invitrogen-Life Technologies, Inc.) and RNAeasy® Mini Kit. Five micrograms of total RNA were reverse transcribed to cDNA with Superscript III reverse transcriptase (Invitrogen, Carlsbad USA). PCR amplification was performed by using primers specific for TFF2 sequence and for CD2 promoter part. Forward primer: 5'-TCTCCAAAGAATTCGCCACCAT-3' (SEQ ID NO: 11), reverse primer: 5'-GGTTGGAAAAGCAGCAGTTTCG-3' (SEQ ID NO: 12), the predicted fragment size 351 bp. PCR amplification was performed for 30 cycles using the following conditions: denaturation for 20 sec at 94° C., annealing at 56° C. for 30 sec, and elongation at 72° C. for 30 sec, followed by a final 7 min at 72° C. Two transgenic lines were maintained by back-crossing with C57BL/6 for at least 10 times before using in experiments.

Isolation of Splenic T- and B-Cells

Splenocytic T- and B-cells were isolated from resting splenocytes by negative selection using immunomagnetic separation kit (Myltenyi Biotech, Inc.). To confirm the validity of the separation procedure the RNA was extracted from T- and B-cell population and subjected to PCR analysis of cell-specific markers Thy 1.2 (marker for T-cells) and CD19 (marker for B-cells) in respective populations.

Semi-Quantitative RT-PCR Analysis

A semi-quantitative reverse transcriptase-polymerase chain reaction (RT-PCR) method was used to measure the relative abundance of TFF2 mRNA transcripts in resting total splenocytes and splenic B- and T-cells. RNA was isolated from whole spleen, and separated splenic B-cells and T-cells, using a Trizol reagent (Invitrogen-Life Technologies, Inc.) and RNeasy® Mini Kit (Qiagen). 5 μg of total RNA was reverse transcribed to cDNA with Superscript III reverse transcriptase (Invitrogen, Carlsbad USA).

PCR amplification was performed using the AB Applied Biosystem device, and amplified PCR products were analyzed in 1.5% agarose gel. All primer pairs, PCR conditions, and predicted sizes of amplified products are listed below. Thy 1.2 antigen forward primer: 5'-GCTGGACTGCCGCCATGAGAA-3' (SEQ ID NO: 13) Thy 1.2 antigen reverse primer: 5'-TGCCGC CACACTTGACCAGC-3' (SEQ ID NO: 14), fragment size 295 bp. PCR amplification was performed for 30 cycles using the following conditions: denaturation for 20 s at 94° C., annealing at 68° C. for 5 s, and elongation at 72° C. for 5 s, followed by a final 7 min at 72° C. CD19 forward primer: 5'-TGCTCAGCGTTGGGCTGCTG-3' (SEQ ID NO: 15). CD19 reverse primer: 5'-TGGGACCCAAGCGAGGATGC-3' (SEQ ID NO: 16), fragment size 390 bp. PCR amplification was performed for 30 cycles using the following conditions: denaturation/annealing for 30 s at 94° C., and elongation at 68° C. for 25 s, followed by a final 7 min at 72° C.

Mouse β-actin sense oligonucleotide: 5'-ACCACACCTTCTACAATGAGCTGC-3' (SEQ ID NO:17). Mouse β-actin anti-sense oligonucleotide: 5'-CTTCTCTTTGATGTCACGCACG-3' (SEQ ID NO: 18), fragment size 386 bp. PCR amplification was performed for 25 cycles using the following conditions: denaturation for 20 s at 94° C., annealing at 55° C. for 30 s, and elongation at 72° C. for 30 s, followed by a final 7 min at 72° C. RNA was purified using Trizol® Reagent (Invitrogen, Scotland, UK) and RNeasy® Mini Kit. Total RNA was reverse transcribed with Superscript III reverse transcriptase (Invitrogen, Carlsbad USA). PCR amplification was performed for 25 cycles using the following conditions: denaturation for 20 s at 94° C., annealing at 55° C. for 30 s, and elongation at 72° C. for 30 s, followed by a final 7 min at 72° C. For calculation of fold augmentation RNA amounts were normalized to β-actin mRNA.

Western Blot Analysis of TFF2 Protein Level

Thymus (spleen) were homogenized in the loading buffer with β-mercaptoethanol and then boiled for 5 min. Proteins were resolved in 18% tris-glycine (or 10-20% Tris-Tricine) SDS-polyacrylamide gel and electrophoretically transferred for 1 hour at 100V onto 0.2 μm-pore-size PVDF membrane (Immobilon-P$^{sq}$, Millipore). The filter was blocked 5% non-fat milk in 0.05% Tween 20/PBS (PBS-T) for 1 hour and incubated night with primary rabbit antibodies (1 μg/ml) raised to C-end of TFF2 (Tu et al., 2007) at 4° C. overnight. After washing in PBS-T the incubation was performed with secondary antibodies conjugated with horseradish peroxidase (GE Healthcare, dilution 1:20000) for 25 min at room temperature and after final washing the membrane was developed with SuperSignal West Femto Maximum Sensitivity Substrate Kit (Pierce ECL).

Quantitative Real-Time PCR for Cytokines.

Total RNA was isolated from tissues using Trizol reagent (GIBCO BRL) according to the manufacturer's guidelines. Total RNA was purified using the RNeasy kit (QIAGEN). After DNase I (Invitrogen) treatment, 2 μg of total RNA was used for reverse transcription reaction (Applied Biosystems). The specific primers for target genes were selected in different exons to avoid/minimize amplification of genomic DNA by using program Primer 3 (fokker.wi.mit.edu). Quantitative real-time PCR was performed on an AB 7300 System (Applied Biosystems, Warrington, U.K.) using SYBR GREEN PCR Master Mix (Applied Biosystems). Amplification conditions were: 50° C. (2 min), 95° C. (15 min), 45 cycles of 95° C. (15 s), and 55° C. (15 s). The expression of each mRNA was normalized to housekeeping gene GAPDH mRNA expression, and subsequently expressed as the fold change relative to non-inflamed controls.

Induction of Colitis

In the experiments involving DSS-induced colitis, 10 to 12-weeks old sex-matched KO, TG and WT mice were used unless specified otherwise. As a control KO, TG and WT mice received only ordinary water without DSS. For induction of chronic colitis, KO, TG and WT mice were given 2.5% DSS (m/w 36 000-50 000; MP Biomedicals, Solon, Ohio, USA) dissolved in drinking water provided ad libitum for 5 days, followed by provision of plain water for 19 days. Mice were daily weighed, and blood in the stool was analyzed at days 3, 5, 7, 9, 11, 13 and 15 using Hemoccult strips (4-5 mice per each group). For stool consistency, a score of 0 points was assigned for well-formed pellets, 2 points for pasty and semiformed stools that did not adhere to the anus, and 4 points for liquid stools that did adhere to the anus. For bleeding, a score of 0 points was assigned for no blood, 2 points for positive hemoccult, and 4 points for gross bleeding. These scores were added together and divided by three, resulting in a total clinical score ranging from 0 (healthy) to 4 (maximal activity of colitis).

For acute colitis induction mice received 2.5% DSS for 5 days and sacrificed at 6 day. In another set of experiments mice received 4% DSS for 7 days followed by plain water for 12 days and were sacrificed at 19 day.

Bone Marrow Transplantation

Bone marrow harvested from the femur and tibia was depleted of erythrocytes by using red blood cell lysis buffer (Sigma, R7757) according to manufacturer's instructions. Mice were lethally irradiated with 9Gy and after 3 h were reconstituted with bone marrow cells ($3.5\times10^{6}$) by using tail injection. For bone marrow chimaeras, where wild-type and SPKO mice were reconstituted with transgenic and wild type bone marrow respectively the presence of mRNA and CD2-TFF2 transcripts was analyzed by qRT-PCR to determine a degree of chimerism. Irradiatiated control mice which did not received transferred bone marrow cells, served as an irradiation control in each experiment. Transplanted mice were allowed to rest 7-8 weeks for full engraftment before DSS water was administrated for 5 days followed plain water. Mice were sacrificed on day 6 and 19 after starting DSS administration and analyzed for progression of colitis (macroscopical and histological colon examination, MPO activity, cytokines level, spleen mass, analysis of splenic cell population)

Assessment of Colitis

Progression of colitis was evaluated by disease activity index (DAI) derived by scoring body weight change (0-4), stool consistency (0-4), and by the presence or absence of fecal blood (0-3) (Xu Y, Hunt N H, Bao S, 2008). These scores were added together and divided by three, resulting in a total clinical score ranging from 0 (healthy) to 4 (maximal activity of colitis). Mice were daily weighed and change in body weight was calculated by the percentage change (gain/loss) from the initial weight (0, less than 5% change; 1, 5-10%; 2, 10-20%; 4, more than 20%). For stool consistency, a score of 0 points was assigned for well-formed pellets, 2 points for pasty and semi formed stools that did not adhere to the anus, and 4 points for liquid stools that did adhere to the anus (Blood in the stool was analyzed both visually and by Hemoccult strip as described previously (Kourt-Jones et al., 2007). Scoring for blood in stool was as follows: 0, none; 1, trace using Hemoccult strips; 2, strong positive using Hemoccult strips; 3, gross hemorrhage.

Colonic inflammation was also evaluated macroscopically by measuring the longitudinal length of the colon from the ileocecal junction to the anal verge.

Histological Scoring

The entire colon was removed from the cecum to the anus, and the colon length was measured as marker of inflammation. For histological examination a 2-cm segment of the distal colon was fixed in 10% formalin overnight then in 70% ethanol for paraffin embedding and sectioning. Slides were stained with Harris hematoxylin-eosin (H&E). Histological scoring was performed in a blinded fashion by a pathologist, with a combined score for inflammatory cell infiltration (score, 0-3) and tissue damage (score, 0-3). The presence of occasional inflammatory cells in the lamina propria was assigned a value of 0; increased numbers of inflammatory cells in the lamina propria as 1; confluence of inflammatory cells, extending into the submucosa, as 2; and transmural extension of the infiltrate as 3. For tissue damage, no mucosal damage was scored as 0; discrete lymphoepithelial lesions were scored as 1; surface mucosal erosion or focal ulceration was scored as 2; and extensive mucosal damage and extension into deeper structures of the bowel wall were scored as 3. The combined histological score ranged from 0 (no changes) to 6 (extensive cell infiltration and tissue damage).

The histology damage score was calculated on a 12-point scale: loss of architecture, 0-3; inflammatory infiltrate, 0-3; goblet cell depletion, 0 or 1; ulceration, 0 or 1; edema, 0 or 1; muscle thickening, 0-2; and presence of crypt abscesses, 0 or 1.

Myeloperoxidase Activity (MPO)

Myeloperoxidase activity in colon tissues was determined as described. Briefly, the colon tissue was rinsed and homogenized in 50 mM potassium-phosphate buffer (pH 6.0) containing 0.5% hexadecyltrimethyl ammonium bromide (HTAB) (Sigma-Aldrich, St. Louis, Mo.). The homogenate centrifuged at 14000×g for 15 min and supernatant was used for measurement of MPO activity normalized on protein concentration. Supernatant was added to 1 mg/ml o-dianisidine hydrochloride (Sigma-Aldrich, ST. Louis, Mo.) and 0.0005% hydrogen peroxide, and the change in absorbance at 460 nm was measured. One unit of MPO activity was defined as the amount that degraded 1 mmol peroxide at 37° C. per minute and expressed in units per milligram protein.

Cytokine ELISA

Colonic tissues (50-100 mg) were homogenized in 1 ml of RIPA buffer containing inhibitors of proteases (Roche), samples were centrifuged at 14000×g for 15 min and supernatant were used for determination of protein concentration by using Bio-Rad DC Protein Assay kit. The concentrations of IL-6, TNF-α, IFN-γ, and IL-1 beta in colon tissue were measured by ELISA using commercial BD OptEIA Set kits (BD Biosciences, Sydney, Australia) and normalized to the concentration of total sample protein. TFF2 expression by T-cells.

Splenocytes from wild type and transgenic mice were depleted from erythrocytes and stimulated with PMA (50 ng/ml) and ionomycin (0.5 μM) for 4 h. Brefeldin (1 μl/ml) was added to prevent TFF2 secretion. Cells were stained for CD3, CD4 and CD8 antigens 30 min on ice, washed twice with cold PBS buffer, fixed and permeabilized with Cytofix/Cytosperm solution (20 min on ice). Then cells were washed twice in Perm/Wash solution and stained (30 min 4° C.) with raised to C-end of TFF2 affinity-purified antibody labeled with Alexa Fluor 488. Rabbit antibodies isolated from preimmune serum and labeled with Alexa Flour 488 were used in parallel as isotypic control. Cells were washed twice in PBS with 2% FBS and analyzed for TFF2 expression in CD4+ and CD8+ cells gated on CD3+ population.

Flow Cytometry Acquisition and Analysis.

Samples were analyzed on LSRII flow cytometer by using software. Typically list mode for 20,000 events for Gr1+ CD11b+ cells in a live-gated mode were acquired. Statistical analysis was done by using isotype matching controls as a reference. Less than 1% positive cells were allowed beyond statistical marker in the appropriate control. The data files were analyzed using FloJo 5.5.5 software.

Cell Sorting.

Gr1+CD11b+ cells were labeled with PerCP5.5 conjugated Gr1 and APS conjugated CD11b+ antibodies and sorted using sorter FASCAria. The purity of sorted cells were more than 95% were used for experiments.

In Vivo Bromodeoxyuridine Labeling

Mice were given 3% DSS water or tap water (control group) for 5 days, and then mice were switched on tap water during next 2 weeks. Mice were injected with BrdU intraperitonally (1 mg per 20 g/body weight) 24, 48 96 h prior to sacrifice them. Splenic cells were stained for CD11b+, Gr1+ and intracellular BrdU according to manufacturer's instructions. Gr1+CD11b+ cells proliferation in vitro assay. Gr1+ CD11b+ cells proliferation was determined by using BrdU Cell Proliferation Assay Kit (Calbiochem). Splenocytes were obtained from spleen TFF2−/− mice treated with DSS on day 19 and Gr1+CD11b+ cells were allowed to bind with antibodies for Gr1 antigen and CD11 b marker labeled with PerCP Cy and APC accordingly and sorted by using sorter FACSAria. Sorted cells were cultured 7 days in complete RPMI 1640 medium (Invitrogen) supplemented with 10% FCS (HyClone), 50 μM β-mercaptoethanol, 1 mM penicillin-streptomycin, GM-CSF in concentrations 5 and 10 ng/ml. Recombinant mouse TFF2 was added in concentration as indicated. Cell proliferation was determined by addition of BrdU during the final 22 h of culture accordingly protocol of manufacture (Calbiochem).

Cell Growth Study.

Sorted Gr1+CD11b+ cells were grown at 37° C. in humidified 95% air and 5% CO2 in RPMI-1640 medium supplemented with 10% heat-inactivated fetal calf serum (HyClone), 2 mM glutamine, 100 U/ml penicillin, 100 μg streptomycin and GM-CSF at concentration 5 or 10 ng/ml. Recombinant TFF2 was added at concentrations as indicated. Cell number was determined by Trypan blue exclusion.

Assessment of Apoptosis

Apoptotic cells were quantified by using annexin V-PE apoptosis detection kit (BD Pharmigen) accordingly company's protocol. Sorted Gr1+CD11b+ cells were grown with 5 ng/ml GM-CSF for 7 days. TFF2 was added at concentrations as indicated at the beginning of experiment.

Tumor Models.

In the AOM/DSS murine model tumorigenesis was induced as described previously with minor modifications (42). Mice (TFF2−/−, WT and TG, age 7-8 weeks) were intraperitonally injected with AOM (10 mg/kg body weight) and maintained on regular water for 7 days. Animals were then given 3% DSS water for 7 days. Control groups were injected with AOM followed only regular water.

For skin tumor model mice were subjected two-step cancerogenesis by using 9,10-dimethylbenz(a)antracene/12-O-tetradecanoylphorbol-13-acetate (DMBA/TPA) treatment ( ). Mice 7-9 week were shaved 2 days prior of initiation of tumorigenesis by single topical application with DMBA (100 μg/200 μl in acetone) to the shaved dorsal skin. One week after initiation mice were treated with topical application of TPA (2 μg/200 μl in acetone) 2 times a week until termination of experiment. Tumors were counted and measured with a caliper once a week. The number of tumors per mouse with the diameter more then 1 mm were counted and data were expressed as tumor burden (the number of tumors per mouse) and tumor incidence (the percentage of mice with tumors).

A, tumor multiplicity (average number of tumors per mouse±SE) and (B) incidence (percentage of mice with tumors) in wild-type (○) and K5.RasGRP1 transgenic (•) mice treated with TPA following initiation with DMBA. C, wild-type (Wt) and K5.RasGRP1 transgenic (Tg) mice bearing tumors. Pictures were taken at the end of the protocol. D, tumor size (diameter in millimeters) at 17 and 28 wk after initiation with DMBA in both wild-type (Wt) and K5.RasGRP1 transgenic (Tg) mice. Values represent the mean±SE of all the tumors in each group (n). *, $P<0.05$; ***,$P<0.0001$ (Student's t test).

Statistical Analysis

Standard errors and significance by Student's two-tailed t-test were calculated by using Microsoft Excel software.

Results

TFF2 Protein is Expressed in the Splenic T Cells and Induced by T Cell Activation.

TFF2 mRNA expression in the murine spleen and thymus has previously been demonstrated (13,34,36). In rat lymphoid organs the peptide TFF2 was detected by radioimmunological assay due to its very low level and it is has been shown that TFF2 is up-regulated several fold upon LPS treatment. However, the source of cells secreting TFF2 was not identified. Consequently, western blot analysis of extracts from spleen of wild type mice was performed, using the previously developed and characterized rabbit polyclonal antibody to the C-terminal peptide of mouse TFF2 (43). Immunoprecipitation of mouse splenic extracts using the affinity-purified rabbit IgG identified TFF2 protein in the spleen as a band that migrates with the same motility as native gastric mouse TFF2 (FIG. 1A). As a negative control, splenic proteins immunoprecipitated by pre-immune rabbit IgG were used. TFF2 peptide was also detected in spleen extracts by western blot using a sensitive methodology (SuperSignal West Femto Trial Kit). TFF2 peptide could be detected in the spleen but not the thymus (FIG. 1B); gastric tissues from wild type and TFF2 knock out mouse were used as positive and negative controls, respectively (FIG. 1B).

To discriminate which major splenic immune cell subset expressed TFF2, resting splenic cells were fractionated into isolated B and T-cell subsets, and these subsets were analyzed for TFF2 mRNA by semi-quantitative RT-PCR analysis. A robust band of amplified TFF2 mRNA was detected in resting splenic T cells (FIG. 1C, lane T), while a minimal signal at best could be detected in the B cell subset (FIG. 1C, lane B). An increase in circulating trefoil proteins was observed in earlier studies in rats challenged with lipopolysaccharides (LPS) (34). To evaluate the possibility of TFF2 regulation in splenic cells by immune activation, murine splenocytes were stimulated with T- and B-cell specific mitogens, concavalin A (Con A) and LPS, respectively. Total mRNA was isolated from stimulated splenocytes, and the level of TFF2 mRNA was analyzed by quantitative real-time PCR. A significant increase in TFF2 mRNA abundance was observed with both treatments (FIG. 1D), with a 2.5-fold increase with LPS and a 40-fold increase with Con A stimulation. Since the increase in TFF2 mRNA expression appeared to be much greater after treatment with the T-cell mitogen, the effect of specific activation of T cells was examined using anti-CD3 antibodies. Treatment with the anti-CD3ε antibody resulted in a 2.6-2.8-fold increase in TFF2 mRNA. Thus, the upregulation of TFF2 expression with the setting of specific T cell stimulation suggests a possible role for TFF2 in T cell function or homeostasis in mice.

It has been long known that trefoil peptides can be overexpressed in the site of ulceration or mucosal damage (44-47). TFF2 mRNA/protein production can be induced in gastric mucosa as rapidly as 1-4 h following injury (10,48). Therefore TFF2 protein/mRNA expression was analyzed in the spleen tissues of wild type and transgenic mice during administration of 3% DSS water (FIGS. 1E, 1F, 1G). A noticeable increase of TFF2 protein was found after 24 h in spleen of both types of mice in response of DSS treatment (FIGS. 1E, 1G), as well as an increase the mRNA TFF2 level (FIG. 1F). The TFF2 mRNA level was also analyzed in sorted T-cells from spleen of mice receiving 3% DSS water.

Transgenic Mice Overexpressing TFF2 in T-Cells Show Attenuated DSS Colitis.

Figures 2A, 2B, 2C:
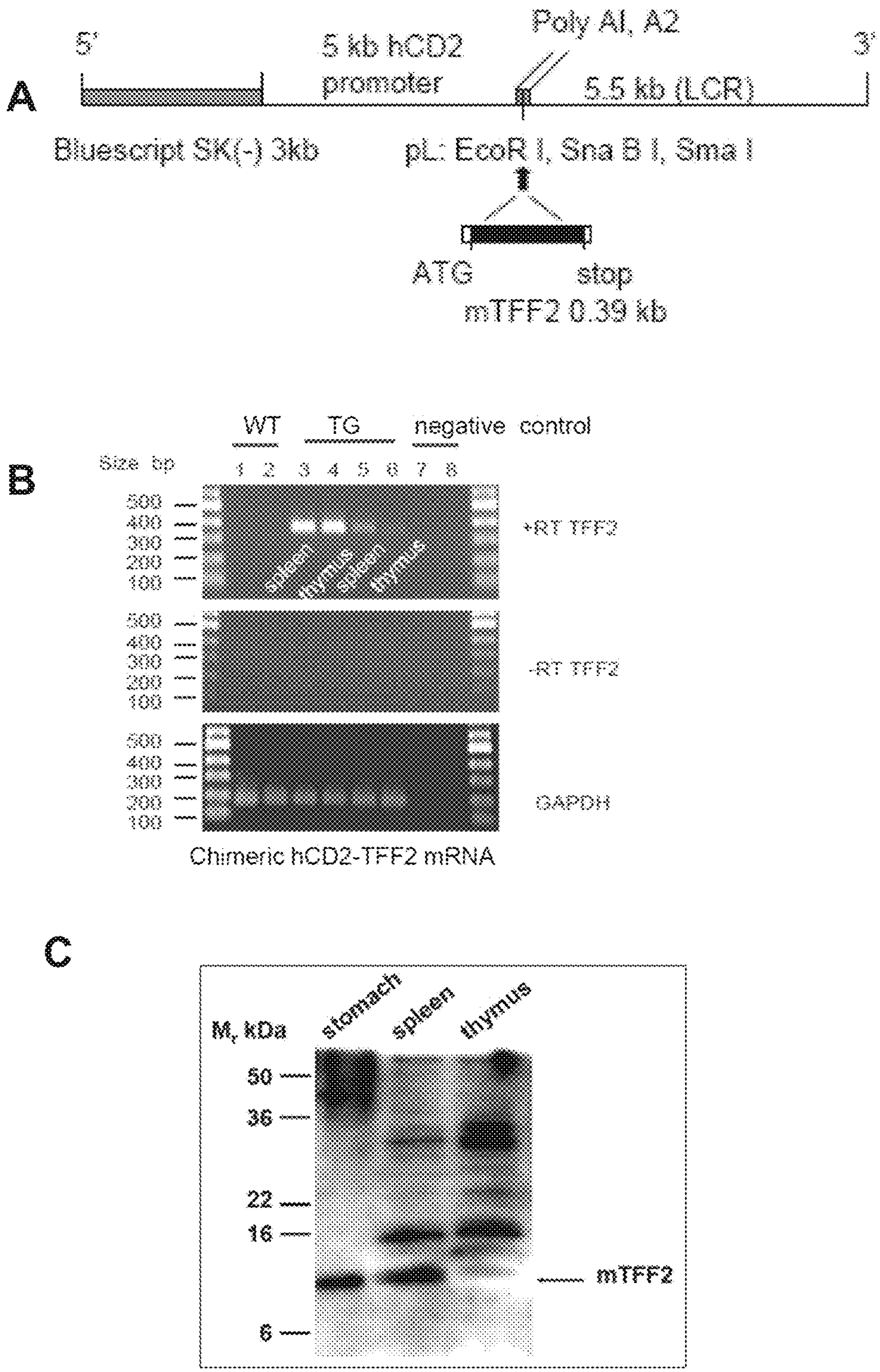
FIGS. 2A-B. Generation and characterization of transgenic CD2-TFF2 mice.
FIG. 2C is a western blot showing expression of TFF2 peptide in spleen and thymus of unchallenged CD2-TFF2 transgenic mice. Cell extracts from whole spleen and thymus were immunoblotted with anti-TFF2 antibodies, stomach extract from wild type mice was used as a positive control.

To further investigate the role of TFF2 specifically in the immune compartment in vivo, transgenic mice were created with the enforced expression of trefoil peptide in T cells. An expression construct in which expression of the murine TFF2 gene (cDNA/ORF) was governed by the human CD2 promoter/enhancer (FIG. 2A) was generated. The latter has previously been shown to drive a T cell-specific transgene expression in the thymus and spleen (49,50). The CD2-TFF2 construct was used to produce 4 transgenic founders lines, identified by PCR-based screen of tail genomic DNA. All four lines showed germline transmission and F1 offspring were tested for CD2/TFF2 mRNA expression in the spleen and thymus. Hybrid CD2-TFF2 transcripts (as amplified RT-PCR products of 351 bp) were detected in both spleen and thymus of tested pups (FIG. 2B). TFF2 protein overexpression was also detected in the spleen and thymus of transgenic mice (FIG. 2C).

Figures 3F, 3G:
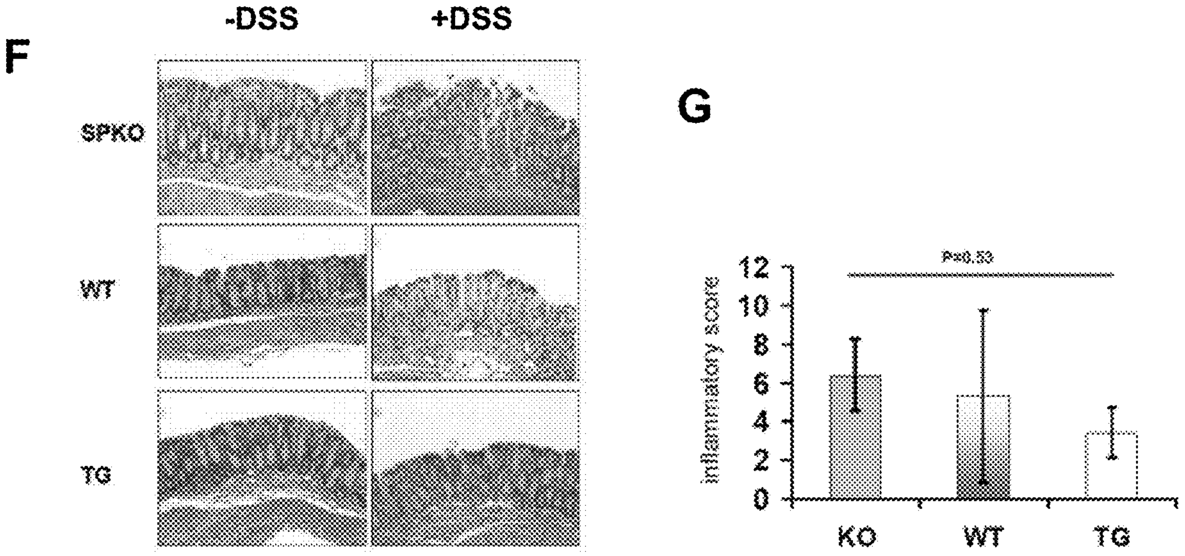
FIGS. 3F-G. TFF2-deficiency results in more severe inflammation upon DSS challenge.

Previously it has been shown that TFF2 knockout mice exhibited an increased susceptibility to DSS colitis (13). Consequently, the susceptibility of CD2-TFF transgenic (TG) mice to DSS colitis was examined and compared to both WT and TFF2−/− mice. DSS (3%) was given continuously in the drinking water and mortality was used as the primary endpoint. TFF2−/− mice as expected showed a higher mortality rate compared to WT and TG mice; however, the CD2-TFF transgenic (TG) mice, overexpressing TFF2 only in their thymus and spleen, were more resistant than wild type mice to DSS treatment (FIG. 3A). In order to examine inflammatory immune response at earlier time points, the same 3 groups of mice (WT, TFF2−/−, TG) mice were given 2.5% DSS for 5 days and observed up to day 19. Again, TFF2−/−mice showed a more severe response, with a marked reduction in colonic length and enlarged spleen mass by day 19 compared to the two other groups (FIGS. 3B, C, D, E). There were no statistically significant differences between the TG and WT mice; however, the DSS-treated TG spleen remain equivalent to that in untreated mice, while the spleen of DSS-treated wild type mice was statistically larger than that of untreated wild type mice (FIG. 3E). Histological examination of the colon at day 19 revealed inflammation, crypt atrophy, and erosions in all groups of mice, with a trend toward less inflammation in the TG mice compared to TFF2−/− but the differences were not statistically significant in this acute colitis model (FIG. 3F, G).

Figures 4A, 4B, 4C, 4D, 4E:
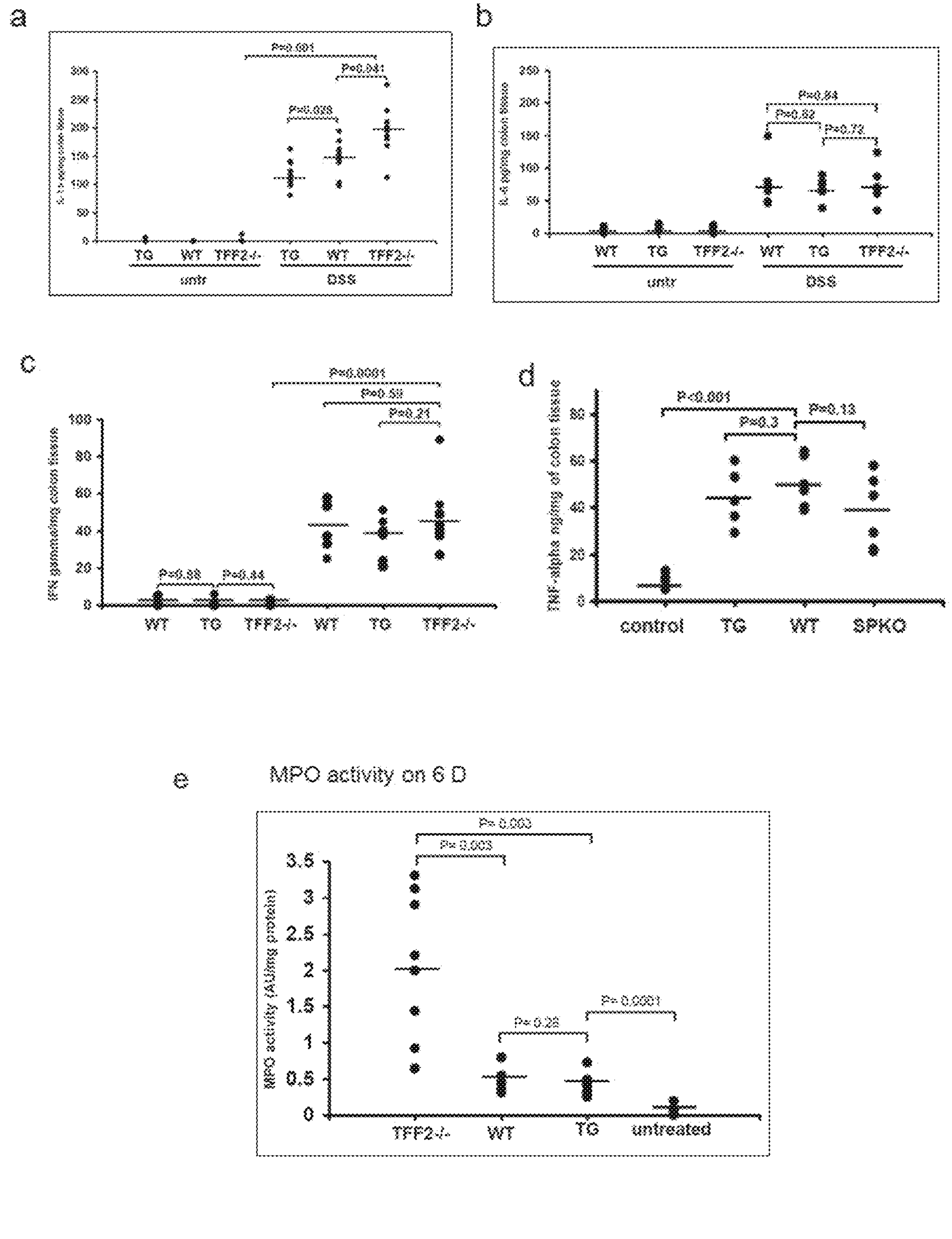
FIGS. 4A-D. Immune response in transgenic, wild type and TFF2−/− mice. Colitis was induced by addition of 2.5% DSS to drinking water for 5 days, mice were sacrificed on day 19; colonic tissues were used for analysis of cytokines IL-1beta, TNF alpha, IFN-gamma and IL-6 by ELISA. Cytokines levels of IL-1beta (FIG. 4A), IL-6 (FIG. 4B), IFN-gamma (FIG. 4C) and TNF alpha (FIG. 4D) normalized to protein content of colonic tissues. Data represent results of 2-3 independent experiments with 5-8 mice per group.
FIG. 4E is a plot showing that TFF2-deficient mice display higher level of myeloperoxidase (MPO) activity at acute phase of colitis (day 6).
Figures 13A, 13B, 13C, 13D:
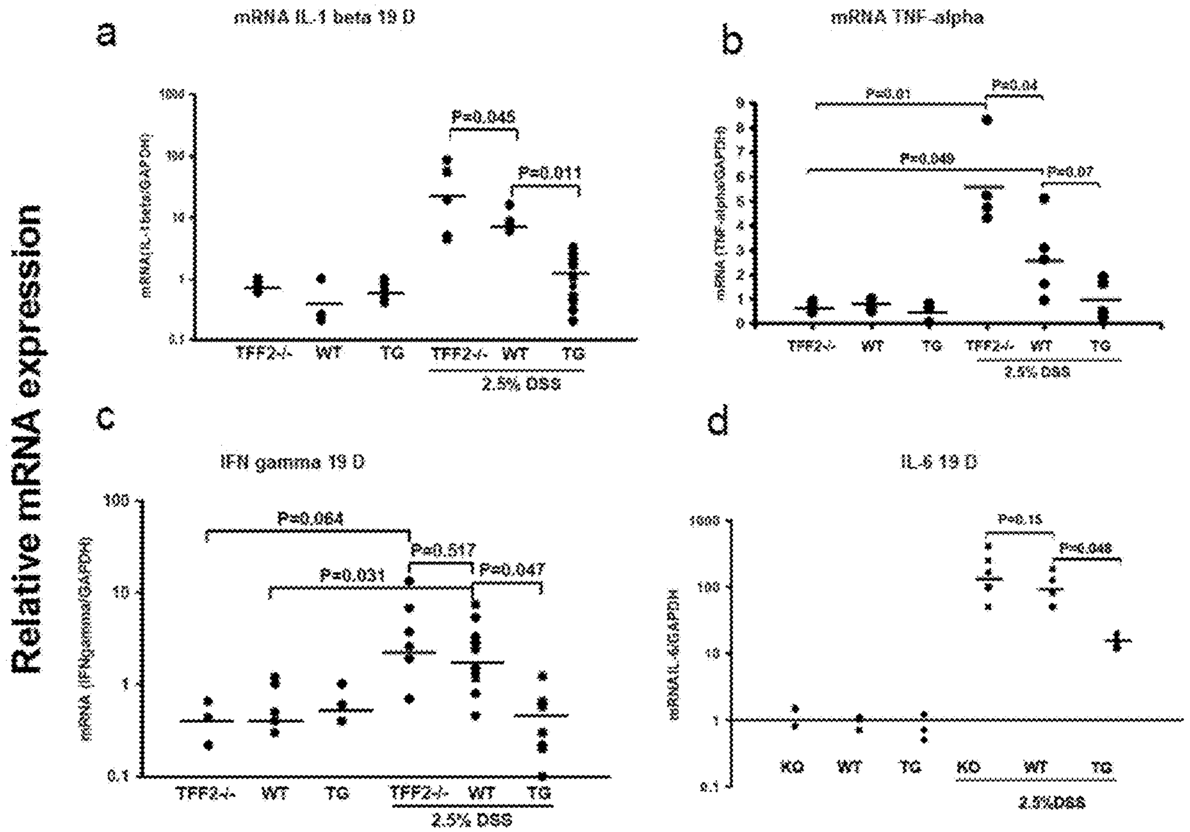
FIGS. 13A-D. Relative mRNA expression of IL-1beta (FIG. 13A), TNF-alpha (FIG. 13B), IFN-gamma (FIG. 13C) and IL-6 (FIG. 13D) in colon tissues. Colitis was induced by addition of 2.5% DSS to drinking water for 5 days, mice were sacrificed on day 19; colonic tissues were used for analysis of mRNA cytokines IL-1beta, TNF alpha, IFN-gamma and IL-6. Data represent results of 2-3 independent experiments with 5-8 mice per group.

Changes in cytokine expression in the three groups of mice were analyzed after a single cycle of DSS for 5 days. In WT C57BL/6 mice, this results in a progressive chronic colitis characterized by increased levels of inflammatory cytokines IL-1β, IL-6, INF-γ and TNF-α in colonic tissues over the time (51-53). In accordance with published data, significant upregulation of mRNA for IL-1β, IL-6, TNF-α and INF-γ in were detected in WT and TFF2−/− mice compared with untreated wild type mice (FIGS. 13A, B, C, D). In contrast, in CD2-TFF2 (TG) mice a statistically lower level of mRNA transcripts for IL-1β, IL-6, TNF-α and INF-γ, and a lower IL-1β protein level, were observed compared with both wild type and KO mice. TFF2−/− mice also had a statistically significant increase in MPO activity compare with WT and TG mice (FIG. 4E). Interestingly, TFF2−/− mice with the highest IL-1β mRNA level had the highest MPO activity, while mice with the lowest MPO activity also showed the lowest IL-1β mRNA level. Since IL-1β expression and MPO activity are typically associated with myeloid cells, it is possible that the absence of TFF2 in TFF2-deficient mice leads to enhanced mobilization and recruitment innate immune myeloid cells.

Figure 14A:
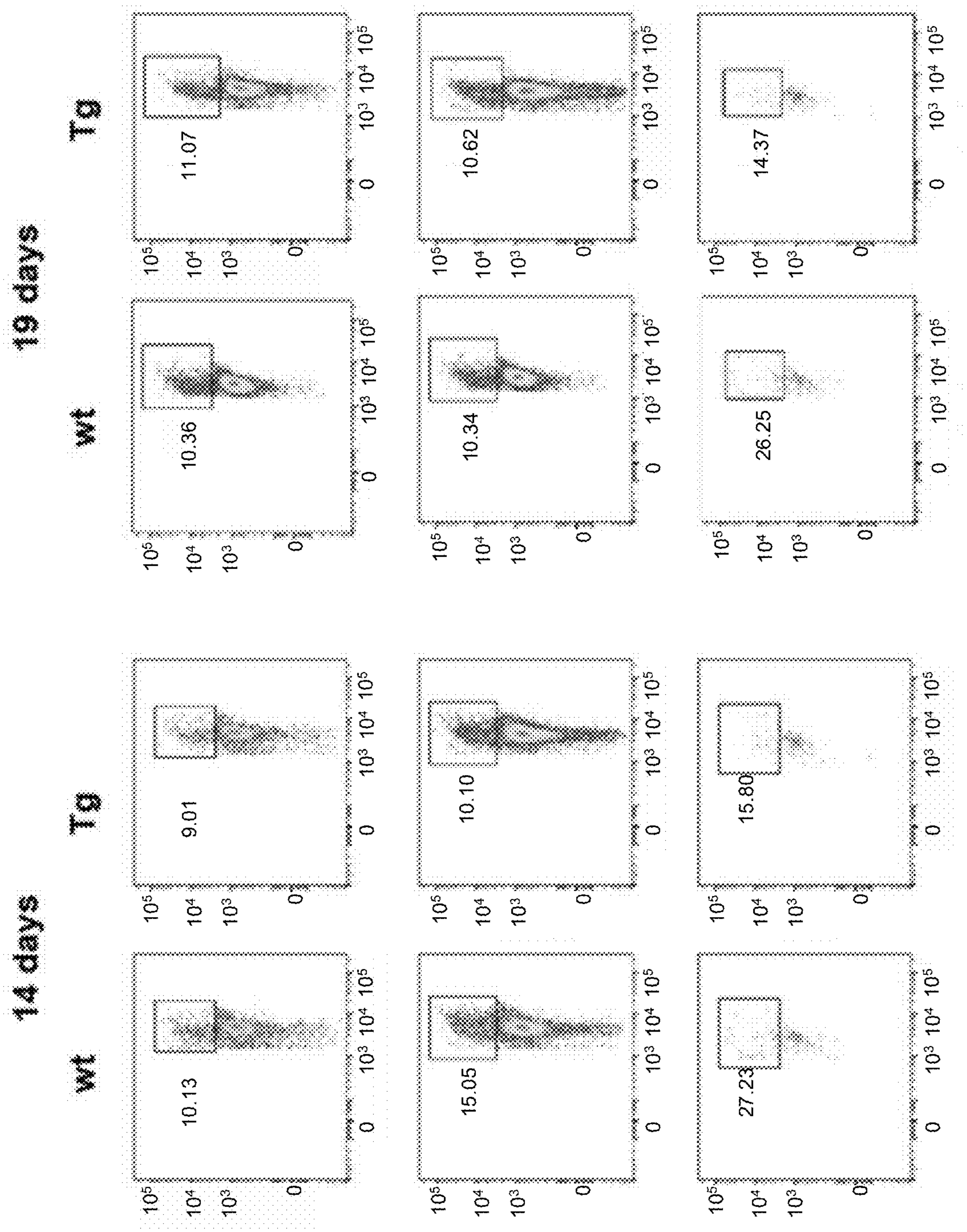
FIGS. 14A-B are plots showing FACS analysis.
Figure 14B:
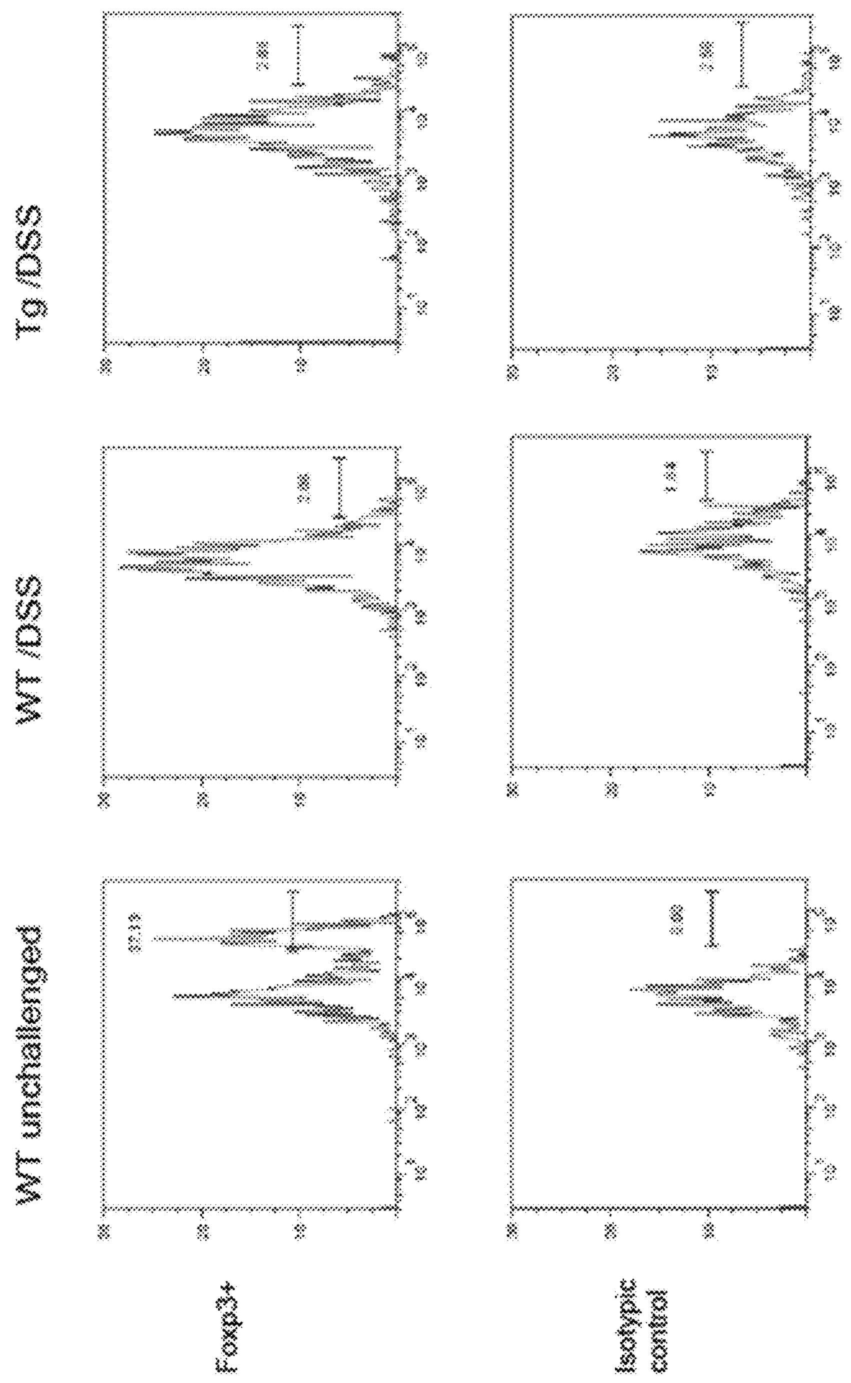

The IL-2 receptor alpha chain CD25 is a marker of activated of CD4+ T-cells (54,55), and previous studies have suggested that expression of the IL-2R alpha chain on CD4 T-cells in both the colon and draining lymphatic nodes from the intestine is associated with increased disease activity in experimental model of colitis (56-58). The proportion of CD4+CD25+ T-cells in TG vs. WT mice after DSS treatment was evaluated; while there was no difference in splenic CD4+CD25+ cells between TG and WT mice at selected time points, the proportion of activated CD4+CD25+ cells in the colon and lymphatic nodes was lower in TG mice compared to WT mice at 14 day after DSS treatment (FIG. 14A). Transgenic mice also had a lower proportion of colonic activated CD4+CD25+ T-cells at 19 day after DSS treatment. Since CD4+CD25+ T-cells expressing Foxp3 are considered as a major population of T regulatory cells that suppress innate and adoptive immune response upon inflammatory change, CD4+CD25+Foxp3 cells were measured in lymphatic nodes in mice WT and TG at 19 day of DSS water treatment. However, the number of CD4+CD25+Foxp3 cells was decreased by this time point in both groups of mice, suggesting that the anti-inflammatory effect of TFF2 is likely unrelated to direct modulation of TReg numbers (FIG. 14B).

Chimaeras Mouse Studies Confirm a Role for Hematopoietic-Derived TFF2 in the Modulation of Acute Inflammatory Response.

Figures 5A, 5B, 5C, 5D, 5E, 5F:
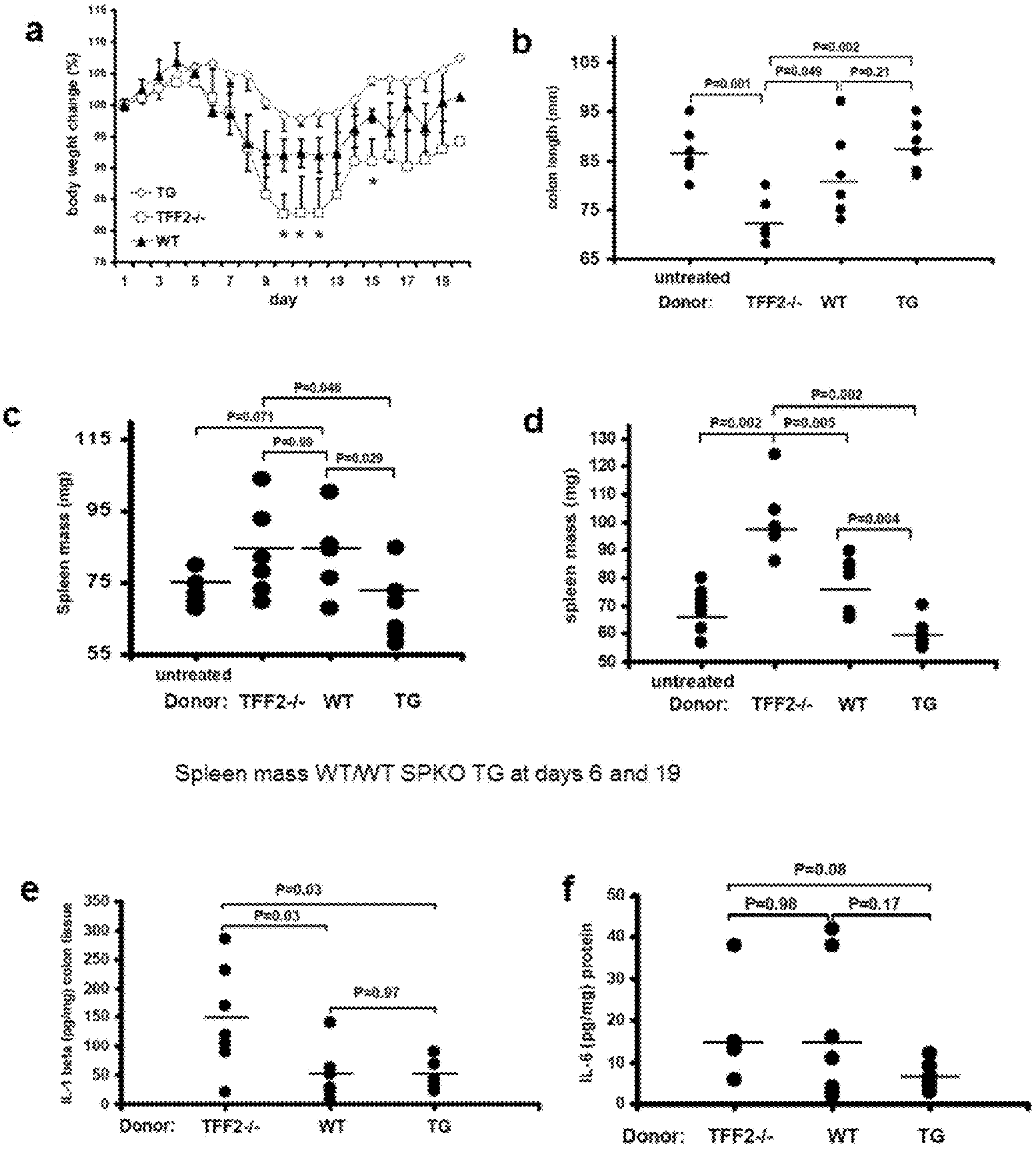
FIGS. 5A-D. Influence of TFF2 expressed in immune compartment on systemic and colonic inflammation. Effect of TFF2 expressed in the lymphohematopoietic compartment on systemic and colonic inflammation. Lethally-irradiated wild type mice were transplanted with bone marrow from WT, TFF2−/− and TG animals. Eight weeks later chimeric animals received 3% DSS water for 5 days followed by tap water for 2 weeks. Mice were analyzed on day 19. Differences in clinical disease parameters between chimaeras transplanted with bone marrow from donor TFF2−/−, WT and TG mice: body weight loss (a statistically significant difference (*, $P<0.05$) in body weight loss is marked by an asterisk.) (FIG. 5A), shrinking colon in mice transplanted with bone marrow from donor TFF2−/− animals (FIG. 5B), lower spleen mass in chimaeras transplanted with bone marrow from donor TG mice at day 6 and 19 (FIG. 5C) and splenomegaly at day 19 (FIG. 5D) in chimaeras wild type mice receiving bone marrow from donor TFF2−/− counterparts.
FIGS. 5E-F. Influence of TFF2 expressed in immune compartment on systemic and colonic inflammation. Plots show the level of IL-1β (FIG. 5E) and IL-6 (FIG. 5F) in colon tissues at day 19 in ELISA.
Figure 5G:
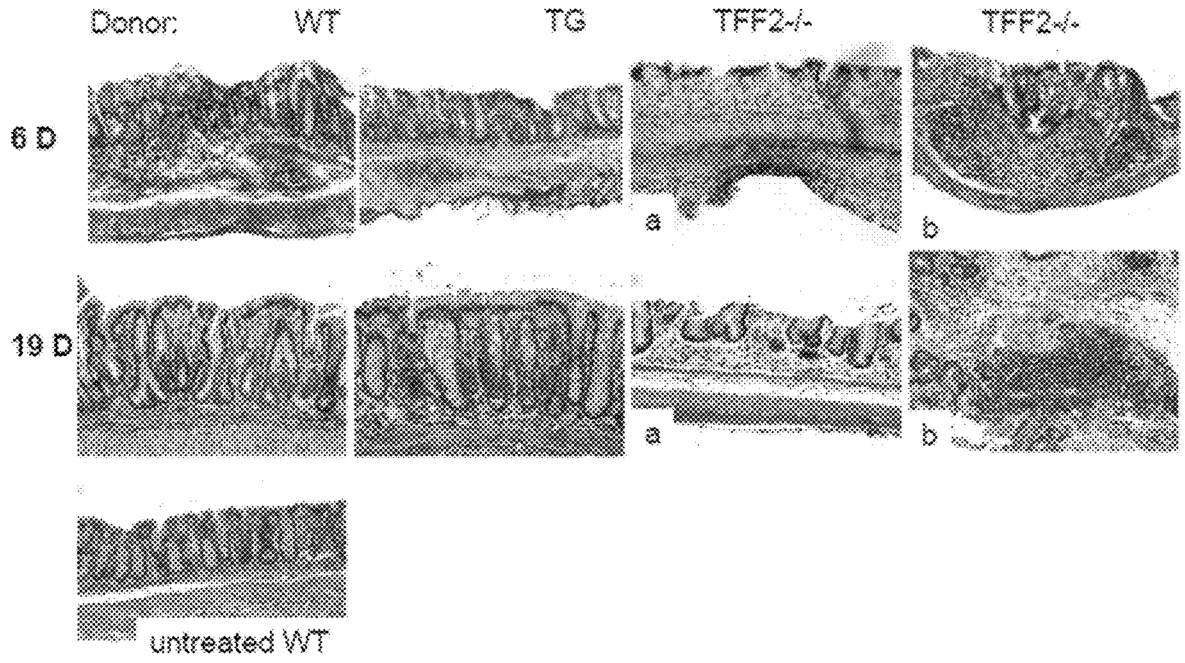
FIGS. 5G-H show histology (G) and inflammatory score (H) of colon of wild type transplanted with bone marrow from donor wild type, transgenic and SPKO mice on days 6 and 19 (FIG. 5G). Histology, upper panel, day 6: donor WT and TG mice, atrophy; donor TFF2−/− mice, atrophy (a) and infiltration of inflammatory cells under mucosa (b). Bottom panel, day 19: donor WT and TG mice, atrophy; donor TFF2−/− mice, atrophy (a) and infiltration of inflammatory cells under mucosa (b). Magnification ×200. Histological score on day 19 (FIG. 5H).
Figure 5H:
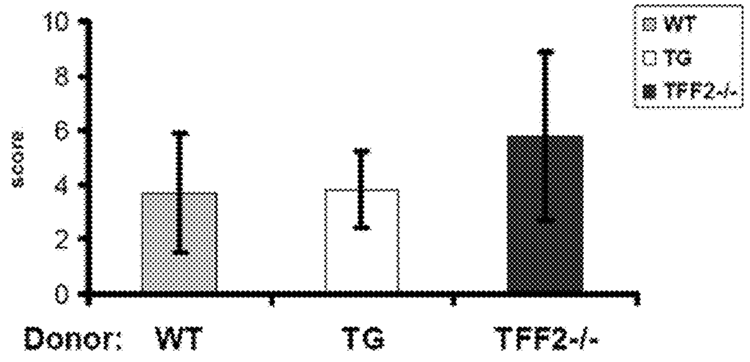

Since TFF2 is expressed in the gastric epithelial cell compartment as well as the immune compartment, bone marrow transplantation experiments were carried out to assess further the importance of hematopoietic cell-derived TFF2. wild type mice were lethally irradiated, and transplanted with bone marrow from TFF2−/−, WT and TG mice. Colitis was induced using 5% DSS in the drinking water for 5 days followed by regular water for 19 days. At 6 days, mice transplanted with TFF2−/− bone marrow mice had worse (gross) rectal bleeding, while mice transplanted with bone marrow from TG mice showed a smaller spleen size and greater body weight (FIG. 5A, C). By day 19, mice receiving bone marrow from TFF2−/−mice retained a statistically bigger spleen (FIG. 5C) and shorter colon (FIG. 5B) compared with the other two groups. In addition, mice that received TFF2−/− bone marrow showed a higher protein level of IL-1 beta relative to the other two groups (FIG. 5E). In contrast, mice that received bone marrow from transgenic mice displayed an amelioration in their colitis, including a greater body weight, normal spleen mass and colon length (FIG. 5A, B, C, D). On histological examination, mice receiving TFF2−/− bone marrow had a greater degree of mucosal injury with gross infiltration of immune cells in submucosa (FIG. 5G), however these differences did not reached statistical significance (FIG. 5H). The fact that wild-type mice transplanted with bone-marrow from TFF2-deficient mice had an overall stronger colitis phenotype (such higher body loss, gross bleeding, shorter colon, larger spleen, higher level of IL-1β) as compared to those transplanted with bone marrow from wild-type or transgenic mice revealed protective effect of bone marrow derived TFF2 in colonic homeostasis.

Figures 6A, 6B, 6C:
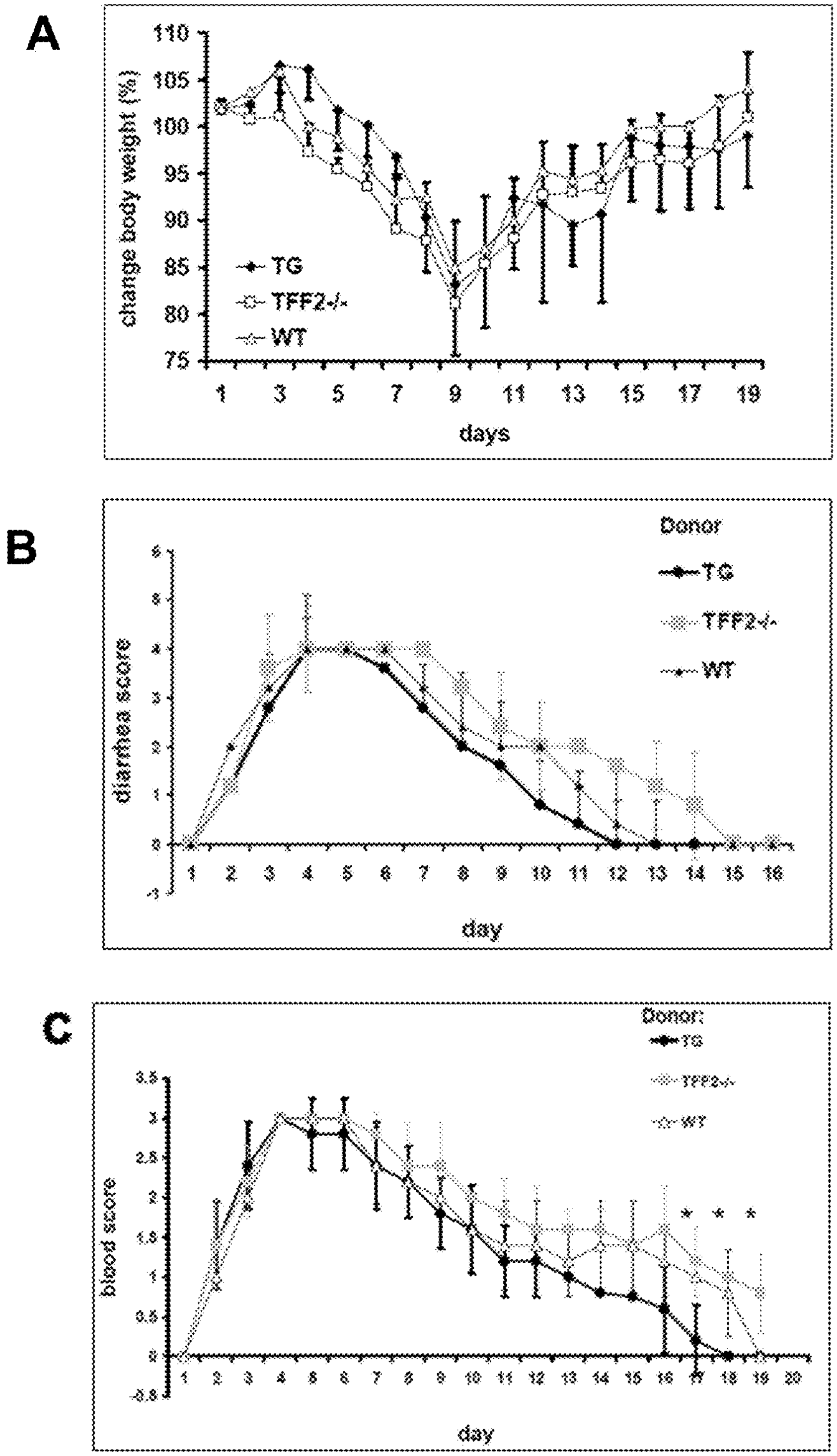
FIGS. 6A-G show the effect of TFF2 expressed in immune cells on colon and systemic inflammation upon DSS challenge in TFF2−/− mice substituted with bone marrow from wild type, TFF2−/− and TG mice. All groups were given 2.5% DSS water for 5 days followed by tap water. Mice were sacrificed on day 19. Clinical disease parameters between TFF2−/− mice transplanted with bone marrow from TFF2−/−, WT and TG animals: body weight change (FIG. 6A), chimaeras mice received bone marrow from TFF2−/− animals have higher diarrhea (FIG. 6B) and bleeding score (FIG. 6C) compare with mice receiving bone marrow from TG animals, colon length (FIG. 6D), splenomegaly in TFF2−/− mice that received bone marrow from TFF2−/− mice and normal mass of spleen in TFF2−/− mice received bone marrow from TG mice (FIG. 6E). ELISA for IL-1b in colon tissues (FIG. 6F). Myeloperoxidase activity at day 6 (FIG. 6G).
Figures 6D, 6E, 6F, 6G:
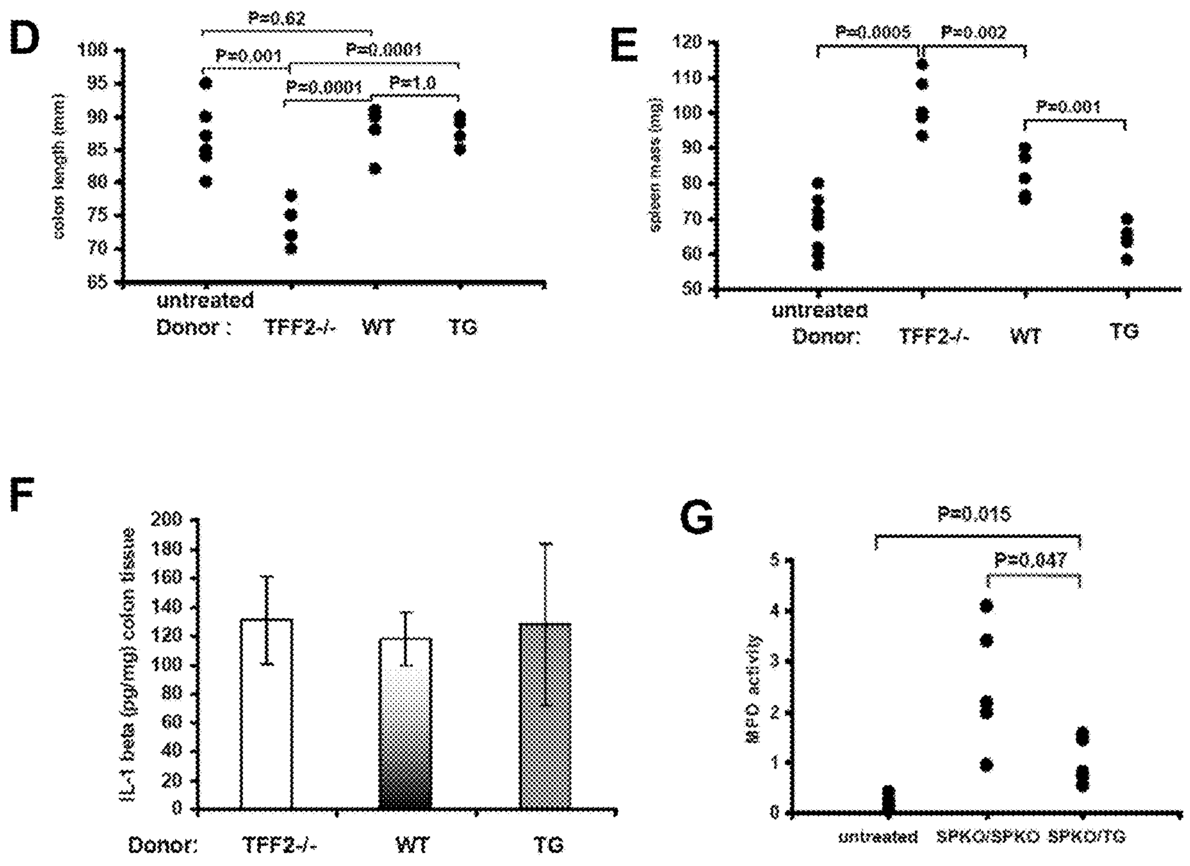

In order to determine whether TFF2-expressing bone marrow could rescue the TFF2-deficient phenotype lethally-irradiated TFF2-deficient mice were transplanted with bone marrow derived from WT, TG or TFF2−/− mice. The transplanted mice were studied after exposure to DSS at a slightly lower concentration (2.5%). Mice receiving bone marrow from TFF2-deficient mice showed higher body weight loss at day 4 and 5 then mice received bone marrow from transgenic mice, however, there was not a difference compared to mice with bone marrow transplanted from wild-type mice (FIG. 6A). In addition, mice receiving bone-marrow from WT or TG mice showed less severe diarrhea, lower colonic MPO activity and a longer duration of rectal bleeding than mice receiving TFF2−/− bone marrow (FIGS. 6B, C, G). On day 19, the chimaeras with bone marrow from TFF2−/− mice still showed the traces of blood in feces, displayed shorter colon and larger spleens compared with the other two groups (FIGS. 6C, D, E). Thus, transplantation of bone marrow from wild-type or CD2-TFF2 transgenic mice into TFF2-deficient mice can partially rescue the inflammatory phenotype.

Finally, the relative contribution of epithelial-derived TFF2 versus bone marrow-derived TFF2 on survival rate when DSS (5%) was continuously administered in the drinking water were compared. Chimaeras TFF2-deficient mice received bone marrow from knockout or wild type or transgenic mice died faster then chimaeras wild-type transplanted with bone marrow from wild type or transgenic or knockout mice upon continuous treatment with 5% DSS (FIG. 6H, upper and lower panel). Without being bound by theory, these experiments showed that TFF2 expressed in epithelial cells of the GI tract likely has a greater protective effect compared with TFF2 from non-epithelial cells.

DSS Treatment Results in Greater Accumulation of Myeloid Cells in Spleen in TFF2-Deficient and Wild Type but not in Transgenic Mice.

Figure 15:
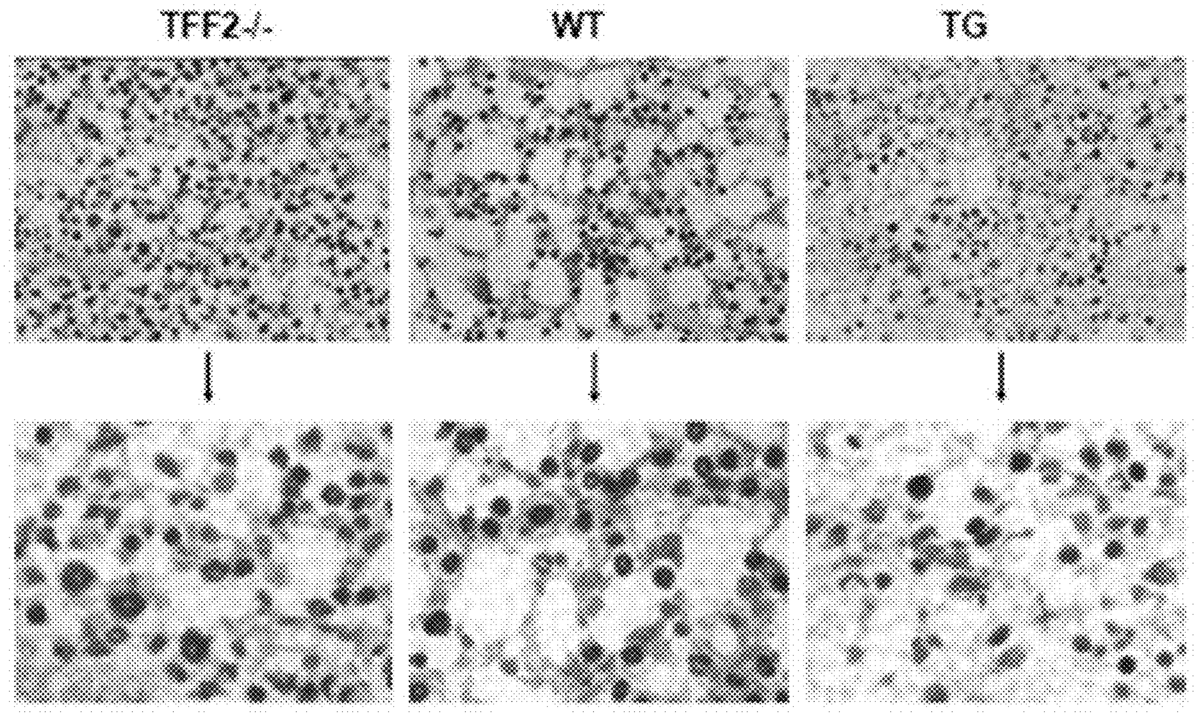
FIG. 15 shows photomicrographs of hematoxylin and eosin-stained spleen (frozen tissue) from TFF2−/−, WT and TG mice (Magnification 60×). Mice were treated with DSS water and spleen was stained for hematoxylin and eosin. Spleen from TG mice displays lowest proportion cells with ring shaped nuclei compare with WT and TFF2−/− mice.

While the data above indicated some degree of protective effect from hematopoietic-derived TFF2 on colonic inflammation, it was also noted in the chimeric studies that TFF2-deficiency was associated with a larger spleen size, while CD2-TFF2 transgenic mice exhibited a lower spleen size after DSS colitis. Under normal conditions, less than 4% of cells in the spleen are myeloid cells expressing CD11b+Ly6C+(59), but during the chronic phase following DSS treatment, the WT spleen enlarges with a significant increase in the total number and proportion of myeloid cells (51,60). Consequently, the possibility that the increase in spleen weight in the setting of TFF2 deficiency might result from the expansion of Gr1CD11b+ cell population was investigated. Histological examination of heamotoxylin/eosin stained spleens on day 19 after DSS treatment revealed that cells with the typical ovoid or circular nucleus, characteristic of immature myeloid cells (IMC), were much more abundant in TFF2−/− and WT mice than in CD2-TFF2 transgenic mice (FIG. 15). In order to determine the cause for this expansion of IMCs, the spleens from TFF2−/−, WT and TG mice of SPKO mice were stained intensively for proliferative marker Ki67. Increased proliferation was observed in TFF2-deficient mice, while decreased proliferation was seen in TG mice (FIGS. 7A, B). Staining of serial sections for Ki67 and Gr1 antigens revealed that TFF2−/− mice showed significantly more actively proliferating Gr1+ cells than WT mice, while TG mice showed fewer proliferating Gr1+ cells than WT mice. Importantly, staining for Ki67 and Gr1 antigens was found in the red pulp zone where myeloid cells typically reside (FIGS. 7A, B). These observations suggested that splenomegaly in DSS-treated TFF2−/− mice indeed might associate with expansion of immature myeloid cells likely due to intensive extramedullary hematopoiesis.

Figure 7C:
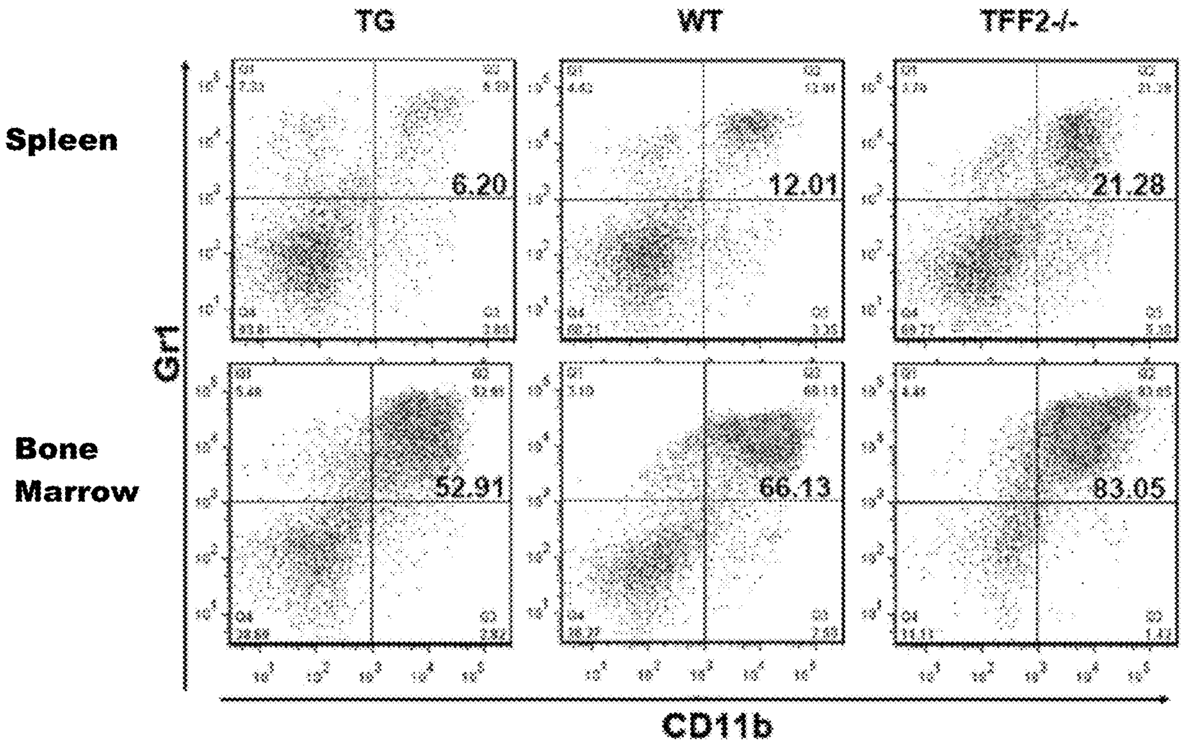
FIG. 7C. TFF2 suppresses expansion of CD11b+Gr1+ cells in spleen and bone marrow upon DSS treatment. Flow cytometry analysis of CD11b1+ staining versus Gr1+ staining gated on live cells from the spleen of spleen of mice with DSS colitis on Day 19 (splenic cells—upper row, bone marrow cells—lower row). Numbers indicate percentage of CD11b+Gr1+.
Figures 7D, 7E, 7F:
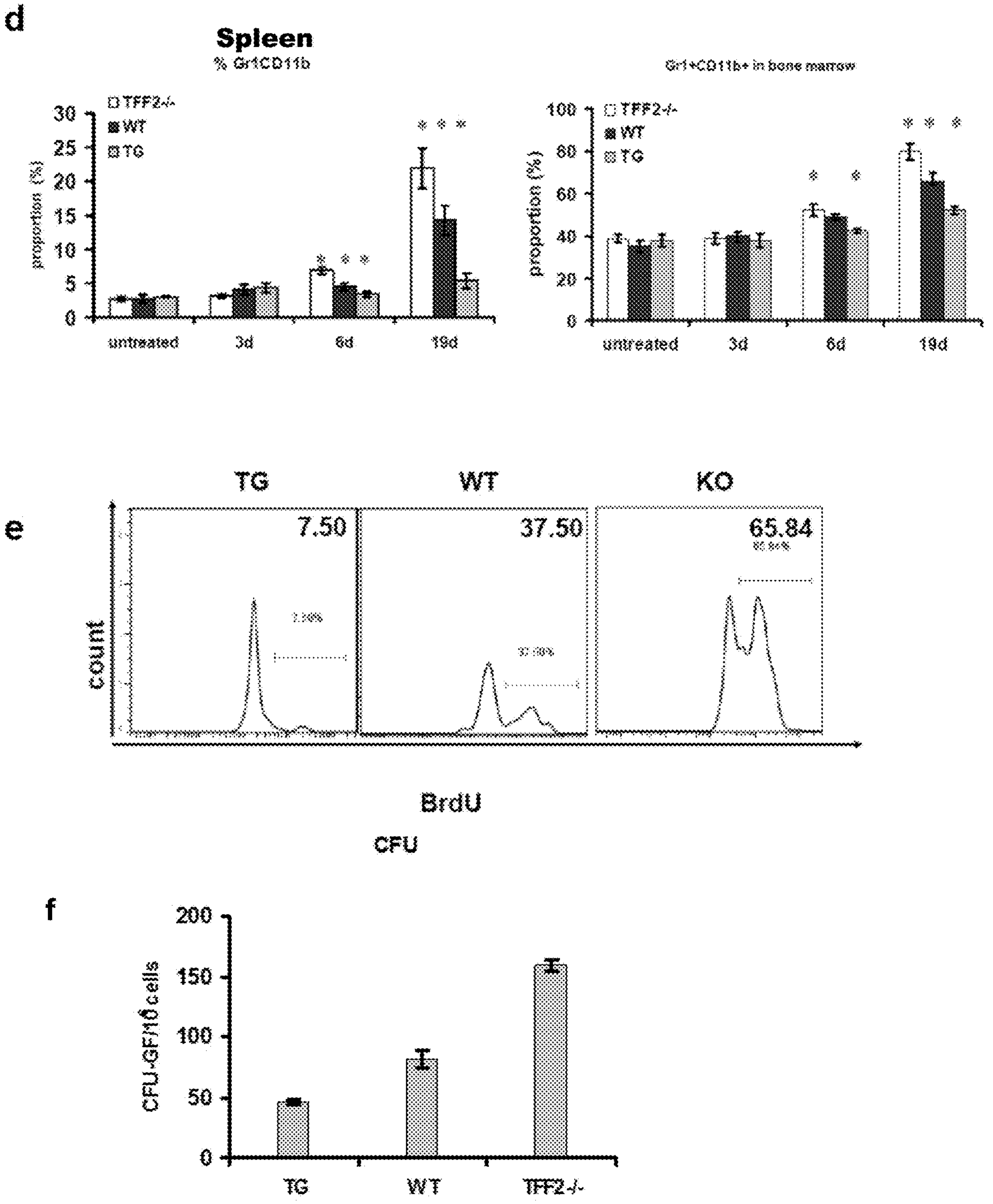
FIGS. 7D-E. Graphical representation of FACS analysis data (D). Percentages of CD11b+Gr1+ cells from spleen (left) and bone marrow (right). Data represent the mean and standard deviation of 3-6 animals per group. Asterisks $P<0.05$ by analysis of variance and the Student's test. Mice were given 3% DSS water for 5 days, and then they switched to tap water and sacrificed at indicated time points.
FIG. 7F is a bar graph of a CFU assay of splenocytes from TG, WT and TFF2−/− mice after DSS treatment. Bar graphs enumerate colonies in cultures.
Figure 16A:
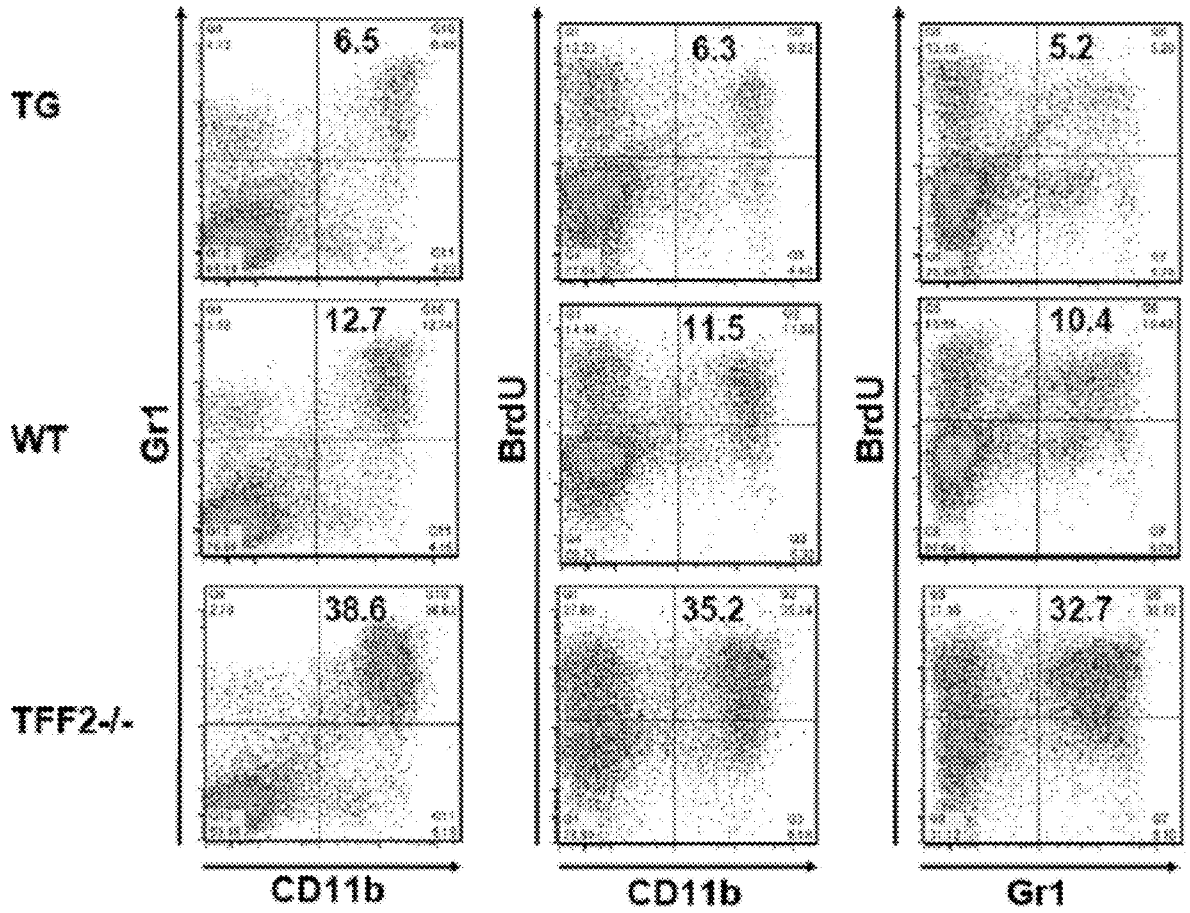
FIG. 16A. Gr1+ and CD11b+ cells from spleen of transgenic, wild type and TFF2−/− deficient mice proliferate during recovery phase of DSS-induced colitis. Proliferative capacity was assessed by BrdU uptake on Gr1+ and Cd11b+ cells from spleen taken from mice treated with 3% DSS on day 19. Cells were analyzed 72 h after first injection of BrdU.

To further explore the role of TFF2 in the modulation of splenocytes, changes in myeloid cells were examined by FACS analysis over the course of DSS-treatment using antibodies to CD11b and Gr-1. TFF2-deficient mice accumulated the highest proportion of CD11b+Gr1+ cells, while CD2-TFF2 transgenic mice showed the lowest percentage (FIG. 7D, FIG. 16A, B). The proportion of CD11b+Gr1+ cells increased over time in TFF2−/− and wild type mice with a peak on day 19, in contrast to the CD2-TFF2 transgenic mice which showed an insignificant increase in proportion of these cells at all time points (FIG. 7D, left). The absolute number of double positive CD11bGr1 cells significantly increased in TFF2−/− and to a lesser extent in wild type mice, while in transgenic mice there was much less accumulation of IMCs (FIG. 7C-E).

Changes in the numbers of Gr1+CD11b+ cells in the bone marrow over the course of DSS-induced colitis were investigated. An increase in Gr1+CD11b+ cells in bone marrow of all groups of mice was found; however TFF2−/− mice showed the highest percentage of IMSc while the TG mice exhibited the statistically lowest percentage of Gr1+CD11b+ cells (FIG. 7D, right).

Recently it has been proven that myelopoisis in spleen significantly contributes in accumulation of myeloid cells under various conditions including injury and cancer. Gr1+ CD11b+ cells comprise heterogeneous population including immature macrophages, dendritic and myeloid cells at various stages of differentiation as well their precursors (61) Almand, 2001). Expansion of myeloid cells in spleen was likely as a result of both recruitment from bone marrow and local proliferation their precursors in spleen of tumor-bearing mice ((62) Cortez-Retamozo et al., 2012) and in case of myocardial infracture.

To determine whether the accumulation of splenic Gr1+ CD11b+ cells occurred due to active proliferation in periphery BrdU was injected in mice to label in vivo dividing cells. After 96 h splenic cells were isolated and stained for CD11b+, Gr1+ and intracellular BrdU incorporation was detected according to manufacturer's instructions. It was observed that splenic cells stained for Gr1 and CD1b markers actively proliferate during recovery phase of DSS-induced colitis, however cells from TFF2-deficient mice display higher BrdU uptake then other two groups (FIG. 16A, B). Approximately 66% Gr1+CD11b+ cells incorporated BrdU in TFF2−/− mice, in WT mice around 38% of Gr1+CD11b+ cells were positive for BrdU uptake, while less then 8% of Gr1+CD11b+ cells were positively stained for BrdU (FIG. 7E).

Since granulocyte/macrophage precursors may give rise to myeloid cell population and contribute to their expansion in spleen (63) Leuschner F et al., 2012) colony-forming capacity of splenocytes obtained from all groups of mice on day 19 after DSS treatment was evaluated by using medium MethoCult M3434. This medium support growth of erythroid, granulocyte-macrophage and multi-potential granulocyte, erythroid, macrophage, megakaryocyte progenitors (StemCell Technology). Splenocytes from TG mice showed the lowest capacity to form colonies, while splenocytes from TFF2−/− deficient mice formed significantly more colonies compared with TG and WT mice accordingly (FIG. 7F). Taken together these data suggest that TFF2 suppresses the expansion of Gr1+CD11b+ cells and their precursors in vivo.

TFF2 Suppresses the Proliferation and Growth of Gr1+ CD11b+ Cells in Ex-Vivo Culture.

Figures 9C, 9D:
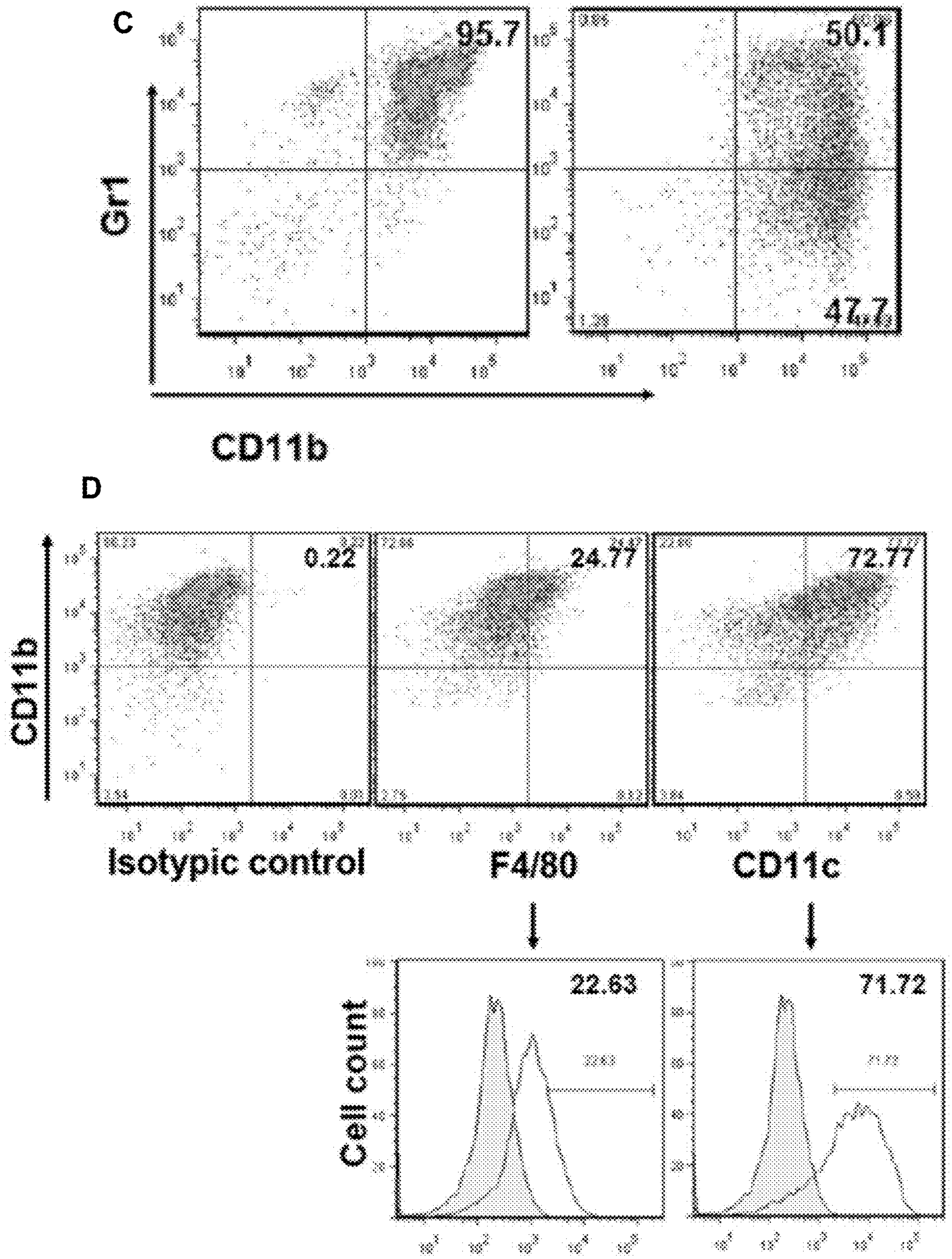
FIG. 9C is a plot showing sorted Gr1+CD11b+ cells loose expression of Gr1 antigen while increase CD11c marker during culture with GM-CSF (10 ng/ml).
FIG. 9D is a plot showing sorted splenic Gr1+CD11b+ cells from TFF2−/− mice, followed by staining for F4/80 or CD11c. Only a small proportion of the cells stain for F4/80 while the majority of the cells are positive for CD11c.
Figures 10A, 10B:
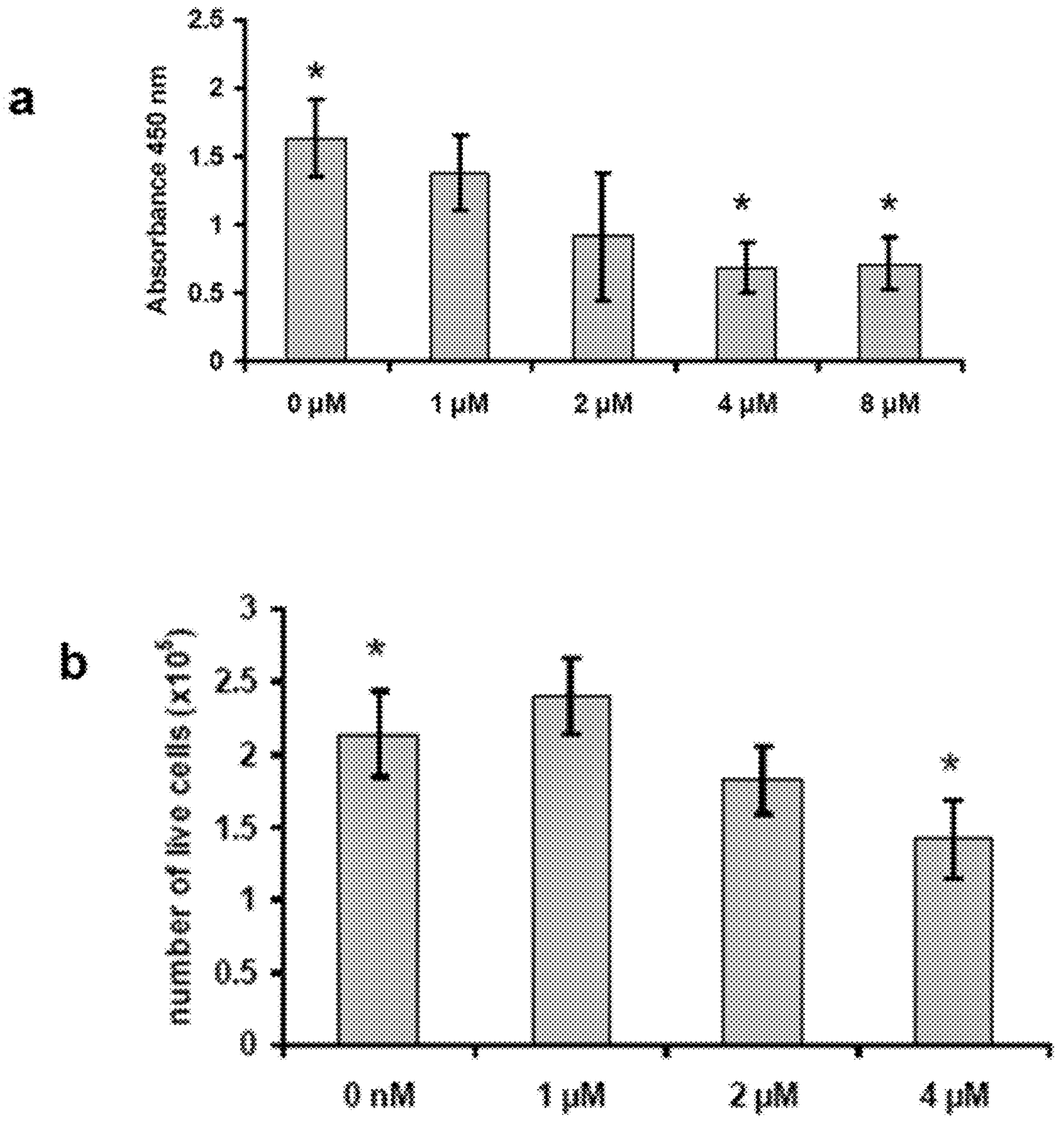
FIGS. 10A-B. Recombinant mouse TFF2 inhibits proliferation of sorted Gr1+CD11b+ cells in vitro. Spleens were obtained from TFF2−/− on day 19 after starting DSS water. Splenic cells from TFF2−/− mice were labeled for Gr1 and CD11b antigen and sorted on sorter FACSAria.
Figure 61A:
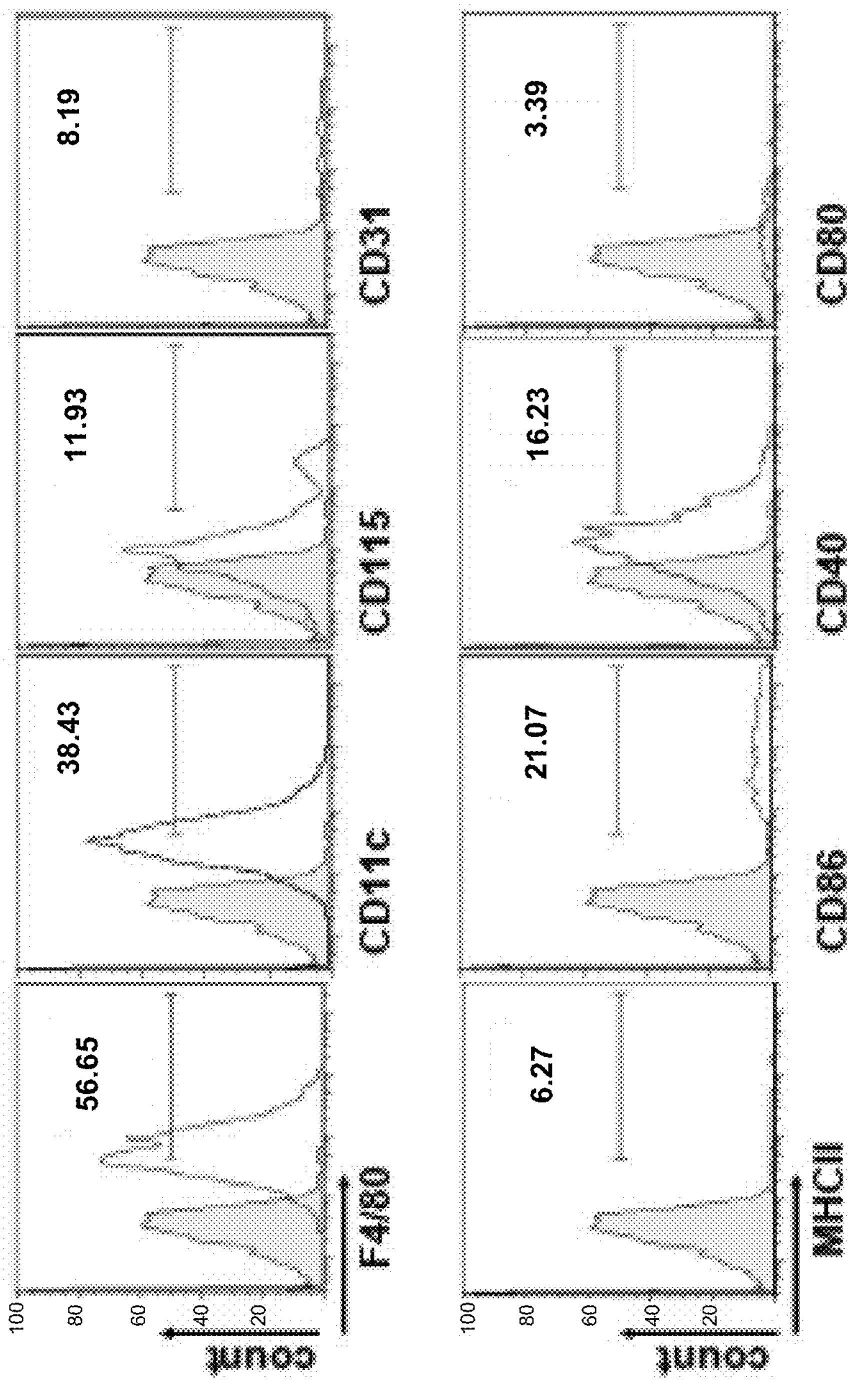
Figure 61B:
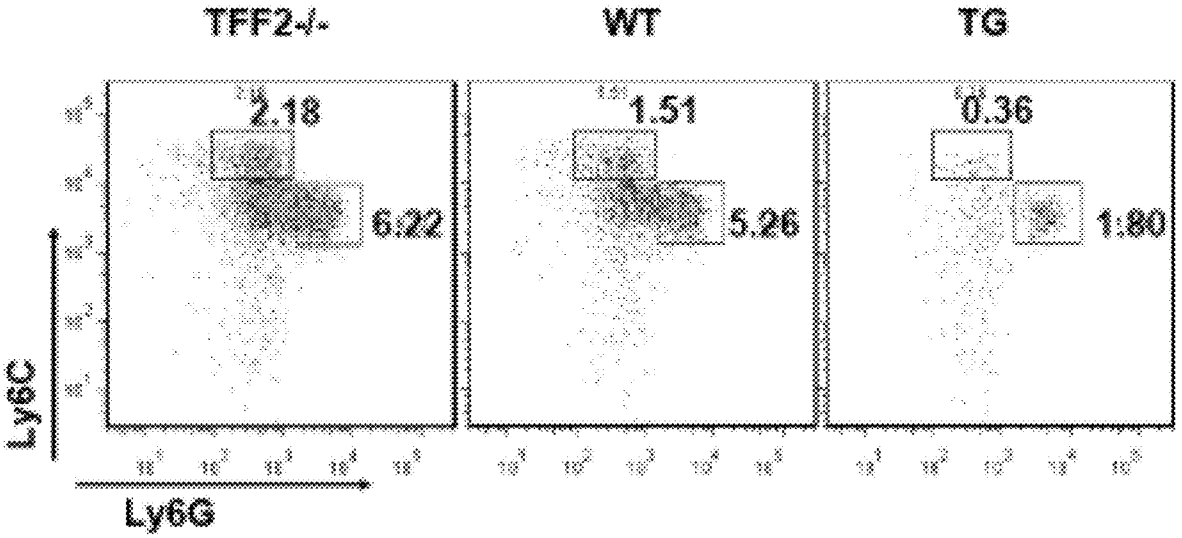
Figure 61C:
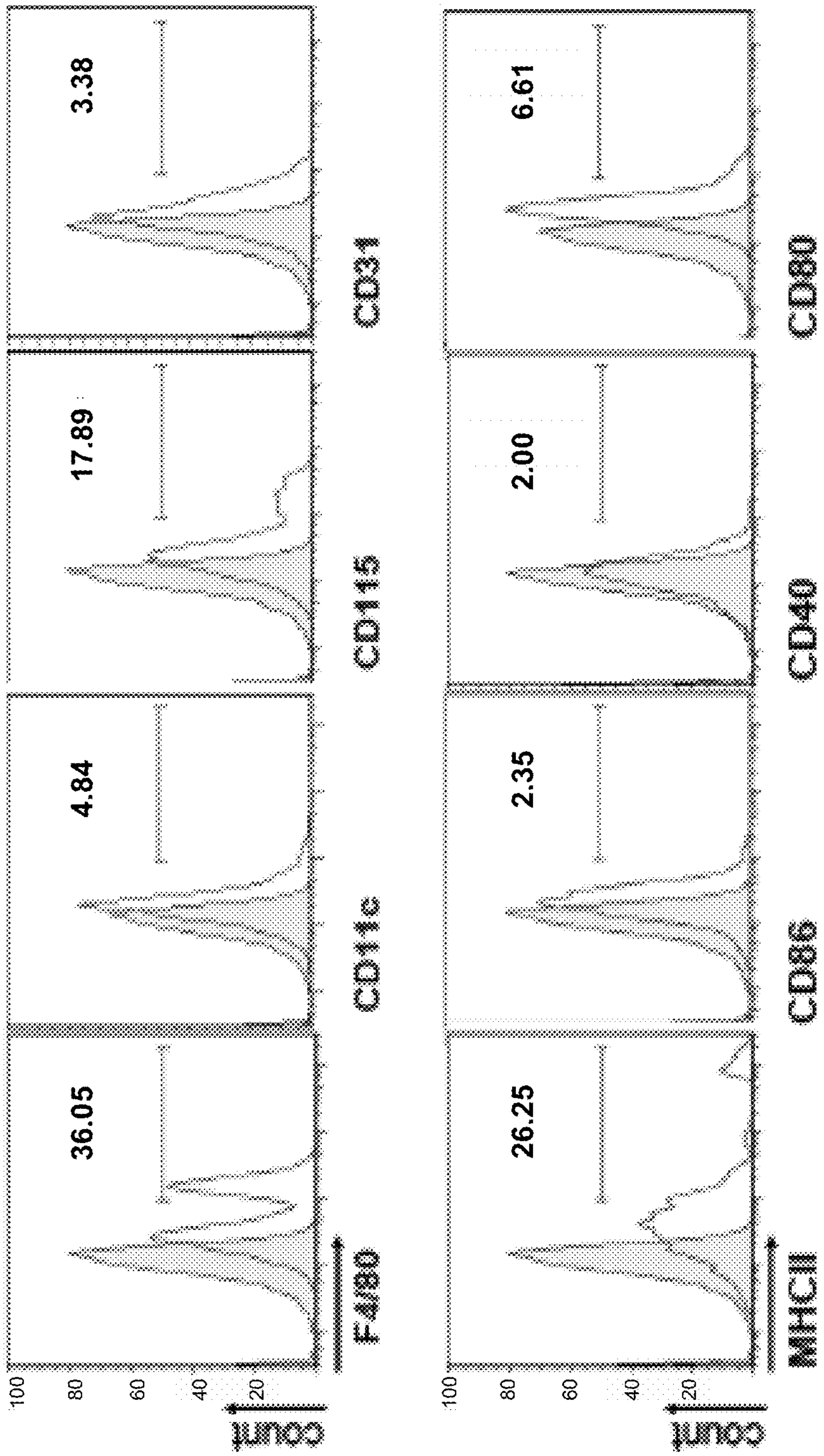

To further explore the effect of TFF2 on Gr1+CD11b+ cells these cells were characterized morphologically and phenotypically. Because Gr1+CD11b+ cells comprise heterogeneous population including immature macrophages, dendritic and myeloid cells at various stages of differentiation (Almand, 2001) splenocytes were labeled with antibodies against antigens Gr1 (which recognizes both monocytic and granulocytic markers) and CD11b then sorted by using sorter FACSAria. Sorted double Gr1+CD11b+ cells with purity around 95% (FIG. 9C) represent heterogeneous population of cells with ring shaped and segmented nuclei (FIG. 9A) and thus show morphological characteristic consistent with phenotype of immature myeloid cells. These cells displayed antigens previously reported being expressed on immature myeloid cells such earlier marker of myeloid progenitors CD31, CD115, macrophage antigen F4/80 and dendritic cell marker CD11c, (FIG. 9B) (64-66; Venkatesh L et al., 2010). They also were positive for monocytic marker Ly6C (FIG. 59C-D, FIG. 61B). These cells are premature as antigen-presenting cells because they express low levels of MHC class II, co-stimulatory molecules CD86, CD80 and CD40. Sorted Gr1+CD11b+ cells grow, loose marker Gr1, decrease expression of macrophage marker F4/80 but increase expression of dendritic cell marker CD11c over 7 days in presence of GM-CSF (10 ng/ml). Next it was investigated whether TFF2 directly affect the growth of sorted Gr1+CD11b+ cells in vitro culture. Because Gr1+ CD11b+ cells died in absence of growth GM-CSF, the effect of TFF2 in presence of low concentration of GM-CSF in medium after 7 days of culture was analyzed. GM-CSF is well-known factor that support viability and differentiation of Gr1+CD11b+ cells (Morales J K & Kmieciak M, Breast Cancer Res Treat 2010). In the initial series of experiments Gr1+CD11b+ cells were cultured with 10 ng/ml GM-CSF only and with addition of TFF2 in parallel setting. Since there was no difference in the number of viable cells and BrdU uptake by Gr1+CD11b+ cells under the above conditions the concentration of GM-CSF was lowered to 5 ng/ml. The number of viable cells decreased in dose-dependent manner upon TFF2 supplementation in the range 0.2 μM-4 μM (FIG. 10A). Addition of TFF2 also resulted to a decreased BrdU uptake by Gr1+CD11b+ cells in dose-concentration manner (FIG. 10B). However, recombinant TFF2 does not seem to induce apoptosis of Gr1+CD11b+ cells even in higher concentrations.

Figures 11F, 11G, 11H, 11I:
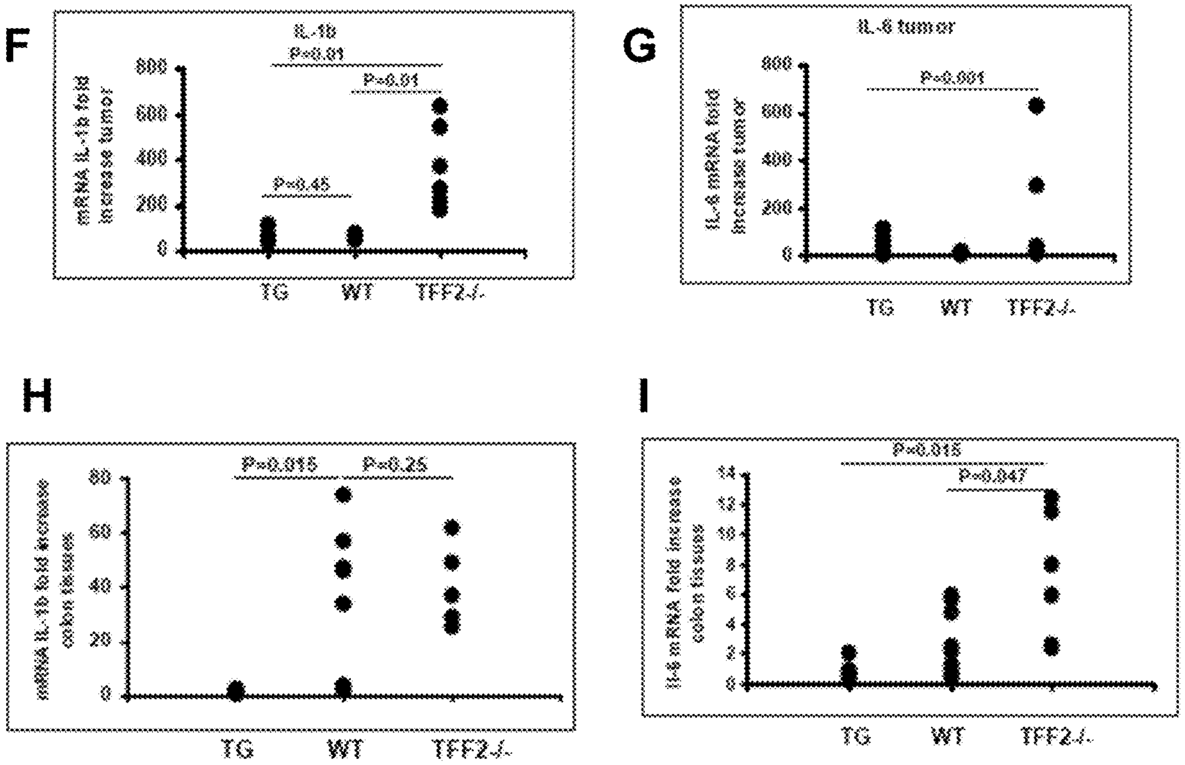
FIG. 11F-I are plots showing gene expression was normalized on GAPDH levels and the expression of each gene relative to untreated colon tissues of wild type mice is depicted. Il-1β (FIG. 11F) and IL-6 (FIG. 11G) level in tumor tissues obtained from TFF2-deficient, TG and wild type mice. Il-1β (FIG. 11H) and IL-6 (FIG. 11I) level and in colon uninvolved in tumor obtained from TFF2-deficient, TG and wild type mice. The data correspond to a representative experiment out of three experiments.
Figure 12:
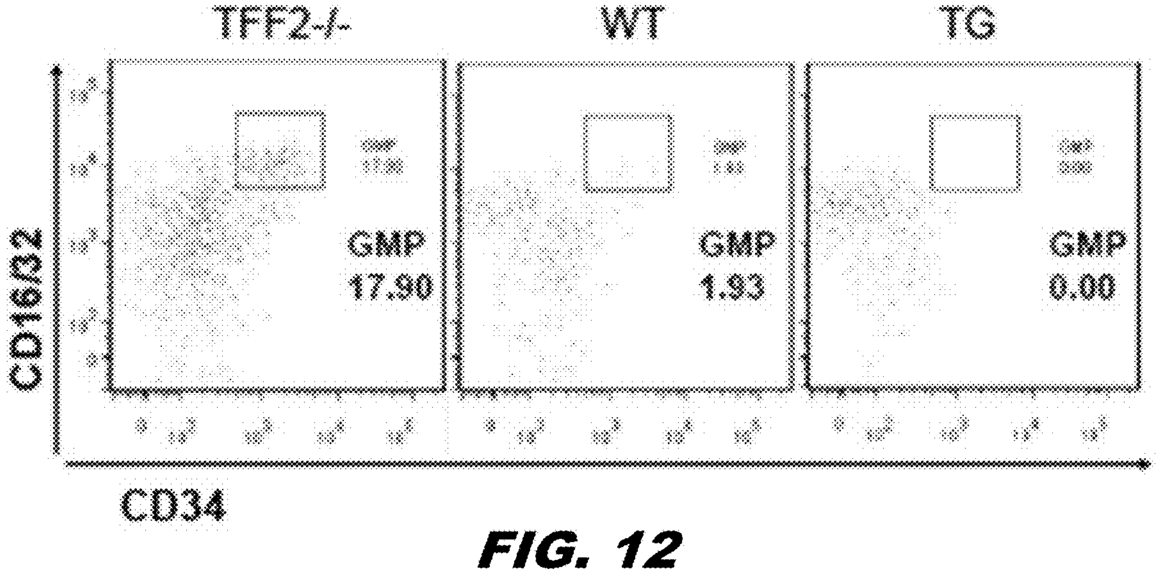
FIG. 12. TFF2−/− deficient mice expand myeloid progenitor cells in spleen (and bone marrow). Identification of GMP cells in spleen of TFF2−/−deficient, WT and TG mice after AOM/DSS treatment (representative data from 4-5 mice of each group).

Expression of TFF2 by Splenic T Cells Suppresses the Development of Colon and Rectal Tumors Following AOM/DSS Treatment Gr1+CD11b+ cells comprise several populations including cells with immunosuppressive function (MDSC). These cells are induced by various conditions including inflammation and inhibit tumor immunity in studies on mouse tumor models and cancer patients (1,67,68). Because TFF2−/− mice developed worse colitis with higher accumulation of Gr1+CD11b+ cells in bone marrow and spleen compare with wild type and transgenic counterparts it is possible TFF2−/− mice were more likely to develop tumors in cancer models associated with inflammation while transgenic mice would be resistant then wild type and TFF−/− deficient mice. Knockout, wild type and transgenic mice were injected with single intraperitoneal injection of procarcinogen azoxymethane (AOM) following 3% DSS regiment during next 7 days. Mice were analyzed for the presence of colon tumor five months later. Both wild type and TFF2−/− mice developed tumors in the third part of distal colon, however TFF2-deficient mice clearly showed higher number of small tumors with size 1-3 and 4 mm (FIG. 11A, B). Transgenic mice showed no tumor at all or only a single tumor, depending on experiment 70-90% of transgenic mice do not develop tumor. Histological examination showed larger adenomas with increased inflammatory cell infiltration in colonic tissues of TFF2−/−deficient mice compare with wild type counterparts (FIG. 11C). Higher tumor burden in TFF2−/− mice correlates with an increased proportion of Gr1+CD11b+ cells in the spleen and bone marrow compare with wild type and transgenic mice (FIG. 11D). Transgenic mice displayed the same proportion of Gr1+CD11b+ cells in bone marrow as wild type, but lower in the spleen and in blood (FIG. 11D). Very recently it has been shown that tumor induces splenic accumulation of hematopoietic stem cells (HSCs) and lineage progenitors cells such GMP and their important contribution in tumor progression (62,68). In order to test the presence of these populations in spleen and bone marrow colony-forming units assay and flow cytometry with markers and gating strategy described earlier (62) (FIG. 40) was performed. TFF2-deficient mice showed a greater proportion of GMP and higher number of CFU compare with WT and TG mice. Thus TFF2 suppresses the expansion of granulocyte-macrophage progenitors in vivo and therefore inhibits cancerogenesis. Interestingly, suppressive TFF2 effect on tumor growth in syngenic model, when tumorigenesis has been initiated by subcutaneous injection of EL-4 cells without application additional inflammatory stimuli was not found. It is well known that the AOM/DSS model associates with colonic inflammation with increase of IL-b, 11-6, TNF alpha cytokines in colon tissues. Indeed, TFF2−/− deficient mice showed significantly higher expression of mRNA for IL-1b and IL-6 in tumor tissues compare with tumor WT and TG mice (FIGS. 11F, G). TFF2−/− deficient mice also showed higher fold change of IL-6 mRNA level in colon tissues uninvolved in tumor compare with other two groups, but the same increase mRNA for IL-1b as in wild type mice. In parallel the lowest increase of mRNA for IL-1b and IL-6 was in colon tissues uninvolved in tumor in transgenic mice (FIGS. 11H, I). Since IL-1b has been shown to promote expansion of myeloid cells these data are consistent with higher tumor incidence in TFF2−/− deficient mice.

From the obtained data, and without being bound be theory, TFF2 attenuates tumor incidence by limiting the number of Gr1+CD11b+ cells in site of tumor.

Discussion

Protective role of TFF2 on stomach and colon is well documented and attributed to gastric origin, where its abundant expression is observed. Earlier studies showed that gastric TFF2 increased the viscosity of mucus which covers and protected cell epithelium and also promoted regenerative process by stimulating migration epithelial cell to places of injury (9,10,69-71).

However, trefoil peptides were detected in immune organs and functional relevance from immune compartment is still not fully understood. Several studies suggest that TFF2 is a negative regulator of gastrointestinal/systemic inflammation and immune cytokine response (13,36). Indeed, recent study showed that TFF2 promotes type 2 immunity by releasing IL-33 from epithelial, macrophages and dendritic cells through CXCR4 receptor (39). This process is beneficial in parasitic infection but pathogenic in context of asthma. In the example presented herein, splenic T-cells were identified as a source of immune cells expressing TFF2 under normal physiological conditions in spleen. For further analysis mice overexpressing TFF2 under human CD2 promoter specifically in T-cells were created and their inflammatory response was examined in a model of oral DSS administration which results in direct colonic injury to intestinal epithelial cells and inflammation due to increasing proinflammatory stimuli (72).

In accordance with earlier published data, results presented herein may not be explained by known barrier and reparative mechanism carried out by gastric TFF2. First, chimaeras WT with TFF2-deficiency in immune compartment showed higher susceptibility to DSS-treatment despite the presence of TFF2 in gastric epithelial cells. Second, chimeras TFF2− null mice with expression of TFF2 only in immune compartment showed less inflammation compared with TFF2− null mice. Thus TFF2 expressed by T-cells exhibits some dampening effect on colonic and systemic inflammation. Remarkably, protective effect was observed despite the fact that quantity of TFF2 in immune compartment is significantly lower than secreted by gastric epithelial cells or recombinant TFF2 used for treatment in earlier reports.

Experiments in the in vivo model indicate that TFF2 besides known barrier and reparative function in gastrointestinal tract also is involved in anti-inflammatory mechanism provided by T-cells expressing TFF2. Exacerbated immune response in TFF2−/− mice was observed in accordance with previous data and lower systemic inflammatory immune response in transgenic mice compare with wild type mice in DSS model. A transient significant increase in the number of Gr1+CD11b+ cells was found in TFF2−/− with less expansion in wild type mice, while only moderate accumulation of these cells was observed in transgenic mice. It has been widely accepted that chronic intestinal inflammation is generally associated with expansion of colitogenic T-cells. However significant increase of Gr1+CD11b+ cells also has been reported under experimental conditions of chronic gut inflammation induced with DSS (51,73) or T-cell adoptive transfer model of chronic colitis (Haile L A et al., Gastroenterology, 2008; Ostanin D et al., I Immunol., 2012). In these mouse models chronic colitis was associated with of accumulation of immature myeloid Gr1+CD11b+ cells similar to those described in tumor-bearing mice. While it is long established that IMC from tumor-bearing mice exhibit suppressive function (MDSC) and contribute in cancer progression, the role of IMC cells in pathogenesis of inflammatory bowel disease is still not clear. Some reports suggest that neutrophils suppress inflammation (Kuhl A A et al, Gastroenterology, 2007; Haile L A et al., Gastroenterology, 2008; Nemoto Y et al, Inflammation Bowel Dis. 2008; Zhang R et al., Inflamm Allergy Drag Targets 2011) but other studies do not support this conclusion (Natsui M et al., J.Gastroent.Hepatol., 1997; Qualls J E et all. J Leuco.Biol 2006; Ostanin D et al, J Immunol, 2012). Latest report suggests that Gr1+ neutrophils isolated from colitic mice induce proliferation of CD4+ T cells and enhance the production of proinflammatory cytokines by activated CD4+ T cells perpetuating gut inflammation (Ostanin et al., J Immunol, 2012).

Importantly, expansion of IMC in the experiments accompanies with an increase of Ki67 marker proliferation in spleen and in vivo BrdU uptake by splenic Gr1+CD11b+ cells suggesting on much higher extramedullar cells proliferation in TFF2-deficient mice compare with other two groups. Splenocytes from TFF2−/− mice treated with DSS form more colonies on medium supporting granulocyte, macrophage, megacaryocyte and erythroid precursors then splenocytes from wild type and transgenic mice. In addition recombinant TFF2 directly suppresses Gr1+CD11b+ cells proliferation in vitro culture, supporting in vivo data.

Expansion of myeloid cells in spleen due to increase in their turnover has been noticed earlier under other pathological conditions such thermal injury (Noel J et al., 2005). The idea that spleen may be as a source of immature myeloid cells due to active extramedullar hematopoiesis came from observation on massive accumulation of these cells in spleen of tumor-bearing mice (Johnson J R et al., 1985, Int.J Cell Cloning; Serafini P. et al., 2004, Cancer Immunol Immunoter; du'Pre S A et Hunter K W Jr, Exp Mol Path., 2007). An expanded red pulp with megacaryoblasts and metamyeloblasts and reduction of white pulp area in spleen of tumor-bearing mice suggest on extramedullar hematopoiesis (du'Pre S A et Hunter K W, 2007). So called leukemoid reactions characterized by splenomegaly due to massive granulocytic infiltrates have been also reported in human cancers and are associated with a poor prognosis (Sato K et al., J. Urol., 1994; Kasuga I et al., 2001; Nimieri et al., 2003, Annal Hematol; Schniewind B et al., 2005, Cancer Biol. Ther.) However, studies on syngenic tumor model suggest that expansion of IMC in spleen during cancer progression occurs as a result of proliferation and differentiation of these cells in bone marrow and subsequent migration from bone marrow to the blood but not due to proliferation in spleen (Ueha S et al., 2011). Indeed, by using a parabiosis system and in vivo BrdU incorporation these authors showed that immature myeloid cells have proliferated primarily in the bone marrow and not in peripheral tissues (Sawanobori Y et al., Blood, 2005). From earlier experiments it has been suggested that myeloid cells undergo extramedullar proliferation in response to soluble tumor-derived factors (Young M R, Young M E, Cancer Res., 1988; Kusmartsev S A, Li Y, J.Immunol., 2000). Recently it has been shown that spleen become reservoir of monocytes/macrophages that mobilize and migrate to inflamed tissue in response to myocardial infraction-induced heart injury and participate in wound healing (Swirski et al., 2009; Leuschner F et al., 2012). Later it has been shown that spleen also contributes inflammatory monocytes to atheroma in atherosclerosis (Robbins C S et al., Circulation, 2012) and monocytes/granulocytes in tumor sites during cancer progression (Cortez-Retamozo V et al., 2012).

Recent studies on RAG−/− mouse model clearly showed that chronic colitis is accompanied by the massive infiltration of myeloid cells in lamina propria and also associated with dramatic myelopoiesis with around 10 folds more myeloid cells (primary neutrophils) than T-cells in spleen (Ostanin D et al., J Immunol., 2012). Moreover, these infiltrated immature myeloid cells acquire the phenotype and function of APC within the inflamed bowel and contribute to disease progression. Therefore it is possible that some conditions such injury, inflammation and tumor growth stimulate extramedullar hematopoiesis in spleen that become an additional source of IMC which may contribute to outcome of disease. Although it has not been found directly how spleen-derived IMC contribute in cancer progression based on presented data it seems TFF2 to be the factor that suppresses proliferation of Gr1+CD11b+ cells in spleen and this accounts on less tumor incidence in cancer models associated with inflammation.

Anti-tumor activity of TFF2 was evaluated in two types of cancer models associated with inflammation: in colon cancer model initiated by AOM following DSS treatment and in skin cancer model initiated by DMBA following TPA treatment. In the first model it was found that TFF2−/− deficient mice are more susceptible while TG mice are more resistant to tumorigenesis. what is consistent with their higher susceptibility to inflammation and higher proportion of inflammatory Gr1+CD11b+ cells observed for these mice upon DSS treatment.

Extensive studies on mechanisms by which MDSCs exert their immunosuppressive function have been done as well factors that promote their expansion have been revealed. Attention should be dedicated to point which factors restrict expansion of MDSC.

REFERENCES

1. Gabrilovich, D. I., Nagaraj, S., Bronte, V., Chappell, D. B., Apolloni, E., Cabrelle, A., Wang, M., Hwu, P., Restifo, N. P., Gabriele, P., Malinverni, G., Moroni, G. L., Gatti, M., Regge, D., Versari, A., Serafini, D., Fraternali, A., Salvo, D., Serafini, P., Carbley, R., Noonan, K. A., Tan, G., Borrello, I., Dolcetti, L., Peranzoni, E., Ugel, S., Marigo, I., Fernandez Gomez, A., Mesa, C., Geilich, M., Winkels, G., Traggiai, E., Casati, A., Grassi, F., Elkabets, M., Ribeiro, V. S., Dinarello, C. A., Ostrand-Rosenberg, S., Di Santo, J. P., Apte, R. N., Vosshenrich, C. A., Li, H., Han, Y., Guo, Q., Zhang, M., Cao, X., Gabrilovich, D., Ishida, T., Oyama, T., Ran, S., Kravtsov, V., Nadaf, S., Carbone, D. P., Playford, R. J., Dignass, A., Lynch-Devaney, K., Kindon, H., Thim, L., Podolsky, D. K., Mashimo, H., Wu, D. C., Fishman, M. C., Kurt-Jones, E. A., Cao, L., Sandor, F., Rogers, A. B., Whary, M. T., Nambiar, P. R., Cerny, A., Bowen, G., Yan, J., Takaishi, S., Chi, A. L., Reed, G., Houghton, J., Fox, J. G., Wang, T. C., Lefebvre, O., Chenard, M. P., Masson, R., Linares, J., Dierich, A., LeMeur, M., Wendling, C., Tomasetto, C., Chambon, P., Rio, M. C., Farrell, J. J., Taupin, D., Koh, T. J., Chen, D., Zhao, C. M., Tomita, H., Menheniott, T. R., Yang, X., Shibata, W., Jin, G., Betz, K. S., Kawakami, K., Minamoto, T., Lerkowit, N., Varro, A., Giraud, A. S., Kim, H., Eun, J. W., Lee, H., Nam, S. W., Rhee, H., and Koh, K. H. (2009) Nat Rev Immunol 9, 162-174
2. Bronte, V., Chappell, D. B., Apolloni, E., Cabrelle, A., Wang, M., Hwu, P., and Restifo, N. P. (1999) *J Immunol* 162, 5728-5737
3. Serafini, P., Carbley, R., Noonan, K. A., Tan, G., Bronte, V., and Borrello, I. (2004) *Cancer Res* 64, 6337-6343
4. Dolcetti, L., Peranzoni, E., Ugel, S., Mango, I., Fernandez Gomez, A., Mesa, C., Geilich, M., Winkels, G., Traggiai, E., Casati, A., Grassi, F., and Bronte, V. *Eur J Immunol* 40, 22-35
5. Mango, I., Bosio, E., Solito, S., Mesa, C., Fernandez, A., Dolcetti, L., Ugel, S., Sonda, N., Bicciato, S., Falisi, E., Calabrese, F., Basso, G., Zanovello, P., Cozzi, E., Mandruzzato, S., and Bronte, V. *Immunity* 32, 790-802
6. Elkabets, M., Ribeiro, V. S., Dinarello, C. A., Ostrand-Rosenberg, S., Di Santo, J. P., Apte, R. N., and Vosshenrich, C. A. *Eur J Immunol* 40, 3347-3357
7. Li, H., Han, Y., Guo, Q., Zhang, M., and Cao, X. (2009) *J Immunol* 182, 240-249
8. Gabrilovich, D., Ishida, T., Oyama, T., Ran, S., Kravtsov, V., Nadaf, S., and Carbone, D. P. (1998) *Blood* 92, 4150-4166
9. Thim, L., Madsen, F., and Poulsen, S. S. (2002) *Eur J Clin Invest* 32, 519-527
10. Playford, R. J., Marchbank, T., Chinery, R., Evison, R., Pignatelli, M., Boulton, R. A., Thim, L., and Hanby, A. M. (1995) *Gastroenterology* 108, 108-116
11. Dignass, A., Lynch-Devaney, K., Kindon, H., Thim, L., and Podolsky, D. K. (1994) *J Clin Invest* 94, 376-383
12. Mashimo, H., Wu, D. C., Podolsky, D. K., and Fishman, M. C. (1996) *Science* 274, 262-265
13. Kurt-Jones, E. A., Cao, L., Sandor, F., Rogers, A. B., Whary, M. T., Nambiar, P. R., Cerny, A., Bowen, G., Yan, J., Takaishi, S., Chi, A. L., Reed, G., Houghton, J., Fox, J. G., and Wang, T. C. (2007) *Infect Immun* 75, 471-480
14. Lefebvre, O., Chenard, M. P., Masson, R., Linares, J., Dierich, A., LeMeur, M., Wendling, C., Tomasetto, C., Chambon, P., and Rio, M. C. (1996) *Science* 274, 259-262
15. Farrell, J. J., Taupin, D., Koh, T. J., Chen, D., Zhao, C. M., Podolsky, D. K., and Wang, T. C. (2002) *J Clin Invest* 109, 193-204
16. Tomasetto, C., and Rio, M. C. (2005) *Cell Mol Life Sci* 62, 2916-2920

17. Tomita, H., Takaishi, S., Menheniott, T. R., Yang, X., Shibata, W., Jin, G., Betz, K. S., Kawakami, K., Minamoto, T., Tomasetto, C., Rio, M. C., Lerkowit, N., Varro, A., Giraud, A. S., and Wang, T. C. *Gastroenterology* 140, 879-891

18. Shi, S. Q., Cai, J. T., and Yang, J. M. (2006) *World J Gastroenterol* 12, 3119-3122

19. Kim, H., Eun, J. W., Lee, H., Nam, S. W., Rhee, H., and Koh, K. H. *Exp Mol Pathol* 90, 201-209

20. Hong, S. J., Oh, J. H., Jung, Y. C., Kim, Y. H., Kim, S. J., Kang, S. J., Seo, E. J., Choi, S. W., Kang, M. I., and Rhyu, M. G. *J Korean Med Sci* 25, 405-417

21. Peterson, A. J., Menheniott, T. R., O'Connor, L., Walduck, A. K., Fox, J. G., Kawakami, K., Minamoto, T., Ong, E. K., Wang, T. C., Judd, L. M., and Giraud, A. S. (2005) *Gastroenterology* 139, 2005-2017

22. Fox, J. G., Rogers, A. B., Whary, M. T., Ge, Z., Ohtani, M., Jones, E. K., and Wang, T. C. (2007) *Am J Pathol* 171, 1520-1528

23. Kjellev, S., Thim, L., Pyke, C., and Poulsen, S. S. (2007) *Dig Dis Sci* 52, 1050-1059

24. Soriano-Izquierdo, A., Gironella, M., Massaguer, A., May, F. E., Salas, A., Sans, M., Poulsom, R., Thim, L., Pique, J. M., and Panes, J. (2004) *J Leukoc Biol* 75, 214-223

25. Tran, C. P., Cook, G. A., Yeomans, N. D., Thim, L., and Giraud, A. S. (1999) *Gut* 44, 636-642

26. FitzGerald, A. J., Pu, M., Marchbank, T., Westley, B. R., May, F. E., Boyle, J., Yadollahi-Farsani, M., Ghosh, S., and Playford, R. J. (2004) *Peptides* 25, 793-801

27. Babyatsky, M. W., deBeaumont, M., Thim, L., and Podolsky, D. K. (1996) *Gastroenterology* 110, 489-497

28. Vandenbroucke, K., Hans, W., Van Huysse, J., Neirynck, S., Demetter, P., Remaut, E., Rottiers, P., and Steidler, L. (2004) *Gastroenterology* 127, 502-513

29. Semple, J. I., Newton, J. L., Westley, B. R., and May, F. E. (2001) *Gut* 48, 648-655

30. Kjellev, S., Vestergaard, E. M., Nexo, E., Thygesen, P., Eghoj, M. S., Jeppesen, P. B., Thim, L., Pedersen, N. B., and Poulsen, S. S. (2007) *Peptides* 28, 1197-1206

31. Poulsen, S. S., Thulesen, J., Christensen, L., Nexo, E., and Thim, L. (1999) *Gut* 45, 516-522

32. Poulsen, S. S., Thulesen, J., Nexo, E., and Thim, L. (1998) *Gut* 43, 240-247

33. Poulsen, S. S., Kissow, H., Hare, K., Hartmann, B., and Thim, L. (2005) *Regul Pept* 126, 163-171

34. Cook, G. A., Familari, M., Thim, L., and Giraud, A. S. (1999) *FEBS Lett* 456, 155-159

35. Giraud, A. S., Pereira, P. M., Thim, L., Parker, L. M., and Judd, L. M. (2004) *Peptides* 25, 803-809

36. Baus-Loncar, M., Kayademir, T., Takaishi, S., and Wang, T. (2005) *Cell Mol Life Sci* 62, 2947-2955

37. Dubeykovskaya, Z., Dubeykovskiy, A., Solal-Cohen, J., and Wang, T. C. (2009) *J Biol Chem* 284, 3650-3662

38. Shibata, W., Ariyama, H., Westphalen, C. B., Worthley, D. L., Muthupalani, S., Asfaha, S., Dubeykovskaya, Z., Quante, M., Fox, J. G., and Wang, T. C. *Gut* 2012, 23

39. Wills-Karp, M., Rani, R., Dienger, K., Lewkowich, I., Fox, J. G., Perkins, C., Lewis, L., Finkelman, F. D., Smith, D. E., Bryce, P. J., Kurt-Jones, E. A., Wang, T. C., Sivaprasad, U., Hershey, G. K., and Herbert, D. R. *J Exp Med* 209, 607-622

40. Loos, M., De Creus, A., Thim, L., Remaut, E., and Rottiers, P. (2007) *Scand J Immunol* 66, 35-42

41. Zhumabekov, T., Corbella, P., Tolaini, M., and Kioussis, D. (1995) *J Immunol Methods* 185, 133-140

42. Tanaka, T., Kohno, H., Suzuki, R., Yamada, Y., Sugie, S., and Mori, H. (2003) *Cancer Sci* 94, 965-973

43. Tu, S., Chi, A. L., Lim, S., Cui, G., Dubeykovskaya, Z., Ai, W., Fleming, J. V., Takaishi, S., and Wang, T. C. (2007) *Am J Physiol Gastrointest Liver Physiol* 292, G1726-1737

44. Poulsom, R., Chinery, R., Sarraf, C., Lalani, E. N., Stamp, G., Elia, G., and Wright, N. (1992) *Scand J Gastroenterol Suppl* 192, 17-28

45. Rio, M. C., Chenard, M. P., Wolf, C., Marcellin, L., Tomasetto, C., Lathe, R., Bellocq, J. P., and Chambon, P. (1991) *Gastroenterology* 100, 375-379

46. Cook, G. A., Yeomans, N. D., and Giraud, A. S. (1997) *Am J Physiol* 272, G1540-1549

47. Henry, J. A., Bennett, M. K., Piggott, N. H., Levett, D. L., May, F. E., and Westley, B. R. (1991) *Br J Cancer* 64, 677-682

48. Alison, M. R., Chinery, R., Poulsom, R., Ashwood, P., Longcroft, J. M., and Wright, N. A. (1995)*J Pathol* 175, 405-414

49. Lang, G., Wotton, D., Owen, M. J., Sewell, W. A., Brown, M. H., Mason, D. Y., Crumpton, M. J., and Kioussis, D. (1988) *EMBO J* 7, 1675-1682

50. Lake, R. A., Wotton, D., and Owen, M. J. (1990) *EMBO J* 9, 3129-3136

51. Melgar, S., Karlsson, A., and Michaelsson, E. (2005)*Am J Physiol Gastrointest Liver Physiol* 288, G1328-1338

52. Melgar, S., Drmotova, M., Rehnstrom, E., Jansson, L., and Michaelsson, E. (2006) *Cytokine* 35, 275-283

53. Mikami, S., Nakase, H., Yamamoto, S., Takeda, Y., Yoshino, T., Kasahara, K., Ueno, S., Uza, N., Oishi, S., Fujii, N., Nagasawa, T., and Chiba, T. (2008) *J Pharmacol Exp Ther* 327, 383-392

54. Maloy, K. J., and Powrie, F. (2001) *Nat Immunol* 2, 816-822

55. Shevach, E. M. (2002) *Nat Rev Immunol* 2, 389-400

56. Stallmach, A., Wittig, B., Giese, T., Pfister, K., Hoffmann, J. C., Bulfone-Paus, S., Kunzendorf, U., Meuer, S. C., and Zeitz, M. (1999) *Gastroenterology* 117, 866-876

57. Veltkamp, C., Tonkonogy, S. L., De Jong, Y. P., Albright, C., Grenther, W. B., Balish, E., Terhorst, C., and Sartor, R. B. (2001) *Gastroenterology* 120, 900-913

58. Siegmund, B., Lehr, H. A., Fantuzzi, G., and Dinarello, C. A. (2001) *Proc Natl Acad Sci USA* 98, 13249-13254

59. Liu, C., Yu, S., Kappes, J., Wang, J., Grizzle, W. E., Zinn, K. R., and Zhang, H. G. (2007) *Blood* 109, 4336-4342

60. Hall, L. J., Faivre, E., Quinlan, A., Shanahan, F., Nally, K., and Melgar, S. (2011) *Dig Dis Sci* 56, 79-89

61. Almand, B., Clark, J. I., Nikitina, E., van Beynen, J., English, N. R., Knight, S. C., Carbone, D. P., and Gabrilovich, D. I. (2001) *J Immunol* 166, 678-689

62. Cortez-Retamozo, V., Etzrodt, M., Newton, A., Rauch, P. J., Chudnovskiy, A., Berger, C., Ryan, R. J., Iwamoto, Y., Marinelli, B., Gorbatov, R., Forghani, R., Novobrantseva, T. I., Koteliansky, V., Figueiredo, J. L., Chen, J. W., Anderson, D. G., Nahrendorf, M., Swirski, F. K., Weissleder, R., and Pittet, M. J. *Proc Natl Acad Sci USA* 109, 2491-2496

63. Leuschner, F., Rauch, P. J., Ueno, T., Gorbatov, R., Marinelli, B., Lee, W. W., Dutta, P., Wei, Y., Robbins, C., Iwamoto, Y., Sena, B., Chudnovskiy, A., Panizzi, P., Keliher, E., Higgins, J. M., Libby, P., Moskowitz, M. A., Pittet, M. J., Swirski, F. K., Weissleder, R., and Nahrendorf, M. *J Exp Med* 209, 123-137

64. Ling, V., Luxenberg, D., Wang, J., Nickbarg, E., Leenen, P. J., Neben, S., and Kobayashi, M. (1997) *Eur J Immunol* 27, 509-514

65. Angulo, I., de las Heras, F. G., Garcia-Bustos, J. F., Gargallo, D., Munoz-Fernandez, M. A., and Fresno, M. (2000) *Blood* 95, 212-220
66. Delano, M. J., Scumpia, P. O., Weinstein, J. S., Coco, D., Nagaraj, S., Kelly-Scumpia, K. M., O'Malley, K. A., Wynn, J. L., Antonenko, S., Al-Quran, S. Z., Swan, R., Chung, C. S., Atkinson, M. A., Ramphal, R., Gabrilovich, D. I., Reeves, W. H., Ayala, A., Phillips, J., Laface, D., Heyworth, P. G., Clare-Salzler, M., and Moldawer, L. L. (2007) *J Exp Med* 204, 1463-1474
67. Bunt, S. K., Sinha, P., Clements, V. K., Leips, J., and Ostrand-Rosenberg, S. (2006) J *Immunol* 176, 284-290
68. Ostrand-Rosenberg, S., and Sinha, P. (2009) *J Immunol* 182, 4499-4506
69. Poulsom, R., Begos, D. E., and Modlin, I. M. (1996) *Yale J Biol Med* 69, 137-146
70. Longman, R. J., Douthwaite, J., Sylvester, P. A., Poulsom, R., Corfield, A. P., Thomas, M. G., and Wright, N. A. (2000) *Gut* 47, 792-800
71. Podolsky, D. K. (2002) *Best Pract Res Clin Gastroenterol* 16, 933-943
72. Kitajima, S., Takuma, S., and Morimoto, M. (1999) *Exp Anim* 48, 137-143
73. Zhang, R., Ito, S., Nishio, N., Cheng, Z., Suzuki, H., and Isobe, K. I. (1111) *Clin Exp Immunol* 164, 417-427

Example 6: Splenic T-Cell Derived TFF2 Inhibits Inflammatory Carcinogenesis Through Suppression of Immature CD11b+Gr1+ Myeloid Cells Myeloid-derived suppressor cells (MDSCs) are a heterogeneous population of CD11b+Gr1+ cells that expand during cancer and can contribute to neoplastic progression. Trefoil factor 2 (TFF2), a small protease resistant protein expressed by the gastric epithelial cells and splenic T cells, can function in part as an anti-inflammatory peptide. Here, it is shown that in response to carcinogenic stimuli, TFF2 is upregulated in memory T cells in the spleen through a vagal neural circuit and functions to suppress proliferation of myeloid progenitor cells. Knockout of the TFF2 gene leads to an expansion of MDSC, and marked acceleration of tumor growth in response to AOM/DSS treatment. Moreover, overexpression of TFF2 in splenic T cells completely suppressed both MDSC expansion and colon cancer induction. Suppression of CD11b+Gr1+ cellular expansion by TFF2 correlated with an increase in CD8+ T cells in response to AOM/DSS colon carcinogenesis. In vitro studies showed that the effect of TFF2 involved a direct suppression of proliferation by granulocyte-macrophage progenitors (GMP) and CD11b+Gr1+ immature myeloid cells (IMC). Bone marrow transplant studies confirmed the role of hematopoietic TFF2 expression in inhibition of the cancer phenotype. Taken together, these studies validate the role for CD11b+Gr1+ cells in early cancer progression, and point to a possible therapeutic role for TFF2 in suppression of MDSCs and cancer.

Introduction

Tumor growth and progression can be accompanied by expansion of myeloid-derived suppressive cells (MDSCs), immune cells characterized in mice by the co-expression of surface markers Gr1 and CD11b (A1). MDSCs are a heterogeneous population of immature myeloid cells that accumulate in the bone marrow, spleen and peripheral blood of tumor-bearing mice, and can be elevated up to ten-fold in the blood of patients with diverse types of cancer. The accumulation and activation of MDSCs can occur in response to factors secrete by tumors, such as VEGF, GM-CSF, IL-6 and PGE2 (A2-A5, A6, A7, A8, A9, A10), which can also be increased in the setting of chronic inflammation. These carcinogenic and/or inflammatory factors can result in the expansion of MDSC through stimulation of myelopoiesis and inhibition of myeloid cell differentiation.

Expansion of CD11b+Gr1+ myeloid cells can also occur following trauma, infection and acute inflammation, but in cancer these cells persist and can acquire the profound ability to suppress T cell activation through multiple mechanisms (A1). Thus, the sustained expansion of MDSCs with immunosuppressive ability that can be seen in cancer is typically absent in acute inflammation. Resolution of inflammatory responses can be mediated by endogenous anti-inflammatory factors secreted by host immune cells in response to inflammatory signals (A2-A4). One anti-inflammatory pathway, termed the inflammatory reflex involves a neural reflex, whereby stimulation of the vagus nerve can activate acetycholine-synthesizing memory (CD4+ $CD44^{hi}$ $CD69L^{lo}$) T cells, which can inhibit cytokine release and attenuate inflammation-mediated injury (A5). These observations suggest the possibility that failure of these reflex anti-inflammatory mechanisms, which can normally limit the expansion of myeloid cells, can contribute to nonresolving inflammation and cancer.

The central nervous system can regulate the innate immune responses via the vagus nerve, a mechanism termed the cholinergic anti-inflammatory pathway. Vagus nerve stimulation can inhibit proinflammatory cytokine production by signaling through the alpha7 nicotinic acetylcholine receptor subunit expressed on macrophages, lymphocytes, neurons and other cells. The mechanism is called the inflammatory reflex. Administration of nicotine, an alpha7 agonist that mimics vagus nerve stimulation, can increase proinflammatory cytokine production and lethality from promicrobial sepsis in splenectomized mice, indicating that the spleen can be a major contributor to the anti-inflammatory effect via the cholinergic pathway.

Trefoil factor 2 (TFF2) is a secreted peptide that can function as an anti-inflammatory peptide. TFF2 is a member of the trefoil factor family (TFF), which in mammals includes three secreted proteins (TFF1, TFF2, and TFF3), each of which possesses a highly conserved triple loop structure (the trefoil domain) and are expressed in the gastrointestinal tract. TFF2, similar to other trefoil proteins, can play a role in mucosal repair and the maintenance of mucosal integrity through interactions with epithelial cells (A6-A8). However, TFF2 can also function as an anti-inflammatory peptide. TFF2-deficient mice at baseline show a minimal phenotype, but in response to DSS showed delayed healing and recovery (A14, A15). Studies have suggested that TFF2 can influence leukocyte migration, recruitment or responses (A10, A13, A16-A19). It has been shown that splenic T cells from TFF2-deficient mice are hyper-responsive to IL-1β stimulation, and that TFF2 can modulate signaling through CXCR4 and induce the release of IL-33 from lung epithelial, dendritic cells and macrophages, thus promoting a Th2 type immune response (A15, A20-22). The recognition that TFF2 can play a broader role in immune responses beyond the gastrointestinal tract was supported by the observation that TFF2 mRNA expression can be detected at low levels in rodents primary and secondary lymphatic organs (thymus and spleen), where expression was increased upon LPS treatment (A15, 16).

In addition, several studies have shown that TFF2 can be downregulated in cancer and may function as a tumor suppressor gene. Loss of TFF2 has been observed during the progression of human intestinal-type gastric cancer (A23, A24), and it has been shown that TFF2 expression is downregulated due to aberrant promoter methylation (A25, A26) in the setting of *H. pylori* infection. Moreover, TFF2-deficient mice progress more quickly to dysplasia in inflammatory models of gastric carcinogenesis (A26, A27).

In this example, it is shown that TFF2 is expressed in memory T cells, regulated by a vagal nerve circuit, and can function to suppress myelopoiesis in the spleen in response to inflammatory stimuli. Importantly, it is shown that TFF2 can function to suppress the development of myeloid-derived suppressor cells (MDSCs) in response to carcinogens, and that overexpression of TFF2 can markedly suppress gastrointestinal tumorigenesis.

Results

TFF2 can be Expressed in the Splenic CD4+ Memory T Cells and Regulated by the Vagus Nerve While previous studies revealed that TFF2 mRNA can be expressed in the rodent in spleen and regulated by inflammatory signals (A15, A16, A18), the precise cellular origin of TFF2 was not identified. Antibodies to the TFF2 C-terminus (A15) identified TFF2 protein in whole spleen as a band at the position similar to those detected in stomach of wild type mice by western blot (FIGS. 1A-B). Fractionation of resting splenic cells revealed higher TFF2 mRNA in T cells compared to B cells (FIG. 1C). Consistent with this finding, stimulation of murine splenocytes showed a 40-fold increase in TFF2 mRNA abundance with a T-cell specific mitogen (concavalin A) compared with a 2.5 fold increase with a B-cell specific mitogen (LPS) (FIG. 1D).

Given previous studies suggesting a protective role for trefoil peptides in rodent colitis models, and the upregulation of TFF2 in the gut in response to injury (A28-A31) (A7, A32, A33), TFF2 protein expression was analyzed in the whole spleen of wild type mice during administration of 3% DSS water, a marked increase was observed after 24 hours of DSS, with continued expression through day 19 (FIGS. 1E, 1G). Similar increases were observed in TFF2 mRNA expression in the DSS model.

Figure 18:
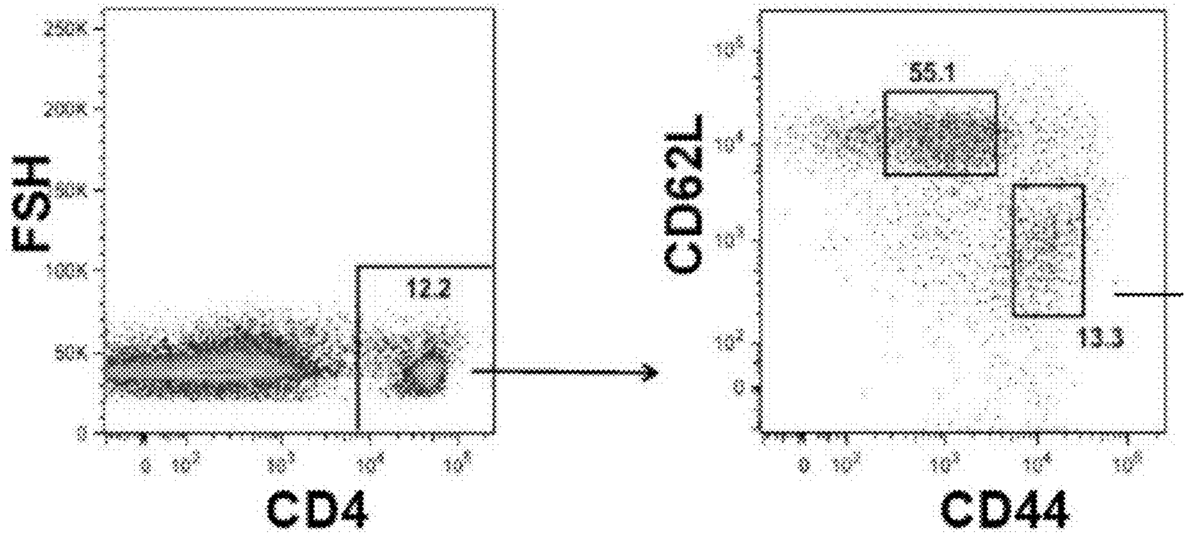
FIG. 18. Gating strategy for sorting of CD4+ memory T+ cells. Cell were gated on CD4+ live cells, then $CD44^{low}CD62L^{high}$ naïve and $CD44^{high}$ $CD62L^{low}$ memory cells were sorted and total mRNA fraction was extracted.
Figure 19:
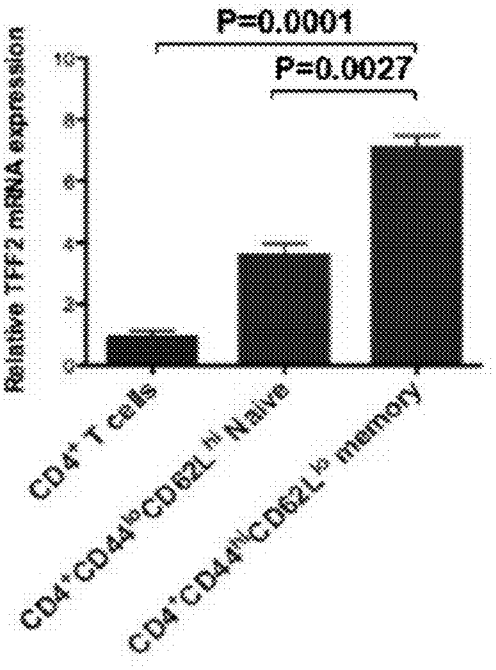
FIG. 19. TFF2 mRNA is up-regulated in splenic memory CD4+ T-cells of wild type mice upon DSS treatment. Wild type mice were challenged with 6% DSS for 48 h. Messenger RNA from total, naïve and memory CD4 T cells was purified and subjected Taqman RT-PCR analysis with TFF2 and GAPDH specific primers and probes. Relative TFF2/GAPDH abundance is plotted on the graph.
Figure 20:
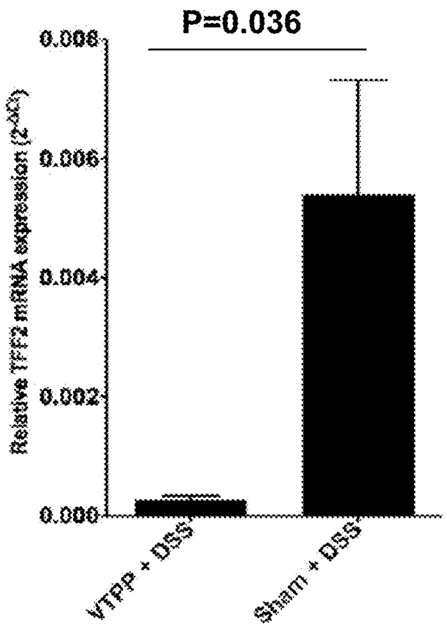
FIG. 20. Vagotomy results in TFF2 mRNA down-regulation in spleen of mice treated with DSS. Mice with vagotomy (VTPP) group and control mice without vagotomy (Sham) were given 6% for 48 h DSS water.
Figure 21:
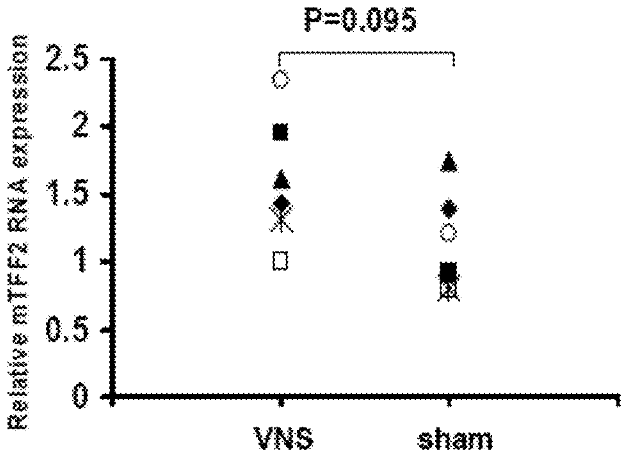
FIG. 21. is a plot showing that vagal nerve stimulation (VNS) does not change level TFF2 mRNA in spleen of untreated mice.
Figure 22:
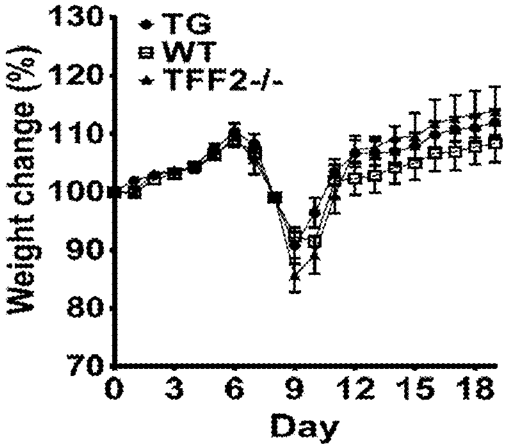
FIG. 22. Change of body weight over 19 days of TFF2−/−, WT and CD2-TFF2 mice. Mice were given 3% DSS in drinking water during 5 days, then mice were given tap water for 14 days. On day 19 mice were sacrificed.
Figure 23:
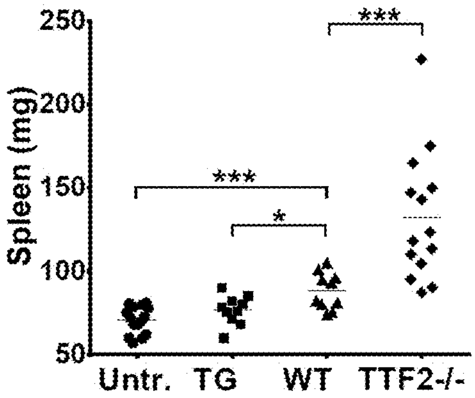
FIG. 23. DSS treatment results in splenomegaly in TFF2−/− mice. Quantification of spleen mass of transgenic, wild type and TFF2−/− mice upon DSS treatment.
Figure 24:
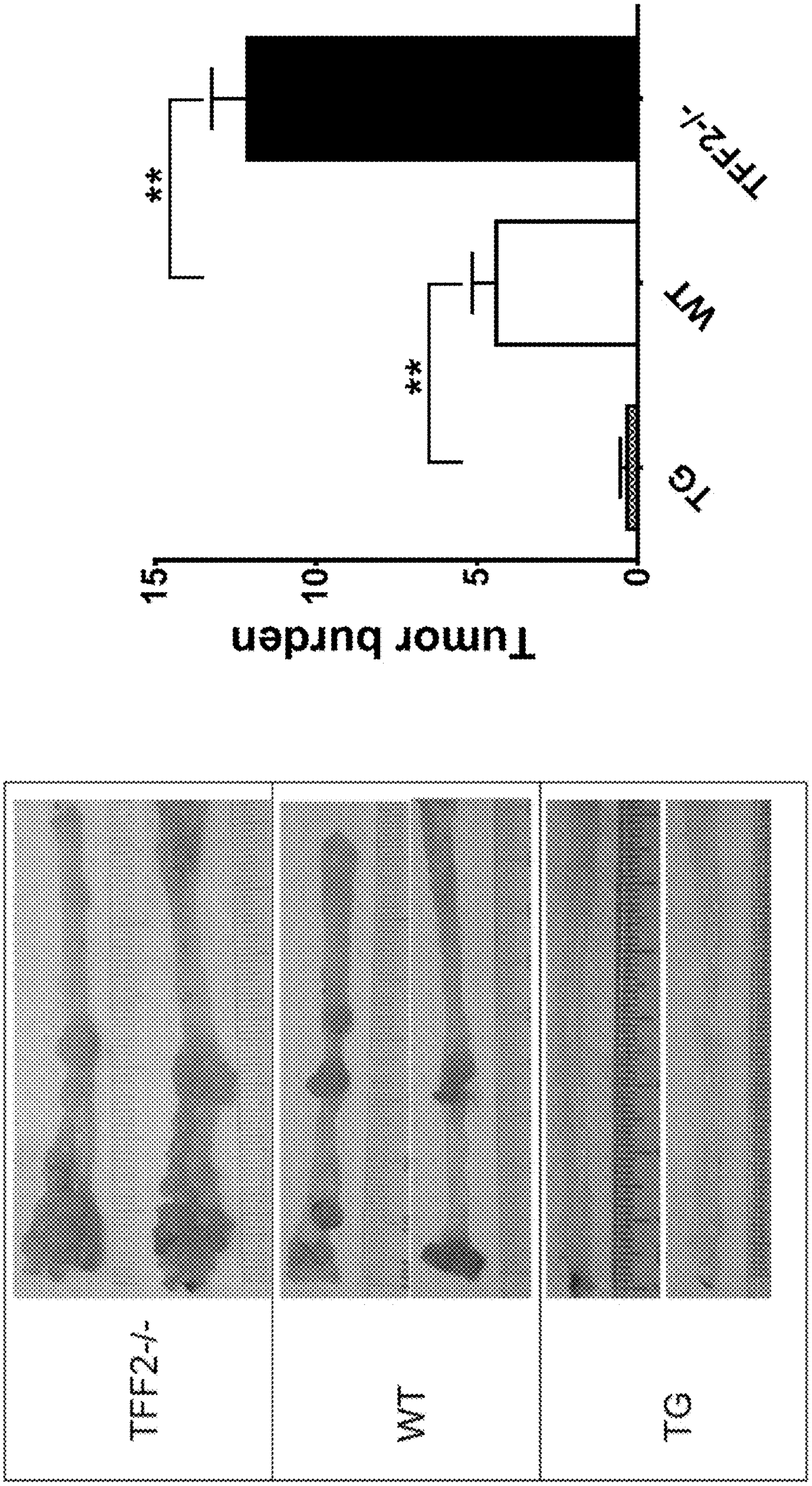
FIG. 24. TG mice are more resistant to AOM/DSS. Representative colons of TFF2/−, WT and TG (upper, middle and lower panels accordingly) mice after AOM/DSS treatment (left) and tumor burden of TFF2/−, WT and TG mice (right).
Figure 25:
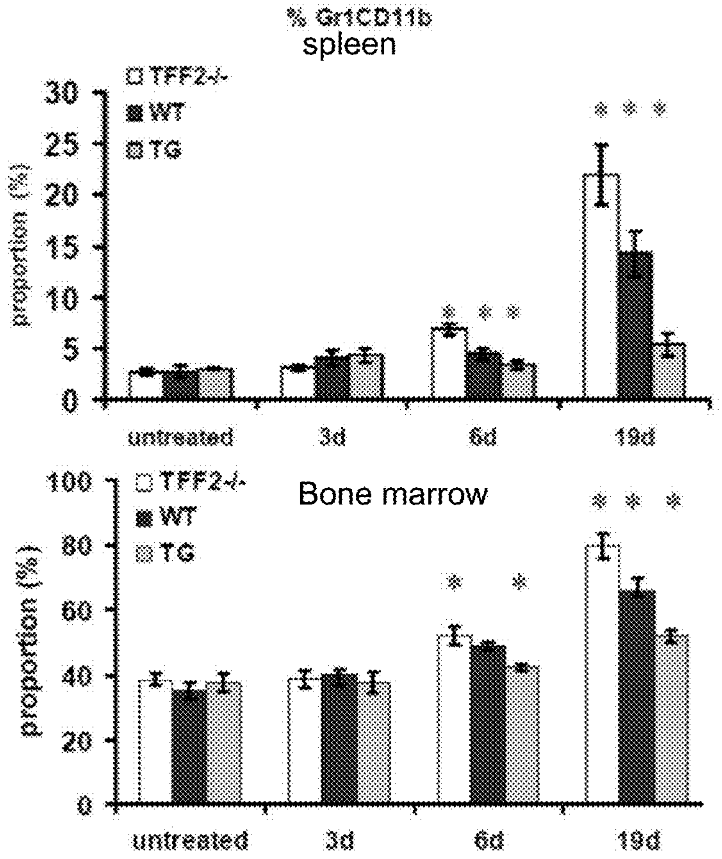
FIG. 25. are bar graphs depicting that TG mice show lowest proportion of CD11b+Gr1+ cells in spleen and bone marrow.

Stimulation of the vagus nerve can inhibit cytokine release and can downregulate systemic inflammation through interactions with memory CD4+ T cells, (A34-A36). TFF2 can also be part of an anti-inflammatory pathway, thus TFF2 expression in the same subset of memory CD4+ T-cells in spleen was analyzed (FIG. 18). Analysis of flow sorted splenic lymphocytes from DSS-treated mice revealed that memory CD4+ $CD44^{high}$ $CD62L^{low}$ T-cells expressed 8-fold higher TFF2 mRNA compared with unsorted total CD4+ T-cells (FIG. 19). Next, TFF2 mRNA levels were analyzed in spleens from mice with bilateral truncal vagotomy with pyloroplasty (VTPP) before and after 6% DSS treatment for 2 days compared with control mice without vagotomy. While VTPP did not alter TFF2 mRNA levels in spleen in untreated mice (FIG. 21), the increase in TFF2 mRNA levels following vagotomy was completely abrogated following vagotomy (FIG. 20). Taken together, these findings suggest that TFF2 can act as an anti-inflammatory peptide expressed in memory T cells and regulated by the vagus through the inflammatory reflex.

Transgenic Mice Overexpressing TFF2 in T-Cells Display Attenuated DSS Colitis.

Figure 27:
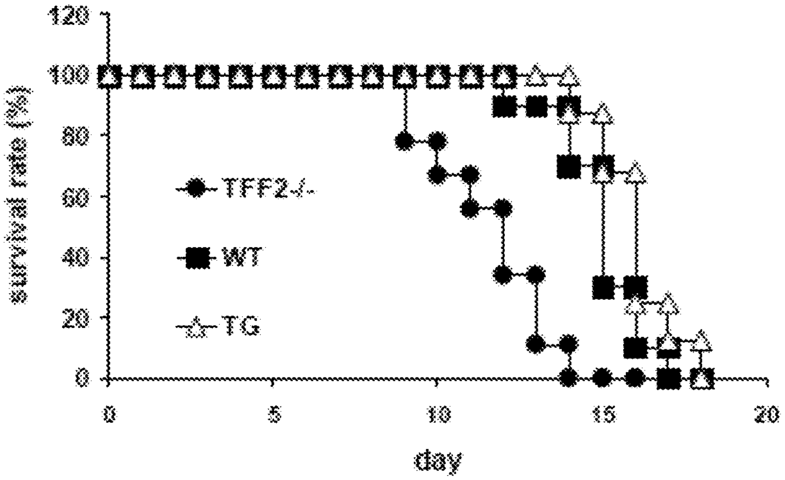
FIG. 27. Survival rate of TFF2−/−, CD2-TFF2, and wild type mice upon 3% DSS treatment. Mortality was assessed as the primary endpoint. Differences in survival curves between two groups were analyzed using the Log-rank (Mantel Cox) test. Representative data of one of two independent experiments (n=12 per TFF2−/−, n=8 per WT, n=7 per TG mice).
Figure 28:
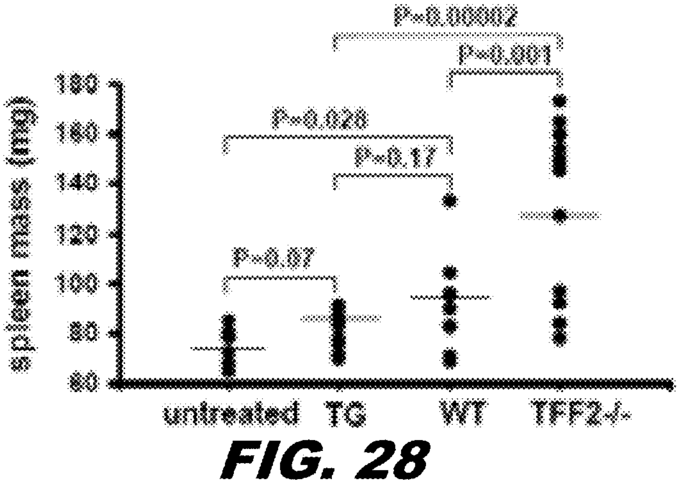
FIG. 28. Change of spleen mass of TFF2−/−, WT and CD2-TFF2 mice. Mice were given 3% DSS in drinking water during 5 days, then mice were given tap water for 14 days. On day 19 mice were sacrificed.
Figure 29:
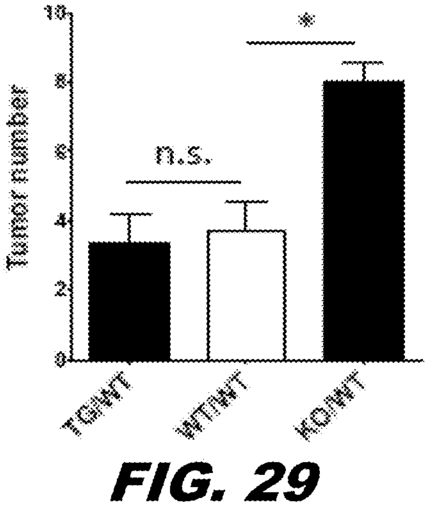
FIG. 29. Mice with bone marrow transplanted from TFF2−/mice develop more tumors compare with wild type and CD2-TFF2 transgenic mice. Wild type mice were lethally irradiated and bone marrow from wild type, CD2-TFF2 and TFF2−/mice was transplanted. Animals were submitted AOM/DSS treatment and analyzed after 5 months.

Given the upregulation of TFF2 in response to inflammation, and its suggested role as an anti-inflammatory peptide, the ability of TFF2 overexpression in the immune compartment to suppress acute or chronic inflammation was tested. Transgenic mice that overexpress murine TFF2 specifically within T cells were generated using a well-established CD2 promoter construct (FIG. 2A) (A37, A38). TFF2 mRNA and protein was detected in the spleen and thymus of CD2-TFF2 F1 offspring (FIGS. 2B-2C). CD2-TFF2 transgenic mice appear phenotypically normal and showed no difference in the proportion of T and B-subsets in spleen and T-cells subsets in thymus. TFF2-null mice exhibited greater susceptibility to colitis following exposure DSS (A15), with increased spleen size (FIG. 28), a marked reduction in colon length (FIG. 3B), increased MPO activity (FIG. 4E), and a higher mortality rate (FIGS. 3A, 27) compared to other groups. However, CD2-TFF2 transgenic mice did not statistically differ from wild type mice, although there was a slight trend towards increased survival. There was no difference in body weight change after one cycle of DSS between all groups. Nevertheless, CD2-TFF2 transgenic mice did show lower levels of IL-1β in their colons compared to WT mice in the DSS model, and IL-1β levels were even higher in TFF2−/− mice (FIG. 4A). Histological examination of the colon at day 19 revealed inflammation, crypt atrophy, and erosions in all groups of mice, with a trend toward less inflammation in the CD2-TFF2 transgenic mice (FIG. 3G).

Since TFF2 can be expressed in the gastric epithelium as well as T-cells, bone marrow transplantation experiments were performed to assess the importance of hematopoietic derived TFF2. Lethally irradiated wild type mice were transplanted with bone marrow from TFF2-null, wild-type and CD2-TFF2 mice; colitis was induced using 3% DSS in the drinking water for 5 days followed by regular water, and animals were assessed on day 19. Transplantation with CD2-TFF2 bone marrow, compared to WT bone marrow, resulted in attenuated colitis as revealed by greater body weight, normal spleen mass and colonic length; in contrast, mice transplanted with TFF2-null bone marrow, compared to WT bone marrow, showed significantly greater loss of body weight, larger spleens, shorter colons and higher levels of IL-1β (FIGS. 5A-5C, 5E). Taken together, these results suggest a role for hematopoietic-derived TFF2 in modulating acute inflammation.

Overexpression of TFF2 by Splenic T Cells can Suppress the Development of AOM/DSS-Induced Colon and Rectal Tumors Previous studies have suggested that TFF2 is a tumor suppressor gene. The influence of overexpression of TFF2 on the development of colon and rectal cancer was tested. TFF2-null, wild type and CD2-TFF2 groups were subjected to the AOM/DSS regimen, and colonic tumors were quantified five months later. Both wild type and TFF2-null mice developed tumors in the third part of distal colon, with the TFF2-null mice showing the greatest tumor load (FIGS. 11A-B). TFF2-null mice showed an average tumor burden that was 3× the tumor burden in WT mice (P=0.0002). Most of the of CD2-TFF2 mice (approximately 80-100%) were tumor free, and no animal in this group developed more than a one lesion. The average tumor burden in CD2-TFF2 transgenic mice was <1 (p−0.004).

Figures 26A, 26B:
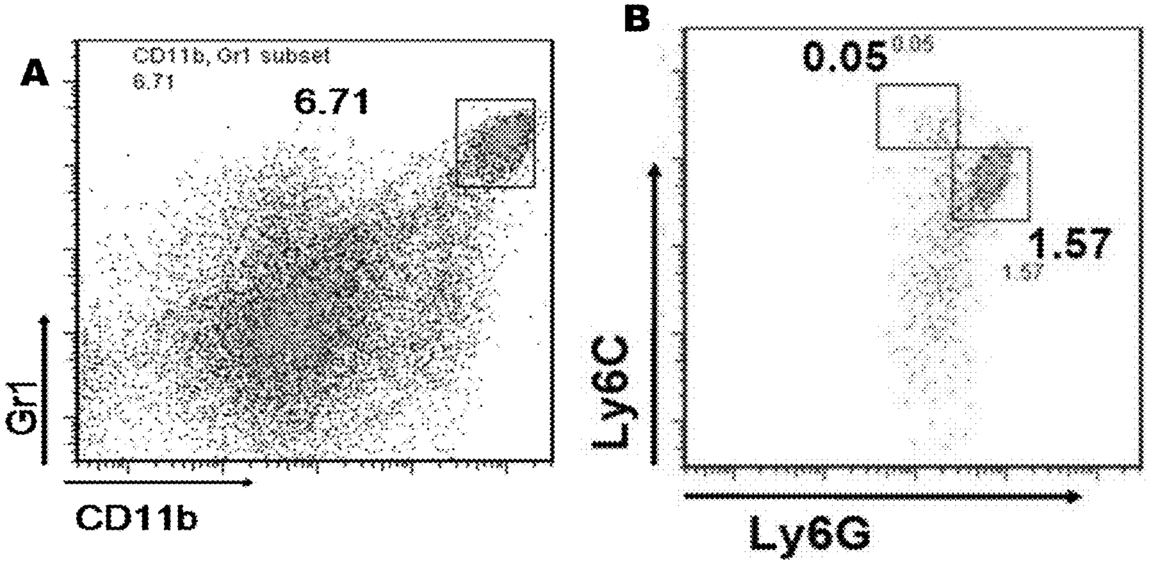
FIGS. 26A-B. Representative flow cytometry dot plots showing the percentage of CD11b+Gr1+ cells in tumor tissue of TFF2−/− mice 5 months after AOM/DSS regimen.

Histological examination of adenomas from TFF2-null mice revealed greater degrees of dysplasia, and increased inflammatory cell infiltration in colonic tissues of TFF2-null mice compared with wild type counterparts (FIG. 11C). The inflammatory cells in the colonic tumors were a heterogeneous population of leukocytes, including CD11b+Gr1+ cells with majority of granulocytic $CD11b+Ly6G+Ly6C^{lo}$ subset (FIGS. 26A-B). The greater tumor burden in the TFF2-null group correlated with an expanded CD11b+Gr1+ cell population in the spleen, bone marrow and blood (FIG. 11D). CD2-TFF2 mice showed the same proportion of CD11b+Gr1+ cells in the bone marrow as wild type mice, but a significantly lower proportion of these cells in the spleen and peripheral blood. Consistent with the increase in colonic myeloid cells, there was increased IL-β mRNA levels in colonic tumors from TFF2−/− deficient mice compared to colonic tumors from wild type and CD2-TFF2 mice (FIGS. 11F, 58, 59A-B), while IL-β (and IL-6) mRNA levels were lower in tumors from CD2-TFF2 transgenic mice. Accumulation of CD11b+Gr1+ cells in tumors correlated with highest IL-1β level in tumor site compare with colonic tissues without visible tumor (FIG. 59C). As has been reported earlier splenic CD11b+Gr1+ cells consist of two populations expressing Ly6G and Ly6C markers with majority of granulocyte antigen Ly6G (FIG. 59D).

TFF2 Inhibits Cancer Through Suppression of MDSCs.

Figure 60:
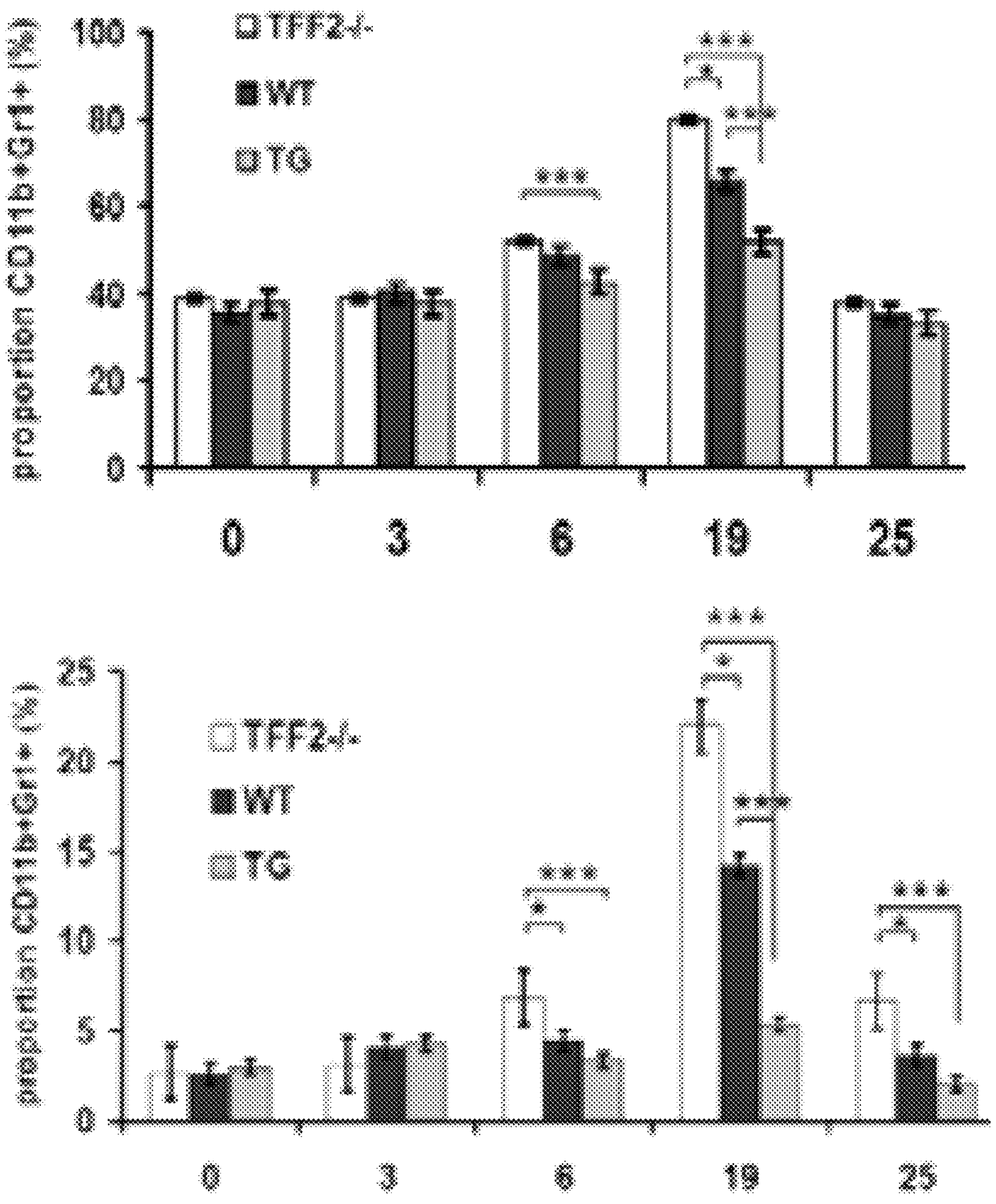
FIG. 60. CD11b+Gr1+ cells expand temporally in spleen and bone marrow upon DSS treatment. Bars represent percentages of CD11b+Gr1+ cells among analyzed live cells. The means and standard deviations were calculated based on data for 3-6 animals per group. Asterisks indicate a statistically significant difference (*P<0.05, ***P<0.001) in CD11b+Gr1+ cell number between tested groups.

The increase in tumorigenesis seen in the TFF2−/− mice was associated with splenomegaly and accumulation of CD11b+Gr1+ myeloid cells, while the suppression of tumors in CD2-TFF2 transgenic mice correlated with a lack of splenic enlargement. DSS-induced colitis has previously been associated with splenic enlargement and a significant increase in CD11b+Gr1+ cells (A39-A41). While under normal physiological conditions, TFF2−/− mice and CD2-TFF2 transgenic mice showed normal spleen size and proportions of CD11b+Gr1+ cells in spleen and bone marrow, in response to DSS, TFF2-null mice showed significantly more Ki67+ proliferating Gr1+ cells than wild-type mice, while CD2-TFF2 mice showed fewer Ki67+ proliferating Gr1+ cells compared to WT mice (FIGS. 7A-B). Importantly, staining for Ki67 was most abundant in the red pulp zone where myeloid cells reside. In response to DSS-treatment, the proportion of CD11b+Gr1+ cells in the spleen and bone marrow increased over time in TFF2-null and wild type mice with a peak occurring on day 19, whilst in the CD2-TFF2 transgenic mice there was a minimal increase in this myeloid lineage (FIGS. 7C, 60).

Figure 39:
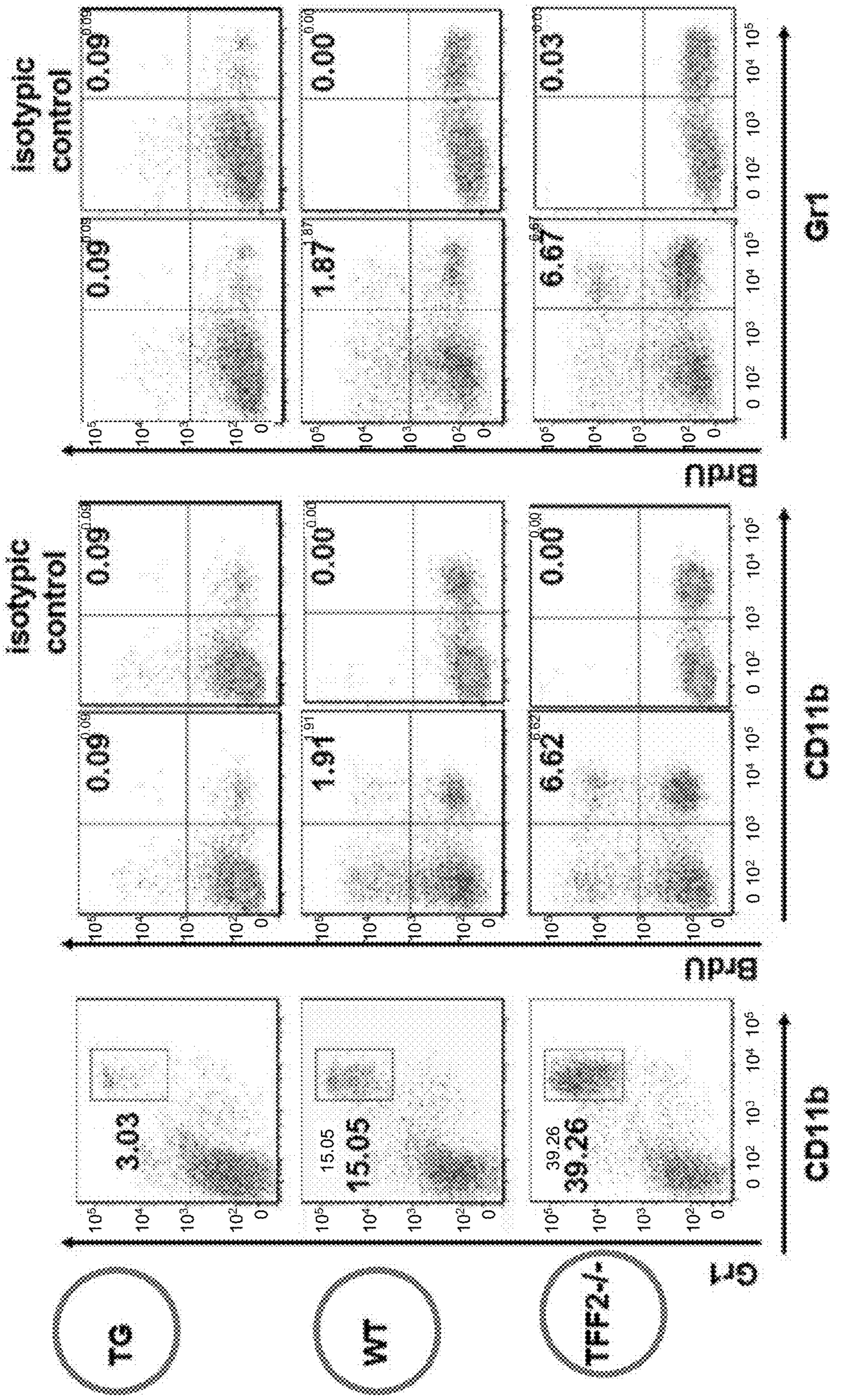
FIG. 39 shows plots that depict splenic CD11b+Gr1+ cells from TFF2−/− mice show higher capacity for proliferation compare with IMCs from wild type and CD2-TFF2 mice. BrdU was injected 3 h before sacrifice.
Figure 41:
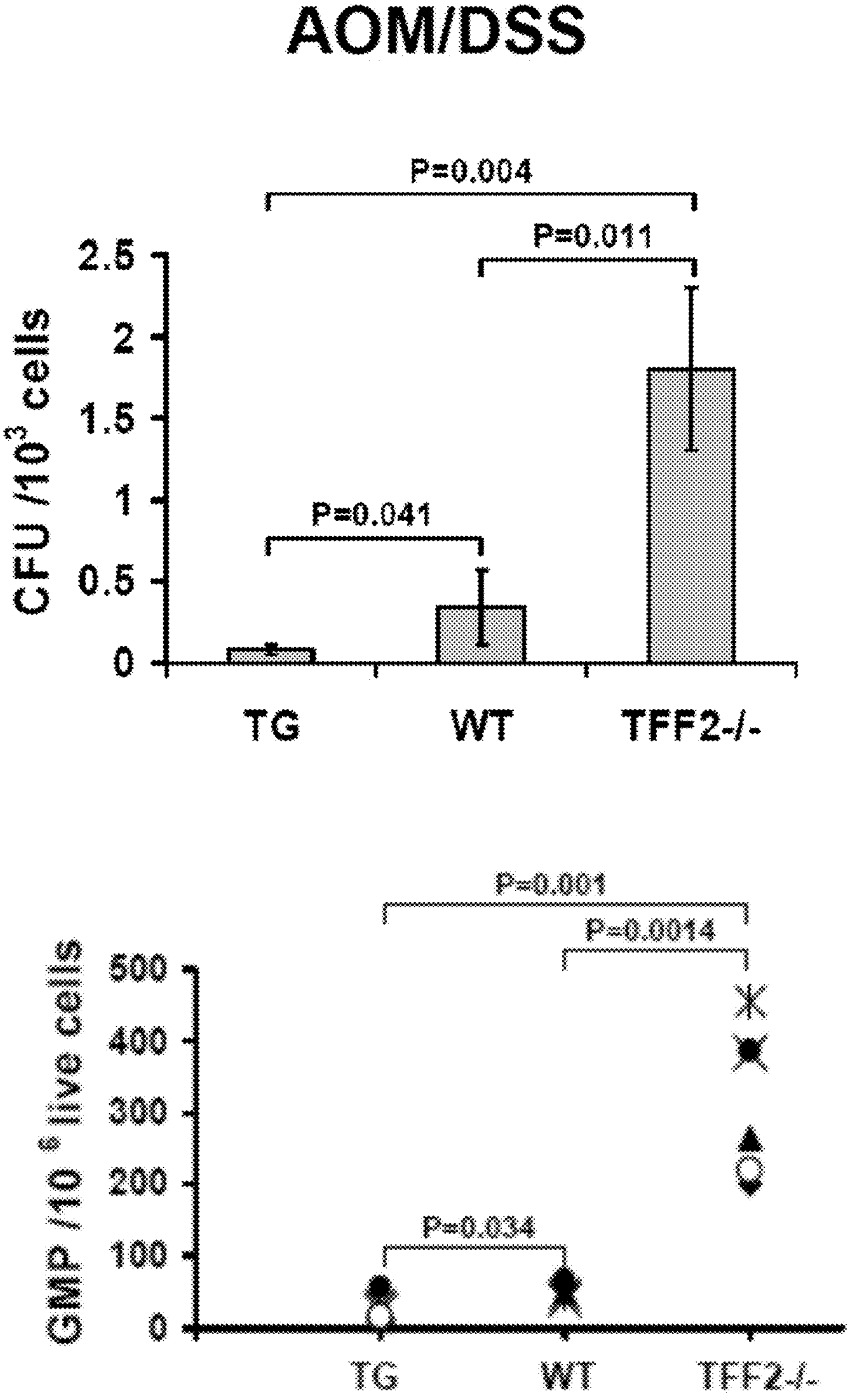
FIG. 41 is a bar graph (top) and plot (bottom) showing TFF2-deficiency results in a higher number of splenic CFU and GMP in the AOM/DSS model.
Figure 42:
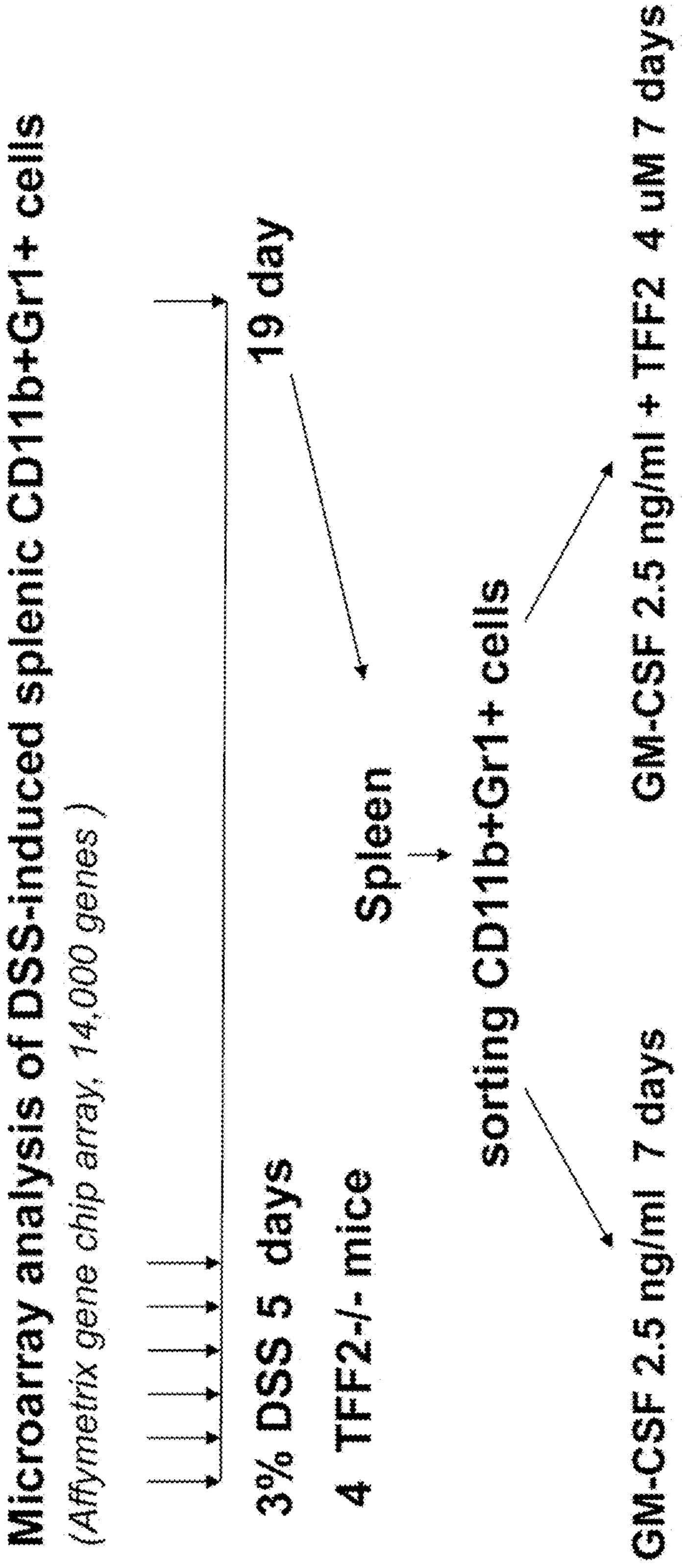
FIG. 42 is a schematic of a microarray analysis of DSS-induced splenic CD11b+Gr1+ cells workflow.
Figure 43:
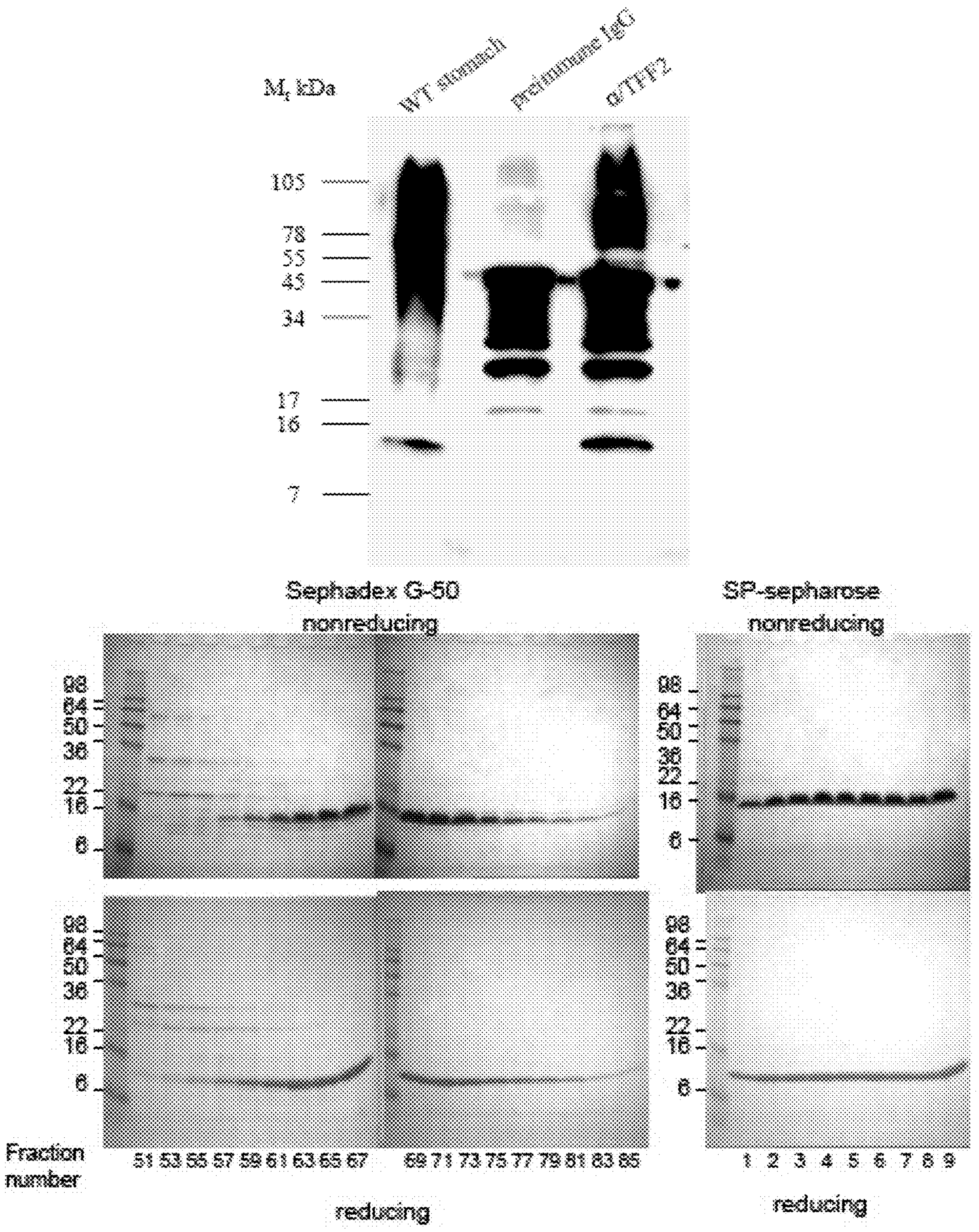
FIG. 43 shows images of western blots of mouse recombinant TFF2 that is expressed by Ad-TFF2 system and secreted in medium.

BrdU labeling studies of DSS treated mice revealed that CD11+Gr1+ myeloid cells in the spleens of WT mice proliferate during the recovery phase of DSS-induced colitis; however, splenic IMC's from TFF2-deficient mice showed greater BrdU uptake than the other two groups (FIG. 39). Up to 7% of CD11b+Gr1+ cells incorporated BrdU in TFF2-null mice, and less than 2% and 0.1% of CD11b+Gr1+ cells from wild-type and CD2-TFF2 animals were positive for BrdU staining.

Figure 16B:
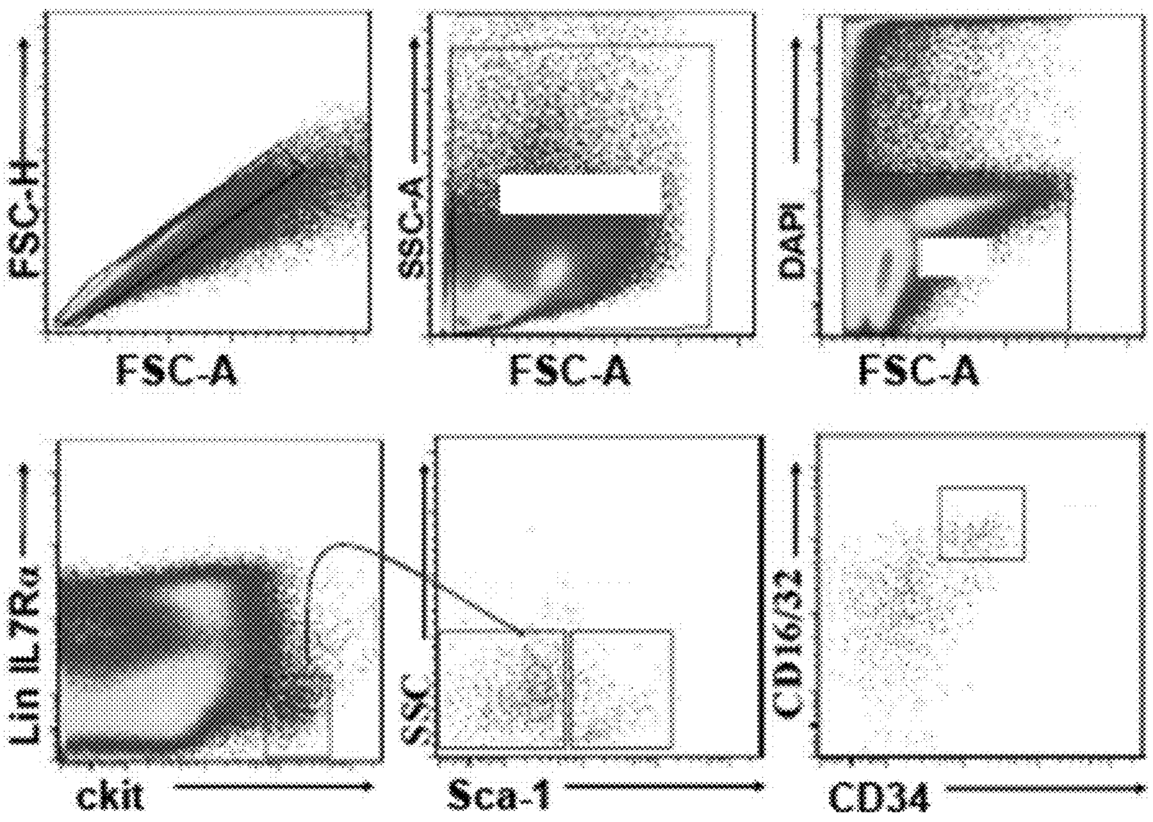
FIG. 16B. Gr1+ and CD11b+ cells from spleen of transgenic, wild type and TFF2−/− deficient mice proliferate during recovery phase of DSS-induced colitis. Gating strategy for analysis of myeloid progenitor cells (GMP). Dead cells were excluded from analysis by staining cells with (DAPI). DAPI-negative population was gated inside of lineage-negative (Lin−) cells along with IL-7Rα-negative cells, and then cells were analyzed for progenitors cells. GMP cells were identified as Lin−IL-7Rα− ckit+ cells, CD34+CD16/32+ population within ckit+Sca− cells.
Figure 17:
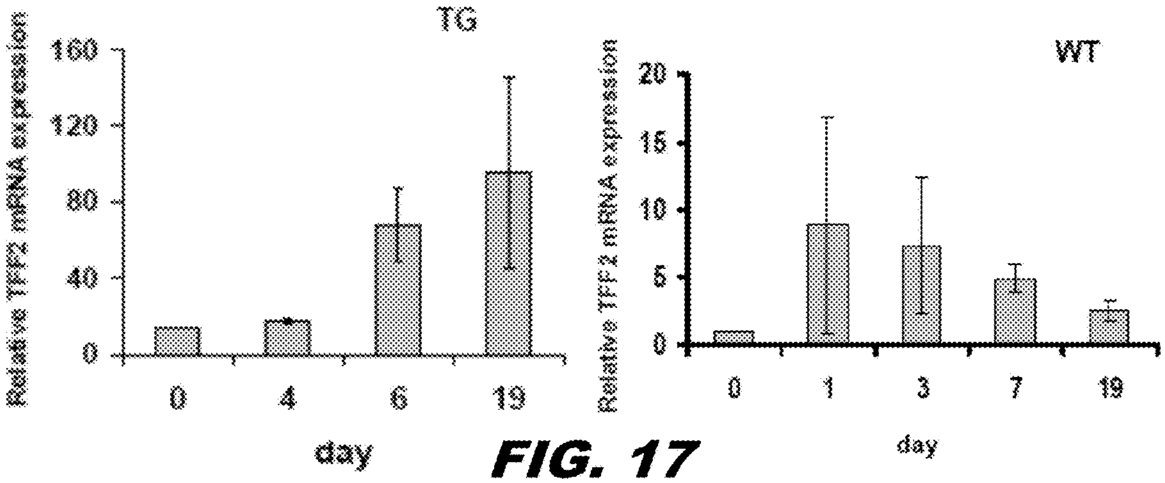
FIG. 17. are bar graphs showing TFF2 is up-regulated in spleen upon DSS treatment.
Figure 30:
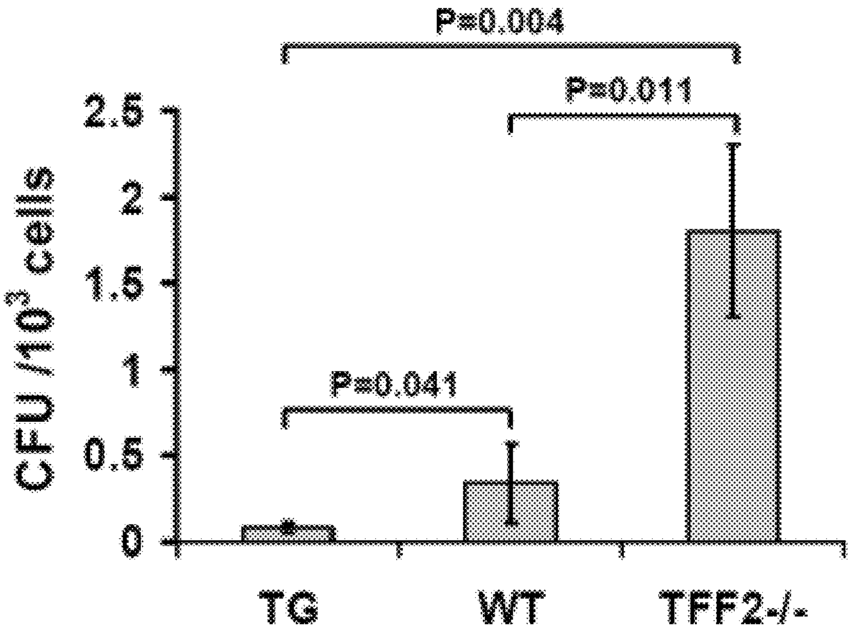
FIG. 30 is a bar graph showing increased CFU in spleen of TFF2−/− but not in CD2-TFF2 transgenic mice treated with DSS, day 19.
Figure 31:
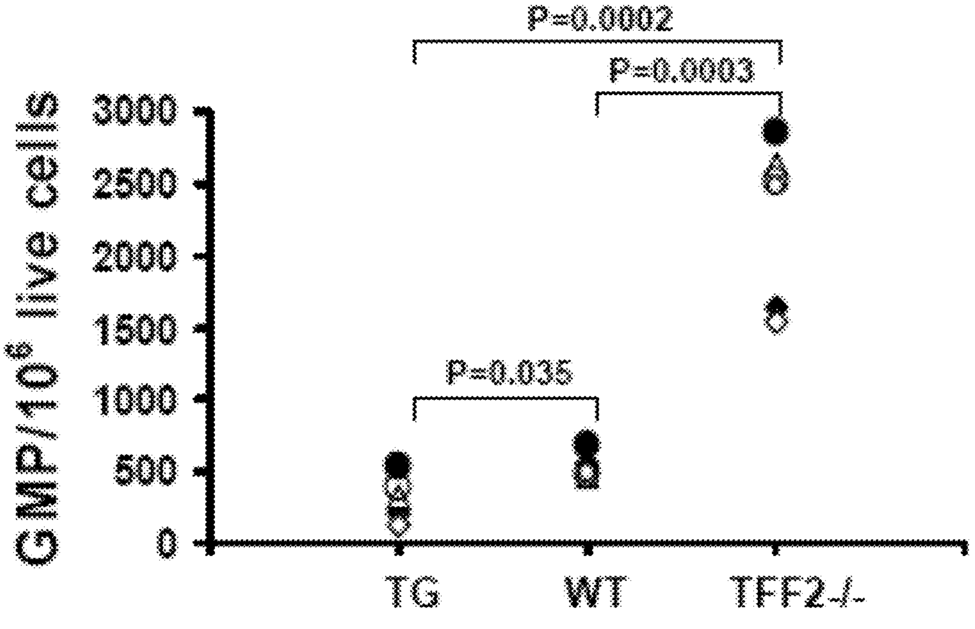
FIG. 31 is a plot showing increased GMP progenitor number in spleen of TFF2−/− but not in CD2-TFF2 transgenic mice treated with DSS, day 19.
Figure 32:
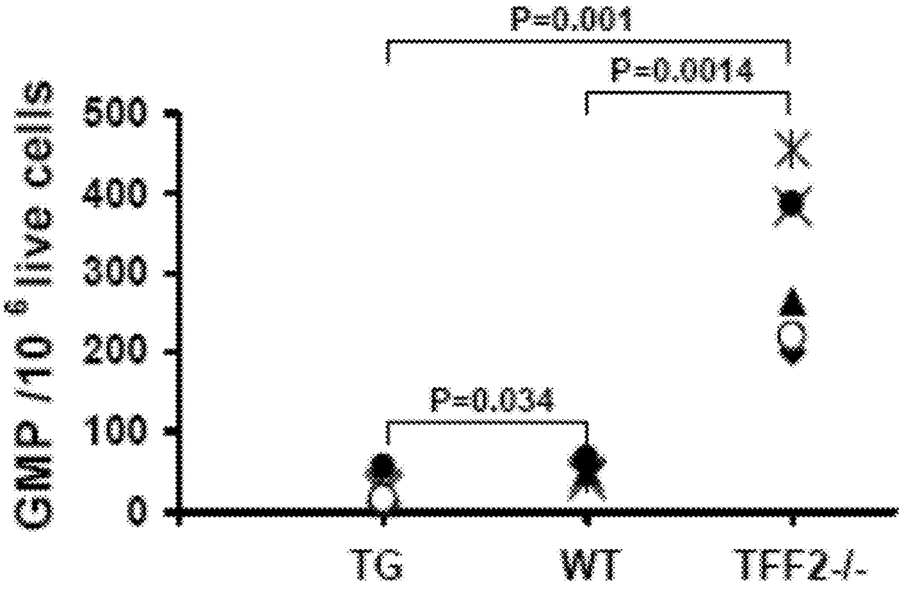
FIG. 32 is a plot showing increased GMP progenitor number in spleen of TFF2−/− but not in CD2-TFF2 transgenic mice treated AOM/DSS

TFF2 can modulate the splenic accumulation of myeloid progenitor cells, such as the granulocyte/macrophage precursor (GMP), what give rise to CD11b+Gr1+ cells following their expansion in the spleen (A42). The relative colony-forming capacity of splenocytes obtained from all groups of mice on day 19 after DSS treatment was studied. Splenocytes from CD2-TFF2 mice showed the lowest capacity to form colonies, while splenocytes from TFF2-null mice formed significantly more colonies compared with those from wild type and CD2-TFF2 counterparts (FIG. 30). In parallel FACS analysis was used to evaluate the number of splenic precursors GMP by defining them as Lin-IL-7Rα-c-kit+Sca-1-CD16/32+CD34+ cells (FIG. 16B) (A43). TFF2-null mice show at least 10 fold higher number of GMP precursors compared with wild and transgenic mice (FIG. 31). In the AOM/DSS model, splenocytes from TFF2-null mice again showed a greater capacity to form colonies on granulocyte/macrophage supporting media and a greater number of splenic GMPs compared to splenocytes from wild-type and CD2-TFF2 mice (FIG. 32).

FACS sorted DSS-induced CD11b+Gr1+ cells from TFF2−/− mice contained a mixed population of cells with ring shaped and large nucleus segmented nuclei (FIG. 9A) that expressed macrophage antigen F4/80, dendritic cell marker CD11c, CD31 and CD115 but low levels of MHC class II and co-stimulatory molecules CD86, CD80 and CD40 (FIG. 61A) (A44-A47). They also were positive for monocytic Ly6C and granulocytic Ly6G markers with a higher proportion of the subpopulation expressing Ly6G antigen (FIG. 61B). DSS-induced CD11b+Gr1+ cells sorted from the spleens of TFF2−/− mice displayed weak or no suppression on proliferation of polyclonally activated CD4+ T-cells in vitro.

Figure 33:
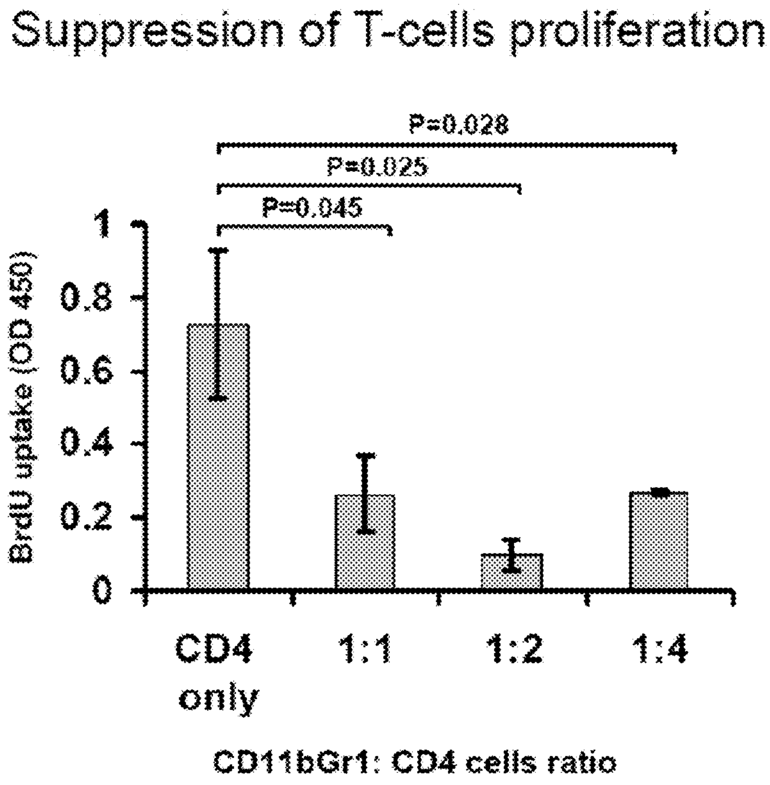
FIG. 33 is a bar graph showing CD11b+Gr1+ cells suppress BrdU uptake by polyclonally activated CD4+ T-cells.
Figure 34:
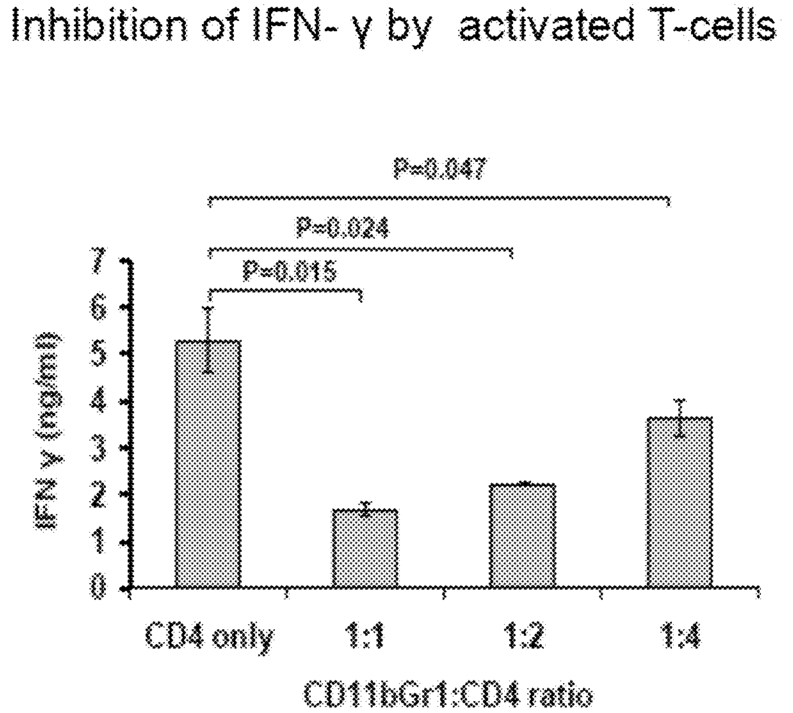
FIG. 34 is a bar graph showing that CD11b+Gr1+ cells suppress INF-γ production by polyclonally activated CD4+ T-cells.
Figure 35:
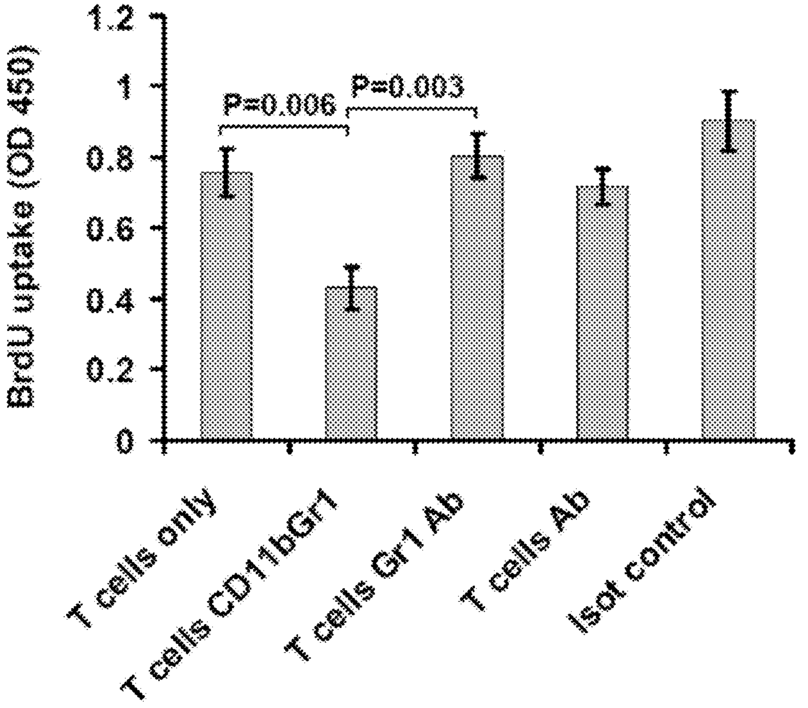
FIG. 35 is a bar graph showing that CD80 Ab abrogate the suppressive effect of CD11b+Gr1+ cells.
Figure 36:
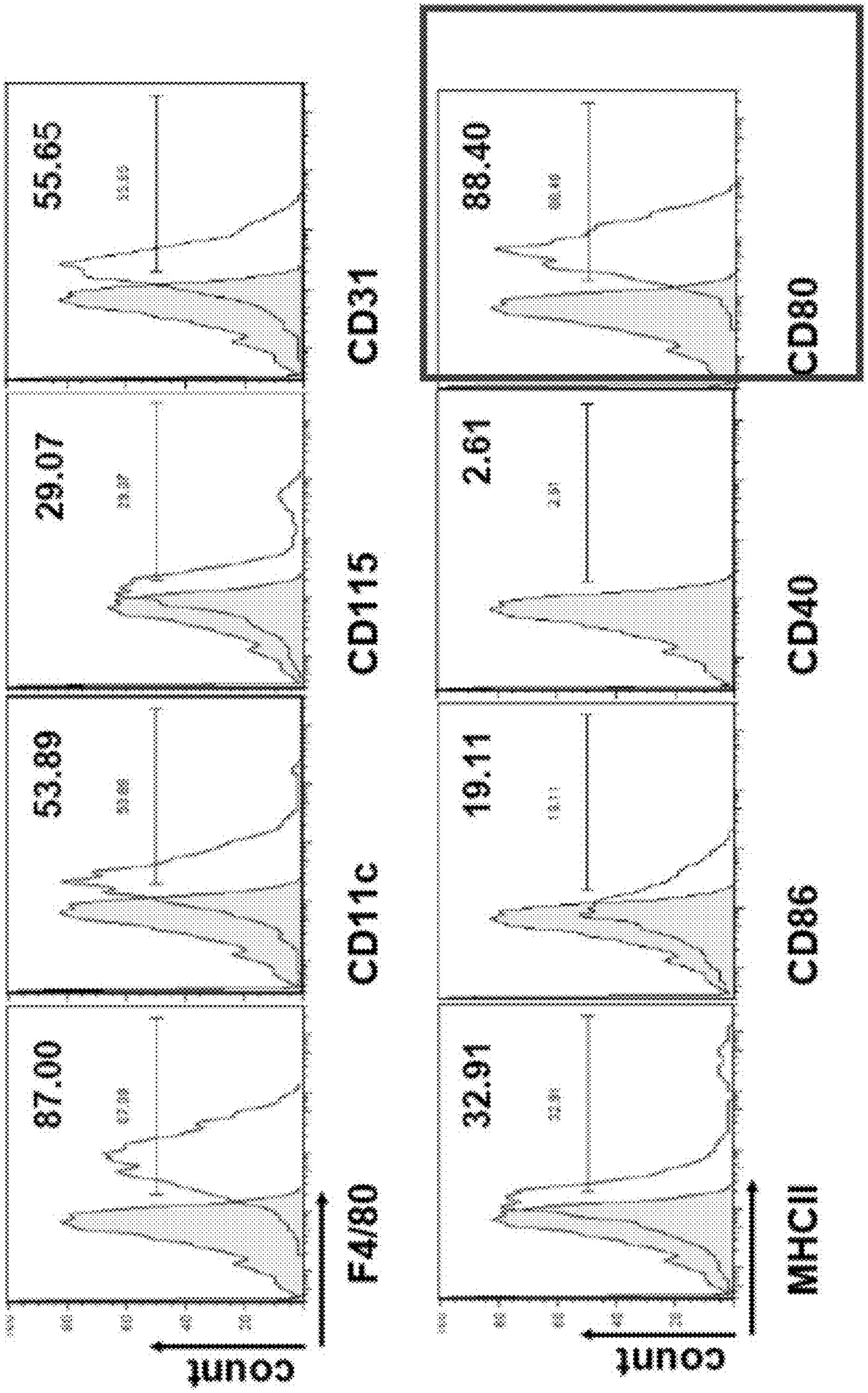
FIG. 36. are plots showing phenotype characterization and increase of CD80 marker expression on MDSCs after AOM/DSS treatment in spleen of TFF2−/− mice.

Splenic CD11b+Gr1+ cells from tumor-bearing TFF2−/− mice highly expressed the CD80 co-stimulatory molecule on their surface (FIG. 36). CD80+CD11b+Gr1+ have been shown to be myeloid derived suppressor cells (MDSC) that accumulated in spleen, ascites and tumor tissue (A48), with CD80 playing a role in suppression of T-cell specific response. Sorted splenic CD11b+Gr1+CD80+ cells significantly inhibited in vitro proliferation of CD4+ T-cells activated with CD3/CD28 antibody and showed a decrease of INF-γ production (FIGS. 33, 34). In contrast, CD11b+Gr1+ cells from spleens of CD2-TFF2 mice that expressed much lower levels of surface CD80 did not suppress proliferation/INF-γ expression of activated T-cells (FIGS. 61A, 61D-E). Addition of CD80 neutralizing CD80 Ab significantly abrogated the suppressive effect of CD11b+Gr1+ cells on T-cells proliferation (FIG. 35). CD11b+Gr1+ cells did not produce nitric oxide or arginase I.

Figure 37:
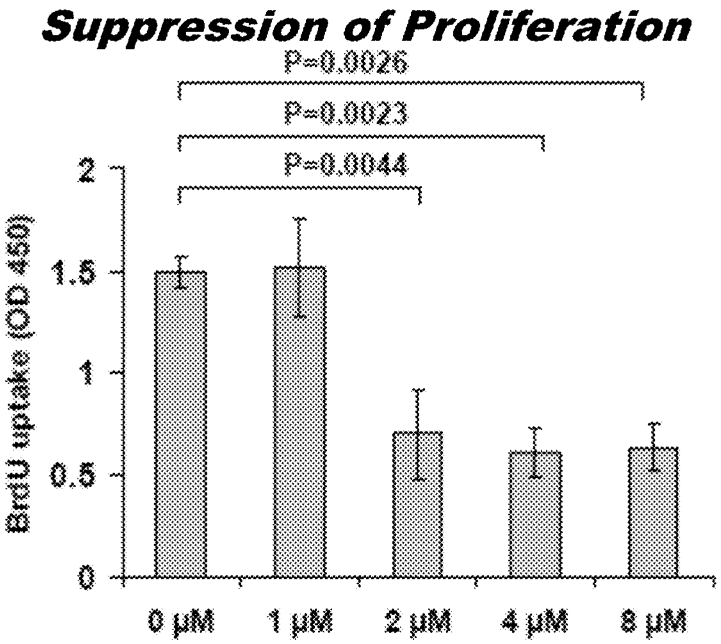
FIG. 37. TFF2 directly suppresses BrdU uptake by IMC in response to GM-CSF. in vitro IMCs were sorted from spleen of TFF2−/− mice treated with DSS and cultured in presence of GM-CSF for 7 days.
Figure 38:
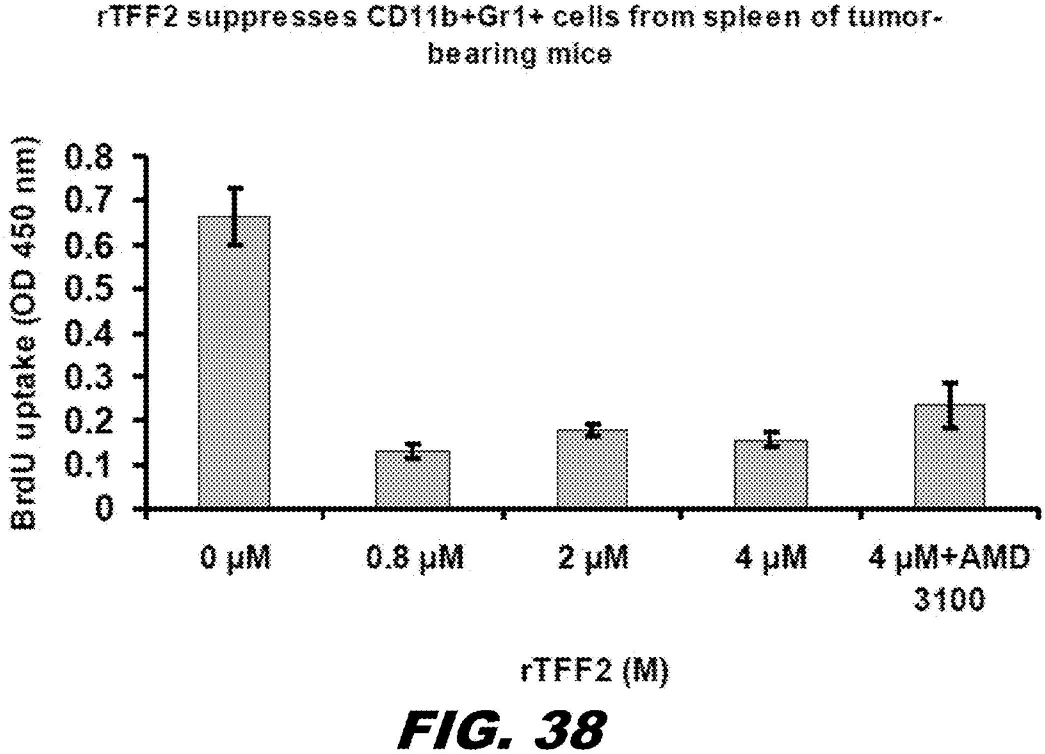
FIG. 38 is a bar graph showing recombinant TFF2 suppresses CD11b+Gr1+ cells from spleen of tumor-bearing mice.
Figure 45:
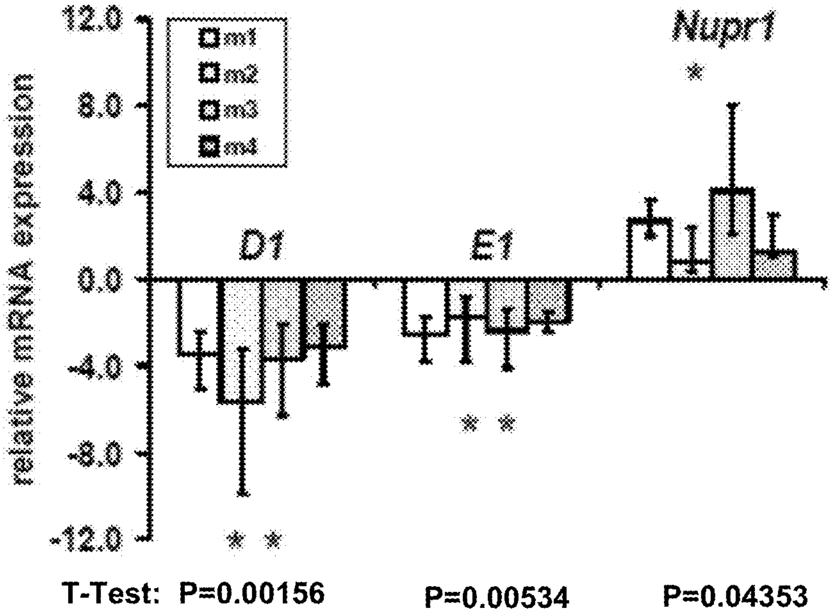
FIG. 45. qPCR Analysis. TFF-2 down-regulates cyclin D1, cyclin E1 and CD11c antigen expression in CD11b+ Gr1+ cells.
Figure 46:
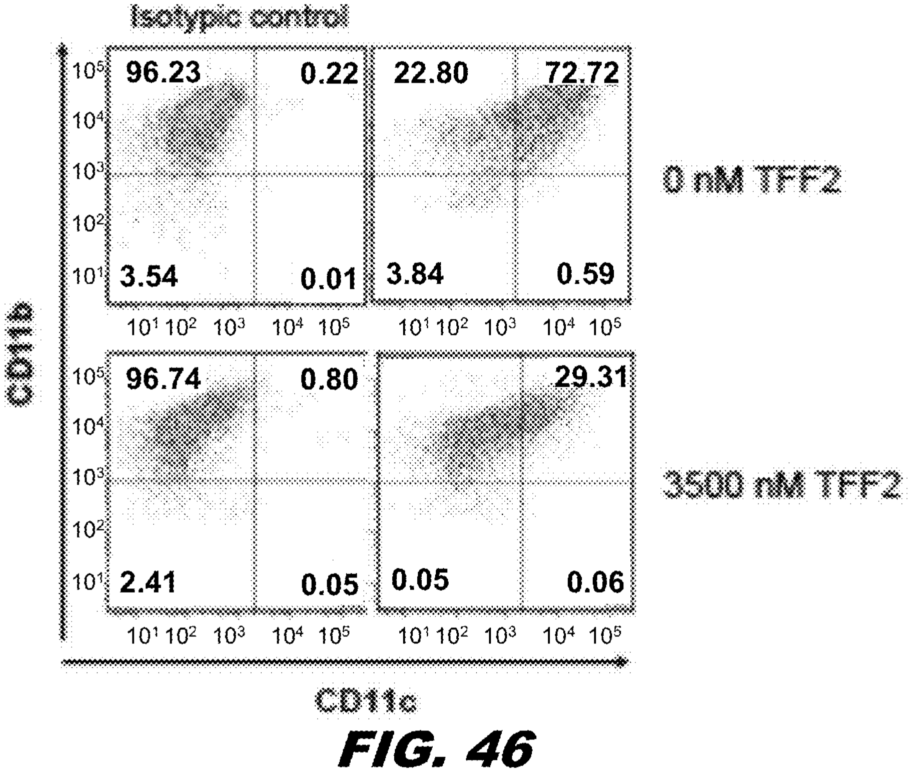
FIG. 46. FACS Analysis. TFF-2 down-regulates cyclin D1, cyclin E1 and CD11c antigen expression in CD11b+ Gr1+ cells.
Figure 48:
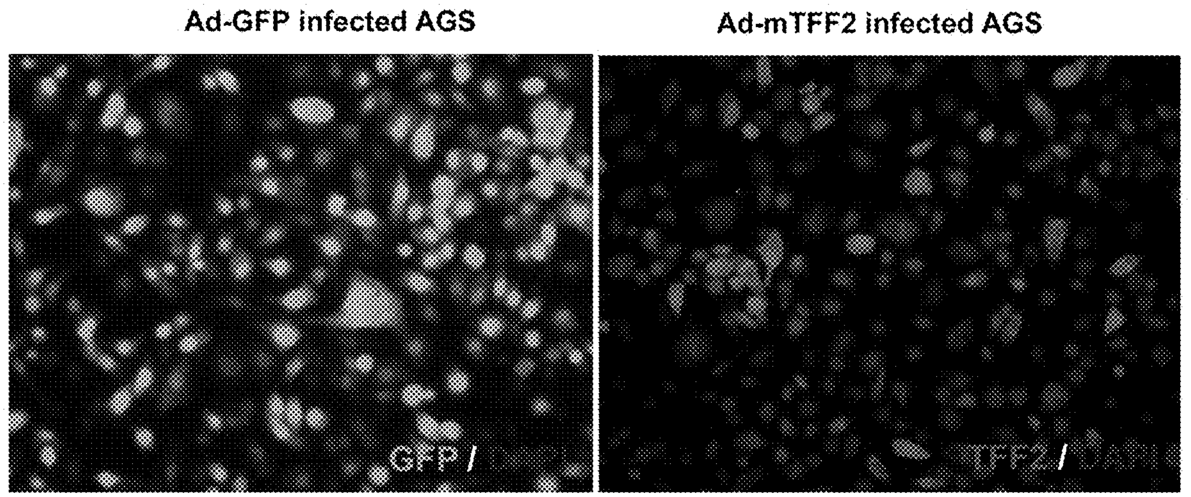
FIG. 48. Recombinant mTFF2 expression in cultured cells. The efficiency of Ad-GFP (80%)/Ad-mTFF2 (60%) infection were identified by immunofluorescence in AGS cells.
Figure 49:
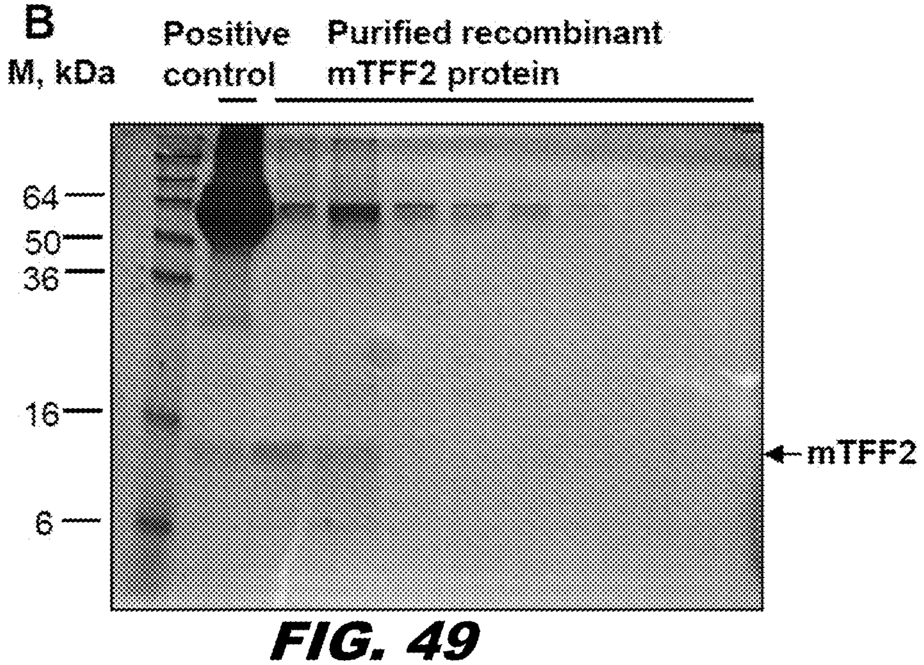
FIG. 49. SDS gel showing purified recombinant mTFF2 protein.

The effect of TFF2 on the in vitro growth of sorted CD11b+Gr1+ cells from spleen of TFF2−/− mice CD11b+Gr1+ cells was tested. The effect of TFF2 on IMCS grown in presence of low concentration (5 ng/ml) of GM-CSF in medium after 7 days of culture was tested. The number of viable cells decreased in a dose-dependent manner upon TFF2 supplementation in range 0.2 μM-4 μM (FIG. 10B). Addition of TFF2 resulted in a decrease of BrdU uptake by CD11b+Gr1+ cells in a dose-dependent manner suggesting that TFF2 inhibited their proliferation (FIG. 37). This was associated with an 8 fold decrease of cyclin-dependent kinase D1 gene expression as has been shown by microarray analysis and validated with qPCR (Table 1). Other cyclin-dependent kinases (for example E1) also were down-regulated as much as 2-fold. Since CDK1 is master positive regulator of cell division (A49) these in vitro studies suggest that TFF2 inhibits proliferation of IMC largely through down-regulation of cyclin D1. Consistently, inhibition of proliferation was accompanied with an increase in the level of negative regulators of the cell cycle such as nuclear protein 1 (Nupr1) (2.68 fold), schlafen 1 (2.16 fold), and large tumor suppressor 2 (1.96 fold). The increase of Nupr1 mRNA was validated by q-PCR (FIG. 45). Although in most cells the increase of intracellular Nupr1 is associated with the induction of apoptosis (A50) recombinant TFF2 did not induce apoptosis of CD11b+Gr1+ cells even at high concentrations. Accordingly, microarray data expression of the CD11c marker on CD11bG1+ cells decreased upon TFF2 treatment which is consistent with flow cytometry results. Similarly, recombinant TFF2 inhibited proliferation of CD11b+Gr1+ cells sorted from tumor-bearing mice presumably through down-regulation of cyclin D1 (FIG. 38).

TABLE 1

TFF2 regulates transcription of cell cycle genes in Gr1+CD11b+ cells

| Symbol | Description | Fold change |
|---|---|---|
| | Positive regulators of cell cycle | |
| Ccnd1 | cyclin D1 | −8.30 |
| Ccnd2 | cyclin D2 | −2.23 |
| Ccne1 | cyclin E1 | −2.29 |
| Sesn3 | sestrin 3 | −3.51 |
| Cep55 | centrosomal protein 55 | −2.34 |
| Prc1 | protein regulator of cytokinesis 1 | −2.32 |
| Spag5 | sperm associated antigen 5 | −2.22 |
| 6-Sep | septin 6 | −2.20 |
| 4-Sep | septin 4 | −2.19 |
| Cenpe | centromere protein E | −2.19 |
| Cenpf | centromere protein F | −2.14 |
| Aurkb | aurora kinase B | −2.09 |
| Kif23 | kinesin family member 23 | −2.13 |
| | Negative regulators of cell cycle | |
| Nupr1 | nuclear protein 1 | 2.68 |
| Slfn1 | schlafen 1 | 2.16 |
| Lats2 | large tumor suppressor 2 | 1.99 |

Recombinant TFF2 Delivered by Adenovirus Vector Suppresses Colonic Cancer Progression in AOM/DSS Model.

Figure 51:
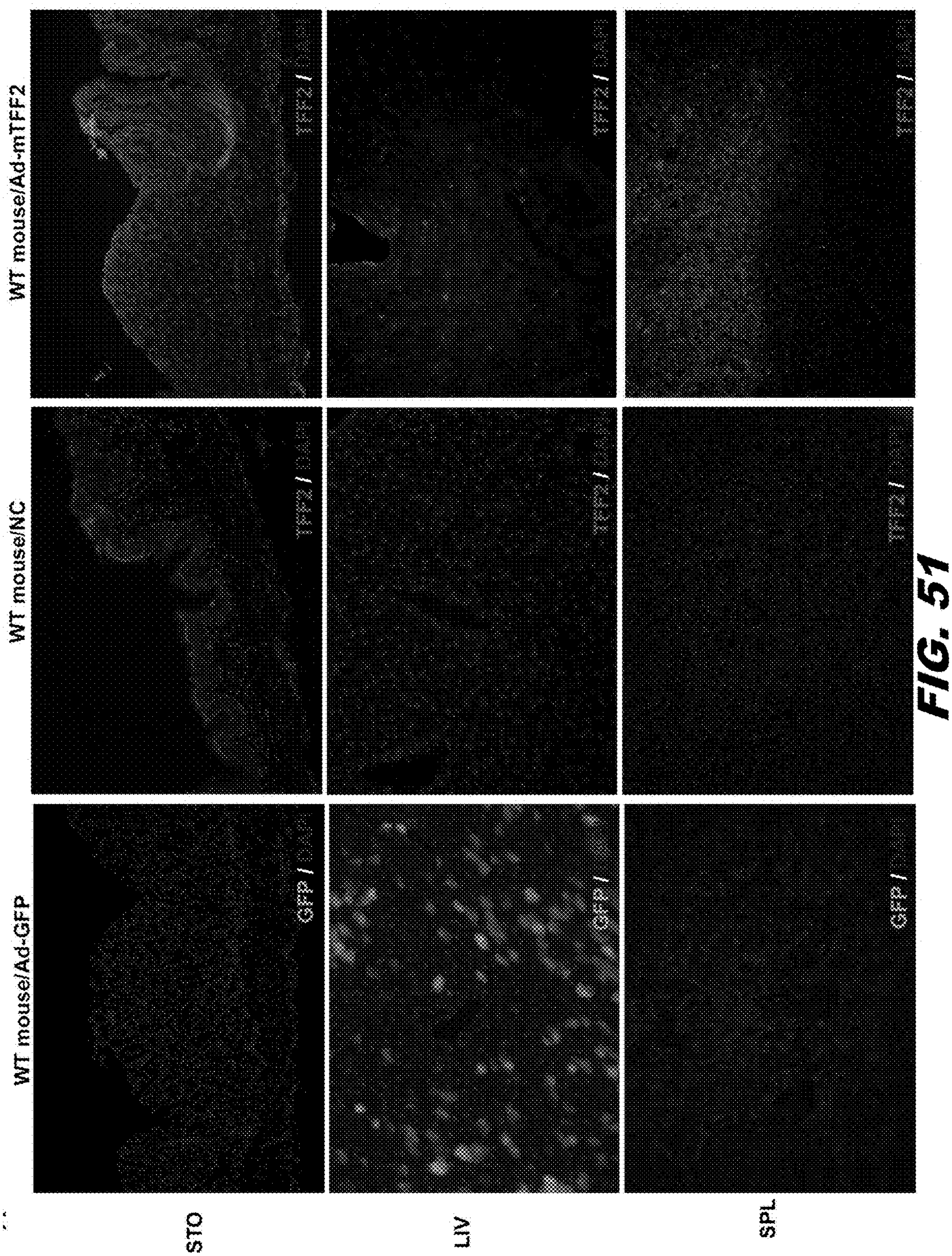
FIG. 51. Recombinant mTFF2 expression in vivo. Recombinant mTFF2 expression in stomach, liver and spleen of WT or TFF2−/− mice with and without Ad-mTFF2 injection. Ad-GFP was used as a control to show the target tissue of Ad-virus. Immunohistochemical and GFP fluorescence evidence for TFF2 expression in the stomach, liver and spleen of WT and TFF2 deficient mice.
Figure 52:
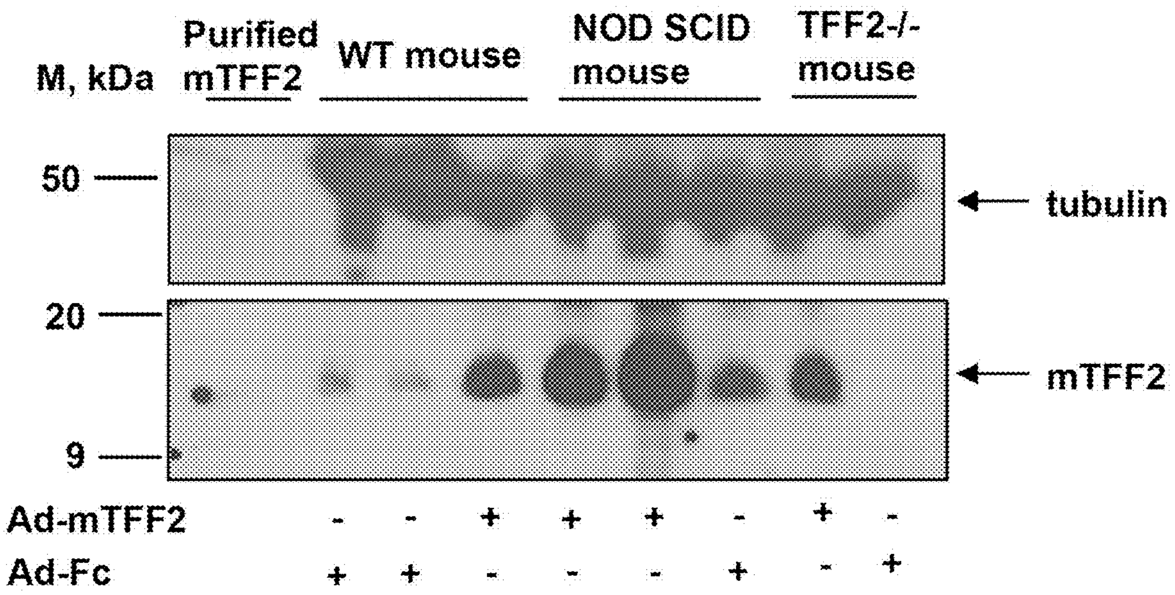
FIG. 52. Recombinant mTFF2 expression in vivo. After one dose of Ad-mTFF2 injection ($5\times10^8$ per mouse), a high level of mTFF2 was found in the serum from NOD-SCID, WT, and TFF2−/− mice, respectively.
Figure 53:
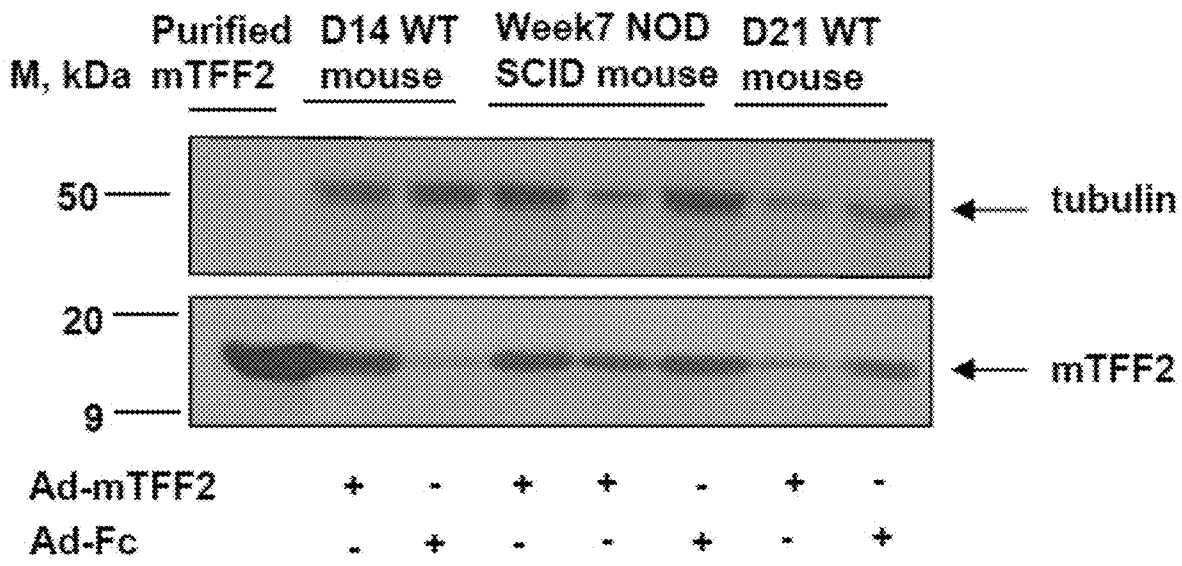
FIG. 53. Recombinant mTFF2 expression in vivo. In NOD-SCID mice, high levels of serum mTFF2 were maintained for at least 7 weeks. In WT mice, levels were maintained for at least 3 weeks.
Figure 54:
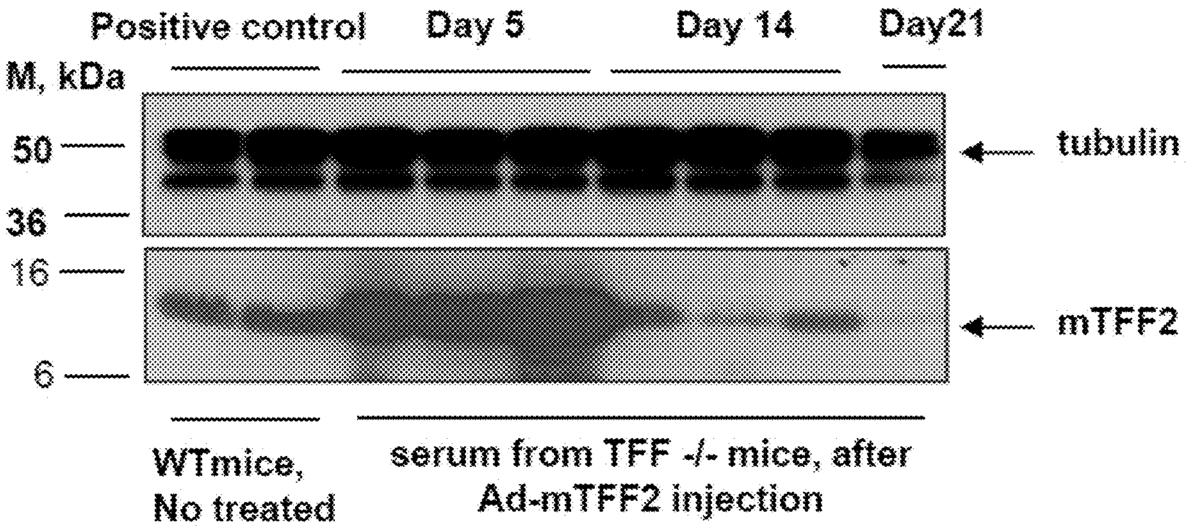
FIG. 54. Recombinant mTFF2 expression in vivo. In TFF2−/− mice, high levels of serum mTFF2 were maintained for 2 weeks.
Figure 55:
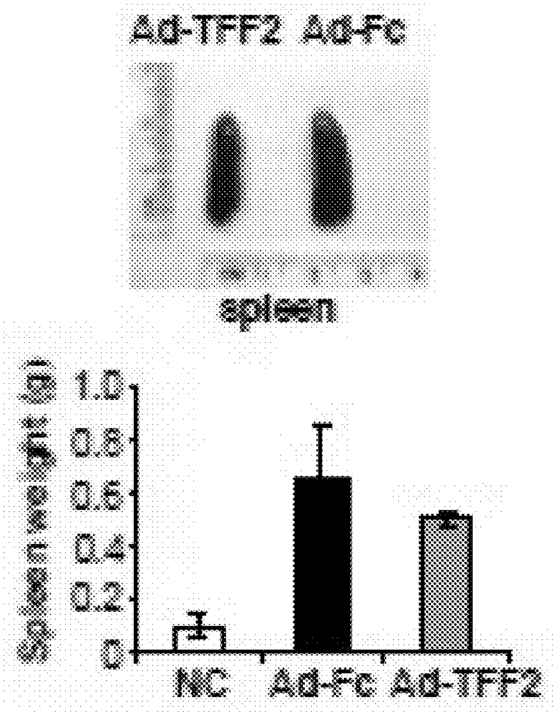
FIG. 55 shows an image of mice spleens and a bar graph depicting the quantitation of spleen size after Ad-TFF2 treatment of TFF2−/− mice after AOM/DSS treatment.
Figure 56:
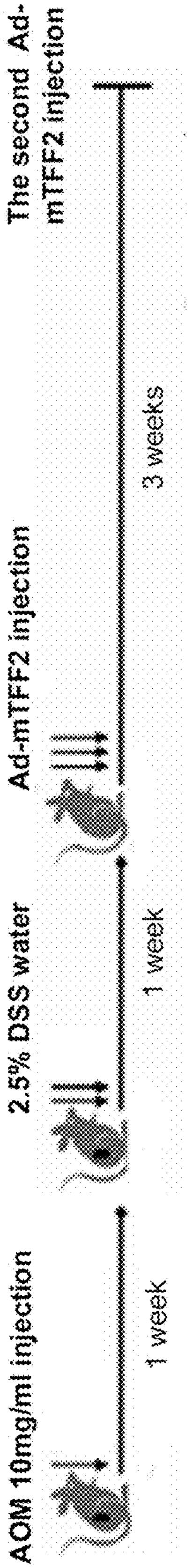
FIG. 56. Effects of adenoviral TFF2 on splenic, BM and circulating IMCs. The time point of Ad-TFF2 injection. The first dose was given at 2 weeks after AOM treatment, then, Ad-mTFF2 treatment was repeated every 3 weeks. Delivery of adenoviral TFF2 to AOM/DSS treated mice suppressed MDSCs. FACS data showing reductions in CD11b+Gr1+ myeloid cells in the blood, spleen and bone marrow after adenoviral delivery of TFF2. Ad-TFF2 treatment significantly alleviated the elevated proportion of Gr1+ CD11b+ cells, which were induced by AOM/DSS treatment, not only in the spleen and peripheral blood from wild-type mice, but also in those from TFF2−/− mice.
Figure 57:
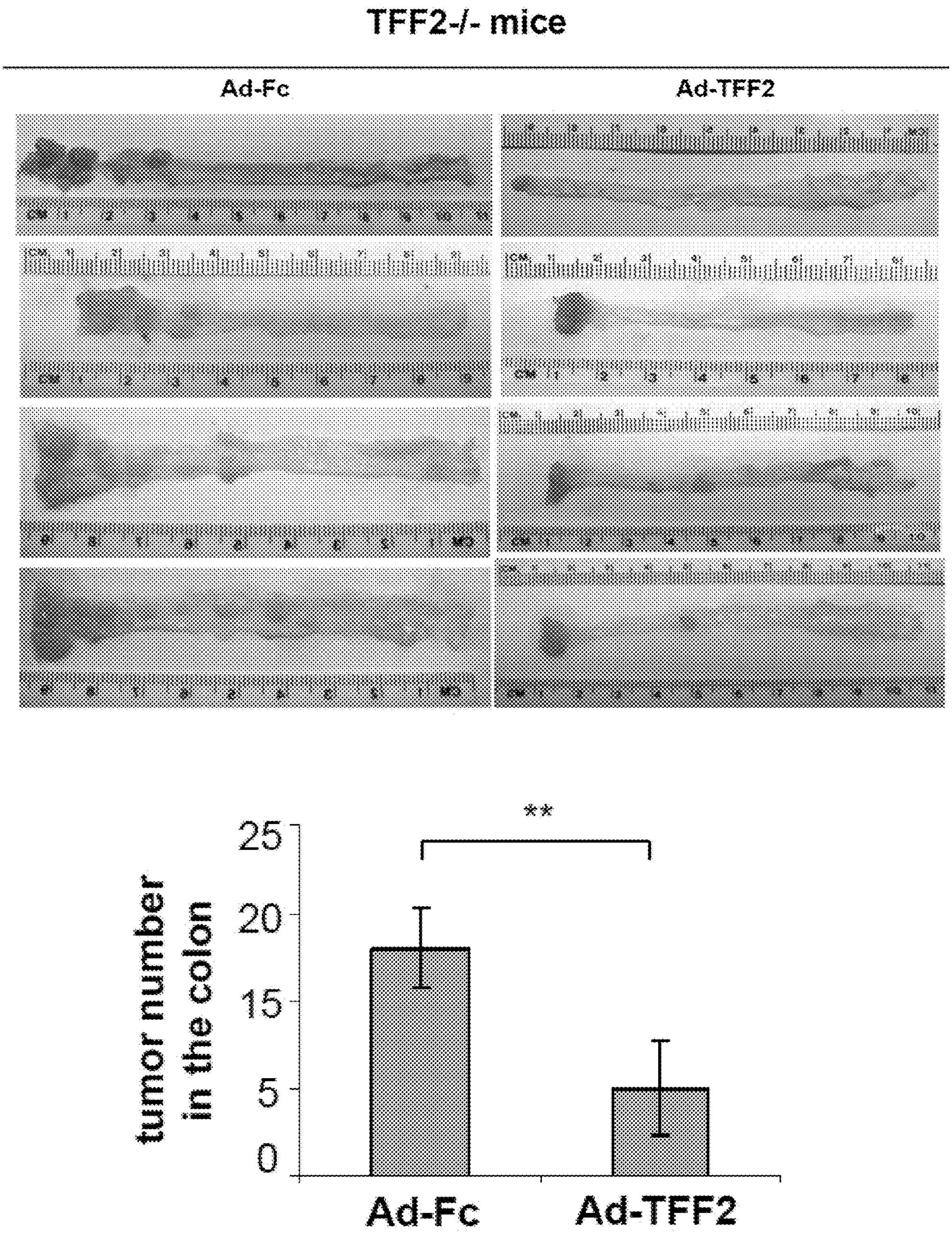
FIG. 57. Suppression of colon tumors by Ad-TFF2. Gross photographs and quantitation of tumor number after Ad-TFF2 treatment of TFF2−/− mice after AOM/DSS treatment (top). 13 weeks after AOM/DSS induction, the number of tumors in the colon of Ad-TFF2 treated mice is much less than that in control mice, especially in TFF2−/− mice (bottom).
Figure 58:
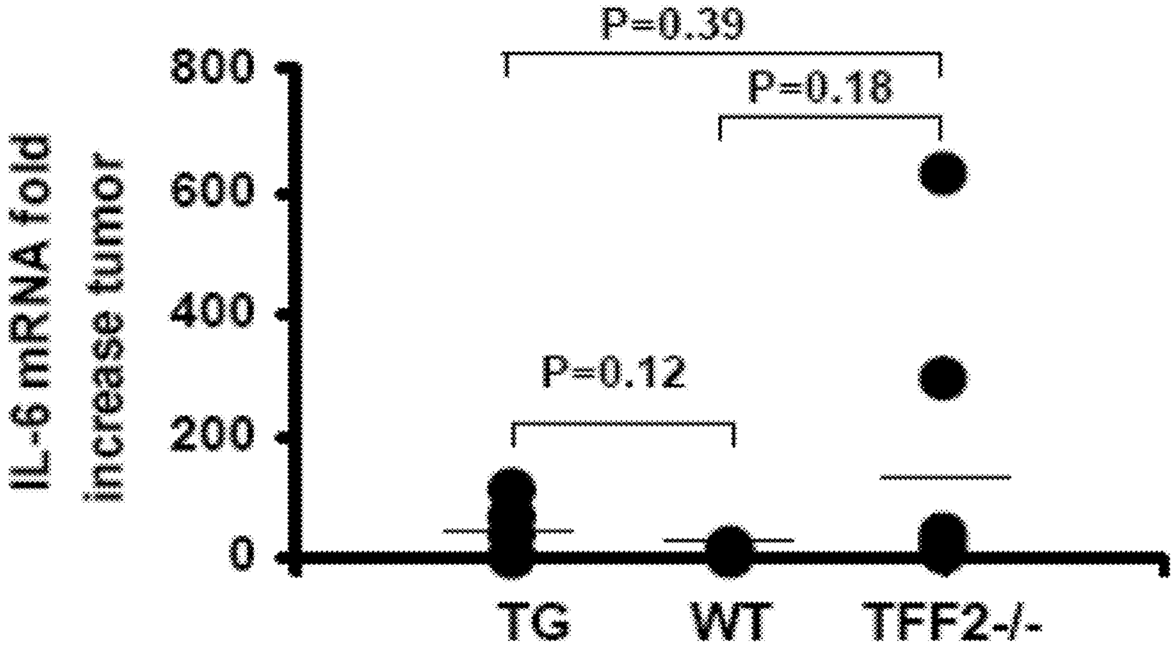
FIG. 58. mRNA level of IL-6 in tumor tissues obtained from TFF2-deficient, TG and wild type mice. Gene expression was normalized on GAPDH levels and the expression of each gene relative to untreated colon tissues of wild type mice is depicted.

To address whether administration of TFF2 is able to suppress cancer development in the AOM/DSS model adenovirus vectors expressing mouse recombinant TFF2 (Ad-TFF2) were generated. mTFF2 protein expression by eukaryotic cells transfected with Ad-TFF2 was validated in western blot (FIG. 50). After one dose of Ad-TFF2 injection ($5\times10^8$ pfu per mouse) TFF2 protein was detected in mouse blood, spleen and liver (FIG. 51). Cancer was initiated by a single injection of AOM following DSS treatment, after 1 week TFF2−/− mice were injected with adenovirus vector expressing recombinant mouse TFF2 (Ad-TFF2) and adenovirus vector alone (Ad-Fc) as a control (FIG. 47). All mice developed tumors by 13 weeks after AOM/DSS administration; however mice injected with Ad-TFF2 developed statistically less number of tumors (FIG. 57). The decrease of tumor burden was associated with a lower proportion of CD11b+Gr1+ cells in spleen and peripheral blood, but not in bone marrow (FIG. 56). TFF2 was detected in the blood by western blot on day 3 after virus administration (FIG. 54). These experiments were repeated with wild type mice with similar results.

Discussion

Gastric epithelial TFF2 can have a mucosal protective and restitutive function in the stomach and colon (A57-A59). Earlier studies showed that TFF2 increased the viscosity of mucus that covers and protects the epithelium, and promoted epithelial restitution by stimulating the migration of epithelial cells to sites of injury (A6, A7, A57, A59, A60). Accumulating data suggest that TFF2 is a modulator of gastrointestinal as well as systemic inflammation (A15, A18).

The role of trefoil peptides derived from an immune cell compartment has not been investigated. Splenic T-cells were identified as a source of TFF2 under normal physiological conditions, as well as under inflammatory conditions (A61). The TFF2 level was controlled in the spleen via the cholinergic anti-inflammatory pathway and was down-regulated by vagotomy. TFF2 derived from T-cells contributes in amelioration of DSS-induced colitis. In a cancer model of AOM/DSS T-cell derived TFF2 plays a role in the suppression of carcinogenesis. Results from the in vivo models indicate that TFF2, in addition to its known barrier and reparative function in gastrointestinal tract, is also involved in an anti-tumor mechanism provided by T-cells. This anti-tumor mechanism can also be provided by adenovirus delivered TFF2 in the AOM/DSS model. Transgenic mice overexpressing TFF2 under hCD2 promoter developed less cancer while TFF2-null mice display highest tumor burden. Recombinant TFF2 delivered by the adenovirus system also suppressed tumor development. Importantly, suppression of tumorigenesis is associated with a decrease in the number of CD11b+Gr1+ cells validating their role in cancer progression.

Expansion of IMCs is associated with an increase in Ki67+ or BrdU+ cells within splenic CD11b+Gr1+ cells, suggesting their higher proliferation in the spleen of TFF2-deficient versus WT and CD2-TFF2 transgenic mice. Splenocytes from TFF2−/− mice treated with DSS form more colonies on medium supporting granulocyte/macrophage precursors than splenocytes from wild type and transgenic mice. In addition, supporting the in vivo observations, recombinant TFF2 directly suppressed CD11b+Gr1+ cell proliferation in vitro.

Splenomegaly in DSS-treated TFF2-null mice resulted from the expansion of immature myeloid cells, presumably as a consequence of extramedullary hematopoiesis. Bone marrow is the major source of CD11b+Gr1+ cells and their precursors under normal and pathological conditions (A51-A53), with egress regulated through the CCR2 receptor (A54). However, recent studies have suggested that the spleen is an important source of extramedullary myelopoiesis under conditions of severe inflammation and cancer (A42, A43, A55, A56).

In the AOM/DSS model spleen-derived CD11b+Gr1+ cells in TFF2−/− mice are MDSCs and show profound suppression on T-cell proliferation and decreased IFN-γ production in vitro. MDSC from the spleen of tumor-bearing TFF2−/− mice express high levels of the surface marker CD80 compared with nonsuppressive CD11b+Gr1+ cells from transgenic CD2-TFF2 mice (without visible tumor in colon) post AOM/DSS regimen. A similar phenotype for CD11b+Gr1+CD80+ cells with suppressive functions has been described for melanoma patients, mouse ovarian carcinoma and 4T1 mammary carcinoma models (A62, A63). CD80 expressed on CD11b+Gr1+ cells ligates with CTLA-4 and transduces inhibitory signals in T-cells (A48). Consistently, the growth of ovarian 1D8 tumors was retarded in CD80-deficient mice due to a decrease of arginase I activity in CD11b+Gr1+ MDSC (A64).

Since MDSCs are an important factor in promoting cancer progression several strategies has been suggested in an attempt to eliminate MDSCs in vivo or suppression their activity. Such as treatments include all-trans-retinoic acid (ATRA) (A66), 1α25-dihydroxyvitamin D (A67), administration of gemcitabine (A68), or 5-Fluorouracil (A69) to induce apoptosis, administration of phosphodiesterase-5 inhibitors in order to downregulate arginase and nitric oxide synthetase activities (A70). Indeed, two widely used anti-cancer cytotoxic agents, 5FU and Gem kill MDSC but they also show side effects by inducing IL-1β release that enhances IL-17 production and accelerates tumor growth (A71). The findings suggest that TFF2 is able to suppress expansion of myeloid cells and delivering recombinant TFF2 in the blood of a subject represents a new strategy to control MDSCs population even under conditions promoting cancer development.

TABLE 2

| Brief Summary of Microarray Dat. GeneChip ® Mouse genome 430A 2.0 Array | |
|---|---|
| Total analyzed genes: | ~14,000 (22,600 probes) |
| with changed mRNA expression upon TFF2 treatment: | 5,810 ($P < 0.05$) |
| (>2 fold) | 807 |
| (>3 fold) | 309 |
| (>4 fold) | 188 |

TABLE 3

22 genes upregulated (>10 fold) by TFF2 in Gr1CD11b cells

| Symbol | Description | Fold Change Up |
|---|---|---|
| Apoe | apolipoprotein E | 89.8 |
| Mcpt8 | mast cell protease 8 | 72.5 |
| Cxcl5 | chemokine (C—X—C motif) ligand 5 | 62.8 |
| Cpa | carboxypeptidase A3, mast cell | 54.7 |
| Il12a | interleukin 12a | 33.1 |
| F2r | coagulation factor II (thrombin) receptor | 30.8 |
| Ctsg | cathepsin G | 20.9 |
| Fcer1a | Fc receptor, IgE, high affinity I, alpha polypeptide | 19.9 |
| Prtn3 | proteinase 3 | 18.2 |
| Mpo | myeloperoxidase | 17.4 |
| Lipg | lipase, endothelial | 16.8 |
| Epx | eosinophil peroxidase | 15.5 |
| Ms4a3 | membrane-spanning 4-domains, subfamily A, member 3 | 15.3 |
| Cyp11a1 | cytochrome P450, family 11, subfamily a, polypeptide 1 | 14.5 |
| Fst | follistatin | 14.1 |
| Akr1c18 | aldo-keto reductase family 1, member C18 | 13.0 |
| Myl10 | myosin, light chain 10, regulatory | 11.9 |
| Saa3 | serum amyloid A 3 | 11.8 |
| Ptgs2 | prostaglandin-endoperoxide synthase 2 | 11.5 |
| Ceacam10 | carcinoembryonic antigen-related cell adhesion molecule 10 | 10.6 |
| Elane | elastase, neutrophil expressed | 10.0 |
| Cd55 | CD55 antigen | 10.0 |

TABLE 4

11 genes downregulated (>10 fold) by TFF2 in Gr1+CD11b + cells

| Symbol | Description | Fold Change Down |
|---|---|---|
| Ly86 | lymphocyte antigen 86 | −19.7 |
| Klrb1b | killer cell lectin-like receptor subfamily B member 1B | −19.3 |
| Hepacam2 | HEPACAM family member 2 | −16.0 |
| Cldn1 | claudin 1 | −15.6 |
| Mfge8 | milk fat globule-EGF factor 8 protein | −14.1 |
| Ciita | class II transactivator | −14.0 |
| Il2ra | interleukin 2 receptor, alpha chain | −12.0 |
| Axl | AXL receptor tyrosine kinase | −10.9 |
| Zbtb46 | zinc finger and BTB domain containing 46 | −10.7 |
| Rtn1 | reticulon 1 | −10.6 |
| Ccl17 | chemokine (C-C motif) ligand 17 | −10.1 |

TABLE 5

TFF2 effect on integrin expression in CD11bGr1 cells

| Symbol | Description | Component of: | Fold Change |
|---|---|---|---|
| Itgax | integrin alpha X | CD11c | −2.3* |
| Itgam | integrin alpha M | CD11b | 1.3 |
| Itga4 | integrin alpha 4/CD49d | VLA-4 | 1.2 |
| Itga4 | integrin alpha 4/CD49d | VLA-4 | 1.1 |

TABLE 5-continued

TFF2 effect on integrin expression in CD11bGr1 cells

| Symbol | Description | Component of: | Fold Change |
|---|---|---|---|
| Itga4 | integrin alpha 4/CD49d | VLA-4 | 1.0 |
| Itgav | integrin alpha V | VNR | 1.3 |
| Itgav | integrin alpha V | VNR | 1.3 |
| Itgav | integrin alpha V | VNR | 1.1 |
| Itgb2l | integrin beta 2-like | Homodimer | 8.8** |
| Itgb2 | integrin beta 2/CD18 | CD11c/Cd11b | 1.1 |

*= Detected by FC

**= Expression in mouse neutrophils only, no orthologs

Summary: Adenoviral delivery of TFF2 suppresses colon cancer in response to AOM/DSS.

Conclusion: These results show that adenoviral delivery of mTFF2 expression can suppress gastrointestinal tumorigenesis through reducing the proliferation of IMCs.

REFERENCES

A1. Gabrilovich, D. I., Nagaraj, S., Bronte, V., Chappell, D. B., Apolloni, E., Cabrelle, A., Wang, M., Hwu, P., and Restifo, N. P. 2009. Myeloid-derived suppressor cells as regulators of the immune system unopposed production of granulocyte-macrophage colony-stimulating factor by tumors inhibits CD8+ T cell responses by dysregulating antigen-presenting cell maturation. Nat Rev Immunol 9:162-174.

A2. Nathan, C. 2002. Points of control in inflammation. Nature 420:846-852.

A3. Delgado, M., and Ganea, D. 2008. Anti-inflammatory neuropeptides: a new class of endogenous immunoregulatory agents. Brain Behav Immun 22:1146-1151.

A4. Banchereau, J., Pascual, V., and O'Garra, A. 1038. From IL-2 to IL-37: the expanding spectrum of anti-inflammatory cytokines. Nat Immunol 13:925-931.

A5. Rosas-Ballina, M., Olofsson, P. S., Ochani, M., Valdes-Ferrer, S. I., Levine, Y. A., Reardon, C., Tusche, M. W., Pavlov, V. A., Andersson, U., Chavan, S., et al. 2011. Acetylcholine-synthesizing T cells relay neural signals in a vagus nerve circuit. Science 334:98-101.

A6. Thim, L., Madsen, F., and Poulsen, S. S. 2002. Effect of trefoil factors on the viscoelastic properties of mucus gels. Eur J Clin Invest 32:519-527.

A7. Playford, R. J., Marchbank, T., Chinery, R., Evison, R., Pignatelli, M., Boulton, R. A., Thim, L., and Hanby, A. M. 1995. Human spasmolytic polypeptide is a cytoprotective agent that stimulates cell migration. Gastroenterology 108:108-116.

A8. Dignass, A., Lynch-Devaney, K., Kindon, H., Thim, L., and Podolsky, D. K. 1994. Trefoil peptides promote epithelial migration through a transforming growth factor beta-independent pathway. J Clin Invest 94:376-383.

A9. Soriano-Izquierdo, A., Gironella, M., Massaguer, A., May, F. E., Salas, A., Sans, M., Poulsom, R., Thim, L., Pique, J. M., and Panes, J. 2004. Trefoil peptide TFF2 treatment reduces VCAM-1 expression and leukocyte recruitment in experimental intestinal inflammation. J Leukoc Biol 75:214-223.

A10. Tran, C. P., Cook, G. A., Yeomans, N. D., Thim, L., and Giraud, A. S. 1999. Trefoil peptide TFF2 (spasmolytic polypeptide) potently accelerates healing and reduces inflammation in a rat model of colitis. Gut 44:636-642.

A11. FitzGerald, A. J., Pu, M., Marchbank, T., Westley, B. R., May, F. E., Boyle, J., Yadollahi-Farsani, M., Ghosh, S., and Playford, R. J. 2004. Synergistic effects of systemic trefoil factor family 1 (TFF1) peptide and epidermal growth factor in a rat model of colitis. Peptides 25:793-801.

A12. Babyatsky, M. W., deBeaumont, M., Thim, L., and Podolsky, D. K. 1996. Oral trefoil peptides protect against ethanol- and indomethacin-induced gastric injury in rats. Gastroenterology 110:489-497.

A13. Vandenbroucke, K., Hans, W., Van Huysse, J., Neirynck, S., Demetter, P., Remaut, E., Rottiers, P., and Steidler, L. 2004. Active delivery of trefoil factors by genetically modified *Lactococcus lactis* prevents and heals acute colitis in mice. Gastroenterology 127:502-513.

A14. Mashimo, H., Wu, D. C., Podolsky, D. K., and Fishman, M. C. 1996. Impaired defense of intestinal mucosa in mice lacking intestinal trefoil factor. Science 274:262-265.

A15. Kurt-Jones, E. A., Cao, L., Sandor, F., Rogers, A. B., Whary, M. T., Nambiar, P. R., Cerny, A., Bowen, G., Yan, J., Takaishi, S., et al. 2007. Trefoil family factor 2 is expressed in murine gastric and immune cells and controls both gastrointestinal inflammation and systemic immune responses. Infect Immun 75:471-480.

A16. Cook, G. A., Familari, M., Thim, L., and Giraud, A. S. 1999. The trefoil peptides TFF2 and TFF3 are expressed in rat lymphoid tissues and participate in the immune response. FEBS Lett 456:155-159.

A17. Giraud, A. S., Pereira, P. M., Thim, L., Parker, L. M., and Judd, L. M. 2004. TFF-2 inhibits iNOS/NO in monocytes, and nitrated protein in healing colon after colitis. Peptides 25:803-809.

A18. Baus-Loncar, M., Kayademir, T., Takaishi, S., and Wang, T. 2005. Trefoil factor family 2 deficiency and immune response. Cell Mol Life Sci 62:2947-2955.

A19. McBerry, C., Egan, C. E., Rani, R., Yang, Y., Wu, D., Boespflug, N., Boon, L., Butcher, B., Mirpuri, J., Hogan, S. P., et al. 2012. Trefoil Factor 2 Negatively Regulates Type 1 Immunity against *Toxoplasma gondii*. J Immunol 2012:15.

A20. Dubeykovskaya, Z., Dubeykovskiy, A., Solal-Cohen, J., and Wang, T. C. 2009. Secreted trefoil factor 2 activates the CXCR4 receptor in epithelial and lymphocytic cancer cell lines. J Biol Chem 284:3650-3662.

A21. Shibata, W., Ariyama, H., Westphalen, C. B., Worthley, D. L., Muthupalani, S., Asfaha, S., Dubeykovskaya, Z., Quante, M., Fox, J. G., and Wang, T. C. 2012. Stromal cell-derived factor-1 overexpression induces gastric dysplasia through expansion of stromal myofibroblasts and epithelial progenitors. Gut 2012:23.

A22. Wills-Karp, M., Rani, R., Dienger, K., Lewkowich, I., Fox, J. G., Perkins, C., Lewis, L., Finkelman, F. D., Smith, D. E., Bryce, P. J., et al. 2012. Trefoil factor 2 rapidly induces interleukin 33 to promote type 2 immunity during allergic asthma and hookworm infection. J Exp Med 209:607-622.

A23. Shi, S. Q., Cai, J. T., and Yang, J. M. 2006. Expression of trefoil factors 1 and 2 in precancerous condition and gastric cancer. World J Gastroenterol 12:3119-3122.

A24. Kim, H., Eun, J. W., Lee, H., Nam, S. W., Rhee, H., and Koh, K. H. 2011. Gene expression changes in patient-matched gastric normal mucosa, adenomas, and carcinomas. Exp Mol Pathol 90:201-209.

A25. Hong, S. J., Oh, J. H., Jung, Y. C., Kim, Y. H., Kim, S. J., Kang, S. J., Seo, E. J., Choi, S. W., Kang, M. I., and Rhyu, M. G. 2010. DNA methylation patterns of ulcer-healing genes associated with the normal gastric mucosa of gastric cancers. J Korean Med Sci 25:405-417.

A26. Peterson, A. J., Menheniott, T. R., O'Connor, L., Walduck, A. K., Fox, J. G., Kawakami, K., Minamoto, T., Ong, E. K., Wang, T. C., Judd, L. M., et al. 2005. *Helicobacter pylori* infection promotes methylation and silencing of trefoil factor 2, leading to gastric tumor development in mice and humans. Gastroenterology 139:2005-2017.

A27. Fox, J. G., Rogers, A. B., Whary, M. T., Ge, Z., Ohtani, M., Jones, E. K., and Wang, T. C. 2007. Accelerated progression of gastritis to dysplasia in the pyloric antrum of TFF2−/− C57BL6×Sv129 *Helicobacter pylori*-infected mice. Am J Pathol 171:1520-1528.

A28. Poulsom, R., Chinery, R., Sarraf, C., Lalani, E. N., Stamp, G., Elia, G., and Wright, N. 1992. Trefoil peptide expression in intestinal adaptation and renewal. Scand J Gastroenterol Suppl 192:17-28.

A29. Rio, M. C., Chenard, M. P., Wolf, C., Marcellin, L., Tomasetto, C., Lathe, R., Bellocq, J. P., and Chambon, P. 1991. Induction of pS2 and hSP genes as markers of mucosal ulceration of the digestive tract. Gastroenterology 100:375-379.

A30. Cook, G. A., Yeomans, N. D., and Giraud, A. S. 1997. Temporal expression of trefoil peptides in the TGF-alpha knockout mouse after gastric ulceration. Am J Physiol 272:G1540-1549.

A31. Henry, J. A., Bennett, M. K., Piggott, N. H., Leven, D. L., May, F. E., and Westley, B. R. 1991. Expression of the pNR-2/pS2 protein in diverse human epithelial tumours. Br J Cancer 64:677-682.

A32. Alison, M. R., Chinery, R., Poulsom, R., Ashwood, P., Longcroft, J. M., and Wright, N. A. 1995. Experimental ulceration leads to sequential expression of spasmolytic polypeptide, intestinal trefoil factor, epidermal growth factor and transforming growth factor alpha mRNAs in rat stomach. J Pathol 175:405-414.

A33. Taupin, D., Wu, D. C., Jeon, W. K., Devaney, K., Wang, T. C., and Podolsky, D. K. 1999. The trefoil gene family are coordinately expressed immediate-early genes: EGF receptor- and MAP kinase-dependent interregulation. J Clin Invest 103:R31-38.

A34. Elenkov, I. J., Wilder, R. L., Chrousos, G. P., and Vizi, E. S. 2000. The sympathetic nerve—an integrative interface between two supersystems: the brain and the immune system. Pharmacol Rev 52:595-638.

A35. Borovikova, L. V., Ivanova, S., Zhang, M., Yang, H., Botchkina, G. I., Watkins, L. R., Wang, H., Abumrad, N., Eaton, J. W., and Tracey, K. J. 2000. Vagus nerve stimulation attenuates the systemic inflammatory response to endotoxin. Nature 405:458-462.

A36. Pavlov, V. A., and Tracey, K. J. 2004. Neural regulators of innate immune responses and inflammation. Cell Mol Life Sci 61:2322-2331.

A37. Lang, G., Wotton, D., Owen, M. J., Sewell, W. A., Brown, M. H., Mason, D. Y., Crumpton, M. J., and Kioussis, D. 1988. The structure of the human CD2 gene and its expression in transgenic mice. EMBO J 7:1675-1682.

A38. Lake, R. A., Wotton, D., and Owen, M. J. 1990. A 3' transcriptional enhancer regulates tissue-specific expression of the human CD2 gene. EMBO J 9:3129-3136.

A39. Melgar, S., Karlsson, A., and Michaelsson, E. 2005. Acute colitis induced by dextran sulfate sodium progresses to chronicity in C57BL/6 but not in BALB/c mice: correlation between symptoms and inflammation. Am J Physiol Gastrointest Liver Physiol 288:G1328-1338.

A40. Hall, L. J., Faivre, E., Quinlan, A., Shanahan, F., Nally, K., and Melgar, S. 2011. Induction and activation of adaptive immune populations during acute and chronic phases of a murine model of experimental colitis. Dig Dis Sci 56:79-89.

A41. Liu, C., Yu, S., Kappes, J., Wang, J., Grizzle, W. E., Zinn, K. R., and Zhang, H. G. 2007. Expansion of spleen myeloid suppressor cells represses NK cell cytotoxicity in tumor-bearing host. Blood 109:4336-4342.

A42. Leuschner, F., Rauch, P. J., Ueno, T., Gorbatov, R., Marinelli, B., Lee, W. W., Dutta, P., Wei, Y., Robbins, C., Iwamoto, Y., et al. 2012. Rapid monocyte kinetics in acute myocardial infarction are sustained by extramedullary monocytopoiesis. J Exp Med 209:123-137.

A43. Cortez-Retamozo, V., Etzrodt, M., Newton, A., Rauch, P. J., Chudnovskiy, A., Berger, C., Ryan, R. J., Iwamoto, Y., Marinelli, B., Gorbatov, R., et al. 2012. Origins of tumor-associated macrophages and neutrophils. Proc Natl Acad Sci USA 109:2491-2496.

A44. Ling, V., Luxenberg, D., Wang, J., Nickbarg, E., Leenen, P. J., Neben, S., and Kobayashi, M. 1997. Structural identification of the hematopoietic progenitor antigen ER-MP12 as the vascular endothelial adhesion molecule PECAM-1 (CD31). Eur J Immunol 27:509-514.

A45. Angulo, I., de las Heras, F. G., Garcia-Bustos, J. F., Gargallo, D., Munoz-Fernandez, M. A., and Fresno, M. 2000. Nitric oxide-producing CD11b(+)Ly-6G(Gr-1)(+) CD31(ER-MP12)(+) cells in the spleen of cyclophosphamide-treated mice: implications for T-cell responses in immunosuppressed mice. Blood 95:212-220.

A46. Delano, M. J., Scumpia, P. O., Weinstein, J. S., Coco, D., Nagaraj, S., Kelly-Scumpia, K. M., O'Malley, K. A., Wynn, J. L., Antonenko, S., A1-Quran, S. Z., et al. 2007. MyD88-dependent expansion of an immature GR-1(+) CD11b(+) population induces T cell suppression and Th2 polarization in sepsis. J Exp Med 204:1463-1474.

A47. Hegde, V. L., Nagarkatti, M., and Nagarkatti, P. S. 2011. Cannabinoid receptor activation leads to massive mobilization of myeloid-derived suppressor cells with potent immunosuppressive properties. Eur J Immunol 40:3358-3371.

A48. Yang, R., Cai, Z., Zhang, Y., Yutzy, W. H. t., Roby, K. F., and Roden, R. B. 2006. CD80 in immune suppression by mouse ovarian carcinoma-associated Gr-1+CD11b+ myeloid cells. Cancer Res 66:6807-6815.

A49. Satyanarayana, A., and Kaldis, P. 2009. Mammalian cell-cycle regulation: several Cdks, numerous cyclins and diverse compensatory mechanisms. Oncogene 28:2925-2939.

A50. Cano, C. E., Hamidi, T., Sandi, M. J., and Iovanna, J. L. 1439. Nupr1: the Swiss-knife of cancer. J Cell Physiol 226:1439-1443.

A51. Bronte, V., Apolloni, E., Cabrelle, A., Ronca, R., Serafini, P., Zamboni, P., Restifo, N. P., and Zanovello, P. 2000. Identification of a CD11b(+)/Gr-1(+)/CD31(+) myeloid progenitor capable of activating or suppressing CD8(+) T cells. Blood 96:3838-3846.

A52. Hock, H., Hamblen, M. J., Rooke, H. M., Traver, D., Bronson, R. T., Cameron, S., and Orkin, S. H. 2003. Intrinsic requirement for zinc finger transcription factor Gfi-1 in neutrophil differentiation. Immunity 18:109-120.

A53. Shi, C., and Pamer, E. G. 1038. Monocyte recruitment during infection and inflammation. Nat Rev Immunol 11:762-774.

A54. Serbina, N. V., and Pamer, E. G. 2006. Monocyte emigration from bone marrow during bacterial infection requires signals mediated by chemokine receptor CCR2. Nat Immunol 7:311-317.

A55. Noel, J. G., Guo, X., Wells-Byrum, D., Schwemberger, S., Caldwell, C. C., and Ogle, C. K. 2005. Effect of thermal injury on splenic myelopoiesis. Shock 23:115-122.

A56. Ostrand-Rosenberg, S., and Sinha, P. 2009. Myeloid-derived suppressor cells: linking inflammation and cancer. J Immunol 182:4499-4506.

A57. Poulsom, R., Begos, D. E., and Modlin, I. M. 1996. Molecular aspects of restitution: functions of trefoil peptides. Yale J Biol Med 69:137-146.

A58. Poulsen, S. S., Kissow, H., Hare, K., Hartmann, B., and Thim, L. 2005. Luminal and parenteral TFF2 and TFF3 dimer and monomer in two models of experimental colitis in the rat. Regul Pept 126:163-171.

A59. Longman, R. J., Douthwaite, J., Sylvester, P. A., Poulsom, R., Corfield, A. P., Thomas, M. G., and Wright, N. A. 2000. Coordinated localisation of mucins and trefoil peptides in the ulcer associated cell lineage and the gastrointestinal mucosa. Gut 47:792-800.

A60. Podolsky, D. K. 2002. The current future understanding of inflammatory bowel disease. Best Pract Res Clin Gastroenterol 16:933-943.

A61. Kitajima, S., Takuma, S., and Morimoto, M. 1999. Changes in colonic mucosal permeability in mouse colitis induced with dextran sulfate sodium. Exp Anim 48:137-143.

A62. Poschke, I., Mougiakakos, D., Hansson, J., Masucci, G. V., and Kiessling, R. 2010. Immature immunosuppressive CD14+HLA−DR−/low cells in melanoma patients are Stat3hi and overexpress CD80, CD83, and DC-sign. Cancer Res 70:4335-4345.

A63. Sinha, P., Okoro, C., Foell, D., Freeze, H. H., Ostrand-Rosenberg, S., Srikrishna, G., Poschke, I., Mougiakakos, D., Hansson, J., Masucci, G. V., et al. 2008. Proinflammatory S100 proteins regulate the accumulation of myeloid-derived suppressor cells Immature immunosuppressive CD14+HLA−DR−/low cells in melanoma patients are Stat3hi and overexpress CD80, CD83, and DC-sign. J Immunol 181:4666-4675.

A64. Liu, Y., Yu, Y., Yang, S., Zeng, B., Zhang, Z., Jiao, G., Zhang, Y., Cai, L., and Yang, R. 2009. Regulation of arginase I activity and expression by both PD-1 and CTLA-4 on the myeloid-derived suppressor cells. Cancer Immunol Immunother 58:687-697.

A65. Movahedi, K., Guilliams, M., Van den Bossche, J., Van den Bergh, R., Gysemans, C., Beschin, A., De Baetselier, P., and Van Ginderachter, J. A. 2008. Identification of discrete tumor-induced myeloid-derived suppressor cell subpopulations with distinct T cell-suppressive activity. Blood 111:4233-4244.

A66. Kusmartsev, S., Cheng, F., Yu, B., Nefedova, Y., Sotomayor, E., Lush, R., and Gabrilovich, D. 2003. All-trans-retinoic acid eliminates immature myeloid cells from tumor-bearing mice and improves the effect of vaccination. Cancer Res 63:4441-4449.

A67. Young, M. R., Lozano, Y., Ihm, J., Wright, M. A., and Prechel, M. M. 1996. Vitamin D3 treatment of tumor bearers can stimulate immune competence and reduce tumor growth when treatment coincides with a heightened presence of natural suppressor cells. Cancer Lett 104:153-161.

A68. Suzuki, E., Kapoor, V., Jassar, A. S., Kaiser, L. R., and Albelda, S. M. 2005. Gemcitabine selectively eliminates splenic Gr-1+/CD11b+ myeloid suppressor cells in tumor-bearing animals and enhances antitumor immune activity. Clin Cancer Res 11:6713-6721.

A69. Vincent, J., Mignot, G., Chalmin, F., Ladoire, S., Bruchard, M., Chevriaux, A., Martin, F., Apetoh, L., Rebe, C., and Ghiringhelli, F. 1158. 5-Fluorouracil selectively kills tumor-associated myeloid-derived suppressor cells resulting in enhanced T cell-dependent antitumor immunity. Cancer Res 70:3052-3061.

A70. Serafini, P., Borrello, I., and Bronte, V. 2006. Myeloid suppressor cells in cancer: recruitment, phenotype, properties, and mechanisms of immune suppression. Semin Cancer Biol 16:53-65.

A71. Bruchard, M., Mignot, G., Derangere, V., Chalmin, F., Chevriaux, A., Vegran, F., Boireau, W., Simon, B., Ryffel, B., Connat, J. L., et al. 1038. Chemotherapy-triggered cathepsin B release in myeloid-derived suppressor cells activates the Nlrp3 inflammasome and promotes tumor growth. Nat Med 19:57-64.

Example 7: Tumor-Associated MDSC

The role of TFF2-mediated suppression of MDSCs in cancer development can also be tested in mouse models of mammary cancer (for example, see Hennighausen (2000) *Breast Cancer Res.* 2(1): 2-7; and Fantozzi et al., (2006) Breast Cancer Res. 2006; 8(4): 212, each of which are hereby incorporated by reference in their entireties). A large number of well validated genetically engineered models (GEM) of breast cancer have been developed over the past few decades, and many (e.g. MMTV-HER2/Neu or MMTV-Wnt-1 or MMTV-PyV-mT) are widely available. In addition, a *H. hepaticus* infection model has recently been utilized to stimulate breast cancer development in Apc/Min mice (Rao V P et al, Cancer Res 2006; 66:7395-400).

The role of TFF2-mediated suppression of MDSCs in cancer development can also be tested in mouse models of prostate cancer (for example, see Jeet et al (2010) *Cancer Metastasis Rev.* 29(1):123-42; Zhou et al., (2010) *J Androl.* 31(3):235-43; Ahmad et al., (2008) *Expert Rev Mol Med.* 10:e16; Havens et al., (2008) *Neoplasia.* 10(4): 371-379; Valkenburg and Williams (2011) *Prostate Cancer*, Volume 2011, Article ID 895238, doi:10.1155/2011/895238, each of which are hereby incorporated by reference in their entireties). A large number of well validated genetically engineered models of prostate cancer have been developed over the past few decades, and many are widely available.

In addition, the role of TFF2-mediated suppression of MDSCs in cancer development can also be tested in mouse models of lung cancer (for example, see Meuwissen and Berns (2005) *GENES & DEVELOPMENT* 19:643-664; Kwon and Berns (2013) *Molecular Oncology* 7(2):165-177; de Serrano and Meuwissen (2010) *Eur Respir J.* 35: 426-443, each of which are hereby incorporated by reference in their entireties). A large number of well validated genetically engineered models of lung cancer have been developed over the past few decades, and many are widely available.

Using one or more of these mouse models, the ability of TFF2 to suppress myeloid progenitors and cancer initiation and progression can be tested. To start with, the CD2-TFF2 transgenic mice can be crossed to a breast cancer mouse model (non-limiting examples include: MMTV-HER2/Neu or MMTV-Wnt-1 or MMTV-PyV-mT), and the development of breast cancer can be followed over time. To study prostate cancer, the CD2-TFF2 transgenic mice can be crossed to a prostate cancer mouse model (non-limiting examples include: Androgen Receptor Knockout mouse, PB-Cre4× PTEN(loxP/loxP) mouse, TRAMP (for transgenic adenocarcinoma mouse prostate), FG-Tag mouse, PB-Neu, and LADY), and the development of prostate cancer can be followed over time. To study lung cancer, the CD2-TFF2 transgenic mice can be crossed to a lung cancer mouse model (non-limiting examples include: CC10-Tag/CC10-hASH1, K5-E6/E7, CCRP-H-Ras, and MMTV-TGF-β1 DN), and the development of lung cancer can be followed over time.

In addition, the use of adenoviral-TFF2 delivery to these animals can be used, through tail vein injection of the recombinant virus. Endpoints can include tumor number, tumor size, and tumor load. This can be correlated with the level of circulating MDSCs and the percentage of MDSCs in the mouse spleen and bone marrow. Without being bound by theory, TFF2 will reduce MDSC expansion and cancer development in either the breast, prostate, or lung.

Figure 62:
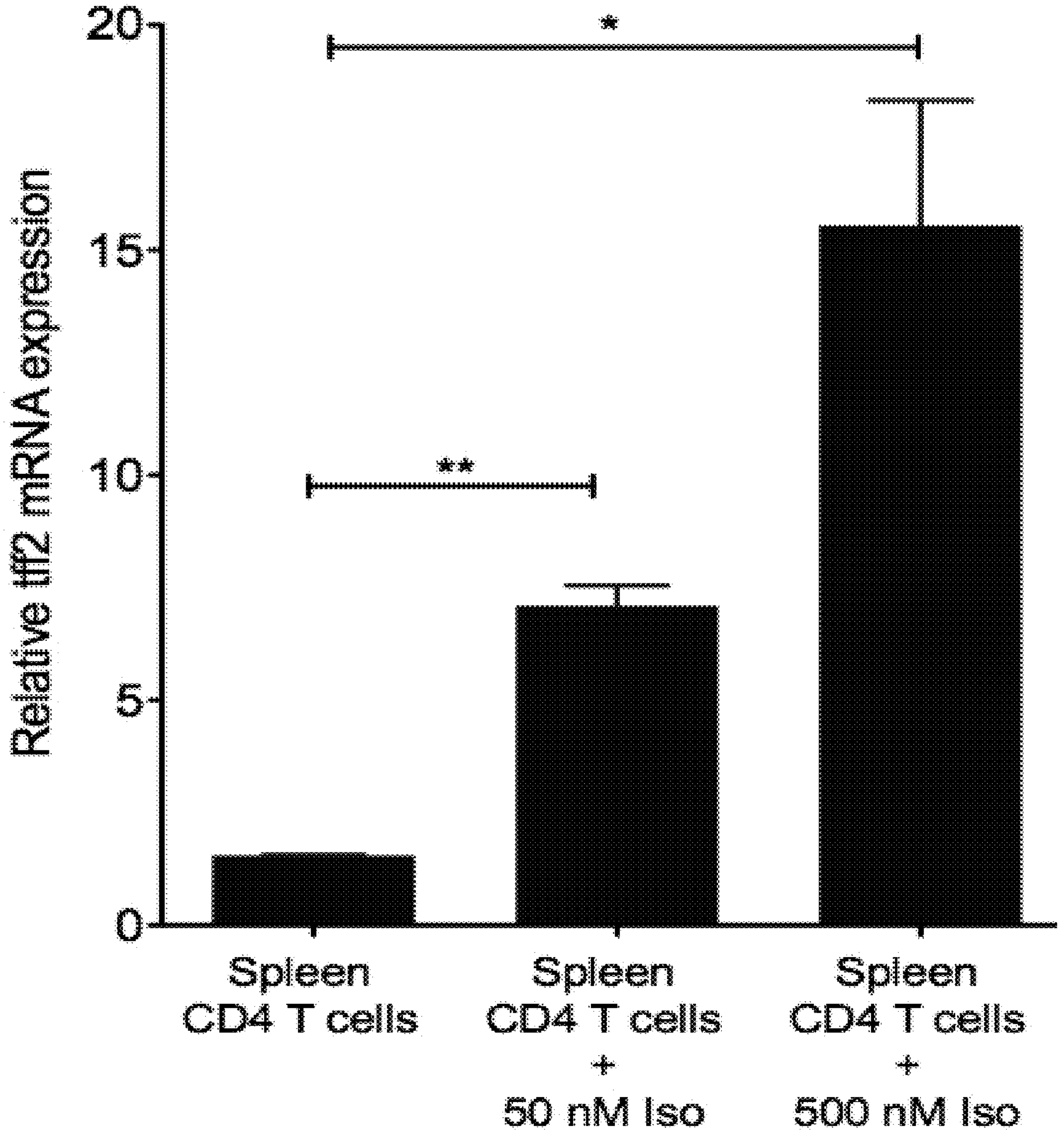
FIG. 62. Splenic CD4+ T cells were sorted and then placed in culture and stimulated with 50 or 500 nM of isoproterenol and then assayed for TFF2 mRNA expression by RT-PCR.

Example 8: TFF2 is Upregulated in Memory T Cells Through Adrenergic Stimulation The studies described herein suggested that the vagus nerve upregulates TFF2 expression in CD4+ memory T cells through an adrenergic (e.g. noradrenaline) pathway. This conclusion was based on previous studies on the inflammatory reflex, which documented that the vagus stimulated splenic nerves, which released noradrenaline to stimulate CD4+ memory T cells. These T cells in turn produce acetylcholine, which inhibit cytokine production (TNF-alpha) by macrophages. However, in order to demonstrate that adrenergic signaling also regulates the production of TFF2 by T cells, studies were carried out with isoproterenol stimulation of memory T cells. These studies (FIG. 62) showed that TFF2 mRNA expression was tightly regulated by adrenergic stimulation with a 15-fold increase seen with 500 nM of isoproterenol.

Example 9: T Cells are the Primary Source of TFF2 in the Hematopoietic System The studies described herein supported the notion that memory CD4+ T cells are the major source of TFF2 mRNA expression in the spleen. They appear to be the same T cells as those targeted by the vagus nerve, which have been reported to be positive for Chat expression.

Figure 63A:
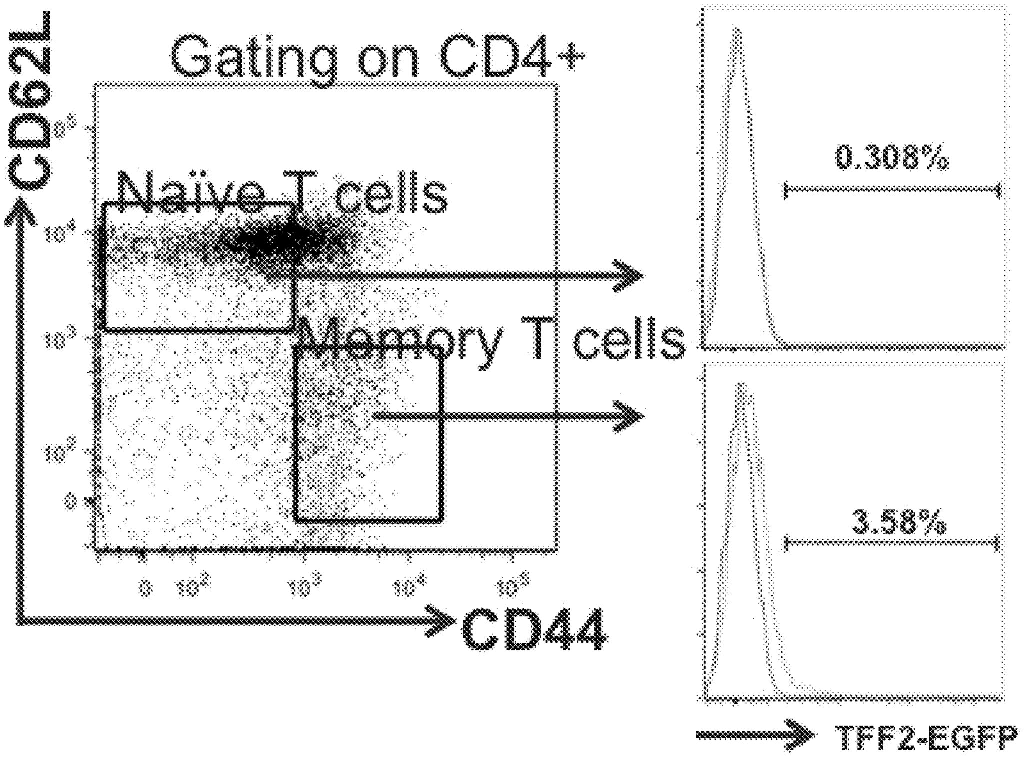
FIGS. 63A-B. (A) FACS plots of CD4+ memory T cells, demonstrating strong EGFP expression in these cells. (B)

To further address this issue, a TFF2-EGFP BAC transgenic mouse was generated. It was confirmed that the transgene was expressed in the stomach, pancreas and spleen. Splenic memory T cells were sorted using CD4+ CD44hiCD62Llo for flow sorting, and it was confirmed that these cells strongly expressed the TFF2-EGFP transgene, while the rest of the splenic T cells did not (FIG. 63A).

Figure 63B:
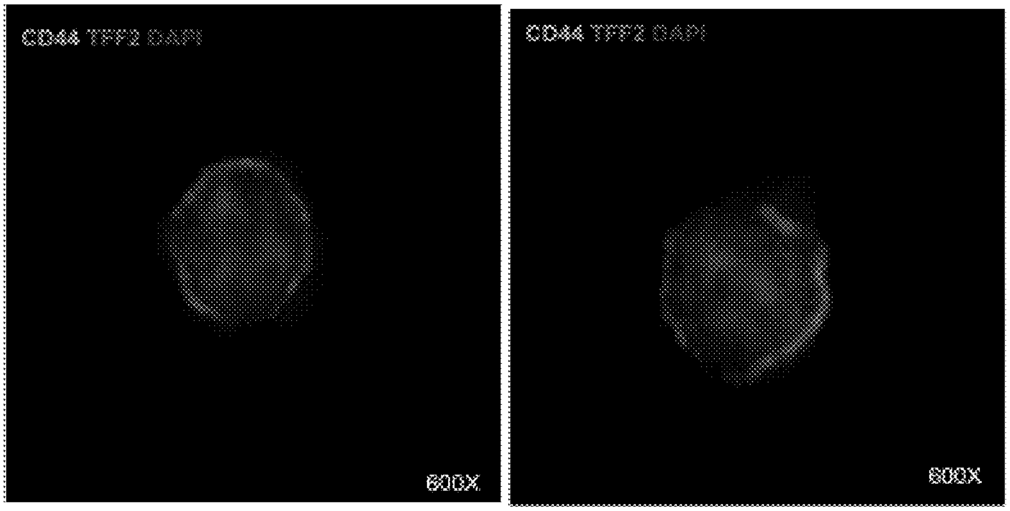

In addition, mouse splenocytes were treated with PMA/ionomycin, which combines cell stimulation with protein transport inhibition, and then FACS sorted memory T cells (CD4+CD44hiCD62Llo), then fixed, permeabilized and performed immunofluorescent staining (FIG. 63B). These studies confirmed colocalizaiton of TFF2 and CD44.

Example 10: T Cells are the Main Source of TFF2 in the Spleen

TFF2 is expressed in most mammals primarily in the gastric mucosa, but as described herein is also in low levels in the spleen. The data described herein suggested that T cells are the major source of TFF2 within the spleen. However, in order to confirm this finding, various hematopoietic populations in the spleen were sorted, and then assessed TFF2 expression by RT-PCR (FIG. 64). These studies showed that TFF2 is most strongly expressed in the CD4+ T cell population, with little expression in other compartments.

Example 11: Decreased Tumor Counts in TFF2-Overexpressing Mice are Due to T Cell Activation The data described herein showed that TFF2 overexpression inhibits expansion of myeloid-derived suppressor cells (MDSCs), which was associated with an increase in CD8+ T cells in the colon and a decrease in colonic tumors. To show that the decreased tumors in the colon are due to increased infiltration with activated T cells studies were carried out to show that CD8+ T cells are essential for the decreased colonic tumors seen in TFF2 transgenic mice (FIG. 65). CD2-TFF2 transgenic mice were treated with AOM/DSS and then treated with an anti-CD8 antibody that depleted CD8+ T cells in the mouse. The antibody was given twice a week for 12 weeks, with an isotype control. This depletion of CD8+ T cells resulted in a marked increase in tumor number and tumor load compared to the control, demonstrating the CD8+ T cells are necessary for the tumor inhibitory effect of TFF2.

Example 12: TFF2 Leads to Activated CD8+ T Cells in CD2-TFF2 Transgenic Mice In order to show that the TFF2-overexpressing mice have activated CD8+ Tcells, CD8+ T cells were sorted from the spleens of transgenic mice, and the amount of interferon-gamma and granzyme B (markers of activated T cells) was measured by ELISASPOT (FIG. 66). These studies showed that CD2-TFF2 transgenic mice had significantly increased IFN-g and Grb in their splenic CD8+ T cells compared to TFF2 null mice, following AOM+DSS.

Example 13: Myeloid Cells Instructed in a TFF2-Deficient Spleen Suppress CD8 T Cells and Promote Colon Cancer As described herein, TFF2 overexpression, whether via the CD2-TFF2 transgene or through Ad-TFF2 overexpression, suppresses MDSCs and suppresses colon tumors. To show that the suppression of colon tumors was through MDSCs, or that MDSCs in TFF2 deficient mice induced colon cancer, adoptive transfer of the MDSCs from TFF2−/− mice treated with AOM/DSS into CD2-TFF2 mice that have been treated with AOM/DSS was carried out. This addressed whether MDSCs from TFF2−/− mice that are prone to cancer can change the cancer-resistant CD2-TFF2 mice to mice that are susceptible to cancer. Is the absence of these MDSCs, instructed in the spleen of mice lacking TFF2, the critical factor missing in the process of cancer initiation by AOM/DSS. FIGS. 67A-B shows MDSCs contribute to carcinogenesis in AOM/DSS-induced colon cancer model.

Example 14: Splenic MDSC from TFF2-Null Mice Promote Colonic Tumorigenesis to a Greater Extent than MDSC from CD2-TFF2 Transgenic Mice Here it was shown the direct suppression of MDSC tumor initiating function by TFF2 overexpression. Myeloid precursors instructed in the spleen in the absence of TFF2 can migrate to the periphery to suppress CD8+ T cell responses, and such instruction can be altered by expression of TFF2 in the spleen. FIGS. 68A-B shows splenic IMC from Tff2-null mice show higher contribution in tumorigenesis vs. splenic IMC from CD2-Tff2 mice.

What is claimed:

1. An isolated polypeptide comprising a carboxy-terminal peptide (CTP) domain fused to a TFF2 protein, wherein the CTP domain comprises the C-terminal domain of the beta subunit of the human chorionic gonadotrophin (hCG).

2. The isolated polypeptide of claim 1 wherein one CTP domain is fused to the C-terminus of the TFF2 protein.

3. The isolated polypeptide of claim 1 wherein two CTP domains are fused in tandem to the C-terminus of the TFF2 protein.

4. The isolated polypeptide of claim 1 wherein three CTP domains are fused in tandem to the C-terminus of the TFF2 protein.

5. A pharmaceutical composition comprising the isolated polypeptide of claim 1 and a pharmaceutically acceptable carrier.

* * * * *

UNITED STATES PATENT AND TRADEMARK OFFICE

CERTIFICATE OF CORRECTION

PATENT NO. : 11,167,010 B2
APPLICATION NO. : 16/189868
DATED : November 9, 2021
INVENTOR(S) : Timothy C. Wang and Jan K. Kitajewski It is certified that error appears in the above-identified patent and that said Letters Patent is hereby corrected as shown below:

In the Specification

Column 1, Lines 16-20, under the Government Support Clause heading delete the following text: "This invention was made with government support under Grant No. NIH 5R01 DK060758-10 awarded by the National Institute of Health and the National Institute of Diabetes and Digestive and Kidney Diseases. The Government has certain rights in the invention."

And insert the following text:
--This invention was made with government support under grant DK060758 awarded by the National Institutes of Health. The government has certain rights in the invention.--

Signed and Sealed this
Twenty-eighth Day of December, 2021

Drew Hirshfeld
*Performing the Functions and Duties of the*
*Under Secretary of Commerce for Intellectual Property and*
*Director of the United States Patent and Trademark Office*